US010807970B2

(12) United States Patent
Garcia-Lopez et al.

(10) Patent No.: US 10,807,970 B2
(45) Date of Patent: Oct. 20, 2020

(54) TETRAHYDROPYRAN AND THIOPYRAN DERIVATIVES HAVING MULTIMODAL ACTIVITY AGAINST PAIN

(71) Applicant: ESTEVE PHARMACEUTICALS, S.A., Barcelona (ES)

(72) Inventors: Monica Garcia-Lopez, Barcelona (ES); Carmen Almansa-Rosales, Barcelona (ES); Ana Virginia Llorente-Fernandez, Barcelona (ES); Ute Christmann, Barcelona (ES); Sergio Rodriguez Escrich, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/301,508

(22) PCT Filed: May 19, 2017

(86) PCT No.: PCT/EP2017/000607
§ 371 (c)(1),
(2) Date: Nov. 14, 2018

(87) PCT Pub. No.: WO2017/198339
PCT Pub. Date: Nov. 23, 2017

(65) Prior Publication Data
US 2019/0241544 A1 Aug. 8, 2019

(30) Foreign Application Priority Data

May 20, 2016 (EP) .................................. 16382222

(51) Int. Cl.
| | | |
|---|---|---|
| *C07D 405/04* | (2006.01) | |
| *C07D 405/14* | (2006.01) | |
| *C07D 487/04* | (2006.01) | |
| *A61P 29/00* | (2006.01) | |
| *C07D 307/04* | (2006.01) | |
| *C07D 407/14* | (2006.01) | |
| *C07D 407/06* | (2006.01) | |

(52) U.S. Cl.
CPC ............ *C07D 405/04* (2013.01); *A61P 29/00* (2018.01); *C07D 307/04* (2013.01); *C07D 405/14* (2013.01); *C07D 407/06* (2013.01); *C07D 407/14* (2013.01); *C07D 487/04* (2013.01)

(58) Field of Classification Search
CPC ..... A61P 29/00; C07D 307/04; C07D 405/04; C07D 405/14; C07D 487/04
See application file for complete search history.

(56) References Cited

U.S. PATENT DOCUMENTS

| | | |
|---|---|---|
| 2010/0009986 A1 | 1/2010 | Zemolka |
| 2011/0071163 A1 | 3/2011 | Woodward |
| 2011/0245287 A1 | 10/2011 | Holaday et al. |
| 2011/0257105 A1 | 10/2011 | Schteingart et al. |
| 2019/0047970 A1 | 2/2019 | Kruegel et al. |

FOREIGN PATENT DOCUMENTS

| | | | |
|---|---|---|---|
| EP | 3328853 | | 6/2018 |
| WO | 2015092009 | * | 6/2015 |
| WO | WO2015091939 | | 6/2015 |
| WO | WO2015092009 | | 6/2015 |
| WO | WO2015185209 | | 12/2015 |

OTHER PUBLICATIONS

Mastrangelo G.,"Antinociceptive and anti-inflammatory profile of (±)-4-chloro-6-(naphthalen-1-yl-tetrahydro-2H-pyran-2-yl-methanol"; Institute of Biological Sciences and Health. Departament of Physiological Sciences, Federal Rural University of Rio de Janeiro, 2016 (Abstract).
Bornot A, Bauer U, Brown A. Firth M, Hellawell C, Engkvist O. Systematic Exploration of Dual-Acting Modulators from a Combined Medicinal Chemistry and Biology Perspective. J. Med. Chem, 56, 1197-1210 (2013).
Chien CC, Pasternak GW. Sigma antagonists potentiate opioid analgesia in rats, Neurosci. Lett. 190. 137-9 (1995).
Dickenson, A.H., Suzuki, R. Opioids in neuropathic pain: Clues from animal studies. Eur J Pain 9, 113-6 (2005).
Goldberg DS, McGee SJ, Pain as a global public health priority. BMC Public Health. 11, 770 (2011).
Harper, N.J. et al. "1-(3,4-Dichlorobenzamidomethyl)cyclohexyldimethylamine and related compounds as Potential Analgesics", Journal of Medicinal Chemistry, 1974, vol. 17, No. 11, pp. 1186-1193.
International Search Report and Written Opinion for PCT/EP2017/000607 dated Jun. 21, 2017.
Liu, et al., "Reductive cleavage of benzyl ethers with lithium naphthalenide. A convenient method for debenzylation", Tetrahedron Lett. 1997, 38, 2253.
Mao J, Gold MS. Backonja M. Combination drug therapy for chronic pain: a call for more clinical studies. J. Pain 12, 157-166 (2011).
McClure. Kelly J. et al. "Discovery of a novel series of selective HCN1 blockers"; Bioorganic & Medicinal Chemistry Letters, 2011, vol. 21, No. 18, pp. 5197-5201.
Turk DC, Wilson HD, Cahana A. Treatment of chronic non-cancer pain. Lancet 377, 2226-2235 (2011).

(Continued)

*Primary Examiner* — Mark L Shibuya
*Assistant Examiner* — Ebenezer O Sackey
(74) *Attorney, Agent, or Firm* — Hueschen and Sage

(57) ABSTRACT

The present invention relates to tetrahydropyran and thiopyran derivatives having dual pharmacological activity towards both the sigma (σ) receptor, and the μ-opioid receptor, to processes of preparation of such compounds, to pharmaceutical compositions comprising them, and to their use in therapy, in particular for the treatment of pain.

24 Claims, No Drawings

(56) References Cited

OTHER PUBLICATIONS

Zamanillo D, Romero L, Merlos M, Vela JM. Sigma 1 receptor: A new therapeutic target for pain. Eur. J. Pharmacol, 716, 78-93 (2013).

* cited by examiner

TETRAHYDROPYRAN AND THIOPYRAN DERIVATIVES HAVING MULTIMODAL ACTIVITY AGAINST PAIN

FIELD OF THE INVENTION

The present invention relates to compounds having dual pharmacological activity towards both the sigma (σ) receptor, and the μ-opioid receptor (MOR or mu-opioid receptor) and more particularly to tetrahydropyran and thiopyran derivatives having this pharmacological activity, to processes of preparation of such compounds, to pharmaceutical compositions comprising them, and to their use in therapy, in particular for the treatment of pain.

BACKGROUND OF THE INVENTION

The adequate management of pain constitutes an important challenge, since currently available treatments provide in many cases only modest improvements, leaving many patients unrelieved [Turk D C, Wilson H D, Cahana A. Treatment of chronic non-cancer pain. Lancet 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economical burden [Goldberg D S, McGee S J. Pain as a global public health priority. BMC Public Health. 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the μ-opioid receptor (MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. Opioids in neuropathic pain: Clues from animal studies. Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. Neurosci. Lett. 190, 137-9 (1995)], who described it as an endogenous anti-opioid system, based on the finding that $\sigma_1$ receptor agonists counteracted opioid receptor mediated analgesia, while $\sigma_1$ receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma 1 receptor: A new therapeutic target for pain. Eur. J. Pharmacol, 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviours than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. J. Pain 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Thus, the technical problem can therefore be formulated as finding compounds that have an alternative or improved pharmacological activity in the treatment of pain.

In view of the existing results of the currently available therapies and clinical practices, the present invention offers a solution by combining in a single compound binding to two different receptors relevant for the treatment of pain. This was mainly achieved by providing the compounds according to the invention that bind both to the μ-opioid receptor and to the $\sigma_1$ receptor.

SUMMARY OF THE INVENTION

The main object of the invention is in one aspect directed to tetrahydropyran and thiopyran derivatives having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a very preferred embodiment if the compound has a binding expressed as $K_i$ which is preferably <1000 nM for both receptors, more preferably <500 nM, even more preferably <100 nM.

More particularly the main aspect of the invention refers to a compound of general Formula (I),

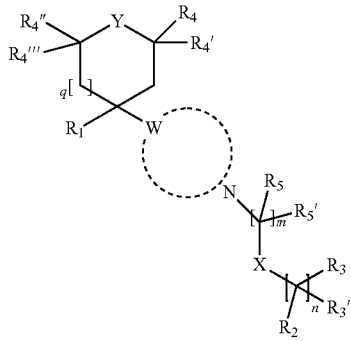

(I)

wherein $R_1$, $R_2$, $R_3$, $R_{3'}$, $R_4$, $R_{4'}$, $R_{4''}$, $R_{4'''}$, $R_5$, $R_{5'}$, X, Y, W, m, n, p and q are as defined below in the detailed description.

In another aspect, the invention refers to a compound of general Formula (I-a),

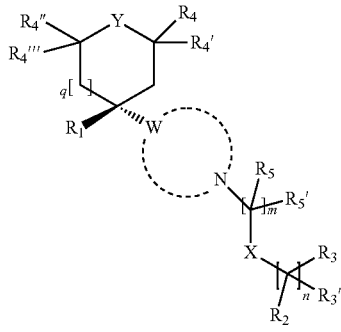

(I-a)

wherein $R_1$, $R_2$, $R_3$, $R_{3'}$, $R_4$, $R_{4'}$, $R_{4''}$, $R_{4'''}$, $R_5$, $R_{5'}$, X, Y, W, m, n, p and q are as defined below in the detailed description.

In another aspect, the invention refers to a compound of general Formula (I-b),

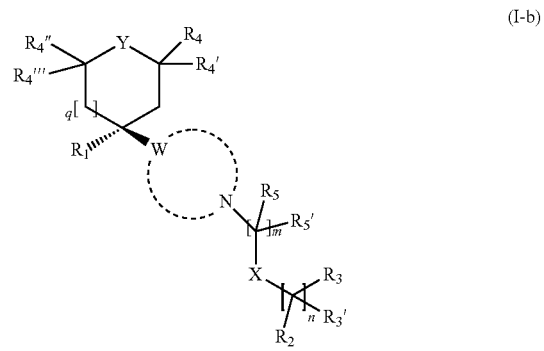

(I-b)

wherein $R_1$, $R_2$, $R_3$, $R_{3'}$, $R_4$, $R_{4'}$, $R_{4''}$, $R_{4'''}$, $R_5$, $R_{5'}$, X, Y, W, m, n, p and q are as defined below in the detailed description.

A further object of the invention refers to the processes for preparation of compounds of general formula (I), (I-a) or (I-b).

A still further object of the invention refers to the use of some intermediate compounds for the preparation of a compound of general formula (I), (I-a) or (I-b).

It is also an object of the invention a pharmaceutical composition comprising a compound of formula (I), (I-a) or (I-b).

Finally, it is an object of the invention the use of compound as a medicament and more particularly for the treatment of pain and pain related conditions.

DETAILED DESCRIPTION OF THE INVENTION

The invention is directed to a family of structurally distinct tetrahydropyran and thiopyran derivatives which have a dual pharmacological activity towards both the sigma (σ) receptor and the μ-opioid receptor, thus solving the above problem of identifying alternative or improved pain treatments by offering such dual compounds.

The invention is directed to compounds having a dual activity binding to the $\sigma_1$ receptor and the μ-opioid receptor for use in the treatment of pain.

As this invention is aimed at providing a compound or a chemically related series of compounds which act as dual ligands of the $\sigma_1$ receptor and the μ-opioid receptor it is a preferred embodiment if the compound has a binding expressed as $K_i$ which is preferably <1000 nM for both receptors, more preferably <500 nM, even more preferably <100 nM.

The applicant has surprisingly found that the problem of providing a new effective and alternative for treating pain and pain related disorders can be solved by using a multi-modal balanced analgesic approach combining two different synergistic activities in a single drug (i.e., dual ligands which are bifunctional and bind to μ-opioid receptor and to $\sigma_1$ receptor), thereby enhancing the opioid analgesia through the $\sigma_1$ activation without increasing the undesirable side effects. This supports the therapeutic value of a dual MOR/

σ₁ receptor compound whereby the σ₁ receptor binding component acts as an intrinsic adjuvant of the MOR binding component.

This solution offered the advantage that the two mechanisms complement each other in order to treat pain and chronic pain using lower and better tolerated doses needed based on the potentiation of analgesia but avoiding the adverse events of μ-opioid receptor agonists.

A dual compound that possess binding to both the μ-opioid receptor and to the σ₁ receptor shows a highly valuable therapeutic potential by achieving an outstanding analgesia (enhanced in respect to the potency of the opioid component alone) with a reduced side-effect profile (safety margin increased compared to that of the opioid component alone) versus existing opioid therapies.

Advantageously, the dual compounds according to the present invention would in addition show one or more the following functionalities: σ₁ receptor antagonism and μ-opioid receptor agonism. It has to be noted, though, that both functionalities "antagonism" and "agonism" are also subdivided in their effect into subfunctionalities like partial agonism or inverse agonism.

Accordingly, the functionalities of the dual compound should be considered within a relatively broad bandwidth.

An antagonist on one of the named receptors blocks or dampens agonist-mediated responses. Known subfunctionalities are neutral antagonists or inverse agonists.

An agonist on one of the named receptors increases the activity of the receptor above its basal level. Known subfunctionalities are full agonists, or partial agonists.

In addition, the two mechanisms complement each other since MOR agonists are only marginally effective in the treatment of neuropathic pain, while σ₁ receptor antagonists show outstanding effects in preclinical neuropathic pain models. Thus, the σ₁ receptor component adds unique analgesic actions in opioid-resistant pain. Finally, the dual approach has clear advantages over MOR agonists in the treatment of chronic pain as lower and better tolerated doses would be needed based on the potentiation of analgesia but not of the adverse events of MOR agonists.

A further advantage of using designed multiple ligands is a lower risk of drug-drug interactions compared to cocktails or multi-component drugs, thus involving simpler pharmacokinetics and less variability among patients.

Additionally, this approach may improve patient compliance and broaden the therapeutic application in relation to monomechanistic drugs, by addressing more complex aetiologies. It is also seen as a way of improving the R&D output obtained using the "one drug-one target" approach, which has been questioned over the last years [Bornot A, Bauer U, Brown A, Firth M, Hellawell C, Engkvist O. Systematic Exploration of Dual-Acting Modulators from a Combined Medicinal Chemistry and Biology Perspective. *J. Med. Chem*, 56, 1197-1210 (2013)].

In its broader aspect, the present invention is directed to compounds of general Formula (I):

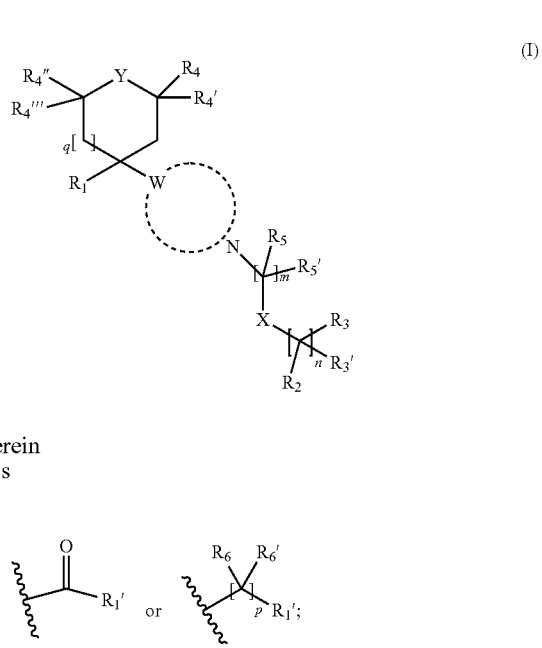

wherein
R₁ is $$\text{or}$$

m is 1, 2 or 3;
n is 0, 1 or 2;
p is 0, 1 or 2;
q is 0 or 1;
W is nitrogen or carbon;
X is a bond, —C(R$_x$R$_{x'}$)—, C=O or —O—;
  wherein R$_x$ is selected from halogen, —OR₇, substituted or unsubstituted C$_{1-6}$ alkyl, substituted or unsubstituted C$_{2-6}$ alkenyl and substituted or unsubstituted C$_{2-6}$ alkynyl;
  R$_{x'}$ is selected from hydrogen, halogen, substituted or unsubstituted C$_{1-6}$ alkyl, substituted or unsubstituted C$_{2-6}$ alkenyl and substituted or unsubstituted C$_{2-6}$ alkynyl;
  R₇ is selected from hydrogen, substituted or unsubstituted C$_{1-6}$ alkyl, substituted or unsubstituted C$_{2-6}$ alkenyl and substituted or unsubstituted C$_{2-6}$ alkynyl;
Y is —S— or —O—;
R$_{1'}$ is selected from substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl;
R₂ is selected from, substituted or unsubstituted C$_{1-6}$ alkyl, substituted or unsubstituted C$_{2-6}$ alkenyl, substituted or unsubstituted C$_{2-6}$ alkynyl, substituted or unsubstituted cycloalkyl, substituted or unsubstituted aryl and substituted or unsubstituted heterocyclyl,
R₃ and R$_{3'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl;
R₄ and R$_{4'}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl,
alternatively, R₄ and R$_{4'}$, may form together with the carbon atom to which they are attached a substituted or unsubstituted cycloalkyl;
R$_{4''}$ and R$_{4'''}$ are independently selected from hydrogen, substituted or unsubstituted C$_{1-6}$ alkyl, substituted or unsubstituted C$_{2-6}$ alkenyl and substituted or unsubstituted C$_{2-6}$ alkynyl, alternatively, $R_{4''}$ and $R_{4'''}$, may form together with the carbon atom to which they are attached a substituted or unsubstituted cycloalkyl;

$R_5$ and $R_{5''}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_8$ and —C(O)OR$_8$;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_6$ and $R_{6'}$ are independently selected from hydrogen, —OR$_9$, substituted or unsubstituted $C_{1-6}$ alkyl, substituted or unsubstituted $C_{2-6}$ alkenyl and substituted or unsubstituted $C_{2-6}$ alkynyl;

wherein $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and wherein

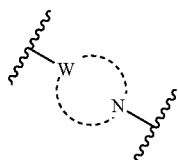

is selected from

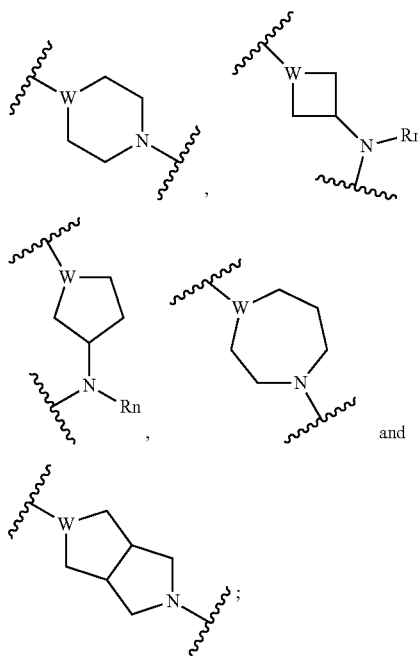

wherein $R_n$ is selected from unsubstituted $C_{1-6}$ alkyl, unsubstituted $C_{2-6}$ alkenyl and unsubstituted $C_{2-6}$ alkynyl.

In one embodiment, the present invention is directed to compounds of general Formula (I-a):

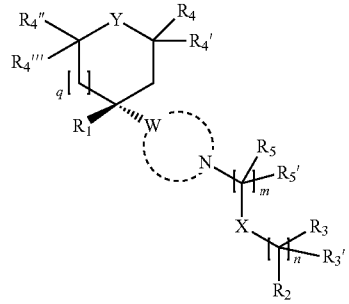

(I-a)

wherein
$R_1$ is

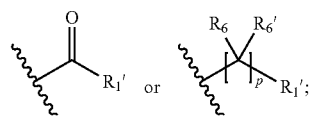

m is 1, 2 or 3;
n is 0, 1 or 2;
p is 0, 1 or 2;
q is 0 or 1;
W is nitrogen or carbon;
X is a bond, —C(R$_x$R$_{x'}$)—, C=O or —O—;
wherein $R_x$ is selected from halogen, —OR$_7$, substituted or unsubstituted $C_{1-6}$ alkyl, substituted or unsubstituted $C_{2-6}$ alkenyl and substituted or unsubstituted $C_{2-6}$ alkynyl;

$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

$R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

Y is —S— or —O—;
$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

$R_2$ is selected from, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_4$ and $R_{4'}$, may form together with the carbon atom to which they are attached a substituted or unsubstituted cycloalkyl;

$R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_{4''}$ and $R_{4'''}$, may form together with the carbon atom to which they are attached a substituted or unsubstituted cycloalkyl;

$R_5$ and $R_{5''}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_8$ and —C(O)OR$_8$;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_6$ and $R_{6'}$ are independently selected from hydrogen, —OR$_9$, substituted or unsubstituted $C_{1-6}$ alkyl, substituted or unsubstituted $C_{2-6}$ alkenyl and substituted or unsubstituted $C_{2-6}$ alkynyl;

wherein $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and wherein

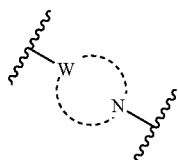

is selected from

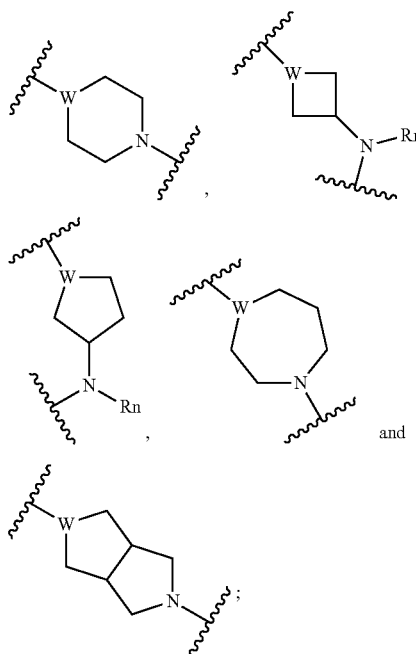

wherein $R_n$ is selected from unsubstituted $C_{1-6}$ alkyl, unsubstituted $C_{2-6}$ alkenyl and unsubstituted $C_{2-6}$ alkynyl.

In one embodiment, the present invention is directed to compounds of general Formula (I-b):

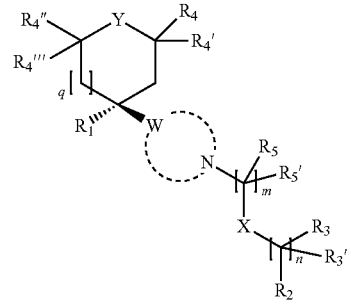

(I-b)

wherein
$R_1$ is

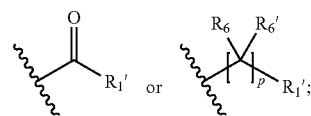

m is 1, 2 or 3;
n is 0, 1 or 2;
p is 0, 1 or 2;
q is 0 or 1;
W is nitrogen or carbon;
X is a bond, —C(R$_x$R$_{x'}$)—, C=O or —O—;
wherein $R_x$ is selected from halogen, —OR$_7$, substituted or unsubstituted $C_{1-6}$ alkyl, substituted or unsubstituted $C_{2-6}$ alkenyl and substituted or unsubstituted $C_{2-6}$ alkynyl;
$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
$R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
Y is —S— or —O—;
$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
$R_2$ is selected from, substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
alternatively, $R_4$ and $R_{4'}$, may form together with the carbon atom to which they are attached a substituted or unsubstituted cycloalkyl;
$R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_{4''}$ and $R_{4'''}$, may form together with the carbon atom to which they are attached a substituted or unsubstituted cycloalkyl;

$R_5$ and $R_{5''}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_8$ and —C(O)OR$_8$;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_6$ and $R_{6'}$ are independently selected from hydrogen, —OR$_9$, substituted or unsubstituted $C_{1-6}$ alkyl, substituted or unsubstituted $C_{2-6}$ alkenyl and substituted or unsubstituted $C_{2-6}$ alkynyl;

wherein $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and wherein

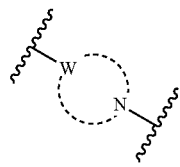

is selected from

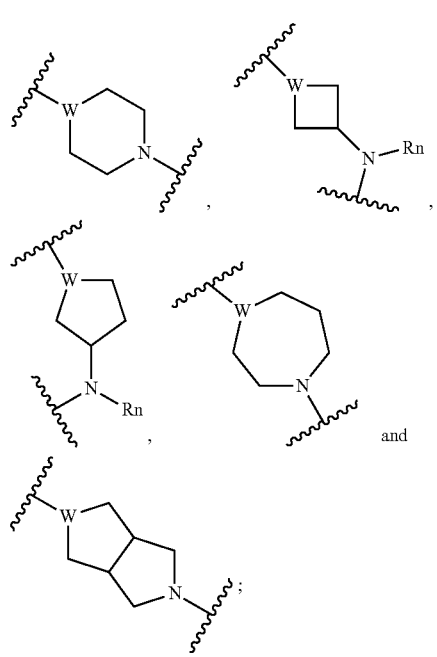

wherein $R_n$ is selected from unsubstituted $C_{1-6}$ alkyl, unsubstituted $C_{2-6}$ alkenyl and unsubstituted $C_{2-6}$ alkynyl.

These compounds above according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment, these compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In a further embodiment the following proviso applies: $R_1$ is not —CH$_2$NH$_2$.

In a further embodiment the following proviso applies: $R_1$ is not —CN.

In a further embodiment the following compound is excluded:

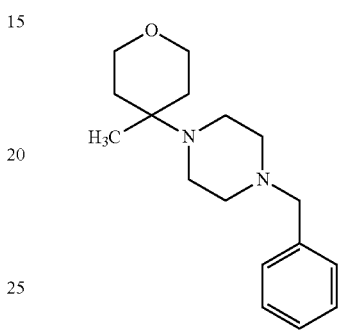

In a further embodiment the following compound is excluded:

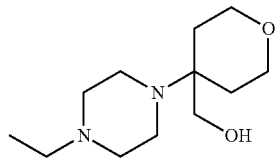

In one further embodiment W is N or CH.
In one further embodiment W is N.
In one further embodiment W is CH.

In a further embodiment the compound according to the invention of general Formula (I) is a compound of general Formula (I')

(I')

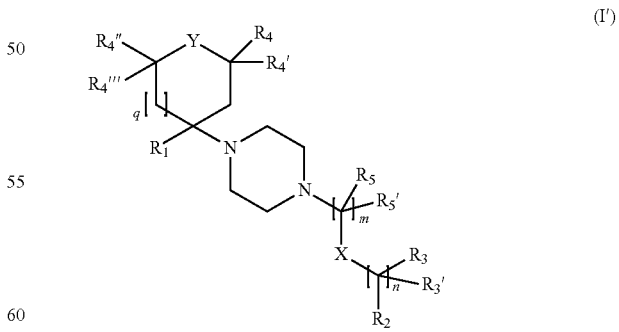

wherein, $R_1$, $R_2$, $R_3$, $R_{3'}$, $R_4$, $R_{4'}$, $R_{4''}$, $R_{4'''}$, $R_5$, $R_{5'}$, X, Y, m, n and q are as defined in the description.

In a further embodiment the compound according to the invention of general Formula (I) is a compound of general Formula (I²')

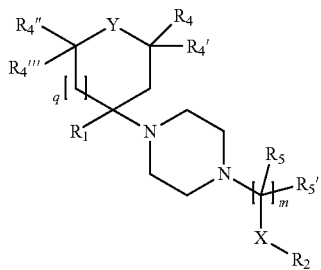

(I²')

wherein $R_1$, $R_2$, $R_4$, $R_{4'}$, $R_{4''}$, $R_{4'''}$, $R_5$, $R_{5'}$, X, Y, m, n and q are as defined in the description.

In a further embodiment, for compounds of general Formula (I) described above in which

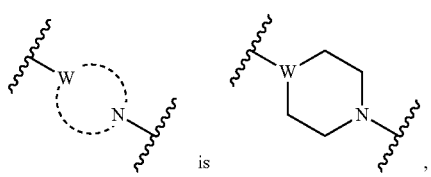

the compounds are thus compounds of general Formula (I³')

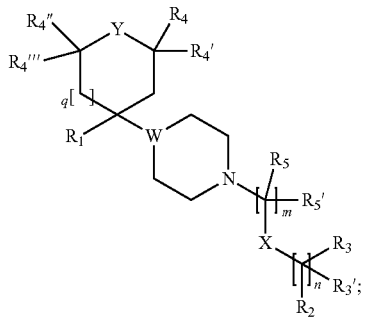

(I³')

wherein $R_1$, $R_2$, $R_3$, $R_{3'}$, $R_4$, $R_{4'}$, $R_{4''}$, $R_{4'''}$, $R_5$, $R_{5'}$, X, Y, W, m, n and q are as defined in the description;
preferably, the compounds of general Formula (I³') are compounds of general Formula (I⁴')

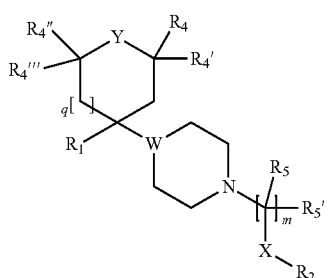

(I⁴')

wherein $R_1$, $R_2$, $R_4$, $R_{4'}$, $R_{4''}$, $R_{4'''}$, $R_5$, $R_{5'}$, X, Y, W, m and q are as defined in the description.

preferably, the compounds of general Formula (I⁴') are compounds of general Formula (I⁴ᵇ')

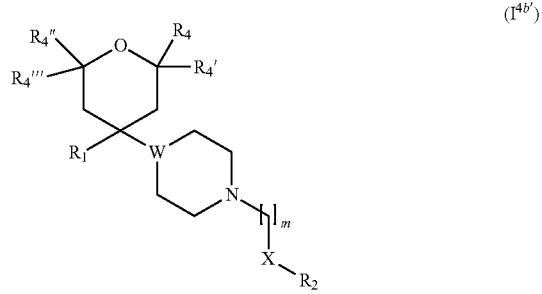

(I⁴ᵇ')

wherein $R_1$, $R_2$, $R_4$, $R_{4'}$, $R_{4''}$, $R_{4'''}$, X, W and m are as defined in the description.

In a further embodiment, for compounds of general Formula (I) described above in which

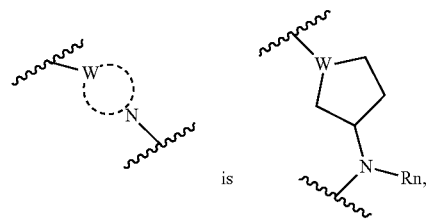

the compounds are thus compounds of general Formula (I⁵')

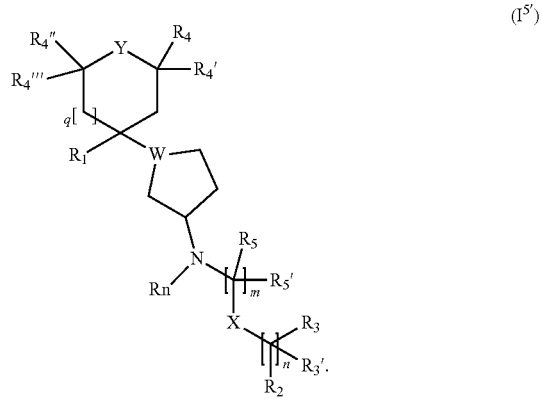

(I⁵')

wherein $R_1$, $R_2$, $R_3$, $R_{3'}$, $R_4$, $R_{4'}$, $R_{4''}$, $R_{4'''}$, $R_5$, $R_{5'}$, $R_n$, X, Y, W, m, n and q are as defined in the description;
preferably, the compounds of general Formula (I⁵') are compounds of general Formula (I⁶')

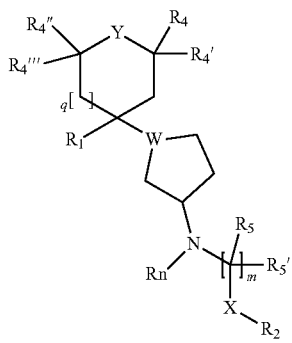
(I6')

wherein $R_1$, $R_2$, $R_4$, $R_{4'}$, $R_{4''}$, $R_{4'''}$, $R_5$, $R_{5'}$, X, Y, W, m and q are as defined in the description;

In a further embodiment, for compounds of general Formula (I) described above in which

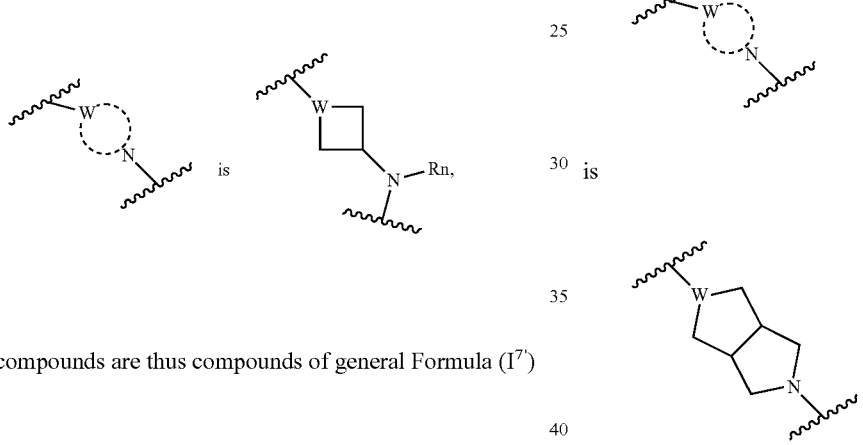

the compounds are thus compounds of general Formula (I7')

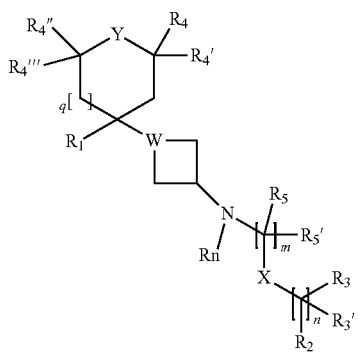
(I7')

wherein $R_1$, $R_2$, $R_3$, $R_{3'}$, $R_4$, $R_{4'}$, $R_{4''}$, $R_{4'''}$, $R_5$, $R_{5'}$, $R_n$, X, Y, W, m, n and q are as defined in the description, preferably, the compounds of general Formula (I7') are compounds of general Formula (I8')

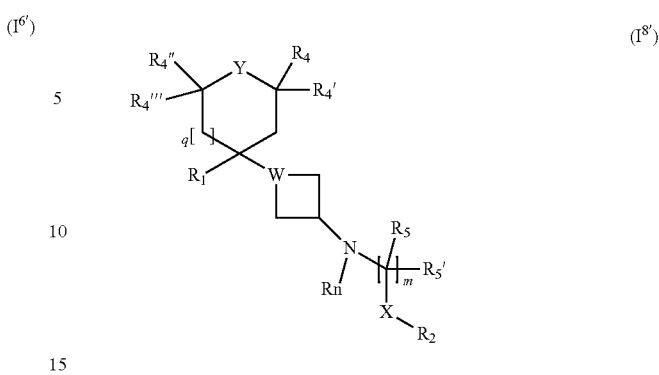
(I8')

wherein $R_1$, $R_2$, $R_4$, $R_{4'}$, $R_{4''}$, $R_{4'''}$, $R_5$, $R_{5'}$, $R_n$, X, Y, W, m and q are as defined in the description.

In a further embodiment, for compounds of general Formula (I) described above in which

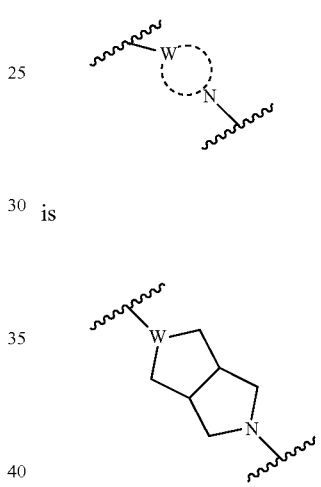

is the compounds are thus compounds of general Formula (I9')

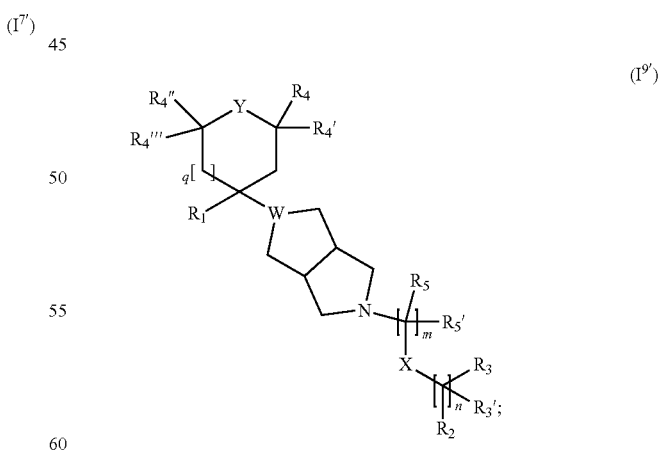
(I9')

wherein $R_1$, $R_2$, $R_3$, $R_{3'}$, $R_4$, $R_{4'}$, $R_{4''}$, $R_{4'''}$, $R_5$, $R_{5'}$, X, Y, W, m, n and q are as defined in the description;

preferably, the compounds of general Formula (I9') are compounds of general Formula (I10')

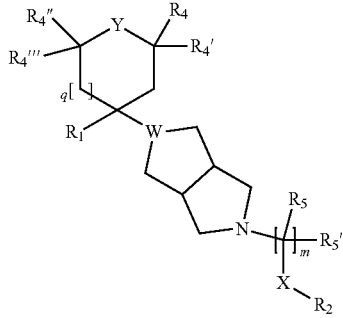 (I¹⁰')

wherein $R_1$, $R_2$, $R_4$, $R_{4'}$, $R_{4''}$, $R_{4'''}$, $R_5$, $R_{5'}$, X, Y, W, m and q are as defined in the description.

In a further embodiment, for compounds of general Formula (I) described above in which

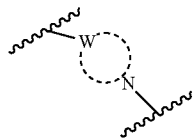

is

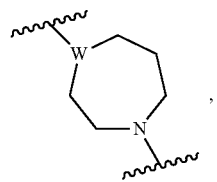, the compounds are thus compounds of general Formula (I¹¹')

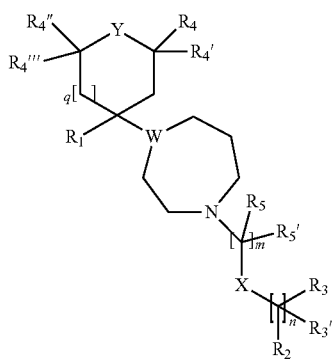 (I¹¹')

wherein $R_1$, $R_2$, $R_3$, $R_{3'}$, $R_4$, $R_{4'}$, $R_{4''}$, $R_{4'''}$, $R_5$, $R_{5'}$, X, Y, W, m, n and q are as defined in the description;
preferably, the compounds of general Formula (I¹¹') are compounds of general Formula (I¹²')

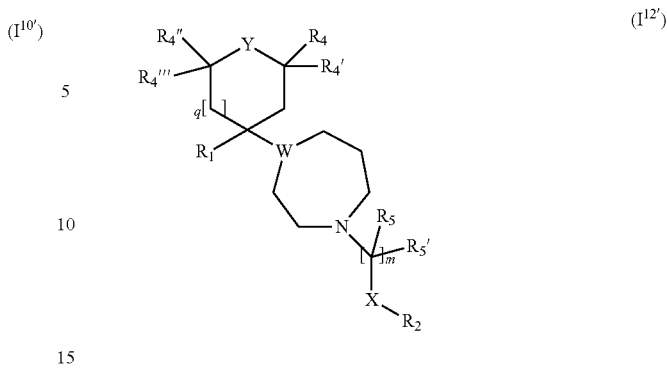 (I¹²')

wherein $R_1$, $R_2$, $R_4$, $R_{4'}$, $R_{4''}$, $R_{4'''}$, $R_5$, $R_{5'}$, X, Y, W, m and q are as defined in the description.

For clarity purposes, reference is also made to the following statements below in the definitions of substitutions on alkyl etc. or aryl etc. that "wherein when different radicals $R_1$ to $R_{14''''}$ and $R_x$, $R_{x'}$ and $R_n$ are present simultaneously in Formula I they may be identical or different". This statement is reflected in the below general Formula (I⁴ᵃ') being derived from and falling into general Formula (I⁴) as well as Formula (I).

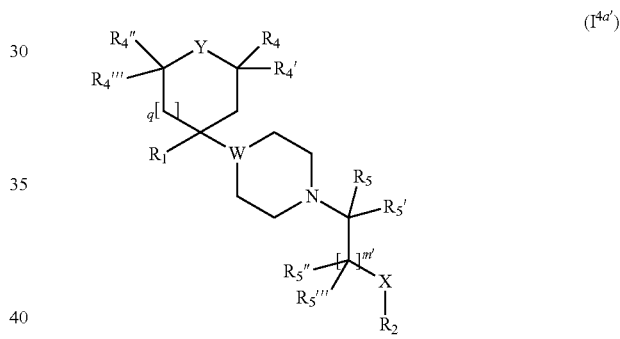 (I⁴ᵃ')

wherein $R_1$, $R_2$, $R_4$, $R_{4'}$, $R_{4''}$, $R_{4'''}$, $R_5$, $R_{5'}$, X, Y, W and q are as defined in the description. In addition, m' (being 0 or 1), $R_{5''}$ and $R_{5'''}$ are added. As said above, this statement is thus reflected in that $R_{5''}$ and $R_{5'''}$ are or could be different from $R_5$ and $R_{5'}$ or not and—accordingly—m' being 0 or 1 is naturally resulting from m (in general Formulas (I) or (I⁴) being 1 or 2).

The same would be applicable mutatis mutandis for general Formulas like general Formula (I) as well as the other general Formulas (I') to (I¹²') above.

For clarity purposes, all groups and definitions described in the description and referring to compounds of general Formula (I), also apply to compounds of general Formula (I-a), (I-b), (I'), (I²'), (I³'), (I⁴'), (I⁵'), (I⁶'), (I⁷'), (I⁸'), (I⁹'), (I¹⁰'), (I¹¹') or (I¹²'), (I⁴ᵃ') and (I⁴ᵇ') and to all synthesis intermediates when those groups are present in the mentioned general Markush formulae, since compounds of general Formula (I-a), (I-b), (I'), (I²'), (I³'), (I⁴'), (I⁵'), (I⁶'), (I⁷'), (I⁸'), (I⁹'), (I¹⁰'), (I¹¹'), (I¹²'), (I⁴ᵃ') or (I⁴ᵇ') are included in the general Formula (I).

For clarity purposes, all compounds described in the description and referring to compounds of general Formula (I), (I'), (I²'), (I³'), (I⁴'), (I⁵'), (I⁶'), (I⁷'), (I⁸'), (I⁹'), (I¹'), (I¹¹') or (I¹²'), and to all synthesis intermediates having the moiety (Q)

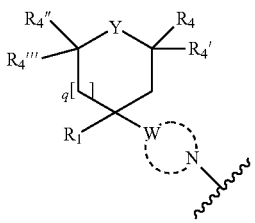

can also refer to compounds exhibiting stereochemistry like (Q1) or (Q2)

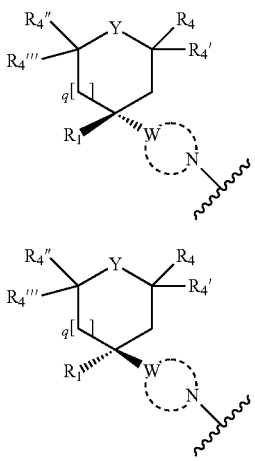

For clarity purposes, the general Markush Formula (I)

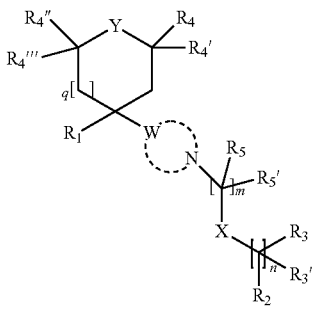

is equivalent to

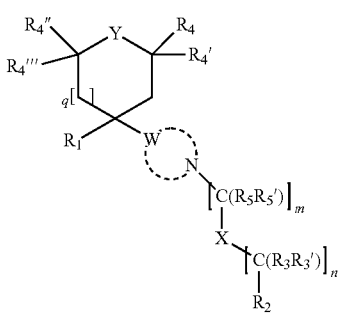

wherein only —C(R$_5$R$_5$')— and —C(R$_3$R$_3$')— are included into the brackets and m or n mean the number of times that —C(R$_5$R$_5$')— or —C(R$_3$R$_3$')— is repeated, respectively. The same would apply to general Markush Formulae (I'), (I-a), (I-b), (I$^{2'}$), (I$^{3'}$), (I$^{4'}$), (I$^{4a'}$), (I$^{4b'}$), (I$^{5'}$), (I$^{6'}$), (I$^{7'}$), (I$^{8'}$), (I$^{9'}$), (I$^{10'}$), (I$^{11'}$) or (I$^{12'}$) and to all synthesis intermediates when applicable. Thus in general, (where applicable) m and n mean in all general Markush Formulae (I), (I'), (I-a), (I-b), (I$^{2'}$), (I$^{3'}$), (I$^{4'}$), (I$^{4a'}$), (I$^{4b'}$) (I$^{5'}$), (I$^{6'}$), (I$^{7'}$), (I$^{8'}$), (I$^{9'}$), (I$^{10'}$), (I$^{11'}$) or (I$^{12'}$) and to all synthesis intermediates when applicable the number of times that —C(R$_5$R$_5$')— or —C(R$_3$R$_3$')— is repeated, respectively.

In addition, and for clarity purposes, it should further be understood that naturally if n is 0, R$_2$ is still present in general Markush Formulae (I'), (I$^{2'}$), (I$^{3'}$), (I$^{4'}$), (I$^{4a'}$), (I$^{4b'}$), (I$^{5'}$), (I$^{6'}$), (I$^{7'}$), (I$^{8'}$), (I$^{9'}$), (I$^{10'}$), (I$^{11'}$) or (I$^{12'}$).

Another additional embodiment of the invention relates to the compounds

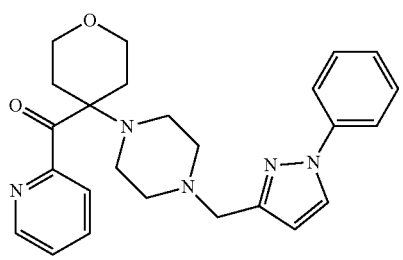

(4-(4-((1-phenyl-1H-pyrazol-3-yl)methyl)piperazin-1-yl) tetrahydro-2H-pyran-4-yl)(pyridin-2-yl)methanone; Compound 206) and

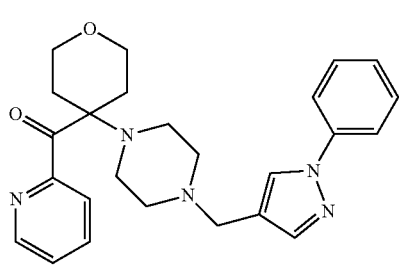 [SMILES: O=C(c1ccccn1)C1(N2CCN(Cc3cnn(-c4ccccc4)c3)CC2)CCOCC1]

(4-(4-((1-phenyl-1H-pyrazol-4-yl)methyl)piperazin-1-yl) tetrahydro-2H-pyran-4-yl)(pyridin-2-yl)methanone; Compound 207).

These Compounds 206 and 207 according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof.

In the context of this invention, alkyl is understood as meaning saturated, linear or branched hydrocarbons, which may be unsubstituted or substituted once or several times. It encompasses e.g. —CH$_3$ and —CH$_2$—CH$_3$. In these radicals, C$_{1-2}$-alkyl represents C1- or C2-alkyl, C$_{1-3}$-alkyl represents C1-, C2- or C3-alkyl, C$_{1-4}$-alkyl represents C1-, C2-, C3- or C4-alkyl, C$_{1-5}$-alkyl represents C1-, C2-, C3-, C4-, or C5-alkyl, C$_{1-6}$-alkyl represents C1-, C2-, C3-, C4-, C5- or C6-alkyl, C$_{1-7}$-alkyl represents C1-, C2-, C3-, C4-, C5-, C6- or C7-alkyl, C$_{1-8}$-alkyl represents C1-, C2-, C3-, C4-, C5-, C6-, C7- or C8-alkyl, C$_{1-10}$-alkyl represents C1-, C2-, C3-, C4-, C5-, C6-, C7-, C8-, C9- or C10-alkyl and $C_{1-18}$-alkyl represents C1-, C2-, C3-, C4-, C5-, C6-, C7-, C8-, C9-, C10-, C11-, C12-, C13-, C14-, C15-, C16-, C17- or C18-alkyl. The alkyl radicals are preferably methyl, ethyl, propyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc. Preferably alkyl is understood in the context of this invention as $C_{1-8}$alkyl like methyl, ethyl, propyl, butyl, pentyl, hexyl, heptyl, or octyl; preferably is $C_{1-6}$alkyl like methyl, ethyl, propyl, butyl, pentyl, or hexyl; more preferably is $C_{1-4}$alkyl like methyl, ethyl, propyl or butyl.

Alkenyl is understood as meaning unsaturated, linear or branched hydrocarbons, which may be unsubstituted or substituted once or several times. It encompasses groups like e.g. $-CH=CH-CH_3$. The alkenyl radicals are preferably vinyl (ethenyl), allyl (2-propenyl). Preferably in the context of this invention alkenyl is $C_{2-10}$-alkenyl or $C_{2-8}$-alkenyl like ethylene, propylene, butylene, pentylene, hexylene, heptylene or octylene; or is $C_{2-6}$-alkenyl like ethylene, propylene, butylene, pentylene, or hexylene; or is $C_{2-4}$-alkenyl, like ethylene, propylene, or butylenes.

Alkynyl is understood as meaning unsaturated, linear or branched hydrocarbons, which may be unsubstituted or substituted once or several times. It encompasses groups like e.g. $-C\equiv CH_3$ (1-propinyl). Preferably alkynyl in the context of this invention is $C_{2-10}$-alkynyl or $C_{2-8}$-alkynyl like ethyne, propyne, butyene, pentyne, hexyne, heptyne, or octyne; or is $C_{2-6}$-alkynyl like ethyne, propyne, butyene, pentyne, or hexyne; or is $C_{2-4}$-alkynyl like ethyne, propyne, butyene, pentyne, or hexyne.

In connection with alkyl (also in alkylaryl, alkylheterocyclyl or alkylcycloalkyl), alkenyl, alkynyl and O-alkyl—unless defined otherwise—the term substituted in the context of this invention is understood as meaning replacement of at least one hydrogen radical on a carbon atom by halogen (F, Cl, Br, I), $-NR_cR_{c'''}$, $-SR_c$, $-S(O)R_c$, $-S(O)_2R_c$, $-OR_c$, $-C(O)OR_c$, $-CN$, $-C(O)NR_cR_{c'}$, haloalkyl, haloalkoxy or $-OC_{1-6}$alkyl, being $R_c$ represented by $R_{11}$, $R_{12}$, $R_{13}$, (being $R_{c'}$ represented by $R_{11'}$, $R_{12'}$, $R_{13'}$; being $R_{c''}$ represented by $R_{11''}$, $R_{12''}$, $R_{13''}$; being $R_{c'''}$ represented by $R_{11'''}$, $R_{12'''}$, $R_{13'''}$), being $R_{c''''}$ represented by $R_{11''''}$, $R_{12''''}$, $R_{13''''}$) wherein $R_1$ to $R_{14''''}$ and $R_x$, $R_{x'}$ and $R_n$ are as defined in the description, and wherein when different radicals $R_1$ to $R_{14''''}$ and $R_x$, $R_{x'}$ and $R_n$ are present simultaneously in Formula I they may be identical or different.

Most preferably in connection with alkyl (also in alkylaryl, alkylheterocyclyl or alkylcycloalkyl), alkenyl, alkynyl or O-alkyl, substituted is understood in the context of this invention that any alkyl (also in alkylaryl, alkylheterocyclyl or alkylcycloalkyl), alkenyl, alkynyl or O-alkyl which, if substituted, is substituted with one or more of halogen (F, Cl, Br, I), $-OR_c$, $-CN$, $-SR_c$, $-S(O)R_c$, $-S(O)_2R_c$, haloalkyl, haloalkoxy or $-OC_{1-6}$alkyl, being $R_c$ represented by $R_{11}$, $R_{12}$, $R_{13}$, (being $R_{c'}$ represented by $R_{11'}$, $R_{12'}$, $R_{13'}$; being $R_{c''}$ represented by $R_{11''}$, $R_{12''}$, $R_{13''}$; being $R_{c'''}$ represented by $R_{11'''}$, $R_{12'''}$, $R_{13'''}$, being $R_{c''''}$ represented by $R_{11''''}$, $R_{12''''}$, $R_{13''''}$), wherein $R_1$ to $R_{14''''}$ and $R_x$, $R_{x'}$ and $R_n$ are as defined in the description, and wherein when different radicals $R_1$ to $R_{14''''}$ and $R_x$, $R_{x'}$ and $R_n$ are present simultaneously in Formula I, they may be identical or different.

More than one replacement on the same molecule and also on the same carbon atom is possible with the same or different substituents. This includes for example 3 hydrogens being replaced on the same C atom, as in the case of $CF_3$, or at different places of the same molecule, as in the case of e.g. $-CH(OH)-CH=CH-CHCl_2$.

In the context of this invention haloalkyl is understood as meaning an alkyl being substituted once or several times by a halogen (selected from F, Cl, Br, I). It encompasses e.g. $-CH_2Cl$, $-CH_2F$, $-CHCl_2$, $-CHF_2$, $-CCl_3$, $-CF_3$ and $-CH_2-CHCl_2$. Preferably haloalkyl is understood in the context of this invention as halogen-substituted $C_{1-4}$-alkyl representing halogen substituted C1-, C2-, C3- or C4-alkyl. The halogen-substituted alkyl radicals are thus preferably methyl, ethyl, propyl, and butyl. Preferred examples include $-CH_2Cl$, $-CH_2F$, $-CHCl_2$, $-CHF_2$, and $-CF_3$.

In the context of this invention haloalkoxy is understood as meaning an $-O$-alkyl being substituted once or several times by a halogen (selected from F, Cl, Br, I). It encompasses e.g. $-OCH_2Cl$, $-OCH_2F$, $-OCHCl_2$, $-OCHF_2$, $-OCCl_3$, $-OCF_3$ and $-OCH_2-CHCl_2$. Preferably haloalkyl is understood in the context of this invention as halogen-substituted $-OC_{1-4}$-alkyl representing halogen substituted C1-, C2-, C3- or C4-alkoxy. The halogen-substituted alkyl radicals are thus preferably O-methyl, O-ethyl, O-propyl, and O-butyl. Preferred examples include $-OCH_2Cl$, $-OCH_2F$, $-OCHCl_2$, $-OCHF_2$, and $-OCF_3$.

In the context of this invention cycloalkyl is understood as meaning saturated and unsaturated (but not aromatic) cyclic hydrocarbons (without a heteroatom in the ring), which can be unsubstituted or once or several times substituted. Furthermore, $C_{3-4}$-cycloalkyl represents C3- or C4-cycloalkyl, $C_{3-5}$-cycloalkyl represents C3-, C4- or C5-cycloalkyl, $C_{3-6}$-cycloalkyl represents C3-, C4-, C5- or C6-cycloalkyl, $C_{3-7}$-cycloalkyl represents C3-, C4-, C5-, C6- or C7-cycloalkyl, $C_{3-8}$-cycloalkyl represents C3-, C4-, C5-, C6-, C7- or C8-cycloalkyl, $C_{4-5}$-cycloalkyl represents C4- or C5-cycloalkyl, $C_{4-6}$-cycloalkyl represents C4-, C5- or C6-cycloalkyl, $C_{4-7}$-cycloalkyl represents C4-, C5-, C6- or C7-cycloalkyl, $C_{5-6}$-cycloalkyl represents C5- or C6-cycloalkyl and $C_{5-7}$-cycloalkyl represents C5-, C6- or C7-cycloalkyl. Examples are cyclopropyl, 2-methylcyclopropyl, cyclopropylmethyl, cyclobutyl, cyclopentyl, cyclopentylmethyl, cyclohexyl, cycloheptyl, cyclooctyl, and also adamantyl. Preferably in the context of this invention cycloalkyl is $C_{3-8}$cycloalkyl like cyclopropyl, cyclobutyl, cyclopentyl, cyclohexyl, cycloheptyl, or cyclooctyl; or is $C_{3-7}$cycloalkyl like cyclopropyl, cyclobutyl, cyclopentyl, cyclohexyl, or cycloheptyl; or is $C_{3-6}$cycloalkyl like cyclopropyl, cyclobutyl, cyclopentyl or cyclohexyl, especially cyclopentyl or cyclohexyl.

Aryl is understood as meaning 5 to 18 membered mono or polycyclic ring systems with at least one aromatic ring but without heteroatoms even in only one of the rings. Examples are phenyl, naphthyl, fluoranthenyl, fluorenyl, tetralinyl, indanyl, 9H-fluorenyl or anthracenyl radicals, which can be unsubstituted or once or several times substituted. Most preferably aryl is understood in the context of this invention as phenyl, naphthyl or anthracenyl, preferably is phenyl.

A heterocyclyl radical or group (also called heterocyclyl hereinafter) is understood as meaning 5 to 18 membered mono or poly heterocyclic ring systems, with at least one saturated or unsaturated ring which contains one or more heteroatoms selected from the group consisting of nitrogen, oxygen and/or sulfur in the ring. A heterocyclic group can also be substituted once or several times.

Examples include non-aromatic heterocyclyls such as tetrahydropyran, oxazepane, morpholine, piperidine, pyrrolidine as well as heteroaryls such as furan, benzofuran, thiophene, benzothiophene, pyrrole, pyridine, pyrimidine, pyrazine, quinoline, isoquinoline, phthalazine, thiazole, benzothiazole, indole, benzotriazole, carbazole and quinazoline.

Subgroups inside the heterocyclyls as understood herein include heteroaryls and non-aromatic heterocyclyls.

the heteroaryl (being equivalent to heteroaromatic radicals or aromatic heterocyclyls) is an aromatic 5 to 18 membered mono or polycyclic heterocyclic ring system of one or more rings of which at least one aromatic 5 to 18 membered ring contains one or more heteroatoms selected from the group consisting of nitrogen, oxygen and/or sulfur in the ring; preferably is an aromatic 5 to 18 membered mono or polycyclic heterocyclic ring system of one or two rings of which at least one aromatic ring contains one or more heteroatoms selected from the group consisting of nitrogen, oxygen and/or sulfur in the ring, more preferably is selected from furan, benzofuran, thiophene, benzothiophene, pyrrole, pyridine, pyrimidine, pyrazine, quinoline, isoquinoline, phthalazine, benzothiazole, indole, benzotriazole, carbazole, quinazoline, thiazole, imidazole, pyrazole, oxazole, thiophene and benzimidazole;

the non-aromatic heterocyclyl is a 5 to 18 membered heterocyclic ring system of one or more rings of which at least one ring—with this (or these) ring(s) then not being aromatic—contains one or more heteroatoms selected from the group consisting of nitrogen, oxygen and/or sulfur in the ring; preferably is a 5 to 18 membered mono or polycyclic heterocyclic ring system of one or two rings of which one or both rings—with this one or two rings then not being aromatic—contain/s one or more heteroatoms selected from the group consisting of nitrogen, oxygen and/or sulfur in the ring, more preferably is selected from oxazepam, pyrrolidine, piperidine, piperazine, tetrahydropyran, morpholine, indoline, oxopyrrolidine, benzodioxane, oxetane, especially is benzodioxane, morpholine, tetrahydropyran, piperidine, oxopyrrolidine, oxetane and pyrrolidine.

Preferably in the context of this invention heterocyclyl is defined as a 5 to 18 membered mono or polycyclic heterocyclic ring system of one or more saturated or unsaturated rings of which at least one ring contains one or more heteroatoms selected from the group consisting of nitrogen, oxygen and/or sulfur in the ring. Preferably it is a 5 to 18 membered mono or polycyclic heterocyclic ring system of one or two saturated or unsaturated rings of which at least one ring contains one or more heteroatoms selected from the group consisting of nitrogen, oxygen and/or sulfur in the ring.

Preferred examples of heterocyclyls include oxetane, oxazepan, pyrrolidine, imidazole, oxadiazole, tetrazole, pyridine, pyrimidine, piperidine, piperazine, benzofuran, benzimidazole, indazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, especially is pyridine, pyrazine, indazole, benzodioxane, thiazole, benzothiazole, morpholine, tetrahydropyran, pyrazole, imidazole, piperidine, thiophene, indole, benzimidazole, pyrrolo[2,3b] pyridine, benzoxazole, oxopyrrolidine, pyrimidine, oxazepane, oxetane and pyrrolidine.

In the context of this invention oxopyrrolidine is understood as meaning pyrrolidin-2-one.

In connection with aromatic heterocyclyls (heteroaryls), non-aromatic heterocyclyls, aryls and cycloalkyls, when a ring system falls within two or more of the above cycle definitions simultaneously, then the ring system is defined first as an aromatic heterocyclyl (heteroaryl) if at least one aromatic ring contains a heteroatom. If no aromatic ring contains a heteroatom, then the ring system is defined as a non-aromatic heterocyclyl if at least one non-aromatic ring contains a heteroatom. If no non-aromatic ring contains a heteroatom, then the ring system is defined as an aryl if it contains at least one aryl cycle. If no aryl is present, then the ring system is defined as a cycloalkyl if at least one non-aromatic cyclic hydrocarbon is present.

In the context of this invention alkylaryl is understood as meaning an aryl group (see above) being connected to another atom through a $C_{1-6}$-alkyl (see above) which may be branched or linear and is unsubstituted or substituted once or several times. Preferably alkylaryl is understood as meaning an aryl group (see above) being connected to another atom through 1 to 4 (—$CH_2$—) groups. Most preferably alkylaryl is benzyl (i.e. —$CH_2$-phenyl).

In the context of this invention alkylheterocyclyl is understood as meaning an heterocyclyl group (see above) being connected to another atom through a $C_{1-6}$-alkyl (see above) which may be branched or linear and is unsubstituted or substituted once or several times. Preferably alkylheterocyclyl is understood as meaning an heterocyclyl group (see above) being connected to another atom through 1 to 4 (—$CH_2$—) groups. Most preferably alkylheterocyclyl is —$CH_2$-pyridine.

In the context of this invention alkylcycloalkyl is understood as meaning an cycloalkyl group (see above) being connected to another atom through a $C_{1-6}$-alkyl (see above) which may be branched or linear and is unsubstituted or substituted once or several times. Preferably alkylcycloalkyl is understood as meaning an cycloalkyl group (see above) being connected to another atom through 1 to 4 (—$CH_2$—) groups. Most preferably alkylcycloalkyl is —$CH_2$-cyclopropyl.

Preferably, the aryl is a monocyclic aryl. More preferably the aryl is a 5, 6 or 7 membered monocyclic aryl. Even more preferably the aryl is a 5 or 6 membered monocyclic aryl.

Preferably, the heteroaryl is a monocyclic heteroaryl. More preferably the heteroaryl is a 5, 6 or 7 membered monocyclic heteroaryl. Even more preferably the heteroaryl is a 5 or 6 membered monocyclic heteroaryl.

Preferably, the non-aromatic heterocyclyl is a monocyclic non-aromatic heterocyclyl. More preferably the non-aromatic heterocyclyl is a 4, 5, 6 or 7 membered monocyclic non-aromatic heterocyclyl. Even more preferably the non-aromatic heterocyclyl is a 5 or 6 membered monocyclic non-aromatic heterocyclyl.

Preferably, the cycloalkyl is a monocyclic cycloalkyl. More preferably the cycloalkyl is a 3, 4, 5, 6, 7 or 8 membered monocyclic cycloalkyl. Even more preferably the cycloalkyl is a 3, 4, 5 or 6 membered monocyclic cycloalkyl.

In connection with aryl (including alkyl-aryl), cycloalkyl (including alkyl-cycloalkyl), or heterocyclyl (including alkyl-heterocyclyl), substituted is understood—unless defined otherwise—as meaning substitution of the ring-system of the aryl or alkyl-aryl, cycloalkyl or alkyl-cycloalkyl; heterocyclyl or alkyl-heterocyclyl with one or more of halogen (F, Cl, Br, I), —$R_c$, —$OR_c$, —CN, —$NO_2$, —$NR_cR_{c'''}$, —$C(O)OR_c$, $NR_cC(O)R_c$, —$C(O)NR_cR_c$, —$NR_cS(O)_2R_{c'}$, =O, —$OCH_2CH_2OH$, —$NR_cC(O)NR_cR_{c''}$, —$S(O)_2NR_cR_{c'}$, —$NR_cS(O)_2R_cR_{c''}$, haloalkyl, haloalkoxy, —$SR_c$, —$S(O)R_c$, —$S(O)_2R_c$ or $C(CH_3)OR_c$; $NR_cR_{c'''}$, with $R_c$, $R_{c'}$, $R_{c''}$ and $R_{c'''}$ independently being either H or a saturated or unsaturated, linear or branched, substituted or unsubstituted $C_{1-6}$-alkyl; a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl-group; a saturated or unsaturated, linear or branched, substituted or unsubstituted —C(O)—O—$C_{1-6}$-alkyl-group; a substituted or unsubstituted aryl or alkyl-aryl; a substituted or unsubstituted cycloalkyl or alkyl-cycloalkyl; a substituted or unsubstituted heterocyclyl or alkyl-heterocyclyl, being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{14''''}$ and $R_x$, $R_{x'}$ and $R_n$ are as defined in the description, and wherein when different radicals $R_1$ to $R_{14''''}$ and $R_x$, $R_{x'}$ and $R_n$ are present simultaneously in Formula I they may be identical or different.

Most preferably in connection with aryl (including alkyl-aryl), cycloalkyl (including alkyl-cycloalkyl), or heterocyclyl (including alkyl-heterocyclyl), substituted is understood in the context of this invention that any aryl, cycloalkyl and heterocyclyl which is substituted is substituted (also in an alyklaryl, alkylcycloalkyl or alkylheterocyclyl) with one or more of halogen (F, Cl, Br, I), —$R_c$, —$OR_c$, —CN, —$NO_2$, —$NR_cR_{c'''}$, $NR_cC(O)R_{c'}$, —$NR_cS(O)_2R_{c'}$, =O, haloalkyl, haloalkoxy, or $C(CH_3)OR_{c'}$; —$OC_{1-4}$alkyl being unsubstituted or substituted with one or more of $OR_c$ or halogen (F, Cl, I, Br), —CN, or —$C_{1-4}$alkyl being unsubstituted or substituted with one or more of $OR_c$ or halogen (F, Cl, I, Br), being $R_c$ one of $R_{11}$, $R_{12}$ or $R_{14}$, (being $R_{c'}$ one of $R_{11'}$, $R_{12'}$ or $R_{14'}$; being $R_{c''}$ one of $R_{11''}$, $R_{12''}$ or $R_{14''}$; being $R_{c'''}$ one of $R_{11'''}$, $R_{12'''}$ or $R_{14'''}$; being $R_{c''''}$ one of $R_{11''''}$, $R_{12''''}$ or $R_{14''''}$), wherein $R_1$ to $R_{14''''}$ and $R_x$, $R_{x'}$ and $R_n$ are as defined in the description, and wherein when different radicals $R_1$ to $R_{14''''}$ and $R_x$, $R_{x'}$ and $R_n$ are present simultaneously in Formula I they may be identical or different.

Moreover, in connection with cycloalkyl (including alkyl-cycloalkyl), or heterocycyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with

(leading to a spiro structure) or =O.

Moreover, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl is spirosubstituted or substituted with =O.

Moreover, in connection with cycloalkyl (including alkyl-cycloalkyl), or heterocyclyl (including alkylheterocyclyl) namely non-aromatic heterocyclyl (including non-aromatic alkyl-heterocyclyl), substituted is also understood—unless defined otherwise—as meaning substitution of the ring-system of the cycloalkyl or alkyl-cycloalkyl; non-aromatic heterocyclyl or non aromatic alkyl-heterocyclyl with =O.

A ring system is a system consisting of at least one ring of connected atoms but including also systems in which two or more rings of connected atoms are joined with "joined" meaning that the respective rings are sharing one (like a spiro structure), two or more atoms being a member or members of both joined rings.

The term "leaving group" means a molecular fragment that departs with a pair of electrons in heterolytic bond cleavage. Leaving groups can be anions or neutral molecules. Common anionic leaving groups are halides such as Cl—, Br—, and I—, and sulfonate esters, such as tosylate (TsO—) or mesylate.

The term "salt" is to be understood as meaning any form of the active compound used according to the invention in which it assumes an ionic form or is charged and is coupled with a counter-ion (a cation or anion) or is in solution. By this are also to be understood complexes of the active compound with other molecules and ions, in particular complexes via ionic interactions.

The term "physiologically acceptable salt" means in the context of this invention any salt that is physiologically tolerated (most of the time meaning not being toxic—especially not caused by the counter-ion) if used appropriately for a treatment especially if used on or applied to humans and/or mammals.

These physiologically acceptable salts can be formed with cations or bases and in the context of this invention is understood as meaning salts of at least one of the compounds used according to the invention—usually a (deprotonated) acid—as an anion with at least one, preferably inorganic, cation which is physiologically tolerated—especially if used on humans and/or mammals. The salts of the alkali metals and alkaline earth metals are particularly preferred, and also those with $NH_4$, but in particular (mono)- or (di)sodium, (mono)- or (di)potassium, magnesium or calcium salts.

Physiologically acceptable salts can also be formed with anions or acids and in the context of this invention is understood as meaning salts of at least one of the compounds used according to the invention as the cation with at least one anion which are physiologically tolerated—especially if used on humans and/or mammals. By this is understood in particular, in the context of this invention, the salt formed with a physiologically tolerated acid, that is to say salts of the particular active compound with inorganic or organic acids which are physiologically tolerated—especially if used on humans and/or mammals. Examples of physiologically tolerated salts of particular acids are salts of: hydrochloric acid, hydrobromic acid, sulfuric acid, methanesulfonic acid, formic acid, acetic acid, oxalic acid, succinic acid, malic acid, tartaric acid, mandelic acid, fumaric acid, lactic acid or citric acid.

The compounds of the invention may be present in crystalline form or in the form of free compounds like a free base or acid.

Any compound that is a solvate of a compound according to the invention like a compound according to general formula I defined above is understood to be also covered by the scope of the invention. Methods of solvation are generally known within the art. Suitable solvates are pharmaceutically acceptable solvates. The term "solvate" according to this invention is to be understood as meaning any form of the active compound according to the invention in which this compound has attached to it via non-covalent binding another molecule (most likely a polar solvent). Especially preferred examples include hydrates and alcoholates, like methanolates or ethanolates.

Any compound that is a prodrug of a compound according to the invention like a compound according to general formula I defined above is understood to be also covered by the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides. Examples of well known methods of producing a prodrug of a given acting compound are known to those skilled in the art and can be found e.g. in Krogsgaard-Larsen et al. "Textbook of Drug design and Discovery" Taylor & Francis (April 2002).

Any compound that is an N-oxide of a compound according to the invention like a compound according to general formula I defined above is understood to be also covered by the scope of the invention.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon or of a nitrogen by $^{15}$N-enriched nitrogen are within the scope of this invention.

The compounds of formula (I) as well as their salts or solvates of the compounds are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts. This applies also to its solvates or prodrugs.

In a more particular embodiment the compound according to the invention of general Formula (I)

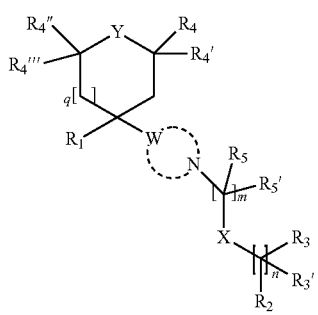

(I)

is a compound wherein
$R_1$ is

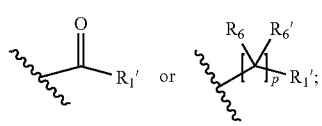

m is 1, 2 or 3;
n is 0, 1 or 2;
p is 0, 1 or 2;
q is 0 or 1;
W is nitrogen or carbon;
X is a bond, —C($R_x R_{x'}$)—, C=O or —O—;
  wherein $R_x$ is selected from halogen, —OR$_7$, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
Y is —S— or —O—;
$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_{1'}$ if substituted, is substituted with one or more substituent/s selected from halogen, —$R_{11}$, —O$R_{11}$, —NO$_2$, —N$R_{11}R_{11'''}$, N$R_{11}$C(O)$R_{11'}$, —N$R_{11}$S(O)$_2R_{11'}$, —S(O)$_2$N$R_{11}R_{11'}$, —N$R_{11}$C(O)N$R_{11'}R_{11'''}$, —S$R_{11}$, —S(O)$R_{11}$, S(O)$_2R_{11}$, —CN, haloalkyl, haloalkoxy, —C(O)O$R_{11}$, —C(O)N$R_{11}R_{11'}$, —OCH$_2$CH$_2$OH, —N$R_{11}$S(O)$_2$N$R_{11'}R_{11''}$ and C(CH$_3$)$_2$O$R_{11}$;
  additionally, cycloalkyl or non-aromatic heterocyclyl in $R_{1'}$, if substituted, may also be substituted

with or =O;
  wherein the alkyl, alkenyl or alkynyl in $R_{1'}$, if substituted, is substituted with one or more substituent/s selected from —O$R_{11}$, halogen, —CN, haloalkyl, haloalkoxy, —S$R_{11}$, —S(O)$R_{11}$, and —S(O)$_2R_{11}$;
  wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
$R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in $R_2$, if substituted, is substituted with one or more substituent/s selected from halogen, —$R_{12}$, —O$R_{12}$, —NO$_2$, —N$R_{12}R_{12'''}$, N$R_{12}$C(O)$R_{12'}$, —N$R_{12}$S(O)$_2R_{12'}$, —S(O)$_2$N$R_{12}R_{12'}$, N$R_{12}$C(O)N$R_{12'}R_{12''}$, —S$R_{12}$, —S(O)$R_{12}$, S(O)$_2R_{12}$, —CN, haloalkyl, haloalkoxy, —C(O)O$R_{12}$, —C(O)N$R_{12}R_{12'}$, —OCH$_2$CH$_2$OH, —N$R_{12}$S(O)$_2$N$R_{12'}R_{12''}$ and —C(CH$_3$)$_2$O$R_{12}$;
  additionally, cycloalkyl or non-aromatic heterocyclyl in $R_2$, if substituted, may also be substituted with

 or =O;

wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_4$ and $R_{4'}$, may form together with the carbon atom to which they are attached a substituted or unsubstituted cycloalkyl;

$R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_{4''}$ and $R_{4'''}$, may form together with the carbon atom to which they are attached a substituted or unsubstituted cycloalkyl;

$R_5$ and $R_{5''}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CHOR_8$ and —$C(O)OR_8$;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_6$ and $R_{6'}$ are independently selected from hydrogen, —$OR_9$, substituted or unsubstituted $C_{1-6}$ alkyl, substituted or unsubstituted $C_{2-6}$ alkenyl and substituted or unsubstituted $C_{2-6}$ alkynyl;

wherein $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

and wherein

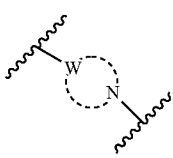

is selected from

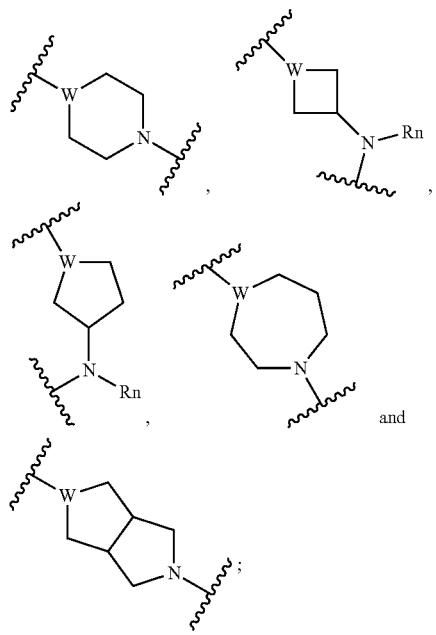

wherein $R_n$ is selected from unsubstituted $C_{1-6}$ alkyl, unsubstituted $C_{2-6}$ alkenyl and unsubstituted $C_{2-6}$ alkynyl;

the alkyl, alkenyl or alkynyl, other than those defined in $R_{1'}$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;

wherein $R_{13}$, and $R_{13'}$ are independently selected from hydrogen, unsubstituted $C_{1-6}$ alkyl, unsubstituted $C_{2-6}$ alkenyl, and unsubstituted $C_{2-6}$ alkynyl;

the aryl, heterocyclyl or cycloalkyl other than those defined in $R_{1'}$ or $R_2$, if substituted, is substituted with one or more substituent/s selected from halogen, —$R_{14}$, —$OR_{14}$, —$NO_2$, —$NR_{14}R_{14'''}$, $NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14}$, $S(O)_2R_{14'}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and $C(CH_3)_2OR_{14}$;

additionally, wherein cycloalkyl or non-aromatic heterocyclyl, other than those defined in $R_{1'}$ or $R_2$, if substituted, may also be substituted with

 or =O;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

These preferred compounds according to the invention are optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In one further embodiment W is N or CH.
In one further embodiment W is N.
In one further embodiment W is CH.
In one further embodiment
R₁ is or

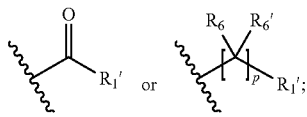

and
R₁‴ is selected from unsubstituted C₁₋₆ alkyl, unsubstituted C₂₋₆ alkenyl, unsubstituted C₂₋₆ alkynyl, substituted or unsubstituted cycloalkyl, substituted or unsubstituted aryl and substituted or unsubstituted heterocyclyl.
wherein said cycloalkyl, aryl or heterocyclyl in R₁ if substituted, is substituted with one or more substituent/s selected from halogen, —R₁₁, —OR₁₁, —NO₂, —NR₁₁R₁₁‴, NR₁₁C(O)R₁₁′, —NR₁₁S(O)₂R₁₁′, —S(O)₂NR₁₁R₁₁′, —NR₁₁C(O)NR₁₁R₁₁‴, —SR₁₁, —S(O)R₁₁, S(O)₂R₁₁, —CN, haloalkyl, haloalkoxy, —C(O)OR₁₁, —C(O)NR₁₁R₁₁′, —OCH₂CH₂OH, —NR₁₁S(O)₂NR₁₁R₁₁‴ and C(CH₃)₂OR₁₁;
additionally, cycloalkyl or non-aromatic heterocyclyl in R₁′, if substituted, may also be substituted with

or =O;
wherein R₁₁, R₁₁′, and R₁₁″ are independently selected from hydrogen, unsubstituted C₁₋₆ alkyl, unsubstituted C₂₋₆ alkenyl and unsubstituted C₂₋₆ alkynyl;
and wherein R₁₁‴ is selected from hydrogen, unsubstituted C₁₋₆ alkyl, unsubstituted C₂₋₆ alkenyl, unsubstituted C₂₋₆ alkynyl and -Boc.

In a further embodiment the compound according to the invention of general Formula (I) is a compound wherein m is 1, 2 or 3;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein n is 0, 1 or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein p is 0, 1 or 2;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein q is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein W is nitrogen or carbon;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein W is nitrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general f Formula (I) is a compound wherein W is carbon;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein X is a bond, —C(R$_x$R$_{x'}$)—, C=O or —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is a bond;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is —C(R$_x$R$_{x'}$)—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is C=O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
X is —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_1$ is

[chemical structures: acyl group with $R_1'$ and O; or phosphorus-containing group with $R_6$, $R_6'$, P, $R_1'$]

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_{1'}$ is selected from substituted or unsubstituted $C_{1-6}$ alkyl, substituted or unsubstituted $C_{2-6}$ alkenyl, substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further embodiment the compound according to the invention of general Formula (I) is a compound wherein
$R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl and substituted or unsubstituted heterocyclyl;
optionally in form of one of the stereoisomers, preferably enantiomers or diastereomers, a racemate or in form of a mixture of at least two of the ratio, or a corresponding salt thereof, or a corresponding solvate thereof.

In a further embodiment the compound according to the invention of general Formula (I) is a compound wherein
$R_2$ is selected from substituted or unsubstituted $C_{1-6}$ alkyl, substituted or unsubstituted $C_{2-6}$ alkenyl, substituted or unsubstituted aryl and substituted or unsubstituted heterocyclyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the according to the invention of general Formula (I) is a compound wherein
$R_3$ and $R_{3'}$ are independently selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_4$ and $R_{4'}$ are independently selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_4$ and $R_{4'}$, may form together with the carbon atom to which they are attached a substituted or unsubstituted cycloalkyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{4''}$ and $R_{4'''}$ are independently selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_{4''}$ and $R_{4'''}$, may form together with the carbon atom to which they are attached a substituted or unsubstituted cycloalkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_5$ and $R_{5''}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_8$ and —C(O)OR$_8$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_5$ and $R_{5''}$ are independently selected from hydrogen, substituted or unsubstituted $C_{1-6}$ alkyl and substituted or unsubstituted $C_{2-6}$ alkenyl; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_5$ and $R_{5''}$ are independently selected from hydrogen and substituted or unsubstituted $C_{1-6}$ alkyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_6$ and $R_{6'}$ are independently selected from hydrogen, —OR$_9$, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound wherein
$R_6$ and $R_{6'}$ are independently selected from hydrogen and —OR$_9$; optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein
$R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11}$, $R_{11'}$, and $R_{11''}$ are independently selected from hydrogen and unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, —$OR_7$, substituted or unsubstituted $C_{1-6}$ alkyl, substituted or unsubstituted $C_{2-6}$ alkenyl and substituted or unsubstituted $C_{2-6}$ alkynyl;

$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_x$ is selected from halogen, —$OR_7$, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound wherein $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_n$ is selected from unsubstituted $C_{1-6}$ alkyl, unsubstituted $C_{2-6}$ alkenyl and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein $R_n$ is unsubstituted $C_{1-6}$ alkyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

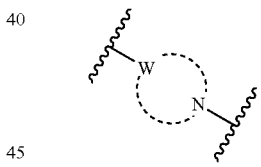

is selected from

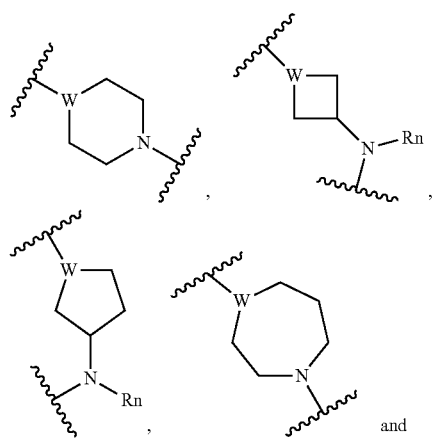

and

-continued

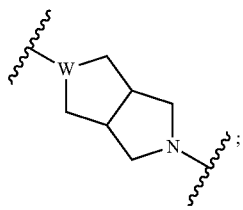

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound wherein

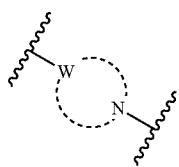

is

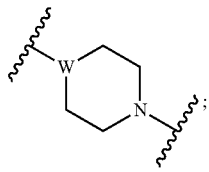

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

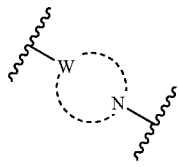

is

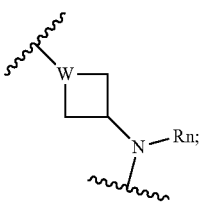

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound wherein

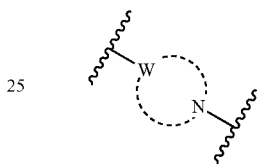

is

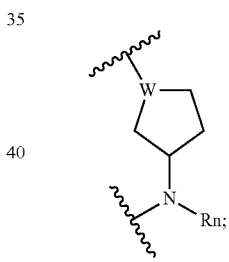

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I) is a compound wherein

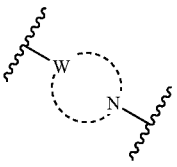

is

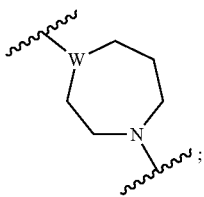

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the compound according to the invention of general Formula (I) is a compound wherein

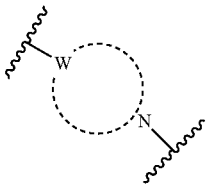

is

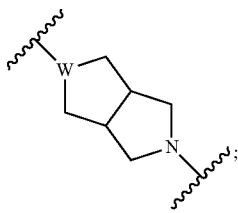

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the compound according to the invention of general Formula (I), is a compound wherein
$R_1$ is

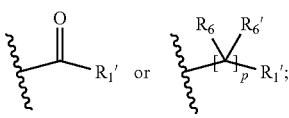

m is 1, 2 or 3;
n is 0, 1 or 2;
p is 0, 1 or 2;
q is 0 or 1;
W is nitrogen or carbon;
X is a bond, —C($R_x$$R_{x'}$)—, C=O or —O—;
Y is —S— or —O—;

$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
wherein
the $C_{1-6}$ alkyl is preferably selected from methyl, ethyl, propyl, butyl, pentyl, hexyl, isopropyl and 2-methylpropyl; more preferably the $C_{1-6}$ alkyl is ethyl, methyl, or isopropyl;
and/or
the $C_{2-6}$-alkenyl is preferably selected from ethylene, propylene, butylene, pentylene and hexylene, more preferably the $C_{2-6}$-alkenyl is vinyl;
and/or
the $C_{2-6}$-alkynyl is preferably selected from ethyne, propyne, butyne, pentyne and hexyne;
and/or
the aryl is selected from phenyl, naphthyl, or anthracene; preferably is naphthyl and phenyl; more preferably is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline, more preferably the heterocyclyl is pyridine;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl, more preferably the cycloalkyl is cyclopropyl;
and/or
$R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
wherein
the $C_{1-6}$ alkyl is preferably selected from methyl, ethyl, propyl, butyl, pentyl, hexyl, isopropyl and 2-methylpropyl; more preferably the $C_{1-6}$ alkyl is methyl, ethyl, isopropyl, isobutyl;
and/or
the $C_{2-6}$-alkenyl is preferably selected from ethylene, propylene, butylene, pentylene and hexylene, more preferably the $C_{2-6}$-alkenyl is 2-methylprop-1-enyl;
and/or
the $C_{2-6}$-alkynyl is preferably selected from ethyne, propyne, butyne, pentyne and hexyne;
and/or
the aryl is selected from phenyl, naphthyl and anthracene; preferably is naphthyl or phenyl; more preferably is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; more preferably the heterocyclyl is pyridine; and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
and/or $R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl; more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or $R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
alternatively, $R_4$ and $R_{4'}$, may form together with the carbon atom to which they are attached a substituted or unsubstituted cycloalkyl;
wherein
the $C_{1-6}$ alkyl is preferably selected from methyl, ethyl, propyl, butyl, pentyl, hexyl, isopropyl and 2-methylpropyl; more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopentyl;
and/or $R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
alternatively, $R_{4''}$ and $R_{4'''}$, may form together with the carbon atom to which they are attached a substituted or unsubstituted cycloalkyl;
wherein
the $C_{1-6}$ alkyl is preferably selected from methyl, ethyl, propyl, butyl, pentyl, hexyl, isopropyl and 2-methylpropyl; more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopentyl;
and/or $R_5$ and $R_{5''}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_8$ and —C(O)OR$_8$;
wherein
the $C_{1-6}$ alkyl is preferably selected from methyl, ethyl, propyl, butyl, pentyl, hexyl, isopropyl and 2-methylpropyl; more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or $R_6$ and $R_{6'}$ are independently selected from hydrogen, —OR$_9$, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
$R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
$R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

$R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl, more preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or the aryl is selected from phenyl, naphthyl and anthracene; preferably is naphthyl or phenyl;

and/or the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

and/or $R_x$ is selected from halogen, $-OR_7$, substituted or unsubstituted $C_{1-6}$ alkyl, substituted or unsubstituted $C_{2-6}$ alkenyl and substituted or unsubstituted $C_{2-6}$ alkynyl;

wherein the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

and/or $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

wherein
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
the $C_{2-6}$-alkynyl is preferably selected from ethyne, propyne, butyne, pentyne and hexyne;
and/or
$R_n$ is selected from unsubstituted $C_{1-6}$ alkyl, unsubstituted $C_{2-6}$ alkenyl and unsubstituted $C_{2-6}$ alkynyl;
wherein
the $C_{1-6}$ alkyl is preferably selected from methyl, ethyl, propyl, butyl, pentyl, hexyl, isopropyl and 2-methylpropyl, preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_1$, as defined in any of the embodiments of the present invention,
the $C_{1-6}$ alkyl is preferably selected from methyl, ethyl, propyl, butyl, pentyl, hexyl, isopropyl and 2-methylpropyl; more preferably the $C_{1-6}$ alkyl is ethyl, methyl, or isopropyl;
and/or
the $C_{2-6}$-alkenyl is preferably selected from ethylene, propylene, butylene, pentylene and hexylene, more preferably, the $C_{2-6}$-alkenyl is vinyl;
and/or
the $C_{2-6}$-alkynyl is preferably selected from ethyne, propyne, butyne, pentyne and hexyne;
and/or
the aryl is selected from phenyl, naphthyl, or anthracene; preferably is naphthyl and phenyl; more preferably is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; more preferably the heterocycle is pyridine;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl, more preferably the cycloalkyl is cyclopropyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_2$ as defined in any of the embodiments of the present invention,
the $C_{1-6}$ alkyl is preferably selected from methyl, ethyl, propyl, butyl, pentyl, hexyl, isopropyl and 2-methylpropyl; more preferably the $C_{1-6}$ alkyl is methyl, ethyl, isopropyl, isobutyl;
and/or
the $C_{2-6}$-alkenyl is preferably selected from ethylene, propylene, butylene, pentylene and hexylene, more preferably, the $C_{2-6}$-alkenyl is 2-methylprop-1-enyl;
and/or
the $C_{2-6}$-alkynyl is preferably selected from ethyne, propyne, butyne, pentyne and hexyne;
and/or
the aryl is selected from phenyl, naphthyl and anthracene; preferably is naphthyl or phenyl; more preferably is phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline; more preferably the heterocyclyl is pyridine;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_3$ as defined in any of the embodiments of the present invention, the $C_{1-6}$ alkyl is preferably selected from methyl, ethyl, propyl, butyl, pentyl, hexyl, isopropyl and 2-methylpropyl, more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_4$ and $R_{4'}$ as defined in any of the embodiments of the present invention, the $C_{1-6}$ alkyl is preferably selected from methyl, ethyl, propyl, butyl, pentyl, hexyl, isopropyl and 2-methylpropyl; more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopentyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{4''}$ and $R_{4'''}$ as defined in any of the embodiments of the present invention, the $C_{1-6}$ alkyl is preferably selected from methyl, ethyl, propyl, butyl, pentyl, hexyl, isopropyl and 2-methylpropyl; more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl; more preferably the cycloalkyl is cyclopentyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_5$ and $R_{5'}$ as defined in any of the embodiments of the present invention, the $C_{1-6}$ alkyl is preferably selected from methyl, ethyl, propyl, butyl, pentyl, hexyl, isopropyl and 2-methylpropyl; more preferably the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_6$ and $R_{6'}$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the invention according to general Formula (I) the compound is a compound, wherein in $R_7$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_8$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_9$ and $R_{9'}$ as defined in any of the embodiments of the present invention, the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11}$, $R_{11'}$ and $R_{11''}$ as defined in any of the embodiments of the present invention,
the $C_{1-6}$ alkyl is preferably selected from methyl, ethyl, propyl, butyl, pentyl, hexyl, isopropyl and 2-methylpropyl, more preferably, the $C_{1-6}$ alkyl is methyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{11'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12}$, $R_{12'}$ and $R_{12''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{12'''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{13}$ and $R_{13'}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14}$, $R_{14'}$ and $R_{14''}$ as defined in any of the embodiments of the present invention,
the $C_{1-6}$ alkyl is preferably selected from methyl, ethyl, propyl, butyl, pentyl, hexyl, isopropyl and 2-methylpropyl;
and/or
the $C_{2-6}$-alkenyl is preferably selected from ethylene, propylene, butylene, pentylene and hexylene;
and/or
the $C_{2-6}$-alkynyl is preferably selected from ethyne, propyne, butyne, pentyne and hexyne;
and/or
the aryl is selected from phenyl, naphthyl and anthracene; preferably is naphthyl or phenyl;
and/or
the heterocyclyl is a heterocyclic ring system of one or more saturated or unsaturated rings of which at least one ring contains one or more heteroatoms selected from the group consisting of nitrogen, oxygen and/or sulfur in the ring; preferably is a heterocyclic ring system of one or two saturated or unsaturated rings of which at least one ring contains one or more heteroatoms selected from the group consisting of nitrogen, oxygen and/or sulfur in the ring, more preferably is selected from imidazole, oxadiazole, tetrazole, pyridine, pyrimidine, piperidine, piperazine, benzofuran, benzimidazole, indazole, benzothiazole, benzodiazole, thiazole, benzothiazole, tetrahydropyran, morpholine, indoline, furan, triazole, isoxazole, pyrazole, thiophene, benzothiophene, pyrrole, pyrazine, pyrrolo[2,3b]pyridine, quinoline, isoquinoline, phthalazine, benzo-1,2,5-thiadiazole, indole, benzotriazole, benzoxazole oxopyrrolidine, pyrimidine, benzodioxolane, benzodioxane, carbazole and quinazoline;

and/or the cycloalkyl is $C_{3-8}$ cycloalkyl like cyclopropyl, cyclobutyl, cyclopentyl, cyclohexyl, cycloheptyl, or cyclooctyl; preferably is $C_{3-7}$ cycloalkyl like cyclopropyl, cyclobutyl, cyclopentyl, cyclohexyl, or cycloheptyl; more preferably from $C_{3-6}$ cycloalkyl like cyclopropyl, cyclobutyl, cyclopentyl or cyclohexyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_{14'''}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_n$ as defined in any of the embodiments of the present invention, the $C_{1-6}$ alkyl is preferably selected from methyl, ethyl, propyl, butyl, pentyl, hexyl, isopropyl and 2-methylpropyl, preferably the $C_{1-6}$ alkyl is methyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein in $R_x$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the ratio, or a corresponding salt thereof, or a corresponding solvate thereof.

In another preferred embodiment of the invention according to general Formula (I) the compound is a compound, wherein in $R_{x'}$ as defined in any of the embodiments of the present invention, the $C_{1-6}$ alkyl is preferably selected from methyl, ethyl, propyl, butyl, pentyl, hexyl, isopropyl and 2-methylpropyl;

and/or the $C_{2-6}$-alkenyl is preferably selected from ethylene, propylene, butylene, pentylene and hexylene;

and/or the $C_{2-6}$-alkynyl is preferably selected from ethyne, propyne, butyne, pentyne and hexyne;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein n is 0, 1 or 2; preferably n is 0;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein m is 1, 2 or 3; preferably m is 1 or 2;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein p is 0, 1 or 2; preferably p is 0 or 1;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
q is 0 or 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
W is nitrogen or carbon;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
X is a bond, —C($R_xR_x$)—, C=O or —O—; preferably, X is a bond or —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I) the compound is a compound, wherein
Y is —S— or —O—; preferably, Y is —O—;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein
X is a bond, —C($R_xR_x$)—, C=O or —O—; preferably X is a bond or —O—; and/or
m is 1, 2 or 3; preferably m is 1 or 2; and/or
n is 0, 1 or 2; preferably n is 0; and/or
p is 0, 1 or 2; preferably p is 0 or 1; and/or
q is 0 or 1; preferably q is 1;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

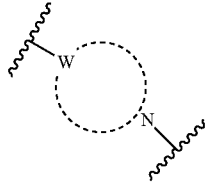

is

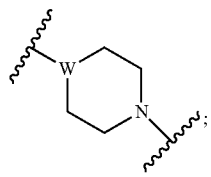

W is nitrogen or carbon; preferably W is nitrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

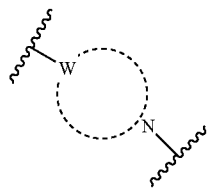

is

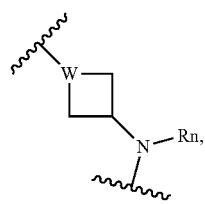

W is nitrogen or carbon; preferably W is nitrogen, and $R_n$ is unsubstituted $C_{1-6}$ alkyl, preferably unsubstituted methyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

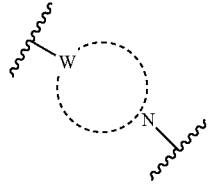

is

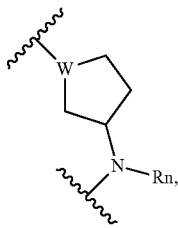

W is nitrogen or carbon; preferably W is nitrogen, and $R_n$ is unsubstituted $C_{1-6}$ alkyl, preferably unsubstituted methyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

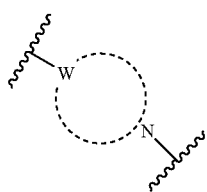

is

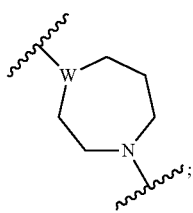

W is nitrogen or carbon; preferably W is nitrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound, wherein

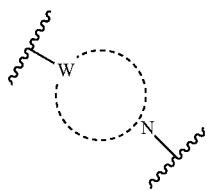

is

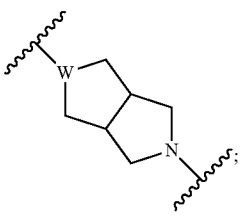

W is nitrogen or carbon; preferably W is nitrogen;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred embodiment of the invention according to general Formula (I), the compound is a compound of Formula (I³')

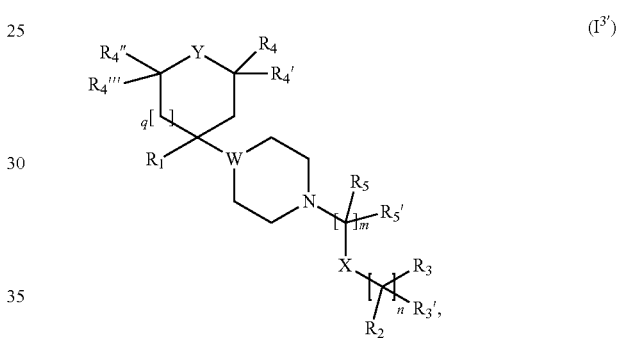

(I³')

wherein
$R_1$ is

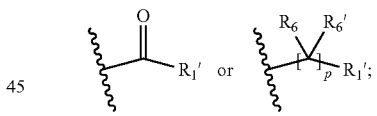

m is 1, 2 or 3;
n is 0, 1 or 2;
p is 0, 1 or 2;
q is 0 or 1;
W is nitrogen or carbon;
X is a bond, —C($R_x R_{x'}$)—, C=O or —O—;
  wherein $R_x$ is selected from halogen, —$OR_7$, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  $R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
Y is —S— or —O—;
$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_{1'}$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11'''}$, and $C(CH_3)_2OR_{11}$;
  additionally, cycloalkyl or non-aromatic heterocyclyl in $R_{1'}$, if substituted, may also be substituted with

or =O;
  wherein the alkyl, alkenyl or alkynyl in $R_{1'}$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;
  wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;
$R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, —$NR_{12}C(O)R_{12'}$, —$NR_{12}S(O)_2R_{12'}$, —$S(O)_2NR_{12}R_{12'}$, —$NR_{12}C(O)NR_{12'}R_{12''}$, —$SR_{12}$, —$S(O)R_{12}$, —$S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and —$C(CH_3)_2OR_{12}$;
  additionally, cycloalkyl or non-aromatic heterocyclyl in $R_2$, if substituted, may also be substituted with

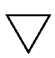

or =O;
  wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
  wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;
  and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;
$R_3$ and $R_{3'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_4$ and $R_{4'}$, may form together with the carbon atom to which they are attached a substituted or unsubstituted cycloalkyl;
$R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
alternatively, $R_{4''}$ and $R_{4'''}$, may form together with the carbon atom to which they are attached a substituted or unsubstituted cycloalkyl;
$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CHOR_8$ and —$C(O)OR_8$;
  wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;
$R_6$ and $R_{6'}$ are independently selected from hydrogen, —$OR_9$, substituted or unsubstituted $C_{1-6}$ alkyl, substituted or unsubstituted $C_{2-6}$ alkenyl and substituted or unsubstituted $C_{2-6}$ alkynyl;
  wherein $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula ($I^{4'}$),

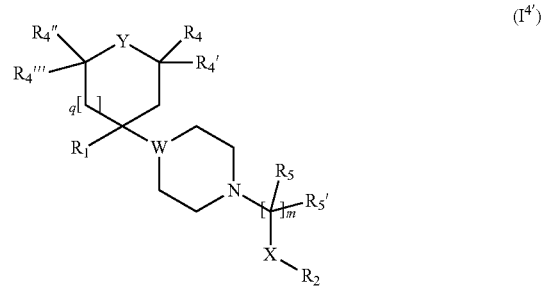

wherein
$R_1$ is

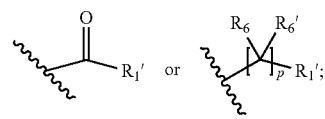

m is 1, 2 or 3;
n is 0, 1 or 2;
p is 0, 1 or 2;
q is 0 or 1;
W is nitrogen or carbon;
X is a bond, —$C(R_xR_{x'})$—, C=O or —O—;

wherein $R_x$ is selected from halogen, —$OR_7$, substituted or unsubstituted $C_{1-6}$ alkyl, substituted or unsubstituted $C_{2-6}$ alkenyl and substituted or unsubstituted $C_{2-6}$ alkynyl;

$R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;

$R_7$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

Y is —S— or —O—;

$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

wherein said cycloalkyl, aryl or heterocyclyl in $R_{1'}$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11'''}$, and $C(CH_3)_2OR_{11}$;

additionally, cycloalkyl or non-aromatic heterocyclyl in $R_{1'}$, if substituted, may also be substituted with

or =O;

wherein the alkyl, alkenyl or alkynyl in $R_{1'}$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

$R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, —$NR_{12}C(O)R_{12'}$, —$NR_{12}S(O)_2R_{12'}$, —$S(O)_2NR_{12}R_{12'}$, —$NR_{12}C(O)NR_{12'}R_{12'''}$, —$SR_{12}$, —$S(O)R_{12}$, —$S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and —$C(CH_3)_2OR_{12}$;

additionally, cycloalkyl or non-aromatic heterocyclyl in $R_2$, if substituted, may also be substituted with

or =O;

wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_4$ and $R_{4'}$, may form together with the carbon atom to which they are attached a substituted or unsubstituted cycloalkyl;

$R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl, alternatively, $R_{4''}$ and $R_{4'''}$, may form together with the carbon atom to which they are attached a substituted or unsubstituted cycloalkyl;

$R_5$ and $R_{5'}$ are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —$CHOR_8$ and —$C(O)OR_8$;

wherein $R_8$ is selected from hydrogen, substituted or unsubstituted $C_{1-6}$ alkyl, substituted or unsubstituted $C_{2-6}$ alkenyl and substituted or unsubstituted $C_{2-6}$ alkynyl;

$R_6$ and $R_{6'}$ are independently selected from hydrogen, —$OR_9$, substituted or unsubstituted $C_{1-6}$ alkyl, substituted or unsubstituted $C_{2-6}$ alkenyl and substituted or unsubstituted $C_{2-6}$ alkynyl;

wherein $R_9$ and $R_{9'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula ($I^{4a'}$),

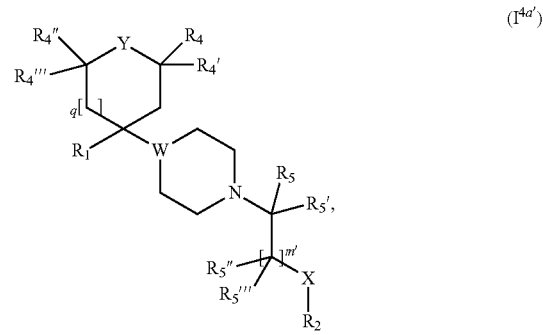

wherein
R₁ is or

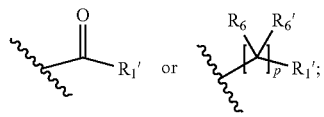

m' is 0, 1 or 2;
n is 0, 1 or 2;
p is 0, 1 or 2;
q is 0 or 1;
W is nitrogen or carbon;
X is a bond, —C($R_x R_{x'}$)—, C=O or —O—;
  wherein $R_x$ is selected from halogen, —OR₇, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from hydrogen, halogen, substituted or unsubstituted $C_{1-6}$ alkyl, substituted or unsubstituted $C_{2-6}$ alkenyl and substituted or unsubstituted $C_{2-6}$ alkynyl;
  R₇ is selected from hydrogen, substituted or unsubstituted $C_{1-6}$ alkyl, substituted or unsubstituted $C_{2-6}$ alkenyl and substituted or unsubstituted $C_{2-6}$ alkynyl;
Y is —S— or —O—;
$R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein said cycloalkyl, aryl or heterocyclyl in $R_{1'}$ if substituted, is substituted with one or more substituent/s selected from halogen, —R₁₁, —OR₁₁, —NO₂, —NR₁₁R₁₁''', NR₁₁C(O)R₁₁', —NR₁₁S(O)₂R₁₁', —S(O)₂NR₁₁R₁₁', —NR₁₁C(O)NR₁₁R₁₁'', —SR₁₁, —S(O)R₁₁, S(O)₂R₁₁, —CN, haloalkyl, haloalkoxy, —C(O)OR₁₁, —C(O)NR₁₁R₁₁', —OCH₂CH₂OH, —NR₁₁S(O)₂NR₁₁R₁₁'' and C(CH₃)₂OR₁₁;
  additionally, cycloalkyl or non-aromatic heterocyclyl in $R_{1'}$ if substituted, may also be substituted with

or =O;
  wherein the alkyl, alkenyl or alkynyl in $R_{1'}$, if substituted, is substituted with one or more substituent/s selected from —OR₁₁, halogen, —CN, haloalkyl, haloalkoxy, —SR₁₁, —S(O)R₁₁, and —S(O)₂R₁₁;
  wherein R₁₁, R₁₁' and R₁₁'' are independently selected from hydrogen, unsubstituted $C_{1-6}$ alkyl, unsubstituted $C_{2-6}$ alkenyl and unsubstituted $C_{2-6}$ alkynyl;
  and wherein R₁₁''' is selected from hydrogen, unsubstituted $C_{1-6}$ alkyl, unsubstituted $C_{2-6}$ alkenyl, unsubstituted $C_{2-6}$ alkynyl and -Boc;
R₂ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
  wherein said cycloalkyl, aryl or heterocyclyl in R₂, if substituted, is substituted with one or more substituent/s selected from halogen, —R₁₂, —OR₁₂, —NO₂, —NR₁₂R₁₂''', —NR₁₂C(O)R₁₂', —NR₁₂S(O)₂R₁₂', —S(O)₂NR₁₂R₁₂', NR₁₂C(O)NR₁₂R₁₂'', —SR₁₂, —S(O)R₁₂, —S(O)₂R₁₂, —CN, haloalkyl, haloalkoxy, —C(O)OR₁₂, —C(O)NR₁₂R₁₂', —OCH₂CH₂OH, —NR₁₂S(O)₂NR₁₂R₁₂'' and —C(CH₃)₂OR₁₂;
  additionally, cycloalkyl or non-aromatic heterocyclyl in R₂, if substituted, may also be substituted with

or =O;
  wherein the alkyl, alkenyl or alkynyl in R₂, if substituted, is substituted with one or more substituent/s selected from —OR₁₂, halogen, —CN, haloalkyl, haloalkoxy, —SR₁₂, —S(O)R₁₂, and —S(O)₂R₁₂;
  wherein R₁₂, R₁₂' and R₁₂'' are independently selected from hydrogen, unsubstituted $C_{1-6}$ alkyl, unsubstituted $C_{2-6}$ alkenyl and unsubstituted $C_{2-6}$ alkynyl;
  and wherein R₁₂''' is selected from hydrogen, unsubstituted $C_{1-6}$ alkyl, unsubstituted $C_{2-6}$ alkenyl, unsubstituted $C_{2-6}$ alkynyl and -Boc;
R₄ and R₄' are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
alternatively, R₄ and R₄', may form together with the carbon atom to which they are attached a substituted or unsubstituted cycloalkyl;
R₄'' and R₄''' are independently selected from hydrogen, substituted or unsubstituted $C_{1-6}$ alkyl, substituted or unsubstituted $C_{2-6}$ alkenyl and substituted or unsubstituted $C_{2-6}$ alkynyl,
alternatively, R₄'' and R₄''', may form together with the carbon atom to which they are attached a substituted or unsubstituted cycloalkyl;
R₅, R₅', R₅'' and R₅''' are independently selected from hydrogen, substituted or unsubstituted $C_{1-6}$ alkyl, substituted or unsubstituted $C_{2-6}$ alkenyl, substituted or unsubstituted $C_{2-6}$ alkynyl, —CHOR₈ and —C(O)OR₈;
  wherein R₈ is selected from hydrogen, substituted or unsubstituted $C_{1-6}$ alkyl, substituted or unsubstituted $C_{2-6}$ alkenyl and substituted or unsubstituted $C_{2-6}$ alkynyl;
R₆ and R₆' are independently selected from hydrogen, —OR₉, substituted or unsubstituted $C_{1-6}$ alkyl, substituted or unsubstituted $C_{2-6}$ alkenyl and substituted or unsubstituted $C_{2-6}$ alkynyl;
  wherein R₉ and R₉' are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a further preferred embodiment of the invention according to general Formula (I) the compound is a compound of Formula ($I^{4b'}$),

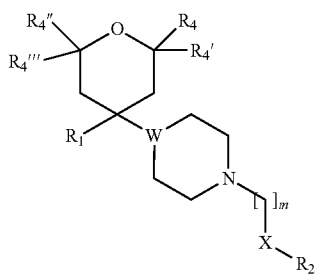

(I<sup>4b'</sup>)

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment
$R_1$ is a substituted or unsubstituted group selected from methyl, ethyl, isopropyl, vinyl, cyclopropyl, phenyl, pyridine, benzyl, —CH(OH)-pyridine, —C(O)-pyridine and —C(O)-phenyl.

In a preferred embodiment
$R_{1'}$ is a substituted or unsubstituted group selected from methyl, ethyl, isopropyl, vinyl, cyclopropyl, phenyl and pyridine.

In a preferred embodiment
$R_2$ is a substituted or unsubstituted group selected from methyl, ethyl, isopropyl, isobutyl, 2-methylprop-1-enyl, $CH_2C(CH_3)_2OH$, $CH_2C(CH_3)_2F$, phenyl and pyridine, more preferably an unsubstituted group selected from methyl, ethyl, isopropyl, isobutyl, 2-methylprop-1-enyl, phenyl and pyridine.

In another preferred embodiment
$R_2$ is a substituted or unsubstituted group selected from methyl, ethyl, isopropyl, isobutyl, 2-methylprop-1-enyl, $CH_2C(CH_3)_2OH$, $CH_2C(CH_3)_2F$, phenyl, pyrazole 1-phenyl-1H-pyrazole-3-yl, 1-phenyl-1H-pyrazole-4-yl and pyridine, more preferably a substituted or unsubstituted group selected from methyl, ethyl, isopropyl, isobutyl, 2-methylprop-1-enyl, phenyl and pyridine, even more preferably a substituted or unsubstituted group selected from isopropyl, isobutyl, phenyl and pyridine In a preferred embodiment
$R_2$ is a substituted or unsubstituted group selected from

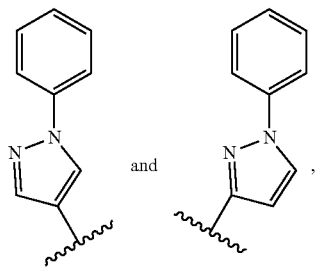 [SMILES: *c1cnn(-c2ccccc2)c1 ; *c1ccn(-c2ccccc2)n1]

preferably, $R_2$ is an unsubstituted group selected from

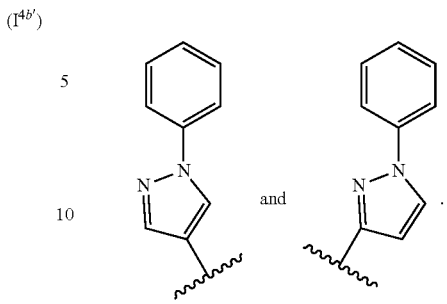

In a preferred embodiment
$R_3$ is hydrogen or substituted or unsubstituted methyl.
In a preferred embodiment
$R_{3'}$ is hydrogen.
In a preferred embodiment
$R_3$ is hydrogen or substituted or unsubstituted methyl, while $R_{3'}$ is hydrogen.
In a preferred embodiment
$R_3$ is substituted or unsubstituted methyl, while $R_{3'}$ is hydrogen.
In a preferred embodiment
$R_3$ and $R_{3'}$ are both hydrogen.
In a preferred embodiment
$R_4$ is hydrogen or substituted or unsubstituted methyl, preferably $R_4$ is hydrogen or unsubstituted methyl.
In a preferred embodiment
$R_{4'}$ is hydrogen or substituted or unsubstituted methyl, preferably $R_{4'}$ is hydrogen or unsubstituted methyl.
In a preferred embodiment
$R_4$ and $R_{4'}$ are both hydrogen.
In a preferred embodiment
$R_4$ and $R_{4'}$ are both substituted or unsubstituted methyl, preferably $R_4$ and $R_{4'}$ are both unsubstituted methyl.
In a preferred embodiment
$R_4$ is substituted or unsubstituted methyl, preferably unsubstituted methyl, while $R_{4'}$ is hydrogen
In a preferred embodiment
$R_4$ is hydrogen, while $R_{4'}$ is substituted or unsubstituted methyl, preferably unsubstituted methyl.
In a preferred embodiment
$R_4$ and $R_{4'}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl;
or
may form together with the carbon atom to which they are attached a substituted or unsubstituted $C_{3-6}$ cycloalkyl; preferably substituted or unsubstituted cyclopentyl
and/or
$R_{4''}$ and $R_{4'''}$ are independently selected from hydrogen, substituted or unsubstituted $C_{1-6}$ alkyl, substituted or unsubstituted $C_{2-6}$ alkenyl and substituted or unsubstituted $C_{2-6}$ alkynyl.

In a preferred embodiment
$R_4$ and $R_{4'}$ are both substituted or unsubstituted methyl, preferably $R_4$ and $R_{4'}$ are both unsubstituted methyl.
or
$R_4$ and $R_{4'}$ form together with the carbon atom to which they are attached a substituted or unsubstituted cyclopentyl, preferably an unsubstituted cyclopentyl.
In a preferred embodiment
$R_4$ and $R_{4'}$ are both substituted or unsubstituted methyl, preferably $R_4$ and $R_{4'}$ are both unsubstituted methyl.

In a preferred embodiment
$R_4$ and $R_{4'}$ form together with the carbon atom to which they are attached a substituted or unsubstituted cyclopentyl, preferably an unsubstituted cyclopentyl.

In a preferred embodiment
$R_{4''}$ is hydrogen or substituted or unsubstituted methyl, preferably $R_{4''}$ is hydrogen or unsubstituted methyl.

In a preferred embodiment
$R_{4'''}$ is hydrogen or substituted or unsubstituted methyl, preferably $R_{4'''}$ is hydrogen or unsubstituted methyl.

In a preferred embodiment
$R_{4''}$ and $R_{4'''}$ are both hydrogen.

In a preferred embodiment
$R_{4''}$ and $R_{4'''}$ are both substituted or unsubstituted methyl, preferably $R_{4''}$ and $R_{4'''}$ are both unsubstituted methyl In a preferred embodiment
$R_{4''}$ and $R_{4'''}$ form together with the carbon atom to which they are attached a substituted or unsubstituted cyclopentyl, preferably unsubstituted cyclopentyl In a preferred embodiment
$R_{4''}$ is substituted or unsubstituted methyl, preferably unsubstituted methyl, while $R_{4'''}$, is hydrogen In a preferred embodiment
$R_{4''}$ is hydrogen, while $R_{4'''}$ is substituted or unsubstituted methyl, preferably unsubstituted methyl.

In a preferred embodiment
$R_5$ is hydrogen or substituted or unsubstituted methyl, preferably $R_5$ is hydrogen or unsubstituted methyl.

In a preferred embodiment
$R_{5'}$ is hydrogen.

In a preferred embodiment
$R_5$ is hydrogen or substituted or unsubstituted methyl, while $R_{5'}$ is hydrogen, preferably $R_5$ is hydrogen or unsubstituted methyl, while $R_{5'}$ is hydrogen.

In a preferred embodiment
$R_5$ is substituted or unsubstituted methyl, while $R_{5'}$ is hydrogen, preferably $R_5$ is unsubstituted methyl, while $R_{5'}$ is hydrogen.

In a preferred embodiment
$R_5$ and $R_{5'}$ are both hydrogen.

In a preferred embodiment
$R_6$ is hydrogen or —OH.

In a preferred embodiment
$R_{6'}$ is hydrogen.

In a preferred embodiment
$R_6$ is hydrogen or —OH, while $R_{6'}$ is hydrogen.

In a preferred embodiment
$R_6$ is —OH, while $R_{6'}$ is hydrogen.

In a preferred embodiment
$R_6$ and $R_{6'}$ are both hydrogen.

In a preferred embodiment
$R_9$ is hydrogen.

In a preferred embodiment
$R_{11}$ is hydrogen or substituted or unsubstituted methyl, more preferably hydrogen or unsubstituted methyl.

In a preferred embodiment
$R_{12}$ is hydrogen.

In a preferred embodiment
$R_n$ is substituted or unsubstituted methyl, preferably unsubstituted methyl.

In a preferred embodiment
X is a bond or —O—.

In a preferred embodiment
Y is —O—.

In a preferred embodiment
W is nitrogen or carbon.

In another preferred embodiment
n is 0.

In another preferred embodiment
m is 1, 2 or 3;

In another preferred embodiment
m is 1 or 2;

In another preferred embodiment
p is 0 or 1.

In another preferred embodiment
q is 0 or 1.

In an particular embodiment
the halogen is fluorine or chlorine.

In an particular embodiment
the haloalkyl is —$CF_3$.

In a preferred further embodiment, the compounds of the general Formula (I) are selected from

| EX | Chemical name |
|---|---|
| 1 | (4-(4-benzylpiperazin-1-yl)-2,2-dimethyltetrahydro-2H-pyran-4-yl)(pyridin-2-yl)methanone |
| 2 | (S)-(4-(4-benzylpiperazin-1-yl)-2,2-dimethyltetrahydro-2H-pyran-4-yl)(pyridin-2-yl)methanone |
| 3 | (R)-(4-(4-benzylpiperazin-1-yl)-2,2-dimethyltetrahydro-2H-pyran-4-yl)(pyridin-2-yl)methanone |
| 4 | (9-(4-benzylpiperazin-1-yl)-6-oxaspiro[4.5]decan-9-yl)(phenyl)methanone |
| 5 | (9-(4-benzylpiperazin-1-yl)-6-oxaspiro[4.5]decan-9-yl)(pyridin-2-yl)methanone |
| 6 | (9-(4-benzylpiperazin-1-yl)-6-oxaspiro[4.5]decan-9-yl)(6-(trifluoromethyl)pyridin-2-yl)methanone |
| 7 | (9-(4-isobutylpiperazin-1-yl)-6-oxaspiro[4.5]decan-9-yl)(phenyl)methanone |
| 8 | (4-(4-benzylpiperazin-1-yl)tetrahydro-2H-pyran-4-yl)(pyridin-2-yl)methanone |
| 9 | (4-(4-benzylpiperazin-1-yl)-2,2-dimethyltetrahydro-2H-pyran-4-yl)(phenyl)methanone |
| 10 | (4-(4-benzylpiperazin-1-yl)-2,2-dimethyltetrahydro-2H-pyran-4-yl)(pyridin-3-yl)methanone |
| 11 | (4-(4-isobutylpiperazin-1-yl)-2,2-dimethyltetrahydro-2H-pyran-4-yl)(phenyl)methanone |
| 12 | (4-(4-isopentylpiperazin-1-yl)-2,2-dimethyltetrahydro-2H-pyran-4-yl)(phenyl)methanone |
| 13 | (4-(4-(2-isopropoxyethyl)piperazin-1-yl)-2,2-dimethyltetrahydro-2H-pyran-4-yl)(phenyl)methanone |
| 14 | (4-(4-isobutylpiperazin-1-yl)-2,2-dimethyltetrahydro-2H-pyran-4-yl)(pyridin-2-yl)methanone |
| 15 | (4-(4-benzylpiperazin-1-yl)-2,2-dimethyltetrahydro-2H-pyran-4-yl)(6-(trifluoromethyl)pyridin-2-yl)methanone |
| 16 | (4-(4-(2-isopropoxyethyl)piperazin-1-yl)-2,2-dimethyltetrahydro-2H-pyran-4-yl)(6-(trifluoromethyl)pyridin-2-yl)methanone |
| 17 | (4-(4-benzylpiperazin-1-yl)-2,2,6,6-tetramethyltetrahydro-2H-pyran-4-yl)(pyridin-2-yl)methanone |
| 18 | (4-(5-benzylhexahydropyrrolo[3,4-c]pyrrol-2(1H)-yl)-2,2-dimethyltetrahydro-2H-pyran-4-yl)(pyridin-2-yl)methanone |
| 19 | (4-(3-(benzyl(methyl)amino)azetidin-1-yl)-2,2-dimethyltetrahydro-2H-pyran-4-yl)(pyridin-2-yl)methanone |
| 20 | (3-(4-benzylpiperazin-1-yl)tetrahydrofuran-3-yl)(pyridin-2-yl)methanone |
| 21 | (4-(1-benzylpiperidin-4-yl)tetrahydro-2H-pyran-4-yl)(pyridin-2-yl)methanone |
| 22 | (4-(1-benzylpiperidin-4-yl)-2,2-dimethyltetrahydro-2H-pyran-4-yl)(pyridin-2-yl)methanone |
| 23 | (4-(3-((2-isopropoxyethyl)(methyl)amino)azetidin-1-yl)-2,2-dimethyltetrahydro-2H-pyran-4-yl)(pyridin-2-yl)methanone |
| 24 | (4-(4-benzyl-1,4-diazepan-1-yl)-2,2-dimethyltetrahydro-2H-pyran-4-yl)(pyridin-2-yl)methanone |
| 25 | 4-(4-benzylpiperazin-1-yl)-2-methyltetrahydro-2H-pyran-4-yl)(pyridin-2-yl)methanone |
| 26 | 2-methyl-4-(4-phenethylpiperazin-1-yl)tetrahydro-2H-pyran-4-yl)(pyridin-2-yl)methanone |
| 27 | (2S,4R)-4-(4-benzylpiperazin-1-yl)-2-methyltetrahydro-2H-pyran-4-yl)(pyridin-2-yl)methanone |
| 28 | (2R,4S)-4-(4-benzylpiperazin-1-yl)-2-methyltetrahydro-2H-pyran-4-yl)(pyridin-2-yl)methanone |
| 29 | 1-benzyl-4-(9-ethyl-6-oxaspiro[4.5]decan-9-yl)piperazine |
| 30 | 1-benzyl-4-(4-phenyltetrahydro-2H-pyran-4-yl)piperazine |
| 31 | 1-benzyl-4-(4-ethyltetrahydro-2H-pyran-4yl)piperazine |

| EX | Chemical name |
|---|---|
| 32 | 1-benzyl-4-(9-phenyl-6-oxaspiro[4.5]decan-9-yl)piperazine |
| 33 | 1-isobutyl-4-(9-phenyl-6-oxaspiro[4.5]decan-9-yl)piperazine |
| 34 | 1-benzyl-4-(9-benzyl-6-oxaspiro[4.5]decan-9-yl)piperazine |
| 35 | 1-benzyl-4-(2,2-dimethyl-4-phenyltetrahydro-2H-pyran-4-yl)piperazine |
| 36 | 1-benzyl-4-(2,2,4-trimethyltetrahydro-2H-pyran-4-yl)piperazine |
| 37 | 1-(2-isopropoxyethyl)-4-(2,2,4-trimethyltetrahydro-2H-pyran-4-yl)piperazine |
| 38 | 1-benzyl-4-(4-ethyl-2,2-dimethyltetrahydro-2H-pyran-4-yl)piperazine |
| 39 | 1-(4-ethyl-2,2-dimethyltetrahydro-2H-pyran-4-yl)-4-(2-isopropoxyethyl)piperazine |
| 40 | 1-benzyl-4-(4-benzyl-2,2-dimethyltetrahydro-2H-pyran-4-yl)piperazine |
| 41 | 1-(2,2-dimethyl-4-propyltetrahydro-2H-pyran-4-yl)-4-phenethylpiperazine |
| 42 | 1-(4-isopropyl-2,2-dimethyltetrahydro-2H-pyran-4-yl)-4-phenethylpiperazine |
| 43 | 1-benzyl-4-(4-isopropyl-2,2-dimethyltetrahydro-2H-pyran-4-yl)piperazine |
| 44 | 1-(4-cyclopropyl-2,2-dimethyltetrahydro-2H-pyran-4-yl)-4-phenethylpiperazine |
| 45 | 1-(2,2-dimethyl-4-vinyltetrahydro-2H-pyran-4-yl)-4-phenethylpiperazine |
| 46 | 1-(4-ethyl-2-methyltetrahydro-2H-pyran-4-yl)-4-phenethylpiperazine |
| 47 | 1-(4-ethyl-4-methyltetrahydro-2H-pyran-4-yl)-4-phenethylpiperazine |
| 48 | 2-(2,2-dimethyl-4-(4-phenethylpiperazin-1-yl)tetrahydro-2H-pyran-4-yl)ethanol |
| 49 | 1-(4-(2-Methoxyethyl)-2,2-dimethyltetrahydro-2H-pyran-4-yl)-4-phenethylpiperazine |
| 50 | (2,2-dimethyl-4-(4-(pyridin-2-ylmethyl)piperazin-1-yl)tetrahydro-2H-pyran-4-yl)(pyridin-2-yl)methanone |
| 51 | (9-(4-isobutylpiperazin-1-yl)-6-oxaspiro[4.5]decan-9-yl)(pyridin-2-yl)methanone |
| 52 | 1-(4-ethyl-2,2-dimethyltetrahydro-2H-pyran-4-yl)-4-phenethylpiperazine |
| 53 | 1-phenethyl-4-(2,2,4-trimethyltetrahydro-2H-pyran-4-yl)piperazine |
| 54 | (2,2-dimethyl-4-(4-phenethylpiperazin-1-yl)tetrahydro-2H-pyran-4-yl)(pyridin-2-yl)methanone |
| 55 | (4-(4-(2-(3-fluoropyridin-2-yl)ethyl)piperazin-1-yl)-2,2-dimethyltetrahydro-2H-pyran-4-yl)(pyridin-2-yl)methanone |
| 56 | (4-(4-(2-(3-chloropyridin-2-yl)ethyl)piperazin-1-yl)-2,2-dimethyltetrahydro-2H-pyran-4-yl)(pyridin-2-yl)methanone |
| 57 | (4-(4-(2-(3-chloropyridin-4-yl)ethyl)piperazin-1-yl)-2,2-dimethyltetrahydro-2H-pyran-4-yl)(pyridin-2-yl)methanone |
| 58 | (2,2-dimethyl-4-(4-(pyridin-3-ylmethyl)piperazin-1-yl)tetrahydro-2H-pyran-4-yl)(pyridin-2-yl)methanone |
| 59 | (2,2-dimethyl-4-(4-(pyridin-4-ylmethyl)piperazin-1-yl)tetrahydro-2H-pyran-4-yl)(pyridin-2-yl)methanone |
| 60 | (4-(4-(4-fluorobenzyl)piperazin-1-yl)-2,2-dimethyltetrahydro-2H-pyran-4-yl)(pyridin-2-yl)methanone |
| 61 | (4-(4-(3-fluorobenzyl)piperazin-1-yl)-2,2-dimethyltetrahydro-2H-pyran-4-yl)(pyridin-2-yl)methanone |
| 62 | (2,2-dimethyl-4-(4-(1-phenylethyl)piperazin-1-yl)tetrahydro-2H-pyran-4-yl)(pyridin-2-yl)methanone |
| 63 | (4-(4-(1-(4-fluorophenyl)ethyl)piperazin-1-yl)-2,2-dimethyltetrahydro-2H-pyran-4-yl)(pyridin-2-yl)methanone |
| 64 | (4-(4-isopentylpiperazin-1-yl)-2,2-dimethyltetrahydro-2H-pyran-4-yl)(pyridin-2-yl)methanone |
| 65 | (4-(4-(2-isopropoxyethyl)piperazin-1-yl)-2,2-dimethyltetrahydro-2H-pyran-4-yl)(pyridin-2-yl)methanone |
| 66 | (4-(4-(2-isobutoxyethyl)piperazin-1-yl)-2,2-dimethyltetrahydro-2H-pyran-4-yl)(pyridin-2-yl)methanone |
| 67 | (4-(4-(2-ethoxyethyl)piperazin-1-yl)-2,2-dimethyltetrahydro-2H-pyran-4-yl)(pyridin-2-yl)methanone |
| 68 | (4-(4-(2-methoxyethyl)piperazin-1-yl)-2,2-dimethyltetrahydro-2H-pyran-4-yl)(pyridin-2-yl)methanone |
| 69 | (2,2-dimethyl-4-(4-(2-(2,2,2-trifluoroethoxy)ethyl)piperazin-1-yl)tetrahydro-2H-pyran-4-yl)(pyridin-2-yl)methanone |
| 70 | (4-(4-(2-(2-hydroxy-2-methylpropoxy)ethyl)piperazin-1-yl)-2,2-dimethyltetrahydro-2H-pyran-4-yl)(pyridin-2-yl)methanone |
| 71 | (4-(4-(3-isopropoxypropyl)piperazin-1-yl)-2,2-dimethyltetrahydro-2H-pyran-4-yl)(pyridin-2-yl)methanone |
| 72 | (4-(4-(2-isopropoxyethyl)piperazin-1-yl)-2,2,6,6-tetramethyltetrahydro-2H-pyran-4-yl)(pyridin-2-yl)methanone |
| 73 | (4-(5-(2-isopropoxyethyl)hexahydropyrrolo[3,4-c]pyrrol-2(1H)-yl)-2,2-dimethyltetrahydro-2H-pyran-4-yl)(pyridin-2-yl)methanone |
| 74 | (3-(4-(2-isopropoxyethyl)piperazin-1-yl)tetrahydrofuran-3-yl)(pyridin-2-yl)methanone |
| 75 | 2-(4-(1-(2-isopropoxyethyl)piperidin-4-yl)-2,2-dimethyltetrahydro-2H-pyran-4-yl)pyridine |
| 76 | (4-(1-isopentylpiperidin-4-yl)-2,2-dimethyltetrahydro-2H-pyran-4-yl)(pyridin-2-yl)methanone |
| 77 | (4-(1-(2-isopropoxyethyl)piperidin-4-yl)-2,2-dimethyltetrahydro-2H-pyran-4-yl)(pyridin-2-yl)methanone |
| 78 | 1-(4-ethyl-2,2-dimethyltetrahydro-2H-pyran-4-yl)-4-isopentylpiperazine |
| 79 | 1-isopentyl-4-(2,2,4-trimethyltetrahydro-2H-pyran-4-yl)piperazine |
| 80 | (2,2-dimethyl-4-(4-(2-(pyridin-3-yl)ethyl)piperazin-1-yl)tetrahydro-2H-pyran-4-yl)(pyridin-2-yl)methanone |
| 81 | (2,2-dimethyl-4-(4-(2-(pyridin-4-yl)ethyl)piperazin-1-yl)tetrahydro-2H-pyran-4-yl)(pyridin-2-yl)methanone |
| 82 | 1-(4-ethyl-2,2-dimethyltetrahydro-2H-pyran-4-yl)-4-(2-(pyridin-4-yl)ethyl)piperazine |
| 83 | 1-(4-ethyl-2,2-dimethyltetrahydro-2H-pyran-4-yl)-4-(2-(pyridin-3-yl)ethyl)piperazine |
| 84 | 1-(4-ethyl-2,2-dimethyltetrahydro-2H-pyran-4-yl)-4-(2-(3-fluoropyridin-4-yl)ethyl)piperazine |
| 85 | (4-(4-(2-(3-fluoropyridin-4-yl)ethyl)piperazin-1-yl)-2,2-dimethyltetrahydro-2H-pyran-4-yl)(pyridin-2-yl)methanone |
| 86 | (4-(4-isopentyl-1,4-diazepan-1-yl)-2,2-dimethyltetrahydro-2H-pyran-4-yl)(pyridin-2-yl)methanone |
| 87 | 1-(4-ethyl-2,2-dimethyltetrahydro-2H-pyran-4-yl)-4-(2-(pyridin-2-yl)ethyl)piperazine |
| 88 | (4-(4-(2-isopropoxyethyl)-1,4-diazepan-1-yl)-2,2-dimethyltetrahydro-2H-pyran-4-yl)(pyridin-2-yl)methanone |
| 89 | 1-(2-fluorophenethyl)-4-(4-isopropyl-2,2-dimethyltetrahydro-2H-pyran-4-yl)piperazine |
| 90 | (4-(4-(3-hydroxy-3-methylbutyl)piperazin-1-yl)-2,2-dimethyltetrahydro-2H-pyran-4-yl)(pyridin-2-yl)methanone |
| 91 | 1-(3-fluorophenethyl)-4-(4-isopropyl-2,2-dimethyltetrahydro-2H-pyran-4-yl)piperazine |
| 92 | 1-(2,5-difluorophenethyl)-4-(4-isopropyl-2,2-dimethyltetrahydro-2H-pyran-4-yl)piperazine |
| 93 | 1-(4-ethyl-2,2-dimethyltetrahydro-2H-pyran-4-yl)-4-(3-fluorophenethyl)piperazine |
| 94 | 1-(4-ethyl-2,2-dimethyltetrahydro-2H-pyran-4-yl)-4-(2-fluorophenethyl)piperazine |
| 95 | (2R,4S)-4-(4-(2-isopropoxyethyl)piperazin-1-yl)-2-methyltetrahydro-2H-pyran-4-yl)(pyridin-2-yl)methanone |
| 96 | (2S,4R)-4-(4-(2-isopropoxyethyl)piperazin-1-yl)-2-methyltetrahydro-2H-pyran-4-yl)(pyridin-2-yl)methanone |
| 97 | (2R,4S)-4-(4-isopentylpiperazin-1-yl)-2-methyltetrahydro-2H-pyran-4-yl)(pyridin-2-yl)methanone |
| 98 | (2S,4R)-4-(4-isopentylpiperazin-1-yl)-2-methyltetrahydro-2H-pyran-4-yl)(pyridin-2-yl)methanone |
| 99 | 1-(2,5-difluorophenethyl)-4-(4-ethyl-2,2-dimethyltetrahydro-2H-pyran-4-yl)piperazine |
| 100 | 1-(2,3-difluorophenethyl)-4-(4-ethyl-2,2-dimethyltetrahydro-2H-pyran-4-yl)piperazine |
| 101 | 1-(2,3-difluorophenethyl)-4-(4-isopropyl-2,2-dimethyltetrahydro-2H-pyran-4-yl)piperazine |
| 102 | (4-(1-isobutylpiperidin-4-yl)-2,2-dimethyltetrahydro-2H-pyran-4-yl)(pyridin-2-yl)methanone |
| 103 | (4-(1-isobutylpiperidin-4-yl)-2,2-dimethyltetrahydro-2H-pyran-4-yl)(pyridin-2-yl)methanone |
| 104 | (4-(1-(3-ethoxypropyl)piperidin-4-yl)-2,2-dimethyltetrahydro-2H-pyran-4-yl)(pyridin-2-yl)methanone |
| 105 | (4-(1-(2-ethoxyethyl)piperidin-4-yl)-2,2-dimethyltetrahydro-2H-pyran-4-yl)(pyridin-2-yl)methanone |
| 106 | (4-(1-(2-isobutoxyethyl)piperidin-4-yl)-2,2-dimethyltetrahydro-2H-pyran-4-yl)(pyridin-2-yl)methanone |
| 107 | (4-(1-(3-isopropoxypropyl)piperidin-4-yl)-2,2-dimethyltetrahydro-2H-pyran-4-yl)(pyridin-2-yl)methanone |
| 108 | (4-(1-(3-fluorobenzyl)piperidin-4-yl)-2,2-dimethyltetrahydro-2H-pyran-4-yl)(pyridin-2-yl)methanone |
| 109 | (4-(1-(4-fluorobenzyl)piperidin-4-yl)-2,2-dimethyltetrahydro-2H-pyran-4-yl)(pyridin-2-yl)methanone |

| EX | Chemical name |
|---|---|
| 110 | (4-(1-(2-fluorobenzyl)piperidin-4-yl)-2,2-dimethyltetrahydro-2H-pyran-4-yl)(pyridin-2-yl)methanone |
| 111 | (4-(4-(2-fluorophenethyl)piperazin-1-yl)-2,2-dimethyltetrahydro-2H-pyran-4-yl)(pyridin-2-yl)methanone |
| 112 | (S)-1-(4-ethyl-2,2-dimethyltetrahydro-2H-pyran-4-yl)-4-phenethylpiperazine |
| 113 | (R) 1-(4-ethyl-2,2-dimethyltetrahydro-2H-pyran-4-yl)-4-phenethylpiperazine |
| 114 | (S)-(4-(1-isopentylpiperidin-4-yl)-2,2-dimethyltetrahydro-2H-pyran-4-yl)(pyridin-2-yl)methanone, |
| 115 | (R)-(4-(1-isopentylpiperidin-4-yl)-2,2-dimethyltetrahydro-2H-pyran-4-yl)(pyridin-2-yl)methanone |
| 116 | (4-(4-(2-(2-fluoro-2-methylpropoxy)ethyl)piperazin-1-yl)-2,2-dimethyltetrahydro-2H-pyran-4-yl)(pyridin-2-yl)methanone |
| 117 | (4-(4-(3-fluoro-3-methylbutyl)piperazin-1-yl)-2,2-dimethyltetrahydro-2H-pyran-4-yl)(pyridin-2-yl)methanone |
| 118 | (2,2-Dimethyl-4-(4-(3-methylbut-3-enyl)piperazin-1-yl)tetrahydro-2H-pyran-4-yl)(pyridin-2-yl)methanone |
| 119 | 1-(9-phenyl-6-oxaspiro[4.5]decan-9-yl)-4-(pyridin-3-ylmethyl)piperazine |
| 120 | 1-(9-phenyl-6-oxaspiro[4.5]decan-9-yl)-4-(pyridin-2-ylmethyl)piperazine |
| 121 | 3-((4-(9-phenyl-6-oxaspiro[4.5]decan-9-yl)piperazin-1-yl)methyl)benzonitrile |
| 122 | 1-(9-benzyl-6-oxaspiro[4.5]decan-9-yl)-4-(pyridin-3-ylmethyl)piperazine |
| 123 | 1-(9-benzyl-6-oxaspiro[4.5]decan-9-yl)-4-isobutylpiperazine |
| 124 | 2-(4-(1-benzylpiperidin-4-yl)tetrahydro-2H-pyran-4-yl)pyridine |
| 125 | 2-(4-(1-benzylpiperidin-4-yl)-2,2-dimethyltetrahydro-2H-pyran-4-yl)pyridine |
| 126 | 2-(4-(1-isobutylpiperidin-4-yl)-2,2-dimethyltetrahydro-2H-pyran-4-yl)pyridine |
| 127 | (2,2-dimethyl-4-(4-(3,3,3-trifluoropropyl)piperazin-1-yl)tetrahydro-2H-pyran-4-yl)(pyridin-2-yl)methanone |
| 128 | (4-(4-(2-cyclopropylethyl)piperazin-1-yl)-2,2-dimethyltetrahydro-2H-pyran-4-yl)(pyridin-2-yl)methanone |
| 129 | (4-(4-benzylpiperazin-1-yl)-2,2-dimethyltetrahydro-2H-pyran-4-yl)(pyridin-2-yl)methanol |
| 130 | (4-(1-benzylpiperidin-4-yl)tetrahydro-2H-pyran-4-yl)(pyridin-2-yl)methanol |
| 131 | (4-(1-benzylpiperidin-4-yl)-2,2-dimethyltetrahydro-2H-pyran-4-yl)(pyridin-2-yl)methanol |
| 132 | (S)-(4-(4-isopentylpiperazin-1-yl)-2,2-dimethyltetrahydro-2H-pyran-4-yl)(pyridin-2-yl)methanone |
| 133 | (R)-(4-(4-isopentylpiperazin-1-yl)-2,2-dimethyltetrahydro-2H-pyran-4-yl)(pyridin-2-yl)methanone |
| 134 | (S)-(4-(4-(2-isopropoxyethyl)piperazin-1-yl)-2,2-dimethyltetrahydro-2H-pyran-4-yl)(pyridin-2-yl)methanone |
| 135 | (R)-(4-(4-(2-isopropoxyethyl)piperazin-1-yl)-2,2-dimethyltetrahydro-2H-pyran-4-yl)(pyridin-2-yl)methanone |
| 136 | (S)-(4-(4-(2-isobutoxyethyl)piperazin-1-yl)-2,2-dimethyltetrahydro-2H-pyran-4-yl)(pyridin-2-yl)methanone |
| 137 | (R)-(4-(4-(2-isobutoxyethyl)piperazin-1-yl)-2,2-dimethyltetrahydro-2H-pyran-4-yl)(pyridin-2-yl)methanone |
| 138 | (4-((S)-3-(benzyl(methyl)amino)pyrrolidin-1-yl)-2,2-dimethyltetrahydro-2H-pyran-4-yl)(pyridin-2-yl)methanone |
| 139 | (R)-(4-(4-(2-isopropoxyethyl)piperazin-1-yl)-2,2-dimethyltetrahydro-2H-pyran-4-yl)(pyridin-2-yl)methanone |
| 140 | ((S)-4-((S)-3-(benzyl(methyl)amino)pyrrolidin-1-yl)-2,2-dimethyltetrahydro-2H-pyran-4-yl)(pyridin-2-yl)methanone |
| 141 | ((R)-4-((S)-3-(benzyl(methyl)amino)pyrrolidin-1-yl)-2,2-dimethyltetrahydro-2H-pyran-4-yl)(pyridin-2-yl)methanone |
| 142 | (R) 4-((R)-3-(benzyl(methyl)amino)pyrrolidin-1-yl)-2,2-dimethyltetrahydro-2H-pyran-4-yl)(pyridin-2-yl)methanone. |
| 143 | (S) 4-((R)-3-(benzyl(methyl)amino)pyrrolidin-1-yl)-2,2-dimethyltetrahydro-2H-pyran-4-yl)(pyridin-2-yl)methanone. | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred further embodiment, the compounds of the general Formula (I) are selected from

| Ex | Structure | Chemical name |
|---|---|---|
| 144 | 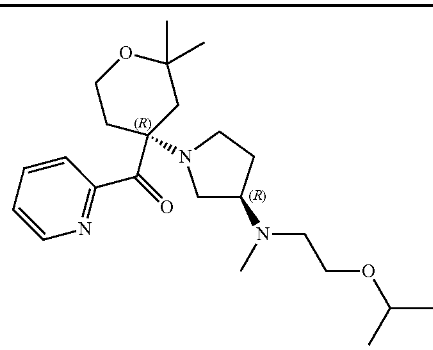 | ((R)-4-((R)-3-((2-isopropoxyethyl)(methyl)amino)pyrrolidin-1-yl)-2,2-dimethyltetrahydro-2H-pyran-4-yl)(pyridin-2-yl)methanone |
| 145 | 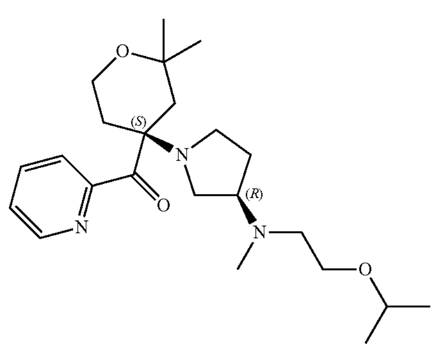 | ((S)-4-((R)-3-((2-isopropoxyethyl)(methyl)amino)pyrrolidin-1-yl)-2,2-dimethyltetrahydro-2H-pyran-4-yl)(pyridin-2-yl)methanone |

| Ex | Structure | Chemical name |
|---|---|---|
| 146 | 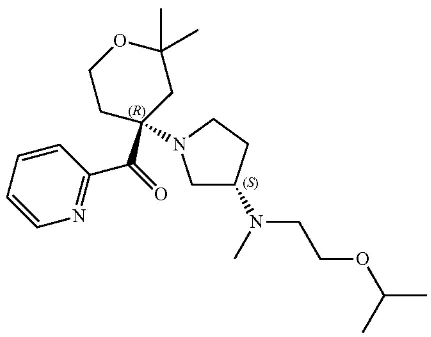 | ((R)-4-((S)-3-((2-isopropoxyethyl)(methyl)amino)pyrrolidin-1-yl)-2,2-dimethyltetrahydro-2H-pyran-4-yl)(pyridin-2-yl)methanone |
| 147 | 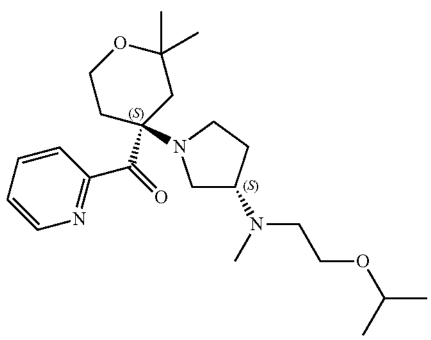 | ((S)-4-((S)-3-((2-isopropoxyethyl)(methyl)amino)pyrrolidin-1-yl)-2,2-dimethyltetrahydro-2H-pyran-4-yl)(pyridin-2-yl)methanone |
| 148 | 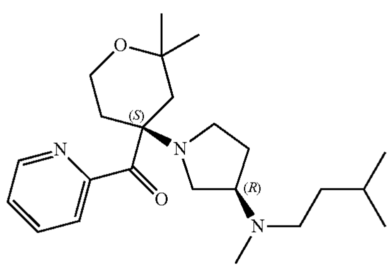 | ((S)-4-((R)-3-(isopentyl(methyl)amino)pyrrolidin-1-yl)-2,2-dimethyltetrahydro-2H-pyran-4-yl)(pyridin-2-yl)methanone |
| 149 | 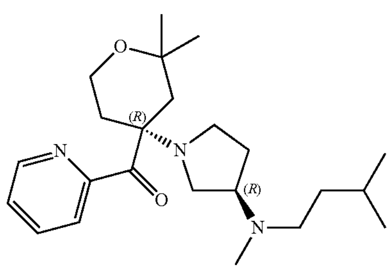 | ((R)-4-((R)-3-(isopentyl(methyl)amino)pyrrolidin-1-yl)-2,2-dimethyltetrahydro-2H-pyran-4-yl)(pyridin-2-yl)methanone |
| 150 | 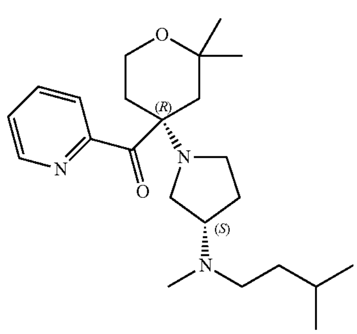 | ((R)-4-((S)-3-(isopentyl(methyl)amino)pyrrolidin-1-yl)-2,2-dimethyltetrahydro-2H-pyran-4-yl)(pyridin-2-yl)methanone |

-continued

| Ex | Structure | Chemical name |
|---|---|---|
| 151 | 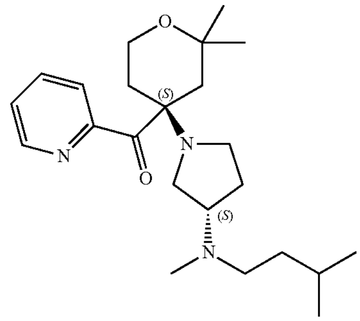 | ((S)-4-((S)-3-(isopentyl(methyl)amino)pyrrolidin-1-yl)-2,2-dimethyltetrahydro-2H-pyran-4-yl)(pyridin-2-yl)methanone |
| 152 | 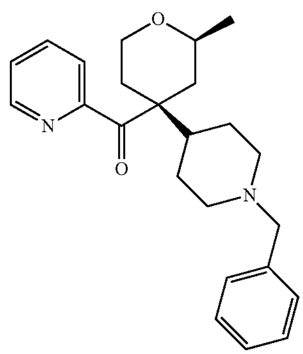 [SMILES: C[C@H]1C[C@@](C(=O)c2ccccn2)(C2CCN(Cc3ccccc3)CC2)CCO1] | 4-(1-benzylpiperidin-4-yl)-2-methyltetrahydro-2H-pyran-4-yl)(pyridin-2-yl)methanone |
| 153 | 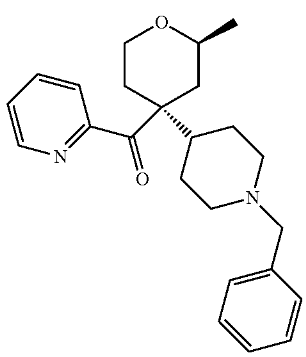 [SMILES: C[C@H]1C[C@](C(=O)c2ccccn2)(C2CCN(Cc3ccccc3)CC2)CCO1] | 4-(1-benzylpiperidin-4-yl)-2-methyltetrahydro-2H-pyran-4-yl)(pyridin-2-yl)methanone |
| 154 | 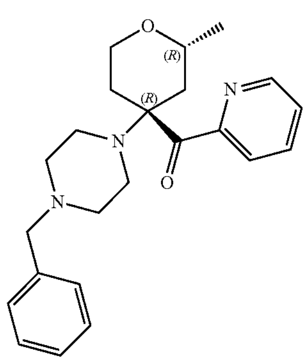 | ((2R,4R)-4-(4-benzylpiperazin-1-yl)-2-methyltetrahydro-2H-pyran-4-yl)(pyridin-2-yl)methanone |

-continued

| Ex | Structure | Chemical name |
|---|---|---|
| 155 | 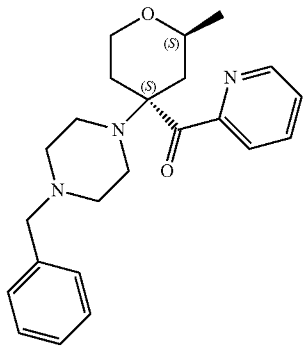 | ((2S,4S)-4-(4-benzylpiperazin-1-yl)-2-methyltetrahydro-2H-pyran-4-yl)(pyridin-2-yl)methanone |
| 156 | 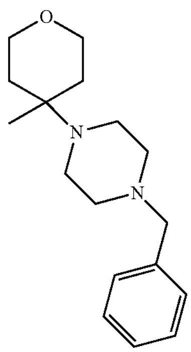 [SMILES: CC1(N2CCN(Cc3ccccc3)CC2)CCOCC1] | 1-Benzyl-4-(4-methyltetrahydro-2H-pyran-4-yl)piperazine |
| 157 | 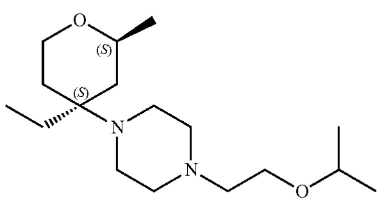 | 1-((2S,4S)-4-ethyl-2-methyltetrahydro-2H-pyran-4-yl)-4-(2-isopropoxyethyl)piperazine |
| 158 | 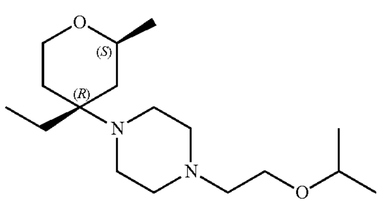 | 1-((2S,4R)-4-ethyl-2-methyltetrahydro-2H-pyran-4-yl)-4-(2-isopropoxyethyl)piperazine |
| 159 | 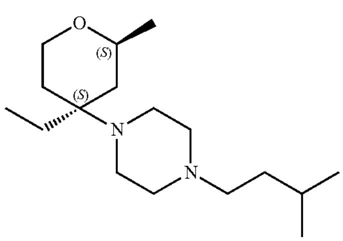 | 1-((2S,4S)-4-ethyl-2-methyltetrahydro-2H-pyran-4-yl)-4-isopentylpiperazine |
| 160 | 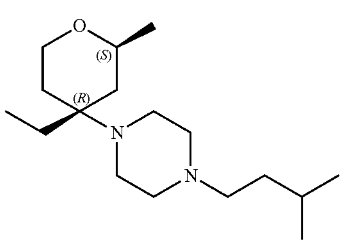 | 1-((2S,4R)-4-ethyl-2-methyltetrahydro-2H-pyran-4-yl)-4-isopentylpiperazine |

-continued

| Ex | Structure | Chemical name |
|---|---|---|
| 161 | 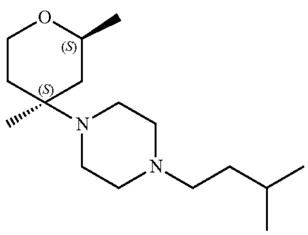 | 1-((2S,4S)-2,4-dimethyltetrahydro-2H-pyran-4-yl)-4-isopentylpiperazine |
| 162 | 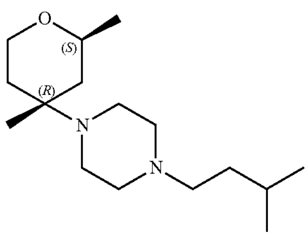 | 1-((2S,4R)-2,4-dimethyltetrahydro-2H-pyran-4-yl)-4-isopentylpiperazine |
| 163 | 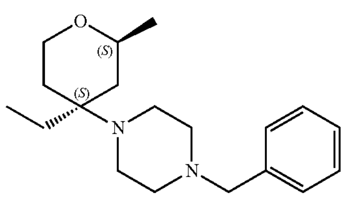 | 1-benzyl-4-((2S,4S)-4-ethyl-2-methyltetrahydro-2H-pyran-4-yl)piperazine |
| 164 | 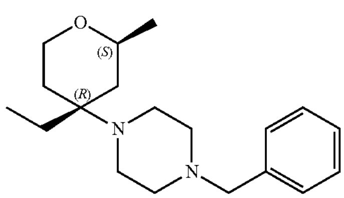 | 1-benzyl-4-((2S,4R)-4-ethyl-2-methyltetrahydro-2H-pyran-4-yl)piperazine |
| 165 | 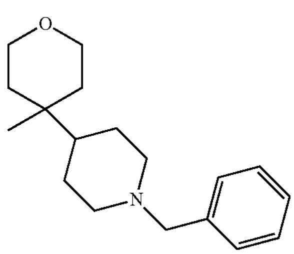 [SMILES: CC1(C2CCN(Cc3ccccc3)CC2)CCOCC1] | 1-benzyl-4-(4-methyltetrahydro-2H-pyran-4-yl)piperidine |
| 166 | 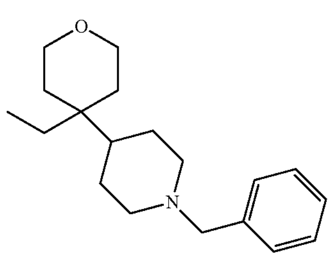 [SMILES: CCC1(C2CCN(Cc3ccccc3)CC2)CCOCC1] | 1-benzyl-4-(4-ethyltetrahydro-2H-pyran-4-yl)piperidine |

-continued

| Ex | Structure | Chemical name |
| --- | --- | --- |
| 167 | 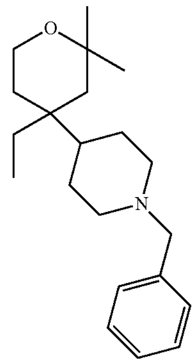 [SMILES: CCC1(C2CCN(Cc3ccccc3)CC2)CCOC(C)(C)C1] | 1-Benzyl-4-(4-ethyl-2,2-dimethyltetrahydro-2H-pyran-4-yl)piperidine |
| 168 | 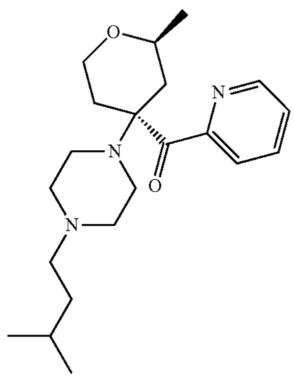 [SMILES: CC(C)CCN1CCN([C@@]2(C(=O)c3ccccn3)CCO[C@@H](C)C2)CC1] | 4-(4-isopentylpiperazin-1-yl)-2-methyltetrahydro-2H-pyran-4-yl)(pyridin-2-yl)methanone |
| 169 | 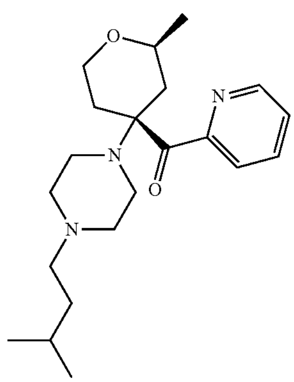 [SMILES: CC(C)CCN1CCN([C@]2(C(=O)c3ccccn3)CCO[C@@H](C)C2)CC1] | 4-(4-isopentylpiperazin-1-yl)-2-methyltetrahydro-2H-pyran-4-yl)(pyridin-2-yl)methanone |
| 170 | 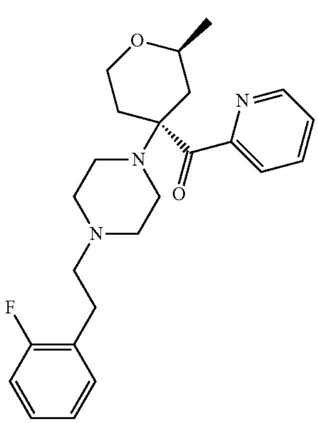 [SMILES: C[C@H]1C[C@@](C(=O)c2ccccn2)(N2CCN(CCc3ccccc3F)CC2)CCO1] | 4-(4-(2-fluorophenethyl)piperazin-1-yl)-2-methyltetrahydro-2H-pyran-4-yl)(pyridin-2-yl)methanone |

-continued

| Ex | Structure | Chemical name |
|---|---|---|
| 171 | 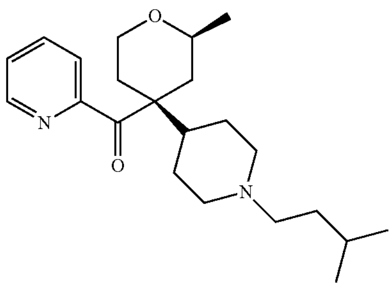 [SMILES: CC(C)CCN1CCC([C@@]2(C(=O)c3ccccn3)CCO[C@@H](C)C2)CC1] | 4-(1-isopentylpiperidin-4-yl)-2-methyltetrahydro-2H-pyran-4-yl)(pyridin-2-yl)methanone |
| 172 | 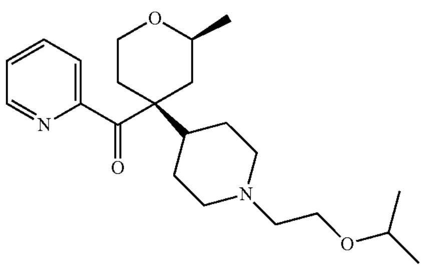 [SMILES: CC(C)OCCN1CCC([C@@]2(C(=O)c3ccccn3)CCO[C@@H](C)C2)CC1] | 4-(1-(2-isopropoxyethyl)piperidin-4-yl)-2-methyltetrahydro-2H-pyran-4-yl)(pyridin-2-yl)methanone |
| 173 | 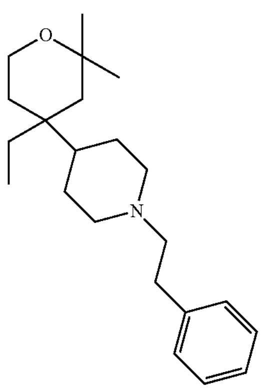 [SMILES: CCC1(C2CCN(CCc3ccccc3)CC2)CCOC(C)(C)C1] | 4-(4-ethyl-2,2-dimethyltetrahydro-2H-pyran-4-yl)-1-phenethylpiperidine |
| 174 | 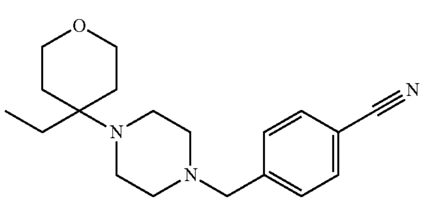 [SMILES: CCC1(N2CCN(Cc3ccc(C#N)cc3)CC2)CCOCC1] | 4-((4-(4-ethyltetrahydro-2H-pyran-4-yl)piperazin-1-yl)methyl)benzonitrile |
| 175 | 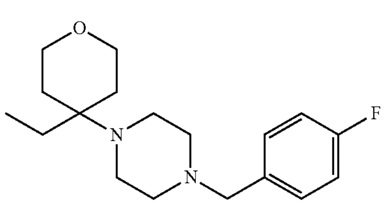 [SMILES: CCC1(N2CCN(Cc3ccc(F)cc3)CC2)CCOCC1] | 1-(4-ethyltetrahydro-2H-pyran-4-yl)-4-(4-fluorobenzyl)piperazine |

-continued

| Ex | Structure | Chemical name |
| --- | --- | --- |
| 176 | 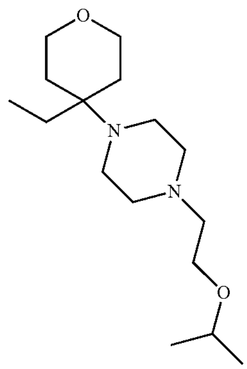 [SMILES: CCC1(N2CCN(CCOC(C)C)CC2)CCOCC1] | 1-(4-ethyltetrahydro-2H-pyran-4-yl)-4-(2-isopropoxyethyl)piperazine |
| 177 | 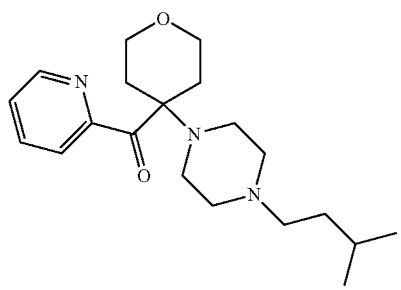 [SMILES: CC(C)CCN1CCN(C2(C(=O)c3ccccn3)CCOCC2)CC1] | (4-(4-isopentylpiperazin-1-yl)tetrahydro-2H-pyran-4-yl)(pyridin-2-yl)methanone |
| 178 | 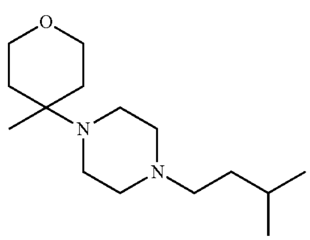 [SMILES: CC(C)CCN1CCN(C2(C)CCOCC2)CC1] | 1-isopentyl-4-(4-methyltetrahydro-2H-pyran-4-yl)piperazine |
| 179 | 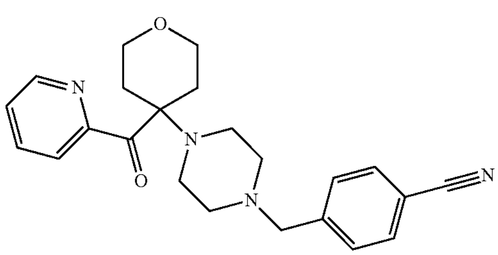 [SMILES: N#Cc1ccc(CN2CCN(C3(C(=O)c4ccccn4)CCOCC3)CC2)cc1] | 4-((4-(4-picolinoyltetrahydro-2H-pyran-4-yl)piperazin-1-yl)methyl)benzonitrile |
| 180 | 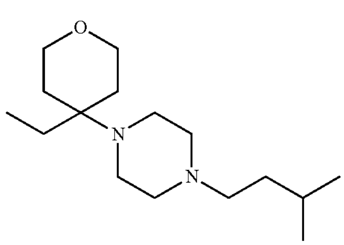 [SMILES: CCC1(N2CCN(CCC(C)C)CC2)CCOCC1] | 1-(4-ethyltetrahydro-2H-pyran-4-yl)-4-isopentylpiperazine |

| Ex | Structure | Chemical name |
|---|---|---|
| 181 | 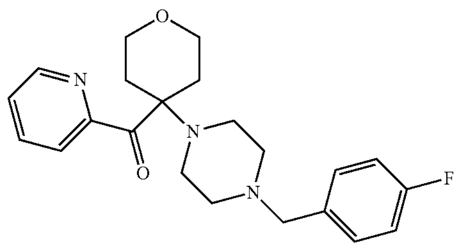 [SMILES: O=C(c1ccccn1)C1(N2CCN(Cc3ccc(F)cc3)CC2)CCOCC1] | (4-(4-(4-fluorobenzyl)piperazin-1-yl)tetrahydro-2H-pyran-4-yl)(pyridin-2-yl)methanone |
| 182 | 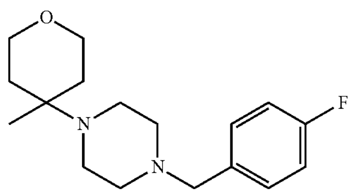 [SMILES: CC1(N2CCN(Cc3ccc(F)cc3)CC2)CCOCC1] | 1-(4-fluorobenzyl)-4-(4-methyltetrahydro-2H-pyran-4-yl)piperazine |
| 183 | 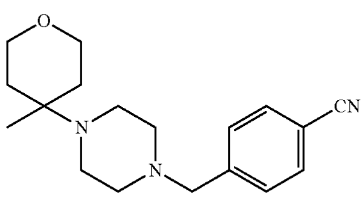 [SMILES: CC1(N2CCN(Cc3ccc(C#N)cc3)CC2)CCOCC1] | 4-((4-(4-methyltetrahydro-2H-pyran-4-yl)piperazin-1-yl)methyl)benzonitrile |
| 184 | 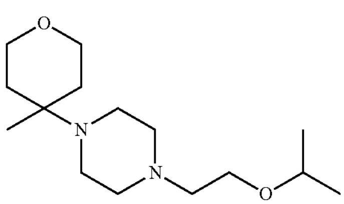 [SMILES: CC(C)OCCN1CCN(C2(C)CCOCC2)CC1] | 1-(2-isopropoxyethyl)-4-(4-methyltetrahydro-2H-pyran-4-yl)piperazine |
| 185 | 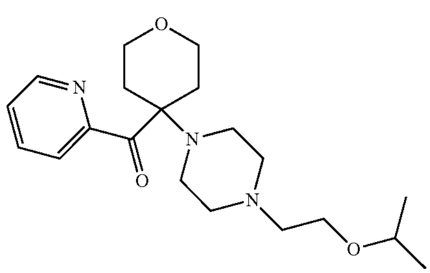 [SMILES: CC(C)OCCN1CCN(C2(C(=O)c3ccccn3)CCOCC2)CC1] | (4-(4-(2-isopropoxyethyl)piperazin-1-yl)tetrahydro-2H-pyran-4-yl)(pyridin-2-yl)methanone |
| 186 | 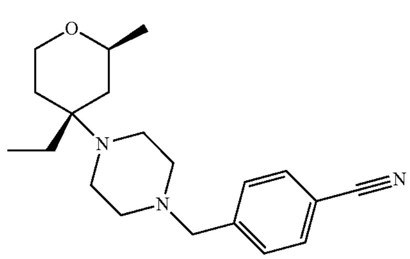 [SMILES: CC[C@@]1(N2CCN(Cc3ccc(C#N)cc3)CC2)CCO[C@@H](C)C1] | 4-((4-(4-ethyl-2-methyltetrahydro-2H-pyran-4-yl)piperazin-1-yl)methyl)benzonitrile |

| Ex | Structure | Chemical name |
| --- | --- | --- |
| 187 | 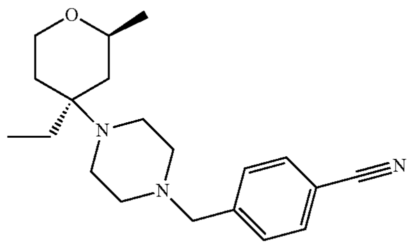 [SMILES: CC[C@]1(N2CCN(Cc3ccc(C#N)cc3)CC2)CCO[C@@H](C)C1] | 4-((4-(4-ethyl-2-methyltetrahydro-2H-pyran-4-yl)piperazin-1-yl)methyl)benzonitrile |
| 188 | 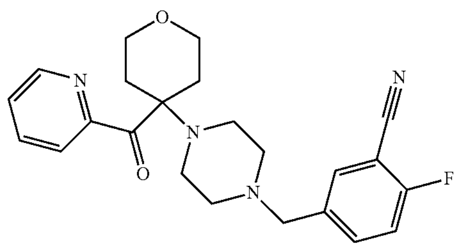 [SMILES: N#Cc1cc(CN2CCN(C3(C(=O)c4ccccn4)CCOCC3)CC2)ccc1F] | 2-fluoro-5-((4-(4-picolinoyltetrahydro-2H-pyran-4-yl)piperazin-1-yl)methyl)benzonitrile |
| 189 | 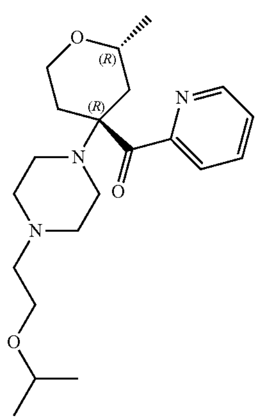 | ((2R,4R)-4-(4-(2-isopropoxyethyl)piperazin-1-yl)-2-methyltetrahydro-2H-pyran-4-yl)(pyridin-2-yl)methanone |
| 190 | 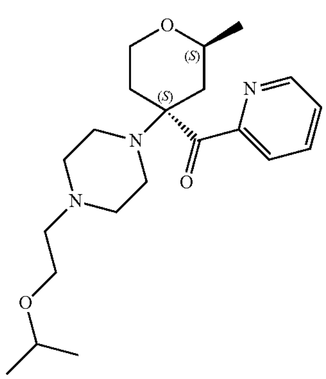 | ((2S,4S)-4-(4-(2-isopropoxyethyl)piperazin-1-yl)-2-methyltetrahydro-2H-pyran-4-yl)(pyridin-2-yl)methanone |
| 191 | 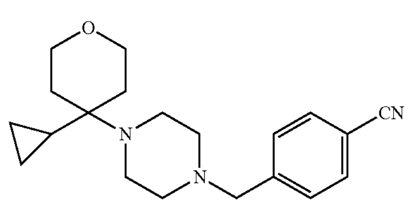 [SMILES: N#Cc1ccc(CN2CCN(C3(C4CC4)CCOCC3)CC2)cc1] | 4-((4-(4-cyclopropyltetrahydro-2H-pyran-4-yl)piperazin-1-yl)methyl)benzonitrile |

| Ex | Structure | Chemical name |
|---|---|---|
| 192 | 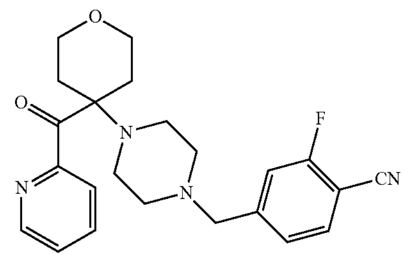 [SMILES: N#Cc1ccc(CN2CCN(C3(C(=O)c4ccccn4)CCOCC3)CC2)cc1F] | 2-fluoro-4-((4-(4-picolinoyltetrahydro-2-pyran-4-yl)piperazin-1-yl)methyl)benzonitrile |
| 193 | 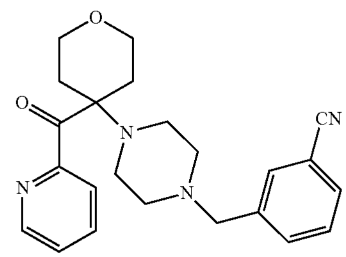 [SMILES: N#Cc1cccc(CN2CCN(C3(C(=O)c4ccccn4)CCOCC3)CC2)c1] | 3-((4-(4-picolinoyltetrahydro-2H-pyran-4-yl)piperazin-1-yl)methyl)benzonitrile |
| 194 | 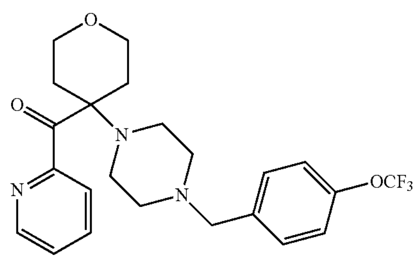 [SMILES: O=C(c1ccccn1)C1(N2CCN(Cc3ccc(OC(F)(F)F)cc3)CC2)CCOCC1] | pyridin-2-yl(4-(4-(4-(trifluoromethoxy)benzyl)piperazin-1-yl)tetrahydro-2H-pyran-4-yl)methanone |
| 195 | 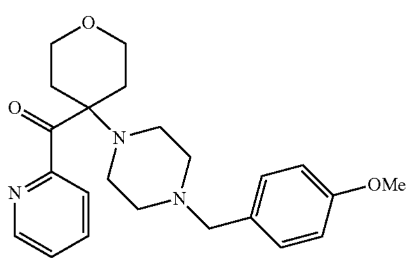 [SMILES: COc1ccc(CN2CCN(C3(C(=O)c4ccccn4)CCOCC3)CC2)cc1] | (4-(4-(4-methoxybenzyl)piperazin-1-yl)tetrahydro-2H-pyran-4-yl)(pyridin-2-yl)methanone |
| 196 | 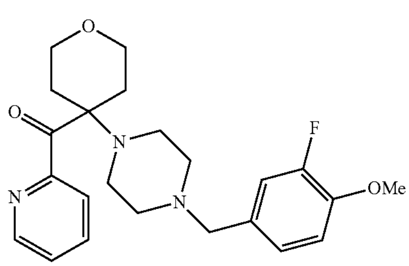 [SMILES: COc1ccc(CN2CCN(C3(C(=O)c4ccccn4)CCOCC3)CC2)cc1F] | (4-(4-(3-fluoro-4-methoxybenzyl)piperazin-1-yl)tetrahydro-2H-pyran-4-yl)(pyridin-2-yl)methanone |
| 197 | 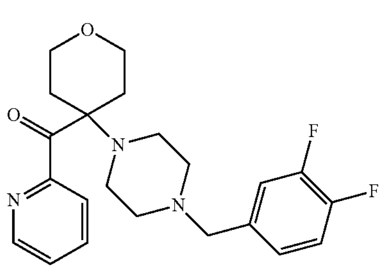 [SMILES: O=C(c1ccccn1)C1(N2CCN(Cc3ccc(F)c(F)c3)CC2)CCOCC1] | (4-(4-(3,4-difluorobenzyl)piperazin-1-yl)tetrahydro-2H-pyran-4-yl)(pyridin-2-yl)methanone |

| Ex | Structure | Chemical name |
|---|---|---|
| 198 | 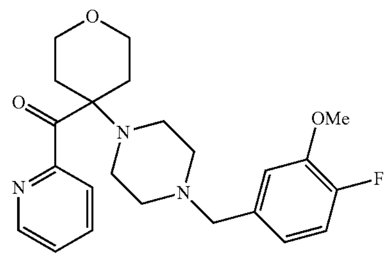 [SMILES: COc1cc(CN2CCN(C3(C(=O)c4ccccn4)CCOCC3)CC2)ccc1F] | (4-(4-(4-fluoro-3-methoxybenzyl)piperazin-1-yl)tetrahydro-2H-pyran-4-yl)(pyridin-2-yl)methanone |
| 199 | 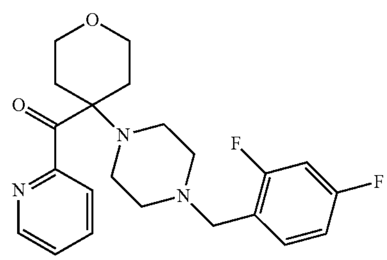 [SMILES: O=C(c1ccccn1)C1(N2CCN(Cc3ccc(F)cc3F)CC2)CCOCC1] | (4-(4-(2,4-difluorobenzyl)piperazin-1-yl)tetrahydro-2H-pyran-4-yl)(pyridin-2-yl)methanone |
| 200 | 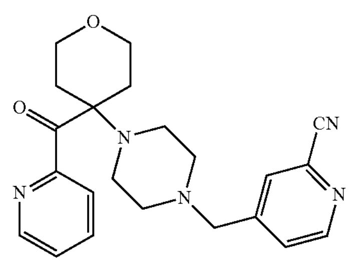 | 4-((4-(4-picolinoyltetrahydro-2H-pyran-4-yl)piperazin-1-yl)methyl)picolinonitrile |
| 201 | 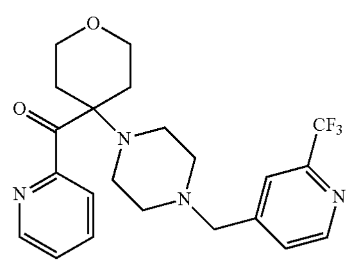 | pyridin-2-yl(4-(4-((2-(trifluoromethyl)pyridin-4-yl)methyl)piperazin-1-yl)tetrahydro-2H-pyran-4-yl)methanone |
| 202 | 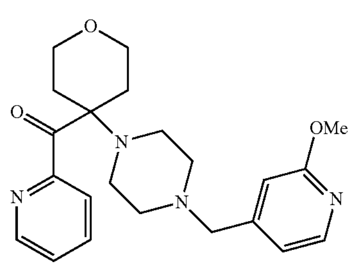 [SMILES: COc1cc(CN2CCN(C3(C(=O)c4ccccn4)CCOCC3)CC2)ccn1] | 4-(4-((2-methoxypyridin-4-yl)methyl)piperazin-1-yl)tetrahydro-2H-pyran-4-yl)(pyridin-2-yl)methanone |
| 203 | 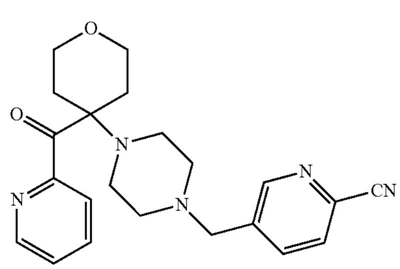 [SMILES: N#Cc1ccc(CN2CCN(C3(C(=O)c4ccccn4)CCOCC3)CC2)cn1] | 5-((4-(4-picolinoyltetrahydro-2H-pyran-4-yl)piperazin-1-yl)methyl)picolinonitrile |

| Ex | Structure | Chemical name |
|---|---|---|
| 204 | 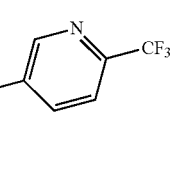 | pyridin-2-yl(4-(4-((6-(trifluoromethyl)pyridin-3-yl)methyl)piperazin-1-yl)tetrahydro-2H-pyran-4-yl)methanone |
| 205 | 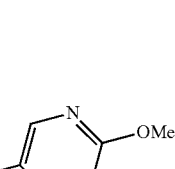 | (4-(4-((6-methoxypyridin-3-yl)methyl)piperazin-1-yl)tetrahydro-2H-pyran-4-yl)(pyridin-2-yl)methanone |
| 206 | 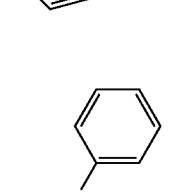 | 4-(4-((1-phenyl-1H-pyrazol-3-yl)methyl)piperazin-1-yl)tetrahydro-2H-pyran-4-yl)(pyridin-2-yl)methanone |
| 207 | 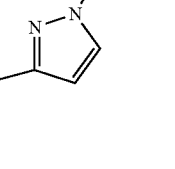 | 4-(4-((1-phenyl-1H-pyrazol-4-yl)methyl)piperazin-1-yl)tetrahydro-2H-pyran-4-yl)(pyridin-2-yl)methanone |
| 208 | 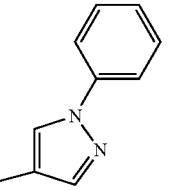 | 4-(1-(4-fluorobenzyl)piperidin-4-yl)tetrahydro-2H-pyran-4-yl)(pyridin-2-yl)methanone |
| 209 | 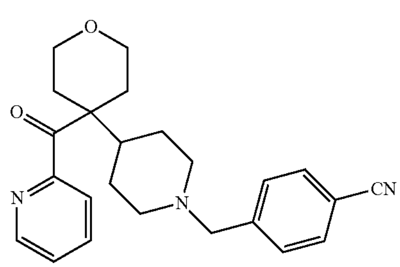 [SMILES: N#Cc1ccc(CN2CCC(C3(C(=O)c4ccccn4)CCOCC3)CC2)cc1] | 4-((4-(4-picolinoyltetrahydro-2H-pyran-4-yl)piperidin-1-yl)methyl)benzonitrile |

| Ex | Structure | Chemical name |
|---|---|---|
| 210 | 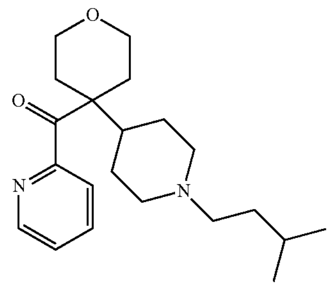 [SMILES: CC(C)CCN1CCC(C2(C(=O)c3ccccn3)CCOCC2)CC1] | (4-(1-isopentylpiperidin-4-yl)tetrahydro-2H-pyran-4-yl)(pyridin-2-yl)methanone |
| 211 | 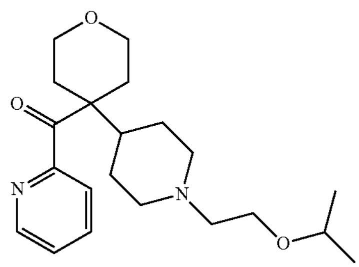 [SMILES: CC(C)OCCN1CCC(C2(C(=O)c3ccccn3)CCOCC2)CC1] | (4-(1-(2-isopropoxyethyl)piperidin-4-yl)tetrahydro-2H-pyran-4-yl)(pyridin-2-yl)methanone |
| 212 | 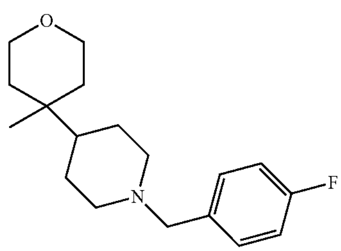 [SMILES: CC1(C2CCN(Cc3ccc(F)cc3)CC2)CCOCC1] | 1-(4-fluorobenzyl)-4-(4-methyltetrahydro-2H-pyran-4-yl)piperidine |
| 213 | 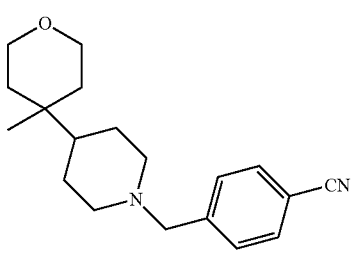 [SMILES: CC1(C2CCN(Cc3ccc(C#N)cc3)CC2)CCOCC1] | 4-((4-(4-methyltetrahydro-2H-pyran-4-yl)piperidin-1-yl)methyl)benzonitrile |
| 214 | 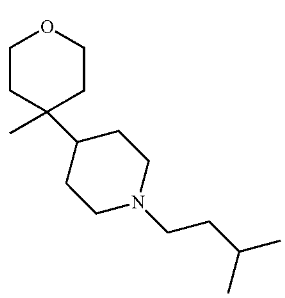 [SMILES: CC(C)CCN1CCC(C2(C)CCOCC2)CC1] | 1-isopentyl-4-(4-methyltetrahydro-2H-pyran-4-yl)piperidine |

-continued

| Ex | Structure | Chemical name |
|---|---|---|
| 215 | 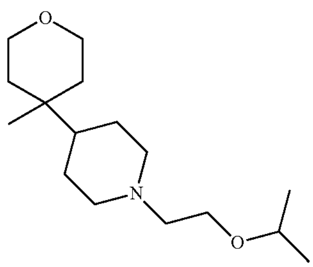 [SMILES: CC(C)OCCN1CCC(C2(C)CCOCC2)CC1] | 1-(2-isopropoxyethyl)-4-(4-methyltetrahydro-2H-pyran-4-yl)piperidine |
| 216 | 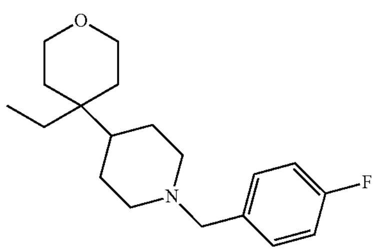 [SMILES: CCC1(C2CCN(Cc3ccc(F)cc3)CC2)CCOCC1] | 4-(4-ethyltetrahydro-2H-pyran-4-yl)-1-(4-fluorobenzyl)piperidine |
| 217 | 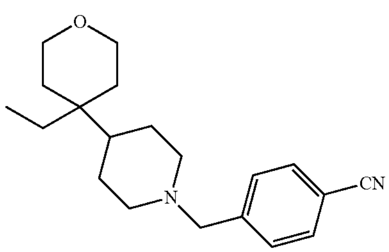 [SMILES: CCC1(C2CCN(Cc3ccc(C#N)cc3)CC2)CCOCC1] | 4-((4-(4-ethyltetrahydro-2H-pyran-4-yl)piperidin-1-yl)methyl)benzonitrile |
| 218 | 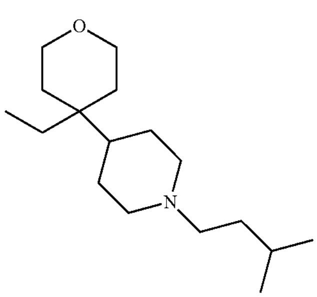 [SMILES: CCC1(C2CCN(CCC(C)C)CC2)CCOCC1] | 4-(4-ethyltetrahydro-2H-pyran-4-yl)-1-isopentylpiperidine |
| 219 | 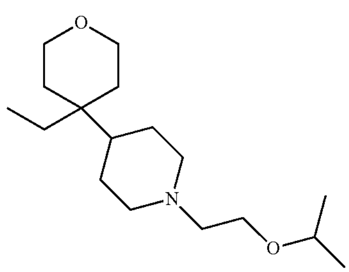 [SMILES: CCC1(C2CCN(CCOC(C)C)CC2)CCOCC1] | 4-(4-ethyltetrahydro-2H-pyran-4-yl)-1-(2-isopropoxyethyl)piperidine |

| Ex | Structure | Chemical name |
|---|---|---|
| 220 | 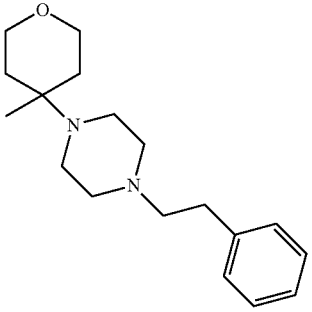 [SMILES: CC1(N2CCN(CCc3ccccc3)CC2)CCOCC1] | 1-(4-methyltetrahydro-2H-pyran-4-yl)-4-phenethylpiperazine |
| 221 | 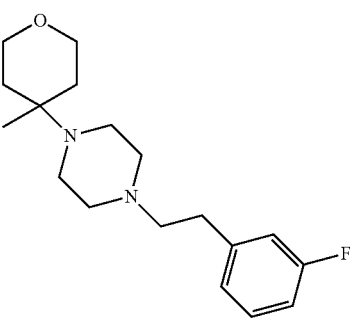 [SMILES: CC1(N2CCN(CCc3cccc(F)c3)CC2)CCOCC1] | 1-(3-fluorophenethyl)-4-(4-methyltetrahydro-2H-pyran-4-yl)piperazine |
| 222 | 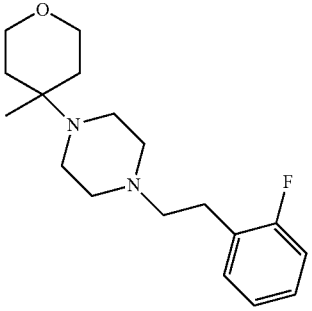 [SMILES: CC1(N2CCN(CCc3ccccc3F)CC2)CCOCC1] | 1-(2-fluorophenethyl)-4-(4-methyltetrahydro-2H-pyran-4-yl)piperazine |
| 223 | 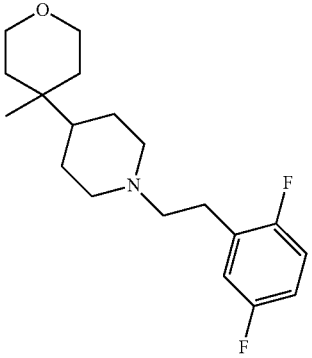 [SMILES: CC1(C2CCN(CCc3cc(F)ccc3F)CC2)CCOCC1] | 1-(2,5-difluorophenethyl)-4-(4-methyltetrahydro-2H-pyran-4-yl)piperazine |

| Ex | Structure | Chemical name |
|---|---|---|
| 224 | 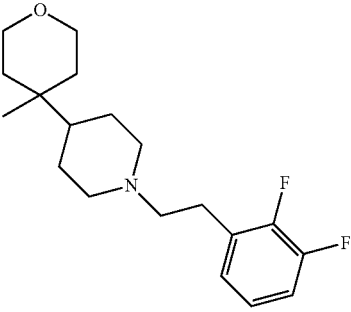 [SMILES: CC1(C2CCN(CCc3cccc(F)c3F)CC2)CCOCC1] | 1-(2,3-difluorophenethyl)-4-(4-methyltetrahydro-2H-pyran-4-yl)piperazine |
| 225 | 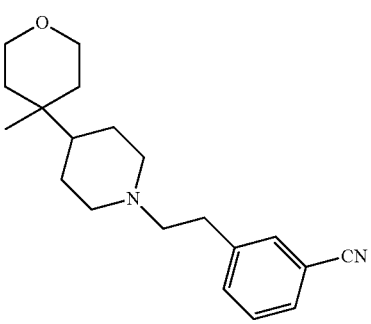 [SMILES: CC1(C2CCN(CCc3cccc(C#N)c3)CC2)CCOCC1] | 3-(2-(4-(4-methyltetrahydro-2H-pyran-4-yl)piperazin-1-yl)ethyl)benzonitrile |
| 226 | 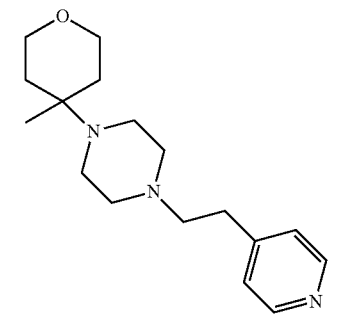 [SMILES: CC1(N2CCN(CCc3ccncc3)CC2)CCOCC1] | 1-(4-methyltetrahydro-2H-pyran-4-yl)-4-(2-(pyridin-4-yl)ethyl)piperazine |
| 227 | 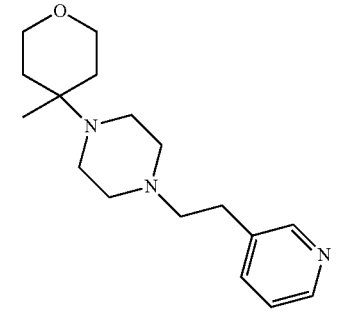 [SMILES: CC1(N2CCN(CCc3cccnc3)CC2)CCOCC1] | 1-(4-methyltetrahydro-2H-pyran-4-yl)-4-(2-(pyridin-3-yl)ethyl)piperazine |
| 228 | 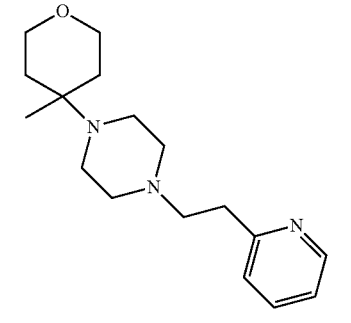 | 1-(4-methyltetrahydro-2H-pyran-4-yl)-4-(2-(pyridin-2-yl)ethyl)piperazine |

| Ex | Structure | Chemical name |
|---|---|---|
| 229 | 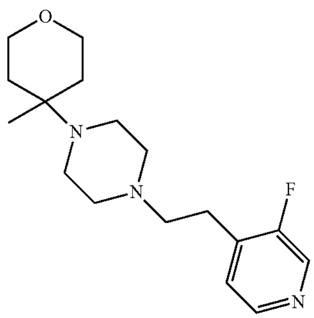 [SMILES: CC1(N2CCN(CCc3ccncc3F)CC2)CCOCC1] | 1-(2-(3-fluoropyridin-4-yl)ethyl)-4-(4-methyltetrahydro-2H-pyran-4-yl)piperazine |
| 230 | 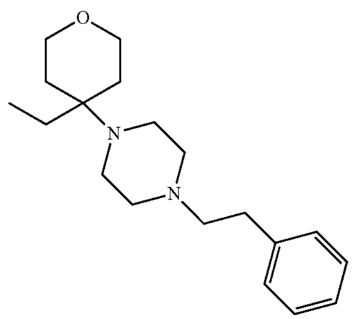 [SMILES: CCC1(N2CCN(CCc3ccccc3)CC2)CCOCC1] | 1-(4-ethyltetrahydro-2H-pyran-4-yl)-4-phenethylpiperazine |
| 231 | 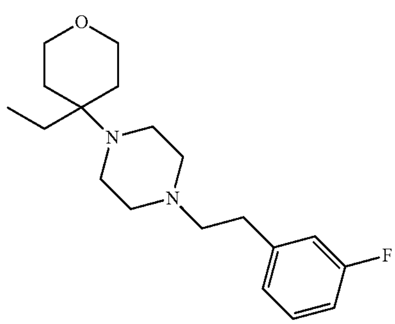 [SMILES: CCC1(N2CCN(CCc3cccc(F)c3)CC2)CCOCC1] | 1-(4-ethyltetrahydro-2H-pyran-4-yl)-4-(3-fluorophenethyl)piperazine |
| 232 | 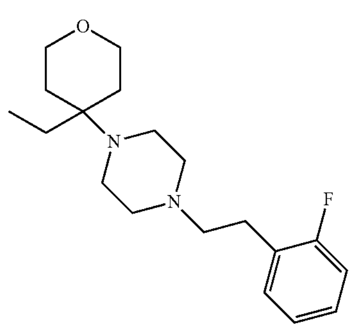 [SMILES: CCC1(N2CCN(CCc3ccccc3F)CC2)CCOCC1] | 1-(4-ethyltetrahydro-2H-pyran-4-yl)-4-(2-fluorophenethyl)piperazine |

-continued

| Ex | Structure | Chemical name |
|---|---|---|
| 233 | 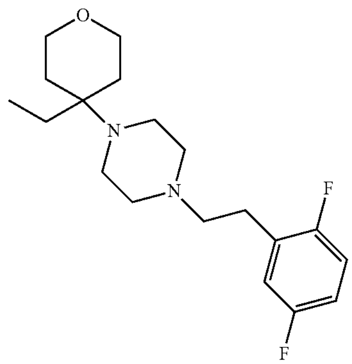 [SMILES: CCC1(N2CCN(CCc3cc(F)ccc3F)CC2)CCOCC1] | 1-(2,5-difluorophenethyl)-4-(4-ethyltetrahydro-2H-pyran-4-yl)piperazine |
| 234 | 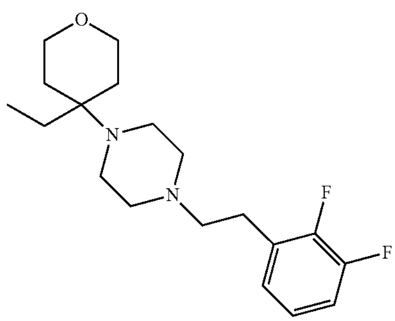 [SMILES: CCC1(N2CCN(CCc3cccc(F)c3F)CC2)CCOCC1] | 1-(2,3-difluorophenethyl)-4-(4-ethyltetrahydro-2H-pyran-4-yl)piperazine |
| 235 | 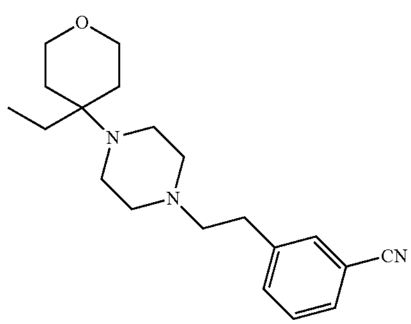 [SMILES: CCC1(N2CCN(CCc3cccc(C#N)c3)CC2)CCOCC1] | 3-(2-(4-(4-ethyltetrahydro-2H-pyran-4-yl)piperazin-1-yl)ethyl)benzonitrile |
| 236 | 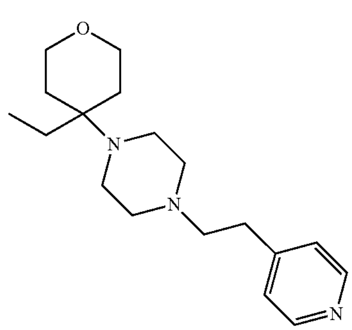 [SMILES: CCC1(N2CCN(CCc3ccncc3)CC2)CCOCC1] | 1-(4-ethyltetrahydro-2H-pyran-4-yl)-4-(2-(pyridin-4-yl)ethyl)piperazine |

| Ex | Structure | Chemical name |
|---|---|---|
| 237 | 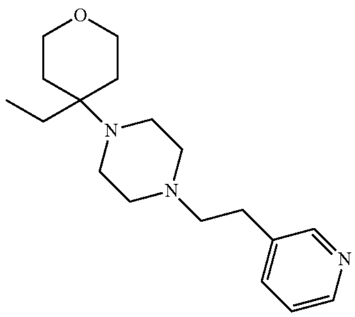 [SMILES: CCC1(N2CCN(CCc3cccnc3)CC2)CCOCC1] | 1-(4-ethyltetrahydro-2H-pyran-4-yl)-4-(2-(pyridin-3-yl)ethyl)piperazine |
| 238 | 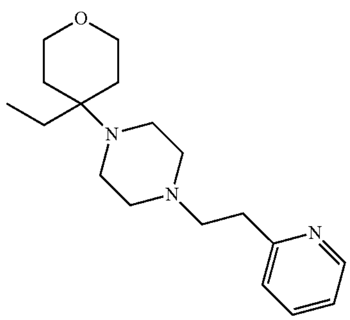 [SMILES: CCC1(N2CCN(CCc3ccccn3)CC2)CCOCC1] | 1-(4-ethyltetrahydro-2H-pyran-4-yl)-4-(2-(pyridin-2-yl)ethyl)piperazine |
| 239 | 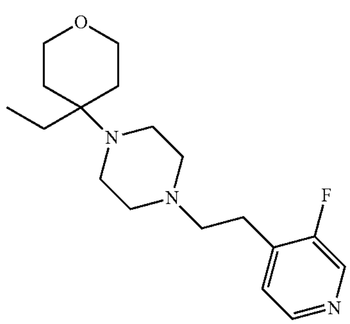 [SMILES: CCC1(N2CCN(CCc3ccncc3F)CC2)CCOCC1] | 1-(4-ethyltetrahydro-2H-pyran-4-yl)-4-(2-(3-fluoropyridin-4-yl)ethyl)piperazine |
| 240 | 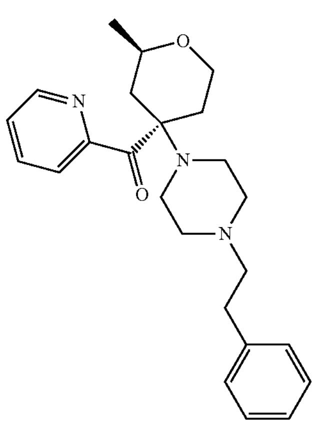 [SMILES: C[C@@H]1C[C@](C(=O)c2ccccn2)(N2CCN(CCc3ccccc3)CC2)CCO1] | ((2R,4R)-2-methyl-4-(4-phenethylpiperazin-1-yl)tetrahydro-2H-pyran-4-yl)(pyridin-2-yl)methanone |

-continued

| Ex | Structure | Chemical name |
|---|---|---|
| 241 | 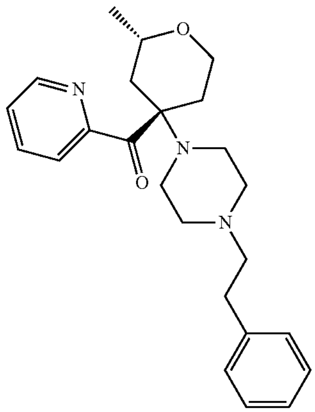 [SMILES: C[C@H]1C[C@@](C(=O)c2ccccn2)(N2CCN(CCc3ccccc3)CC2)CCO1] | ((2S,4S)-2-methyl-4-(4-phenethylpiperazin-1-yl)tetrahydro-2H-pyran-4-yl)(pyridin-2-yl)methanone |
| 242 | 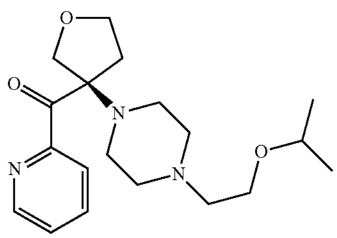 [SMILES: CC(C)OCCN1CCN([C@]2(C(=O)c3ccccn3)CCOC2)CC1] | (R)-(3-(4-(2-isopropoxyethyl)piperazin-1-yl)tetrahydrofuran-3-yl)(pyridin-2-yl)methanone |
| 243 | 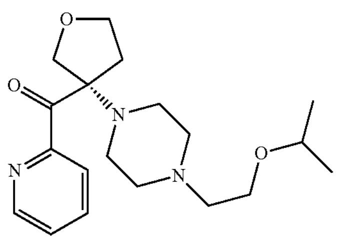 [SMILES: CC(C)OCCN1CCN([C@@]2(C(=O)c3ccccn3)CCOC2)CC1] | (S)-(3-(4-(2-isopropoxyethyl)piperazin-1-yl)tetrahydrofuran-3-yl)(pyridin-2-yl)methanone |
| 244 | 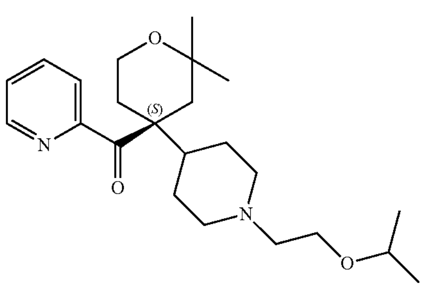 | (S)-(4-(1-(2-isopropoxyethyl)piperidin-4-yl)-2,2-dimethyltetrahydro-2H-pyran-4-yl)(pyridin-2-yl)methanone |
| 245 | 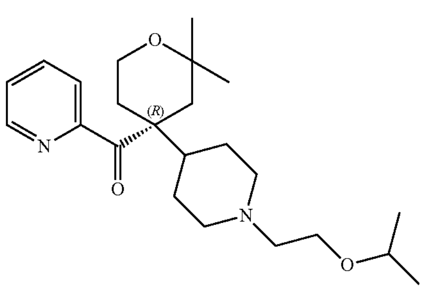 | (R)-(4-(1-(2-isopropoxyethyl)piperidin-4-yl)-2,2-dimethyltetrahydro-2H-pyran-4-yl)(pyridin-2-yl)methanone |

-continued

| Ex | Structure | Chemical name |
|---|---|---|
| 246 | 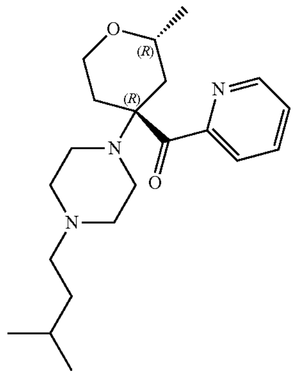 | ((2R,4R)-4-(4-isopentylpiperazin-1-yl)-2-methyltetrahydro-2H-pyran-4-yl)(pyridin-2-yl)methanone |
| 247 | 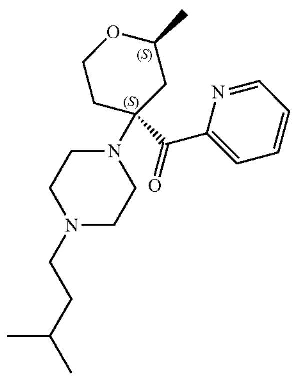 | ((2S,4S)-4-(4-isopentylpiperazin-1-yl)-2-methyltetrahydro-2H-pyran-4-yl)(pyridin-2-yl)methanone |
| 248 | 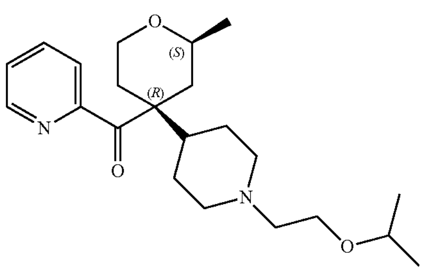 | ((2S,4R)-4-(1-(2-isopropoxyethyl)piperidin-4-yl)-2-methyltetrahydro-2H-pyran-4-yl)(pyridin-2-yl)methanone |
| 249 | 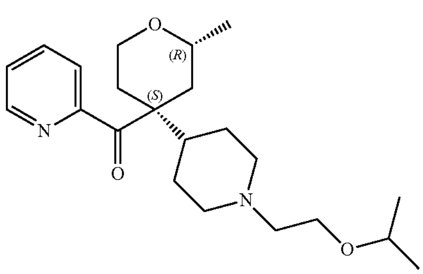 | ((2R,4S)-4-(1-(2-isopropoxyethyl)piperidin-4-yl)-2-methyltetrahydro-2H-pyran-4-yl)(pyridin-2-yl)methanone |
| 250 | 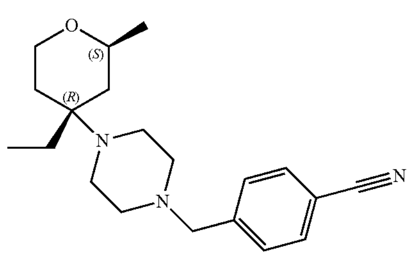 | 4-((4-((2S,4R)-4-ethyl-2-methyltetrahydro-2H-pyran-4-yl)piperazin-1-yl)methyl)benzonitrile |

| Ex | Structure | Chemical name |
|---|---|---|
| 251 | | 4-((4-((2R,4S)-4-ethyl-2-methyltetrahydro-2H-pyran-4-yl)piperazin-1-yl)methyl)benzonitrile | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another preferred further embodiment, the compounds of the general Formula (I) are selected from

| Ex | Structure | Chemical name |
|---|---|---|
| 144 | 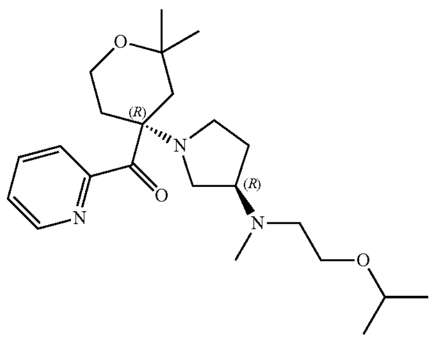 | ((R)-4-((R)-3-((2-isopropoxyethyl)(methyl)amino)pyrrolidin-1-yl)-2,2-dimethyltetrahydro-2H-pyran-4-yl)(pyridin-2-yl)methanone |
| 145 | 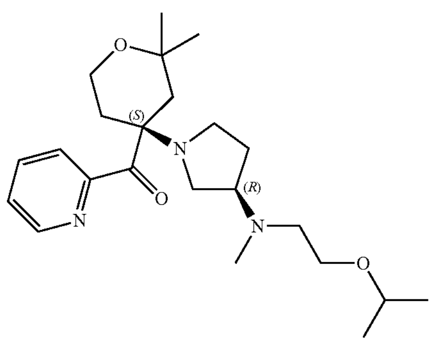 | ((S)-4-((R)-3-((2-isopropoxyethyl)(methyl)amino)pyrrolidin-1-yl)-2,2-dimethyltetrahydro-2H-pyran-4-yl)(pyridin-2-yl)methanone |
| 146 | 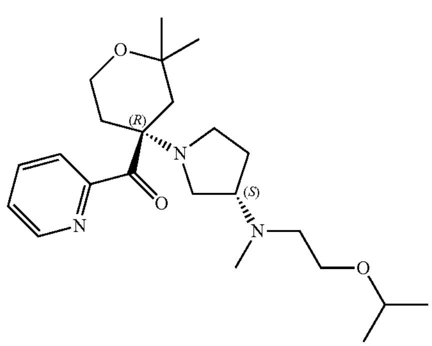 | ((R)-4-((S)-3-((2-isopropoxyethyl)(methyl)amino)pyrrolidin-1-yl)-2,2-dimethyltetrahydro-2H-pyran-4-yl)(pyridin-2-yl)methanone |

-continued

| Ex | Structure | Chemical name |
|---|---|---|
| 147 | 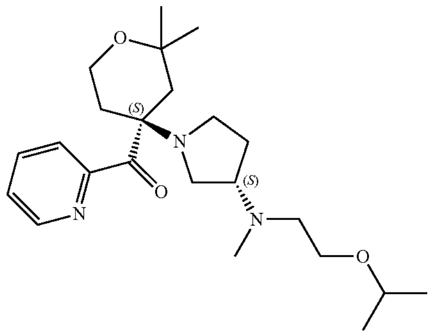 | ((S)-4-((S)-3-((2-isopropoxyethyl)(methyl)amino)pyrrolidin-1-yl)-2,2-dimethyltetrahydro-2H-pyran-4-yl)(pyridin-2-yl)methanone |
| 148 | 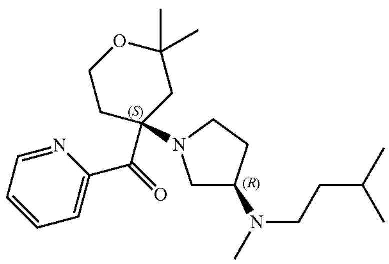 | ((S)-4-((R)-3-(isopentyl(methyl)amino)pyrrolidin-1-yl)-2,2-dimethyltetrahydro-2H-pyran-4-yl)(pyridin-2-yl)methanone |
| 149 | 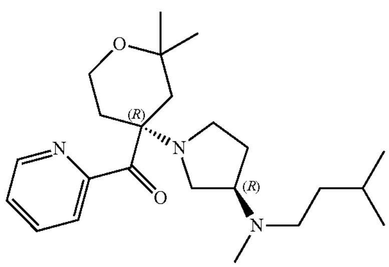 | ((R)-4-((R)-3-(isopentyl(methyl)amino)pyrrolidin-1-yl)-2,2-dimethyltetrahydro-2H-pyran-4-yl)(pyridin-2-yl)methanone |
| 150 | 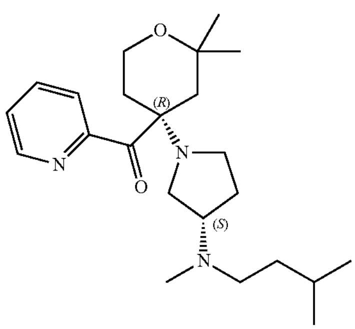 | ((R)-4-((S)-3-(isopentyl(methyl)amino)pyrrolidin-1-yl)-2,2-dimethyltetrahydro-2H-pyran-4-yl)(pyridin-2-yl)methanone |
| 151 | 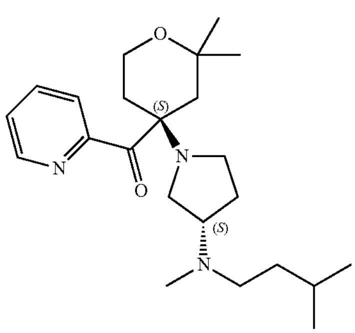 | ((S)-4-((S)-3-(isopentyl(methyl)amino)pyrrolidin-1-yl)-2,2-dimethyltetrahydro-2H-pyran-4-yl)(pyridin-2-yl)methanone |

-continued

| Ex | Structure | Chemical name |
|---|---|---|
| 152 | 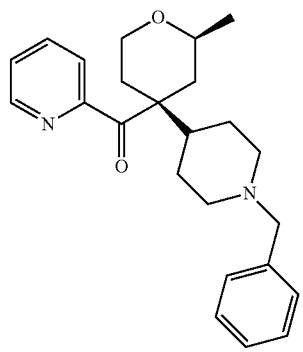 [SMILES: C[C@H]1C[C@@](C(=O)c2ccccn2)(C2CCN(Cc3ccccc3)CC2)CCO1] | 4-(1-benzylpiperidin-4-yl)-2-methyltetrahydro-2H-pyran-4-yl)(pyridin-2-yl)methanone |
| 153 | 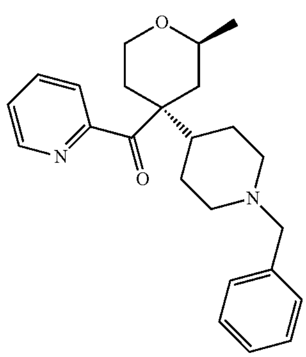 [SMILES: C[C@H]1C[C@](C(=O)c2ccccn2)(C2CCN(Cc3ccccc3)CC2)CCO1] | 4-(1-benzylpiperidin-4-yl)-2-methyltetrahydro-2H-pyran-4-yl)(pyridin-2-yl)methanone |
| 154 | 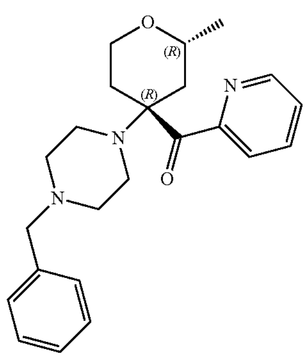 | ((2R,4R)-4-(4-benzylpiperazin-1-yl)-2-methyltetrahydro-2H-pyran-4-yl)(pyridin-2-yl)methanone |
| 155 | 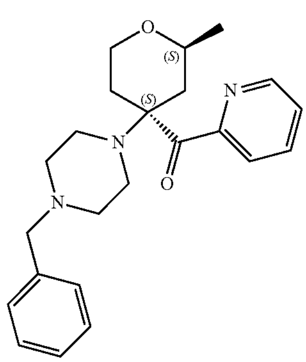 | ((2S,4S)-4-(4-benzylpiperazin-1-yl)-2-methyltetrahydro-2H-pyran-4-yl)(pyridin-2-yl)methanone |

| Ex | Structure | Chemical name |
|---|---|---|
| 156 | 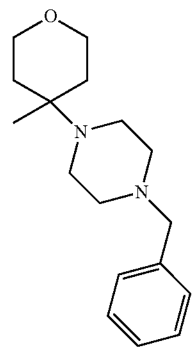 [SMILES: CC1(N2CCN(Cc3ccccc3)CC2)CCOCC1] | 1-Benzyl-4-(4-methyltetrahydro-2H-pyran-4-yl)piperazine |
| 157 | 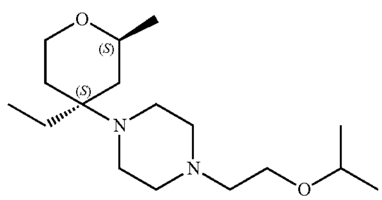 | 1-((2S,4S)-4-ethyl-2-methyltetrahydro-2H-pyran-4-yl)-4-(2-isopropoxyethyl)piperazine |
| 158 | 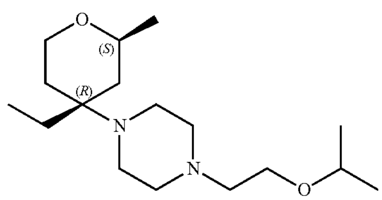 | 1-((2S,4R)-4-ethyl-2-methyltetrahydro-2H-pyran-4-yl)-4-(2-isopropoxyethyl)piperazine |
| 159 | 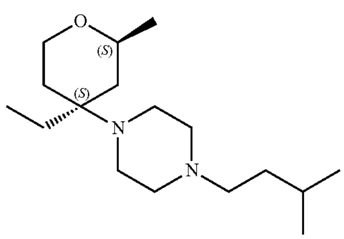 | 1-((2S,4S)-4-ethyl-2-methyltetrahydro-2H-pyran-4-yl)-4-isopentylpiperazine |
| 160 | 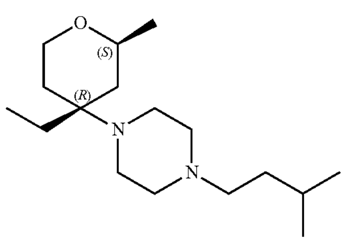 | 1-((2S,4R)-4-ethyl-2-methyltetrahydro-2H-pyran-4-yl)-4-isopentylpiperazine |
| 161 | 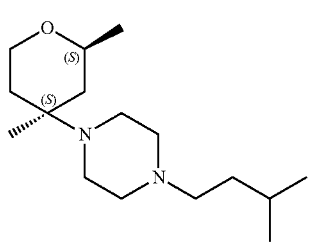 | 1-((2S,4S)-2,4-dimethyltetrahydro-2H-pyran-4-yl)-4-isopentylpiperazine |

-continued

| Ex | Structure | Chemical name |
|---|---|---|
| 162 | 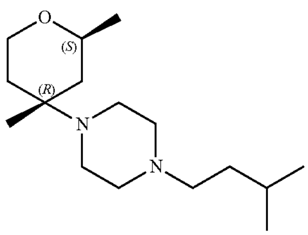 | 1-((2S,4R)-2,4-dimethyltetrahydro-2H-pyran-4-yl)-4-isopentylpiperazine |
| 163 | 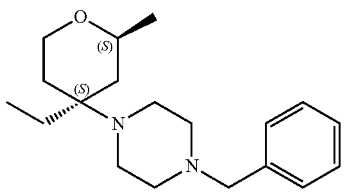 | 1-benzyl-4-((2S,4S)-4-ethyl-2-methyltetrahydro-2H-pyran-4-yl)piperazine |
| 164 | 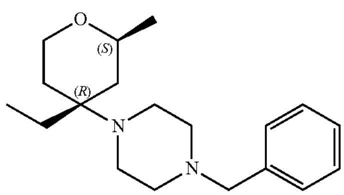 | 1-benzyl-4-((2S,4R)-4-ethyl-2-methyltetrahydro-2H-pyran-4-yl)piperazine |
| 165 | 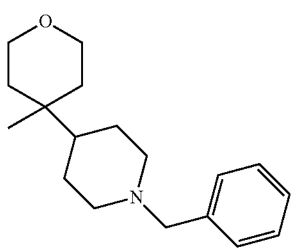 [SMILES: CC1(C2CCN(Cc3ccccc3)CC2)CCOCC1] | 1-benzyl-4-(4-methyltetrahydro-2H-pyran-4-yl)piperidine |
| 166 | 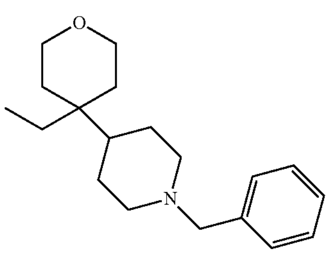 [SMILES: CCC1(C2CCN(Cc3ccccc3)CC2)CCOCC1] | 1-benzyl-4-(4-ethyltetrahydro-2H-pyran-4-yl)piperidine |
| 167 | 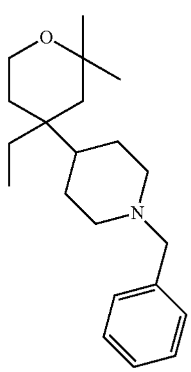 [SMILES: CCC1(C2CCN(Cc3ccccc3)CC2)CCOC(C)(C)C1] | 1-Benzyl-4-(4-ethyl-2,2-dimethyltetrahydro-2H-pyran-4-yl)piperidine |

-continued
| Ex | Structure | Chemical name |
|---|---|---|
| 168 | 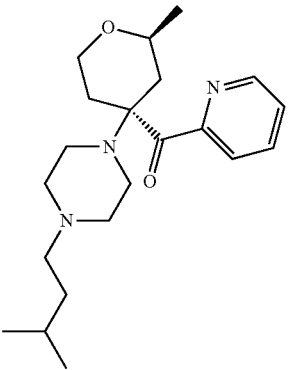 [SMILES: CC(C)CCN1CCN([C@@]2(C(=O)c3ccccn3)CCO[C@@H](C)C2)CC1] | 4-(4-isopentylpiperazin-1-yl)-2-methyltetrahydro-2H-pyran-4-yl)(pyridin-2-yl)methanone |
| 169 | 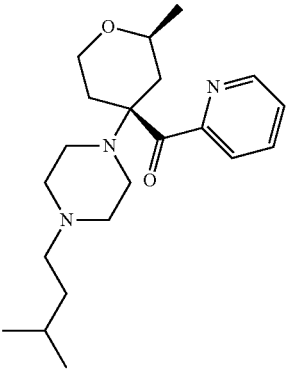 [SMILES: CC(C)CCN1CCN([C@]2(C(=O)c3ccccn3)CCO[C@@H](C)C2)CC1] | 4-(4-isopentylpiperazin-1-yl)-2-methyltetrahydro-2H-pyran-4-yl)(pyridin-2-yl)methanone |
| 170 | 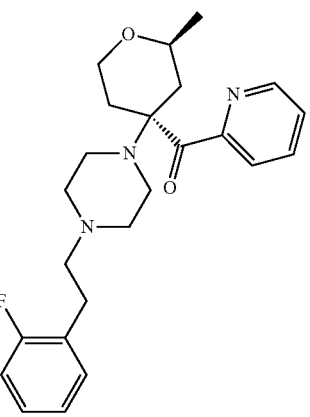 | 4-(4-(2-fluorophenethyl)piperazin-1-yl)-2-methyltetrahydro-2H-pyran-4-yl)(pyridin-2-yl)methanone |
| 171 | 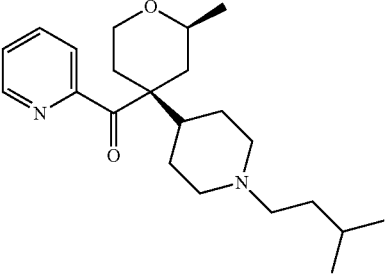 [SMILES: CC(C)CCN1CCC([C@@]2(C(=O)c3ccccn3)CCO[C@@H](C)C2)CC1] | 4-(1-isopentylpiperidin-4-yl)-2-methyltetrahydro-2H-pyran-4-yl)(pyridin-2-yl)methanone |

| Ex | Structure | Chemical name |
|---|---|---|
| 172 | 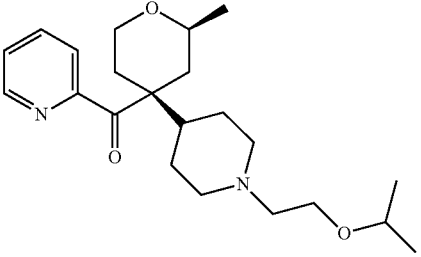 [SMILES: CC(C)OCCN1CCC([C@@]2(C(=O)c3ccccn3)CCO[C@@H](C)C2)CC1] | 4-(1-(2-isopropoxyethyl)piperidin-4-yl)-2-methyltetrahydro-2H-pyran-4-yl)(pyridin-2-yl)methanone |
| 173 | 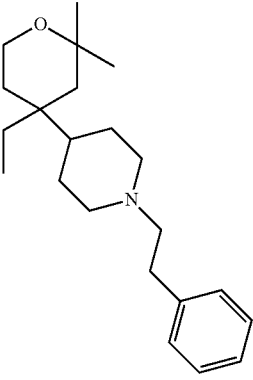 [SMILES: CCC1(C2CCN(CCc3ccccc3)CC2)CCOC(C)(C)C1] | 4-(4-ethyl-2,2-dimethyltetrahydro-2H-pyran-4-yl)-1-phenethylpiperidine |
| 174 | 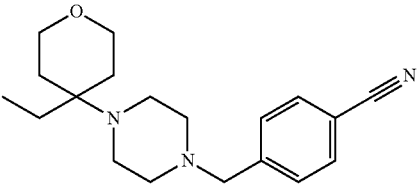 [SMILES: CCC1(N2CCN(Cc3ccc(C#N)cc3)CC2)CCOCC1] | 4-((4-(4-ethyltetrahydro-2H-pyran-4-yl)piperazin-1-yl)methyl)benzonitrile |
| 175 | 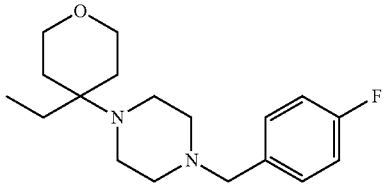 | 1-(4-ethyltetrahydro-2H-pyran-4-yl)-4-(4-fluorobenzyl)piperazine |
| 176 | 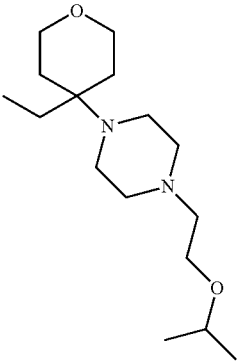 [SMILES: CCC1(N2CCN(CCOC(C)C)CC2)CCOCC1] | 1-(4-ethyltetrahydro-2H-pyran-4-yl)-4-(2-isopropoxyethyl)piperazine |

| Ex | Structure | Chemical name |
|---|---|---|
| 177 | 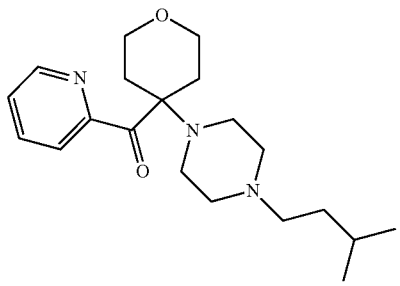 [SMILES: CC(C)CCN1CCN(C2(C(=O)c3ccccn3)CCOCC2)CC1] | (4-(4-isopentylpiperazin-1-yl)tetrahydro-2H-pyran-4-yl)(pyridin-2-yl)methanone |
| 178 | 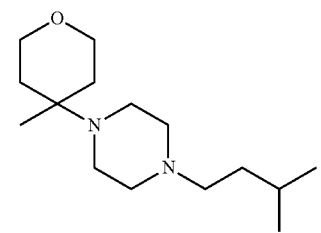 [SMILES: CC(C)CCN1CCN(C2(C)CCOCC2)CC1] | 1-isopentyl-4-(4-methyltetrahydro-2H-pyran-4-yl)piperazine |
| 179 | 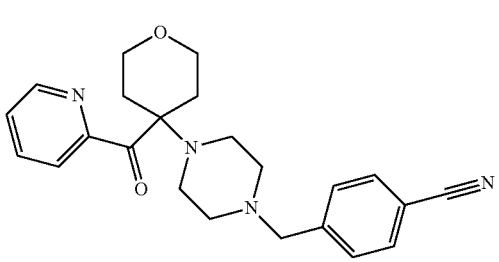 [SMILES: N#Cc1ccc(CN2CCN(C3(C(=O)c4ccccn4)CCOCC3)CC2)cc1] | 4-((4-(4-picolinoyltetrahydro-2H-pyran-4-yl)piperazin-1-yl)methyl)benzonitrile |
| 180 | 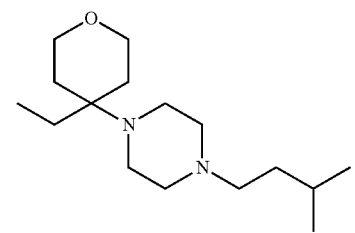 | 1-(4-ethyltetrahydro-2H-pyran-4-yl)-4-isopentylpiperazine |
| 181 | 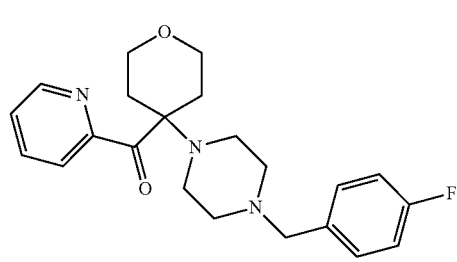 [SMILES: O=C(c1ccccn1)C1(N2CCN(Cc3ccc(F)cc3)CC2)CCOCC1] | (4-(4-(4-fluorobenzyl)piperazin-1-yl)tetrahydro-2H-pyran-4-yl)(pyridin-2-yl)methanone |
| 182 | 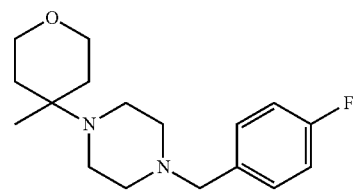 [SMILES: CC1(N2CCN(Cc3ccc(F)cc3)CC2)CCOCC1] | 1-(4-fluorobenzyl)-4-(4-methyltetrahydro-2H-pyran-4-yl)piperazine |

| Ex | Structure | Chemical name |
| --- | --- | --- |
| 183 | 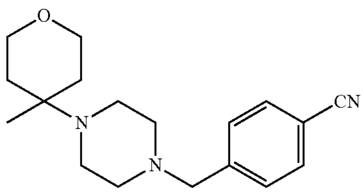 [SMILES: CC1(N2CCN(Cc3ccc(C#N)cc3)CC2)CCOCC1] | 4-((4-(4-methyltetrahydro-2H-pyran-4-yl)piperazin-1-yl)methyl)benzonitrile |
| 184 | 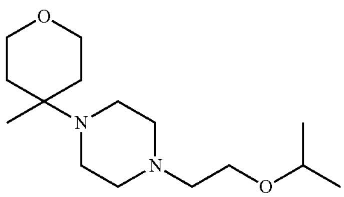 [SMILES: CC(C)OCCN1CCN(C2(C)CCOCC2)CC1] | 1-(2-isopropoxyethyl)-4-(4-methyltetrahydro-2H-pyran-4-yl)piperazine |
| 185 | 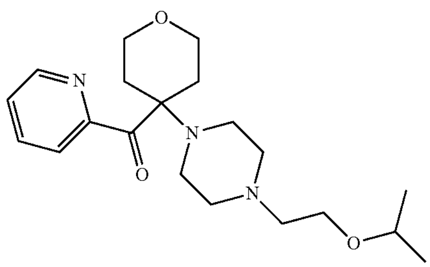 [SMILES: CC(C)OCCN1CCN(C2(C(=O)c3ccccn3)CCOCC2)CC1] | (4-(4-(2-isopropoxyethyl)piperazin-1-yl)tetrahydro-2H-pyran-4-yl)(pyridin-2-yl)methanone |
| 186 | 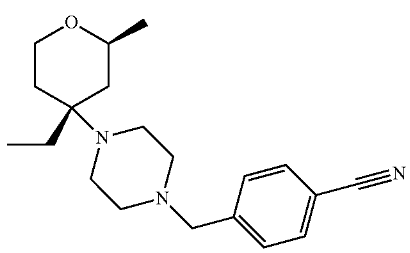 [SMILES: CC[C@@]1(N2CCN(Cc3ccc(C#N)cc3)CC2)CCO[C@@H](C)C1] | 4-((4-(4-ethyl-2-methyltetrahydro-2H-pyran-4-yl)piperazin-1-yl)methyl)benzonitrile |
| 187 | 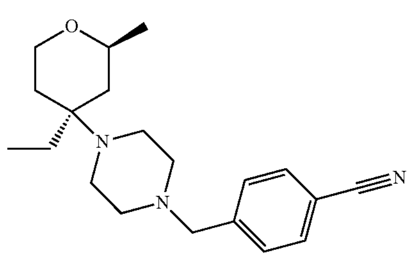 [SMILES: CC[C@]1(N2CCN(Cc3ccc(C#N)cc3)CC2)CCO[C@@H](C)C1] | 4-((4-(4-ethyl-2-methyltetrahydro-2H-pyran-4-yl)piperazin-1-yl)methyl)benzonitrile |
| 188 | 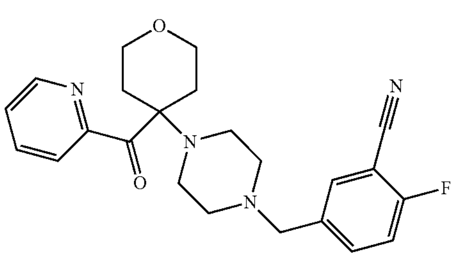 [SMILES: N#Cc1cc(CN2CCN(C3(C(=O)c4ccccn4)CCOCC3)CC2)ccc1F] | 2-fluoro-5-((4-(4-picolinoyltetrahydro-2H-pyran-4-yl)piperazin-1-yl)methyl)benzonitrile |

-continued

| Ex | Structure | Chemical name |
|---|---|---|
| 189 | 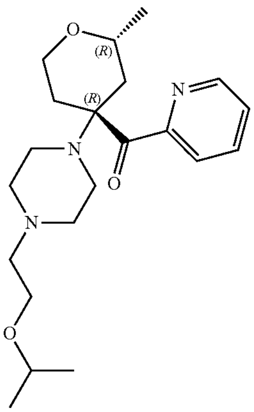 | ((2R,4R)-4-(4-(2-isopropoxyethyl)piperazin-1-yl)-2-methyltetrahydro-2H-pyran-4-yl)(pyridin-2-yl)methanone |
| 190 | 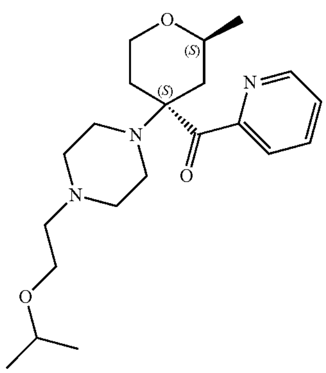 | ((2S,4S)-4-(4-(2-isopropoxyethyl)piperazin-1-yl)-2-methyltetrahydro-2H-pyran-4-yl)(pyridin-2-yl)methanone |
| 191 | 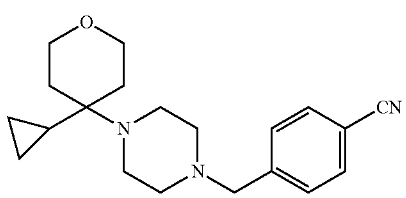 [SMILES: N#Cc1ccc(CN2CCN(C3(C4CC4)CCOCC3)CC2)cc1] | 4-((4-(4-cyclopropyltetrahydro-2H-pyran-4-yl)piperazin-1-yl)methyl)benzonitrile |
| 192 | 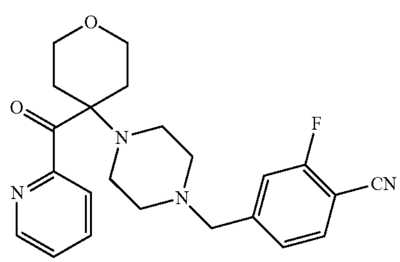 [SMILES: N#Cc1ccc(CN2CCN(C3(C(=O)c4ccccn4)CCOCC3)CC2)cc1F] | 2-fluoro-4-((4-(4-picolinoyltetrahydro-2-pyran-4-yl)piperazin-1-yl)methyl)benzonitrile |
| 193 | 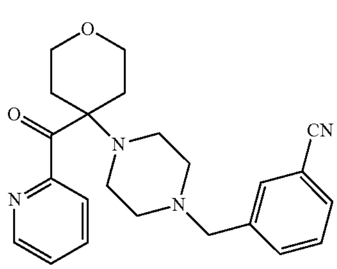 [SMILES: N#Cc1cccc(CN2CCN(C3(C(=O)c4ccccn4)CCOCC3)CC2)c1] | 3-((4-(4-picolinoyltetrahydro-2H-pyran-4-yl)piperazin-1-yl)methyl)benzonitrile |

| Ex | Structure | Chemical name |
|---|---|---|
| 194 | 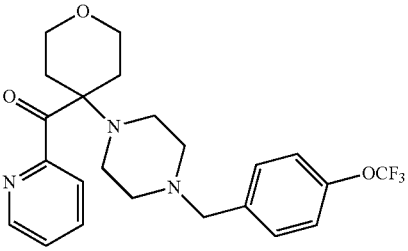 [SMILES: O=C(c1ccccn1)C1(N2CCN(Cc3ccc(OC(F)(F)F)cc3)CC2)CCOCC1] | pyridin-2-yl(4-(4-(4-(trifluoromethoxy)benzyl)piperazin-1-yl)tetrahydro-2H-pyran-4-yl)methanone |
| 195 | 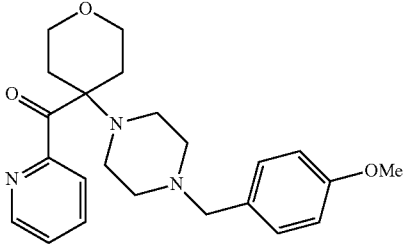 | (4-(4-(4-methoxybenzyl)piperazin-1-yl)tetrahydro-2H-pyran-4-yl)(pyridin-2-yl)methanone |
| 196 | 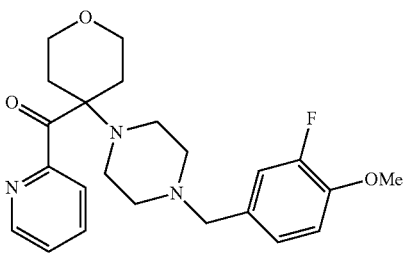 [SMILES: COc1ccc(CN2CCN(C3(C(=O)c4ccccn4)CCOCC3)CC2)cc1F] | (4-(4-(3-fluoro-4-methoxybenzyl)piperazin-1-yl)tetrahydro-2H-pyran-4-yl)(pyridin-2-yl)methanone |
| 197 | 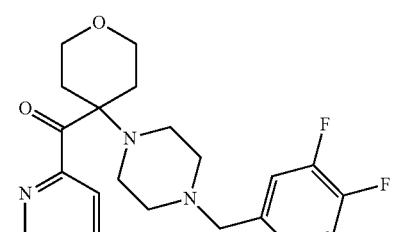 | (4-(4-(3,4-difluorobenzyl)piperazin-1-yl)tetrahydro-2H-pyran-4-yl)(pyridin-2-yl)methanone |
| 198 | 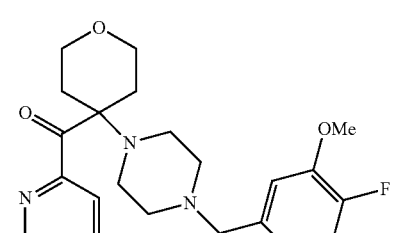 | (4-(4-(4-fluoro-3-methoxybenzyl)piperazin-1-yl)tetrahydro-2H-pyran-4-yl)(pyridin-2-yl)methanone |
| 199 | 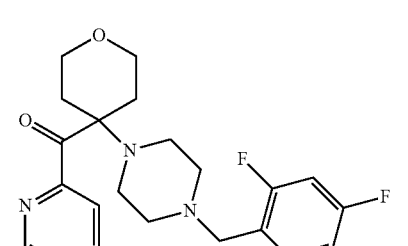 | (4-(4-(2,4-difluorobenzyl)piperazin-1-yl)tetrahydro-2H-pyran-4-yl)(pyridin-2-yl)methanone |

-continued

| Ex | Structure | Chemical name |
|---|---|---|
| 200 | 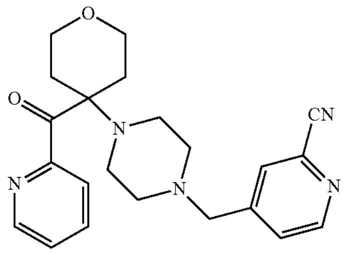 [SMILES: N#Cc1cc(CN2CCN(C3(C(=O)c4ccccn4)CCOCC3)CC2)ccn1] | 4-((4-(4-picolinoyltetrahydro-2H-pyran-4-yl)piperazin-1-yl)methyl)picolinonitrile |
| 201 | 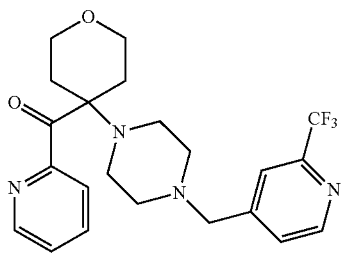 | pyridin-2-yl(4-(4-((2-(trifluoromethyl)pyridin-4-yl)methyl)piperazin-1-yl)tetrahydro-2H-pyran-4-yl)methanone |
| 202 | 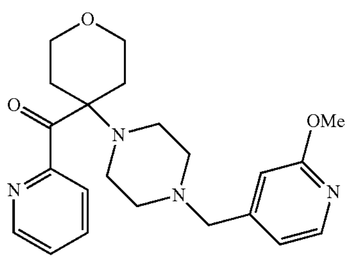 [SMILES: COc1cc(CN2CCN(C3(C(=O)c4ccccn4)CCOCC3)CC2)ccn1] | 4-(4-((2-methoxypyridin-4-yl)methyl)piperazin-1-yl)tetrahydro-2H-pyran-4-yl)(pyridin-2-yl)methanone |
| 203 | 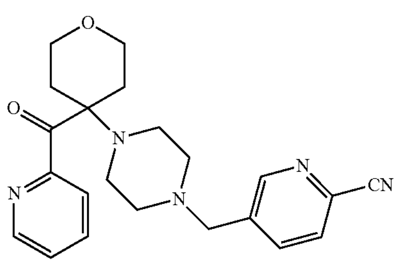 [SMILES: N#Cc1ccc(CN2CCN(C3(C(=O)c4ccccn4)CCOCC3)CC2)cn1] | 5-((4-(4-picolinoyltetrahydro-2H-pyran-4-yl)piperazin-1-yl)methyl)picolinonitrile |
| 204 | 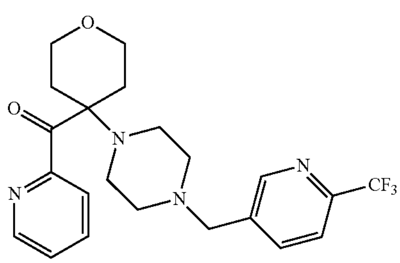 [SMILES: O=C(c1ccccn1)C1(N2CCN(Cc3ccc(C(F)(F)F)nc3)CC2)CCOCC1] | pyridin-2-yl(4-(4-((6-(trifluoromethyl)pyridin-3-yl)methyl)piperazin-1-yl)tetrahydro-2H-pyran-4-yl)methanone |
| 205 | 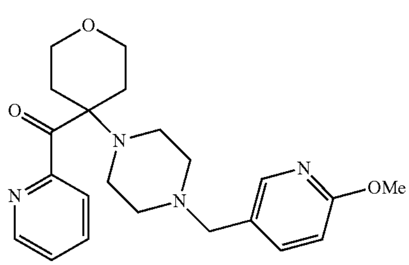 [SMILES: COc1ccc(CN2CCN(C3(C(=O)c4ccccn4)CCOCC3)CC2)cn1] | (4-(4-((6-methoxypyridin-3-yl)methyl)piperazin-1-yl)tetrahydro-2H-pyran-4-yl)(pyridin-2-yl)methanone |

| Ex | Structure | Chemical name |
|---|---|---|
| 208 | 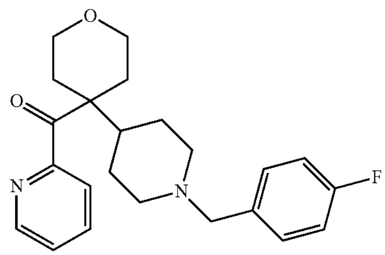 [SMILES: O=C(c1ccccn1)C1(C2CCN(Cc3ccc(F)cc3)CC2)CCOCC1] | 4-(1-(4-fluorobenzyl)piperidin-4-yl)tetrahydro-2H-pyran-4-yl)(pyridin-2-yl)methanone |
| 209 | 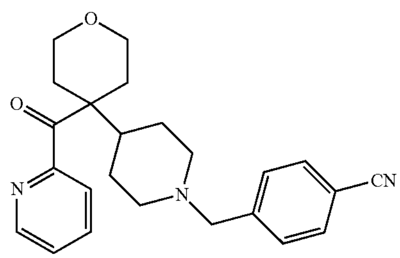 [SMILES: N#Cc1ccc(CN2CCC(C3(C(=O)c4ccccn4)CCOCC3)CC2)cc1] | 4-((4-(4-picolinoyltetrahydro-2H-pyran-4-yl)piperidin-1-yl)methyl)benzonitrile |
| 210 | 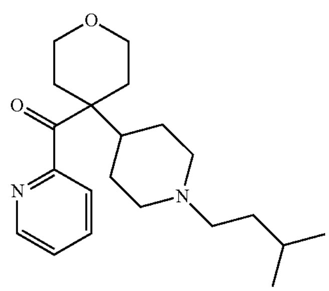 [SMILES: CC(C)CCN1CCC(C2(C(=O)c3ccccn3)CCOCC2)CC1] | (4-(1-isopentylpiperidin-4-yl)tetrahydro-2H-pyran-4-yl)(pyridin-2-yl)methanone |
| 211 | 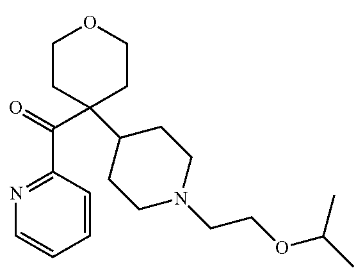 [SMILES: CC(C)OCCN1CCC(C2(C(=O)c3ccccn3)CCOCC2)CC1] | (4-(1-(2-isopropoxyethyl)piperidin-4-yl)tetrahydro-2H-pyran-4-yl)(pyridin-2-yl)methanone |
| 212 | 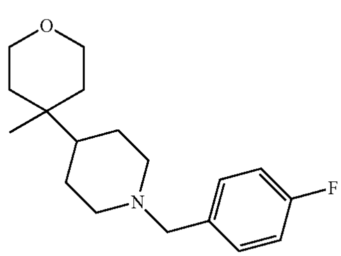 [SMILES: CC1(C2CCN(Cc3ccc(F)cc3)CC2)CCOCC1] | 1-(4-fluorobenzyl)-4-(4-methyltetrahydro-2H-pyran-4-yl)piperidine |
| 213 | 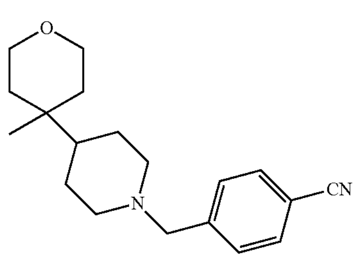 [SMILES: CC1(C2CCN(Cc3ccc(C#N)cc3)CC2)CCOCC1] | 4-((4-(4-methyltetrahydro-2H-pyran-4-yl)piperidin-1-yl)methyl)benzonitrile |

-continued

| Ex | Structure | Chemical name |
|---|---|---|
| 214 | 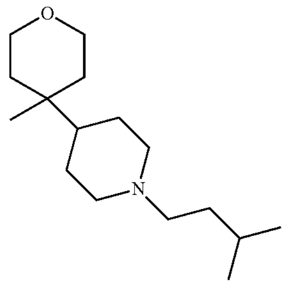 [SMILES: CC(C)CCN1CCC(C2(C)CCOCC2)CC1] | 1-isopentyl-4-(4-methyltetrahydro-2H-pyran-4-yl)piperidine |
| 215 | 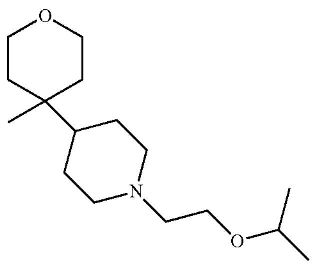 [SMILES: CC(C)OCCN1CCC(C2(C)CCOCC2)CC1] | 1-(2-isopropoxyethyl)-4-(4-methyltetrahydro-2H-pyran-4-yl)piperidine |
| 216 | 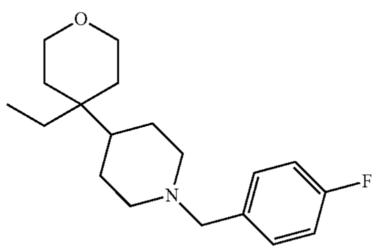 [SMILES: CCC1(C2CCN(Cc3ccc(F)cc3)CC2)CCOCC1] | 4-(4-ethyltetrahydro-2H-pyran-4-yl)-1-(4-fluorobenzyl)piperidine |
| 217 | 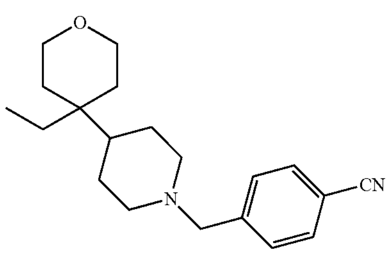 [SMILES: CCC1(C2CCN(Cc3ccc(C#N)cc3)CC2)CCOCC1] | 4-((4-(4-ethyltetrahydro-2H-pyran-4-yl)piperidin-1-yl)methyl)benzonitrile |
| 218 | 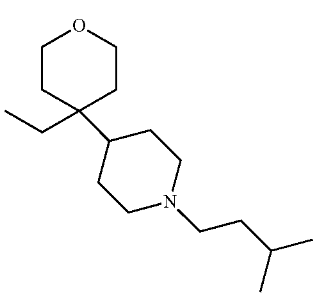 [SMILES: CCC1(C2CCN(CCC(C)C)CC2)CCOCC1] | 4-(4-ethyltetrahydro-2H-pyran-4-yl)-1-isopentylpiperidine |

| Ex | Structure | Chemical name |
|---|---|---|
| 219 | 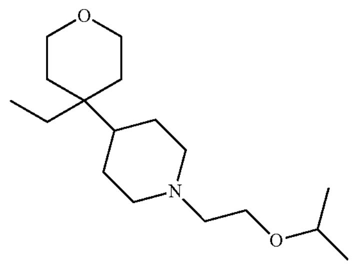 [SMILES: CCC1(C2CCN(CCOC(C)C)CC2)CCOCC1] | 4-(4-ethyltetrahydro-2H-pyran-4-yl)-1-(2-isopropoxyethyl)piperidine |
| 220 | 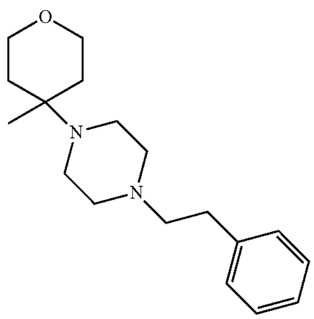 [SMILES: CC1(N2CCN(CCc3ccccc3)CC2)CCOCC1] | 1-(4-methyltetrahydro-2H-pyran-4-yl)-4-phenethylpiperazine |
| 221 | 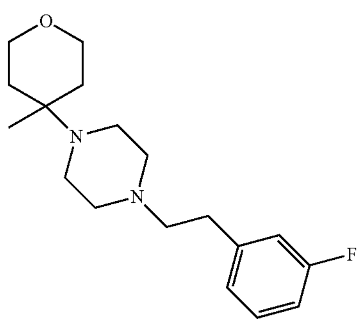 [SMILES: CC1(N2CCN(CCc3cccc(F)c3)CC2)CCOCC1] | 1-(3-fluorophenethyl)-4-(4-methyltetrahydro-2H-pyran-4-yl)piperazine |
| 222 | 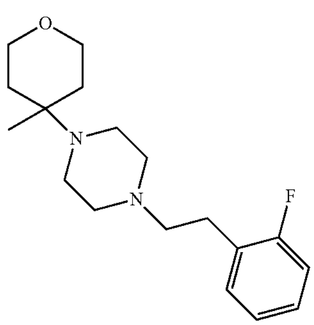 [SMILES: CC1(N2CCN(CCc3ccccc3F)CC2)CCOCC1] | 1-(2-fluorophenethyl)-4-(4-methyltetrahydro-2H-pyran-4-yl)piperazine |
| 223 | 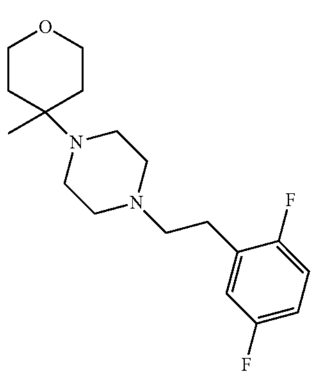 | 1-(2,5-difluorophenethyl)-4-(4-methyltetrahydro-2H-pyran-4-yl)piperazine |

-continued

| Ex | Structure | Chemical name |
|---|---|---|
| 224 | 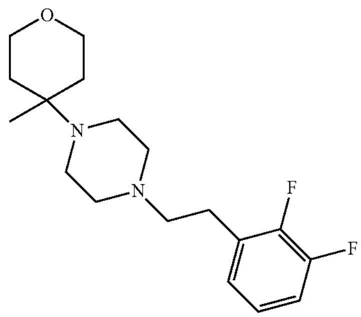 [SMILES: CC1(N2CCN(CCc3cccc(F)c3F)CC2)CCOCC1] | 1-(2,3-difluorophenethyl)-4-(4-methyltetrahydro-2H-pyran-4-yl)piperazine |
| 225 | 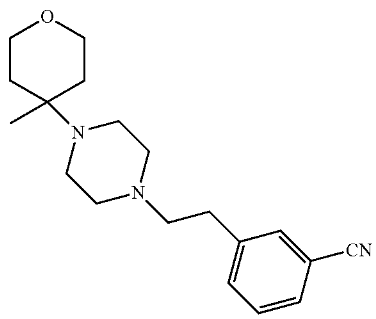 [SMILES: CC1(N2CCN(CCc3cccc(C#N)c3)CC2)CCOCC1] | 3-(2-(4-(4-methyltetrahydro-2H-pyran-4-yl)piperazin-1-yl)ethyl)benzonitrile |
| 226 | 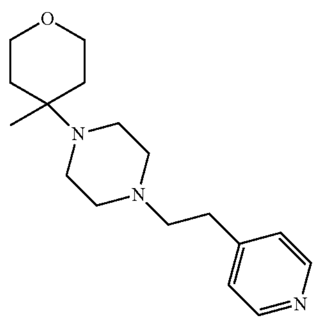 | 1-(4-methyltetrahydro-2H-pyran-4-yl)-4-(2-(pyridin-4-yl)ethyl)piperazine |
| 227 | 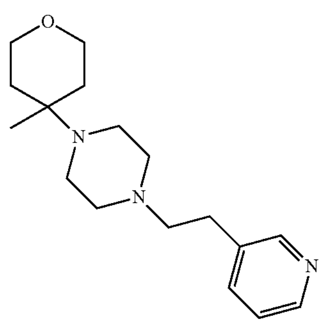 [SMILES: CC1(N2CCN(CCc3cccnc3)CC2)CCOCC1] | 1-(4-methyltetrahydro-2H-pyran-4-yl)-4-(2-(pyridin-3-yl)ethyl)piperazine |
| 228 | 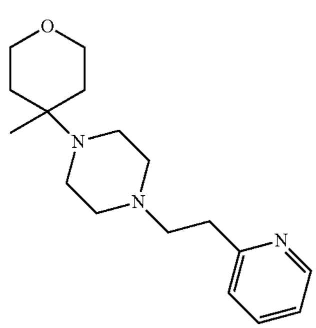 [SMILES: CC1(N2CCN(CCc3ccccn3)CC2)CCOCC1] | 1-(4-methyltetrahydro-2H-pyran-4-yl)-4-(2-(pyridin-2-yl)ethyl)piperazine |

| Ex | Structure | Chemical name |
|---|---|---|
| 229 | 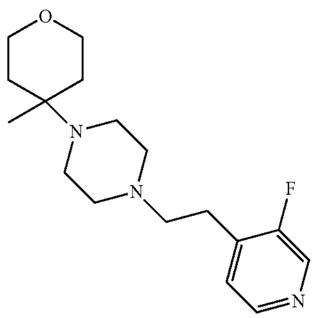 [SMILES: CC1(N2CCN(CCc3ccncc3F)CC2)CCOCC1] | 1-(2-(3-fluoropyridin-4-yl)ethyl)-4-(4-methyltetrahydro-2H-pyran-4-yl)piperazine |
| 230 | 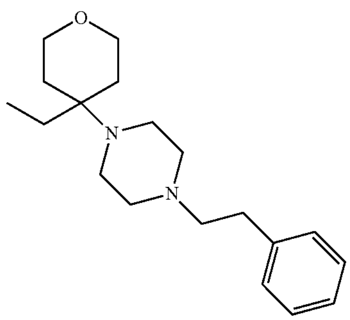 [SMILES: CCC1(N2CCN(CCc3ccccc3)CC2)CCOCC1] | 1-(4-ethyltetrahydro-2H-pyran-4-yl)-4-phenethylpiperazine |
| 231 | 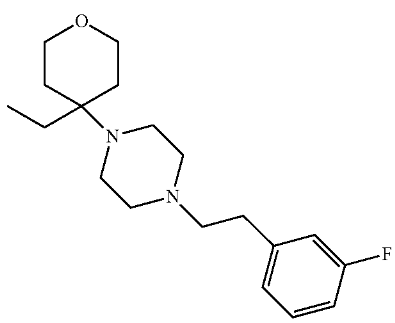 [SMILES: CCC1(N2CCN(CCc3cccc(F)c3)CC2)CCOCC1] | 1-(4-ethyltetrahydro-2H-pyran-4-yl)-4-(3-fluorophenethyl)piperazine |
| 232 | 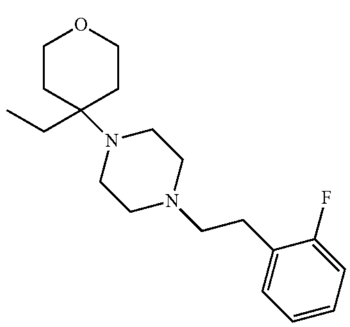 [SMILES: CCC1(N2CCN(CCc3ccccc3F)CC2)CCOCC1] | 1-(4-ethyltetrahydro-2H-pyran-4-yl)-4-(2-fluorophenethyl)piperazine |

-continued

| Ex | Structure | Chemical name |
|---|---|---|
| 233 | 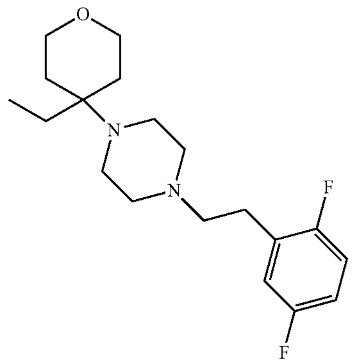 [SMILES: CCC1(N2CCN(CCc3cc(F)ccc3F)CC2)CCOCC1] | 1-(2,5-difluorophenethyl)-4-(4-ethyltetrahydro-2H-pyran-4-yl)piperazine |
| 234 | 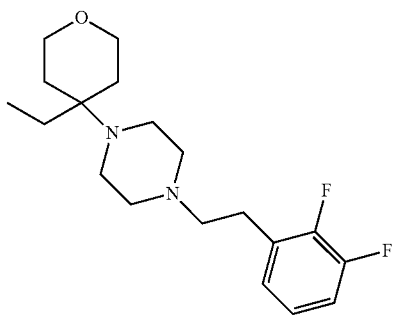 [SMILES: CCC1(N2CCN(CCc3cccc(F)c3F)CC2)CCOCC1] | 1-(2,3-difluorophenethyl)-4-(4-ethyltetrahydro-2H-pyran-4-yl)piperazine |
| 235 | 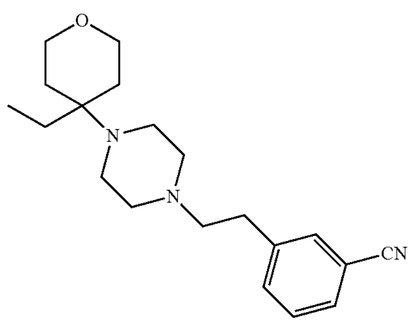 [SMILES: CCC1(N2CCN(CCc3cccc(C#N)c3)CC2)CCOCC1] | 3-(2-(4-(4-ethyltetrahydro-2H-pyran-4-yl)piperazin-1-yl)ethyl)benzonitrile |
| 236 | 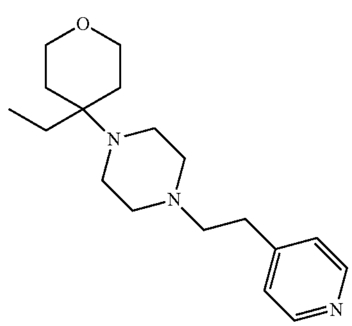 | 1-(4-ethyltetrahydro-2H-pyran-4-yl)-4-(2-(pyridin-4-yl)ethyl)piperazine |

-continued

| Ex | Structure | Chemical name |
|---|---|---|
| 237 | 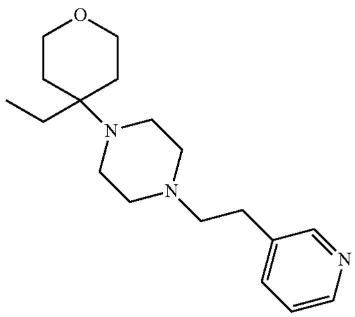 [SMILES: CCC1(N2CCN(CCc3cccnc3)CC2)CCOCC1] | 1-(4-ethyltetrahydro-2H-pyran-4-yl)-4-(2-(pyridin-3-yl)ethyl)piperazine |
| 238 | 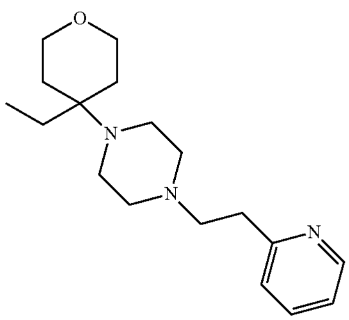 [SMILES: CCC1(N2CCN(CCc3ccccn3)CC2)CCOCC1] | 1-(4-ethyltetrahydro-2H-pyran-4-yl)-4-(2-(pyridin-2-yl)ethyl)piperazine |
| 239 | 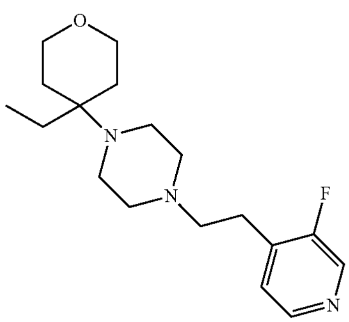 | 1-(4-ethyltetrahydro-2H-pyran-4-yl)-4-(2-(3-fluoropyridin-4-yl)ethyl)piperazine |
| 240 | 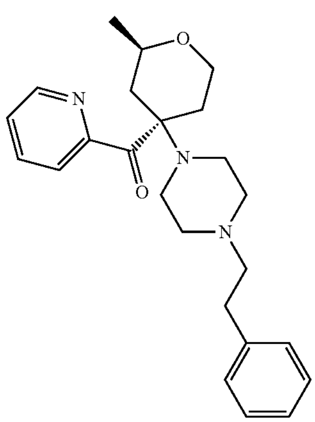 [SMILES: C[C@@H]1C[C@](C(=O)c2ccccn2)(N2CCN(CCc3ccccc3)CC2)CCO1] | ((2R,4R)-2-methyl-4-(4-phenethylpiperazin-1-yl)tetrahydro-2H-pyran-4-yl)(pyridin-2-yl)methanone |

| Ex | Structure | Chemical name |
|---|---|---|
| 241 | 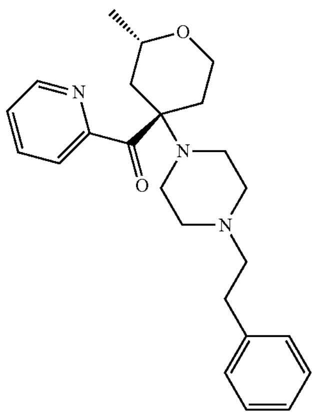 [SMILES: C[C@H]1C[C@@](C(=O)c2ccccn2)(N2CCN(CCc3ccccc3)CC2)CCO1] | ((2S,4S)-2-methyl-4-(4-phenethylpiperazin-1-yl)tetrahydro-2H-pyran-4-yl)(pyridin-2-yl)methanone |
| 242 | 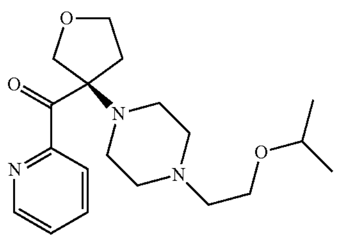 [SMILES: CC(C)OCCN1CCN([C@]2(C(=O)c3ccccn3)CCOC2)CC1] | (R)-(3-(4-(2-isopropoxyethyl)piperazin-1-yl)tetrahydrofuran-3-yl)(pyridin-2-yl)methanone |
| 243 | 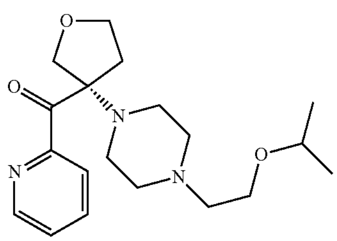 [SMILES: CC(C)OCCN1CCN([C@@]2(C(=O)c3ccccn3)CCOC2)CC1] | (S)-(3-(4-(2-isopropoxyethyl)piperazin-1-yl)tetrahydrofuran-3-yl)(pyridin-2-yl)methanone |
| 244 | 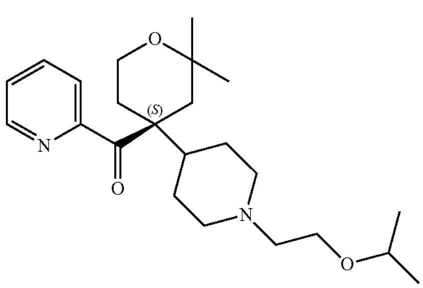 | (S)-(4-(1-(2-isopropoxyethyl)piperidin-4-yl)-2,2-dimethyltetrahydro-2H-pyran-4-yl)(pyridin-2-yl)methanone |
| 245 | 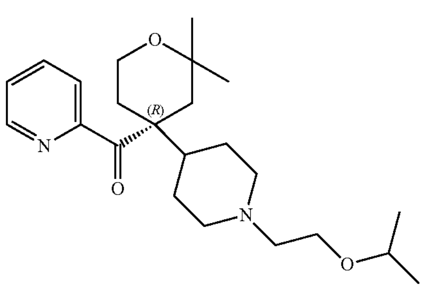 | (R)-(4-(1-(2-isopropoxyethyl)piperidin-4-yl)-2,2-dimethyltetrahydro-2H-pyran-4-yl)(pyridin-2-yl)methanone |

| Ex | Structure | Chemical name |
|---|---|---|
| 246 | 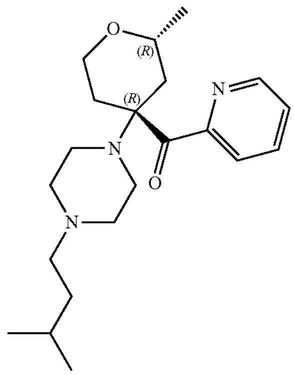 | ((2R,4R)-4-(4-isopentylpiperazin-1-yl)-2-methyltetrahydro-2H-pyran-4-yl)(pyridin-2-yl)methanone |
| 247 | 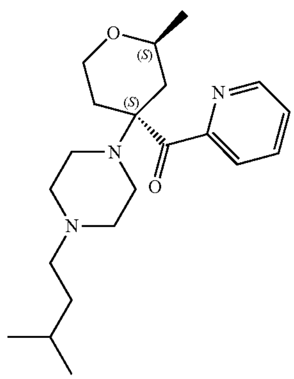 | ((2S,4S)-4-(4-isopentylpiperazin-1-yl)-2-methyltetrahydro-2H-pyran-4-yl)(pyridin-2-yl)methanone |
| 248 | 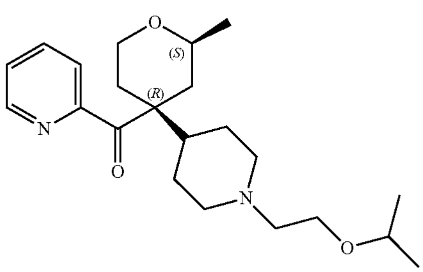 | ((2S,4R)-4-(1-(2-isopropoxyethyl)piperidin-4-yl)-2-methyltetrahydro-2H-pyran-4-yl)(pyridin-2-yl)methanone |
| 249 | 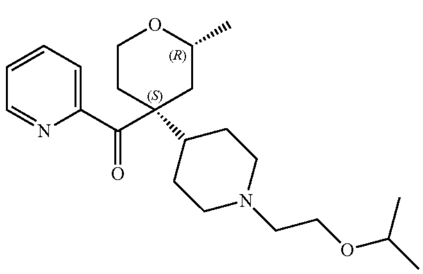 | ((2R,4S)-4-(1-(2-isopropoxyethyl)piperidin-4-yl)-2-methyltetrahydro-2H-pyran-4-yl)(pyridin-2-yl)methanone |
| 250 | 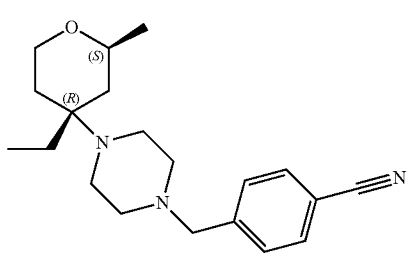 | 4-((4-((2S,4R)-4-ethyl-2-methyltetrahydro-2H-pyran-4-yl)piperazin-1-yl)methyl)benzonitrile |

| Ex | Structure | Chemical name |
|---|---|---|
| 251 |  | 4-((4-((2R,4S)-4-ethyl-2-methyltetrahydro-2H-pyran-4-yl)piperazin-1-yl)methyl)benzonitrile | optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I), $R_{1'}$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;

wherein said cycloalkyl, aryl or heterocyclyl in $R_{1'}$ if substituted, is substituted with one or more substituent/s selected from halogen, —$R_{11}$, —$OR_{11}$, —$NO_2$, —$NR_{11}R_{11'''}$, $NR_{11}C(O)R_{11'}$, —$NR_{11}S(O)_2R_{1'}$, —$S(O)_2$ $NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11'''}$ and $C(CH_3)_2OR_{11}$;

additionally, cycloalkyl or non-aromatic heterocyclyl in $R_{1'}$ if substituted, may also be substituted with

or =O;

wherein the alkyl, alkenyl or alkynyl in $R_{1'}$, if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;

wherein $R_{11}$, $R_{11'}$ and $R_{11''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{11'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), $R_2$ is selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl, wherein said cycloalkyl, aryl or heterocyclyl in $R_2$, if substituted, is substituted with one or more substituent/s selected from halogen, —$R_{12}$, —$OR_{12}$, —$NO_2$, —$NR_{12}R_{12'''}$, $NR_{12}C(O)R_{12'}$, —$NR_{12}S(O)_2R_{12'}$, —$S(O)_2NR_{12}R_{12'}$, $NR_{12}C(O)NR_{12'}R_{12''}$, —$SR_{12}$, —$S(O)R_{12}$, —$S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and —$C(CH_3)_2OR_{12}$;

additionally, cycloalkyl or non-aromatic heterocyclyl in $R_2$, if substituted, may also be substituted with

▽ or =O;

wherein the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;

wherein $R_{12}$, $R_{12'}$ and $R_{12''}$ are independently selected from hydrogen, unsubstituted $C_{1-6}$ alkyl, unsubstituted $C_{2-6}$ alkenyl and unsubstituted $C_{2-6}$ alkynyl;

and wherein $R_{12'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the alkyl, alkenyl or alkynyl, other than those defined in $R_{1'}$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;

wherein $R_{13}$ and $R_{13'}$ are independently selected from hydrogen, unsubstituted $C_{1-6}$ alkyl, unsubstituted $C_{2-6}$ alkenyl, and unsubstituted $C_{2-6}$ alkynyl;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In another embodiment of the invention the compound of general Formula (I), the aryl, heterocyclyl or cycloalkyl other than those defined in $R_{1'}$ or $R_2$, if substituted, is substituted with one or more substituent/s selected from halogen, —$R_{14}$, —$OR_{14}$, —$NO_2$, —$NR_{14}R_{14'''}$, —$NR_{14}C(O)R_{14'}$, —$NR_{14}S(O)_2R_{14'}$, —$S(O)_2NR_{14}R_{14'}$, —$NR_{14}C(O)NR_{14'}R_{14'''}$, —$SR_{14}$, —$S(O)R_{14}$, —$S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and —$C(CH_3)_2OR_{14}$;

additionally, wherein cycloalkyl or non-aromatic heterocyclyl, other than those defined in $R_{1'}$ or $R_2$, if substituted, may also be substituted with

or =O;

wherein $R_{14}$, $R_{14'}$ and $R_{14''}$ are independently selected from hydrogen, unsubstituted $C_{1-6}$ alkyl, unsubstituted $C_{2-6}$ alkenyl, unsubstituted $C_{2-6}$ alkynyl, unsubstituted aryl, unsubstituted cycloalkyl and unsubstituted heterocyclyl;

and wherein $R_{14'''}$ is selected from hydrogen, unsubstituted $C_{1-6}$ alkyl, unsubstituted $C_{2-6}$ alkenyl, unsubstituted $C_{2-6}$ alkynyl and -Boc;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention, the cycloalkyl, aryl or heterocyclyl in $R_1$, if substituted, is substituted with one or more substituent/s selected from halogen, —$R_{11}$, —$OR_{11}$, —$NO_2$, $NR_{11}R_{11'''}$, $NR_{11}C(O)R_{11'}$, —$NR_{11}S(O)_2R_{11'}$, —$S(O)_2NR_{11}R_{11'}$, $NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention, the cycloalkyl, aryl or heterocyclyl in $R_{1'}$ if substituted, is substituted with —$CF_3$ optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention, the cycloalkyl or non-aromatic heterocyclyl in $R_{1'}$ if substituted, may also be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_{1'}$ of any of the embodiments of the present invention, the alkyl, alkenyl or alkynyl in $R_{1'}$ if substituted, is substituted with one or more substituent/s selected from —$OR_{11}$, halogen, —CN, haloalkyl, haloalkoxy, —$SR_{11}$, —$S(O)R_{11}$, and —$S(O)_2R_{11}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl, aryl or heterocyclyl in $R_2$, if substituted, is substituted with one or more substituent/s selected from halogen, —$R_{12}$, —$OR_{12}$, —$NO_2$, $NR_{12}R_{12'''}$, —$NR_{12}C(O)R_{12'}$, —$NR_{12}S(O)_2R_{12'}$, —$S(O)_2NR_{12}R_{12'}$, $NR_{12}C(O)NR_{12'}R_{12'''}$, —$SR_{12}$, —$S(O)R_{12}$, —$S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and —$C(CH_3)_2OR_{12}$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl, aryl or heterocyclyl in $R_2$, if substituted, is substituted with one or more substituent/s selected from fluorine, chlorine, -methoxy, —CN, —$CF_3$ and —$OCF_3$;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention, the cycloalkyl or non-aromatic heterocyclyl in $R_2$, if substituted, may also be substituted with

or =O;

optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the alkyl, alkenyl or alkynyl in $R_2$, if substituted, is substituted with one or more substituent/s selected from —$OR_{12}$, halogen, —CN, haloalkyl, haloalkoxy, —$SR_{12}$, —$S(O)R_{12}$, and —$S(O)_2R_{12}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to $R_2$ of any of the embodiments of the present invention,
the alkyl, alkenyl or alkynyl in $R_2$, if substituted, is substituted with one or more substituent/s selected from —OH, fluorine and —$CF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to alkyls other than those defined in $R_{1'}$ or $R_2$ of any of the embodiments of the present invention,
the alkyl, alkenyl or alkynyl, other than those defined in $R_{1'}$ or $R_2$, if substituted, is substituted with one or more substituent/s selected from —$OR_{13}$, halogen, —CN, haloalkyl, haloalkoxy, —$SR_{13}$, —$S(O)R_{13}$, and —$S(O)_2R_{13}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_{1'}$ or $R_2$ of any of the embodiments of the present invention,
the aryl, heterocyclyl or cycloalkyl other than those defined in $R_{1'}$ or $R_2$, if substituted, is substituted with one or more substituent/s selected from halogen, —$R_{14}$, —$OR_{14}$, —$NO_2$, —$NR_{14}R_{14'''}$, —$NR_{14}C(O)R_{14'}$, —$NR_{14}S(O)_2R_{14'}$, —$S(O)_2NR_{14}R_{14'}$, —$NR_{14}C(O)NR_{14'}R_{14''}$, —$SR_{14}$, —$S(O)R_{14'}$, —$S(O)_2R_{14}$, —CN, haloalkyl, haloalkoxy, —$C(O)OR_{14}$, —$C(O)NR_{14}R_{14'}$, —$OCH_2CH_2OH$, —$NR_{14}S(O)_2NR_{14'}R_{14''}$ and —$C(CH_3)_2OR_{14}$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In a preferred embodiment of the compound according to the invention of general Formula (I) and in relation to the cycloalkyl, aryl or heterocyclyl other than those defined in $R_{1'}$ or $R_2$ of any of the embodiments of the present invention, the cycloalkyl or non-aromatic heterocyclyl, other than those defined in $R_{1'}$ or $R_2$, if substituted, may also be substituted with

or =O;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the halogen is fluorine, chlorine, iodine or bromine, preferably fluorine or chlorine;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

In an embodiment of the compound according to the invention of general Formula (I),
the haloalkyl is —$CF_3$;
optionally in form of one of the stereoisomers, preferably enantiomers or diastereomers, a racemate or in form of a mixture of at least two of the ratio, or a corresponding salt thereof, or a corresponding solvate thereof.

In another embodiment of the compound according to the invention of general Formula (I),
the haloalkoxy is —$OCF_3$;
optionally in form of one of the stereoisomers, preferably enantiomers or diastereomers, a racemate or in form of a mixture of at least two of the stereoisomers, preferably enantiomers and/or diastereomers, in any mixing ratio, or a corresponding salt thereof, or a corresponding solvate thereof.

As this invention is aimed at providing a compound or a chemically related series of compounds which act as dual ligands of the $\sigma_1$ receptor and the µ-opioid receptor it is a very preferred embodiment in which the compounds are selected which act as dual ligands of the $\sigma_1$ receptor and the µ-opioid receptor and especially compounds which have a binding expressed as $K_i$ which is preferably <1000 nM for both receptors, more preferably <500 nM, even more preferably <100 nM.

In the following the phrase "compound of the invention" is used. This is to be understood as any compound according to the invention as described above according to general Formula (I), (I-a), (I-b), (I'), ($I^{2'}$), ($I^{3'}$), ($I^{4'}$), ($I^{5'}$), ($I^{6'}$), ($I^{7'}$), ($I^{8'}$), ($I^{9'}$), ($I^{10'}$), ($I^{11'}$), ($I^{12'}$), ($I^{4a'}$) or ($I^{4b'}$).

The compounds of the invention represented by the above described Formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

In general the processes are described below in the experimental part. The starting materials are commercially available or can be prepared by conventional methods.

A preferred aspect of the invention is also a process for the production of a compound according to Formula (I), following scheme 1.

A preferred aspect of the invention is a process for the production of a compound according to Formula (I), wherein $R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X, Y and W are as defined in the description, following scheme 1.

For the sake of clarity the expression "a compound according to Formula (I), wherein $R_1$, etc are as defined in the description" would (just like the expression "a compound of Formula (I) as defined in, e.g., any one of claims 1 to 10" found in the claims) refer to "a compound according to Formula (I)", wherein the definitions of the respective substituents $R_1$ etc. (also from the cited claims) are applied. In addition, this would also mean, though (especially in regards to the claims) that also one or more disclaimers defined in the description (or used in any of the cited claims like e.g. claim 1) would be applicable to define the respective compound. Thus, a disclaimer found in e.g. claim 1 would be also used to define the compound "of Formula (I) as defined in any one of claims 1 to 10".

In all processes and uses described underneath and in scheme 1, the values of $R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X, Y and W are as defined in the description, L is a leaving group such as halogen, mesylate, tosylate or triflate, Z is chloro or bromo, M is

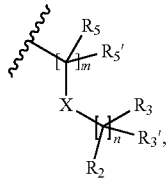

and PG is a protecting group, such as benzyl and tert-butoxycarbonyl.

A preferred embodiment of the invention is a process for the production of a compound according to Formula (I), wherein a) when $R_1$ is $-C(O)R_{1'}$, said process comprises treating a compound of Formula IIb

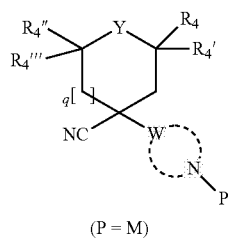

with a lithium salt generated from compounds of general formula IIIa

Z—$R_{1'}$            IIIa with organolithium reagent, and hydrolysing the obtained imine intermediate compound to a ketone compound of formula I in the presence of an aqueous inorganic acid, or b) when $R_1$ is $-C(R_6R_{6'})_pR_{1'}$, said process comprises the reaction of compounds of general formula IIb

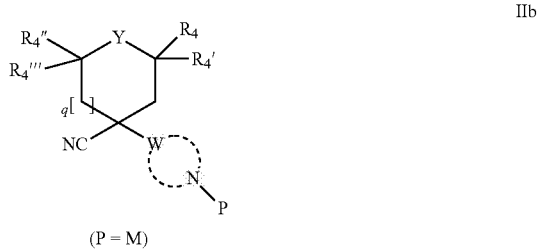

with Grignard reagents of formula IIIb

Z—Mg—$R_1$           IIIb, or c) said process comprises reacting a compound of general formula VII

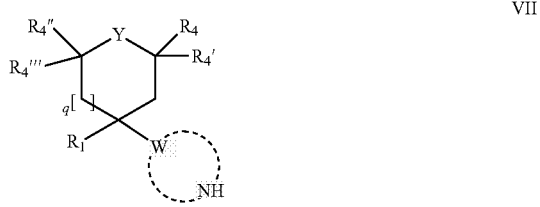

with a compound of general formula VIIIa though an alkylation reaction in the presence of an inorganic or organic base

or with a compound of general formula VIIIb though a reductive amination reaction in the presence of a reductive agent

or with a compound of general formula VIIIc though a condensation reaction

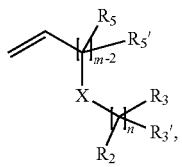

or d) when W is carbon, said process comprises the reductive alkylation of a cyano derivatives of formula V

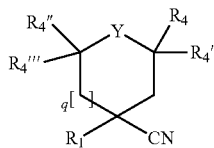

with a compound of formula VIb

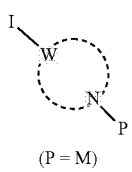

In the presence of lithium naphthalenide.

In a particular embodiment there is a process for the production of a compound of Formula (I) when $R_1$ is —C(O)$R_{1'}$,

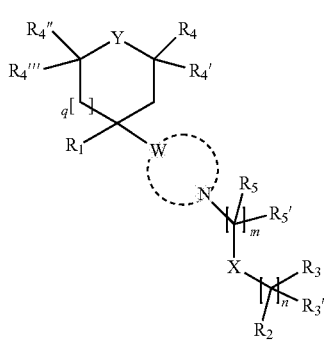

said process comprises treating a compound of Formula IIb

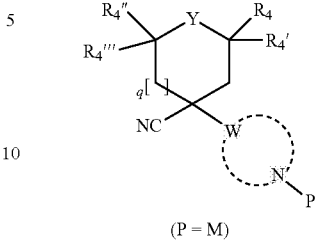

with a lithium salt generated from compounds of general formula IIIa $$Z-R_{1'} \quad \text{IIIa}$$

with an organolithium reagent and hydrolysing the obtained imine intermediate compound to a ketone compound of formula I in the presence of an aqueous inorganic acid.

In a particular embodiment there is a process for the production of a compound of Formula (I) when $R_1$ is —C($R_6R_{6'}$)$_p$$R_{1'}$,

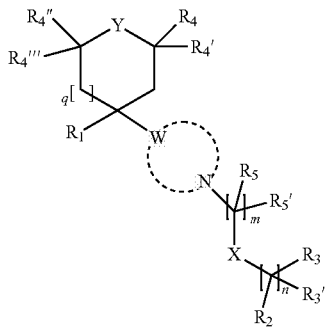

said process comprises the reaction of compounds of general formula IIb

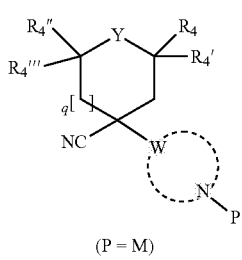

with Grignard reagents of formula IIIb $$Z-Mg-R_1 \quad \text{IIIb.}$$

In a particular embodiment there is a process for the production of a compound of Formula (I),

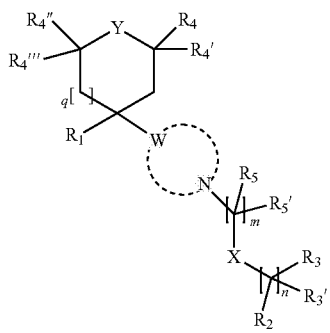

said process comprises reacting a compound of general formula VII

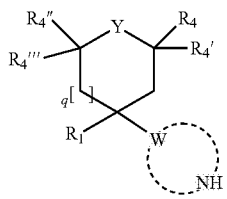

with a compound of general formula VIIIa though an alkylation reaction in the presence of an inorganic or organic base

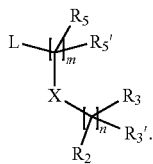

In a particular embodiment there is a process for the production of a compound of Formula (I),

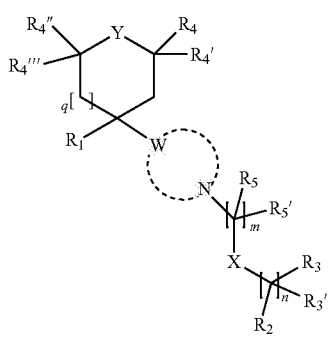

said process comprises reacting a compound of general formula VII

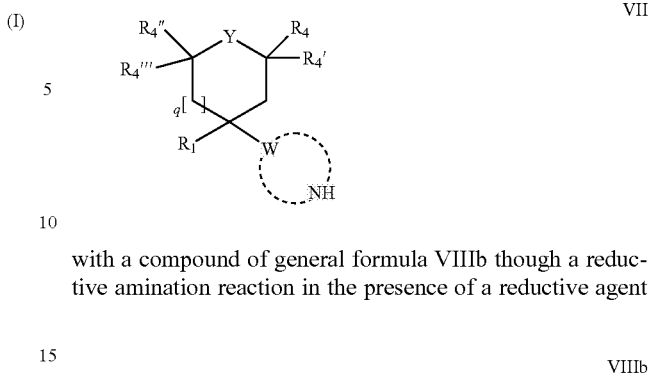

with a compound of general formula VIIIb though a reductive amination reaction in the presence of a reductive agent In a particular embodiment there is a process for the production of a compound of Formula (I),

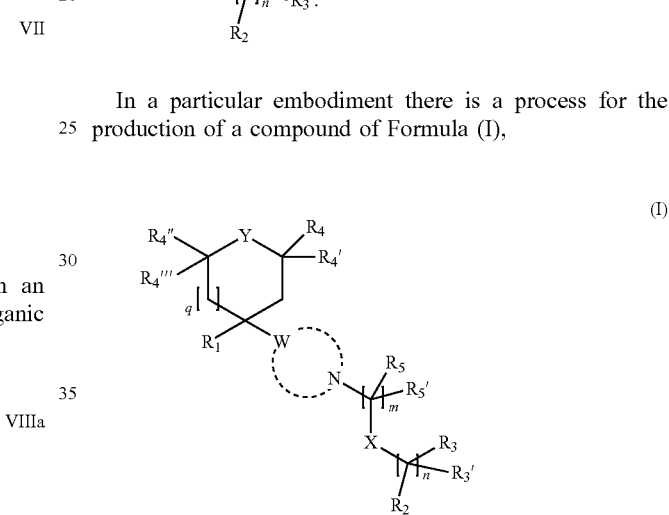

said process comprises reacting a compound of general formula VII

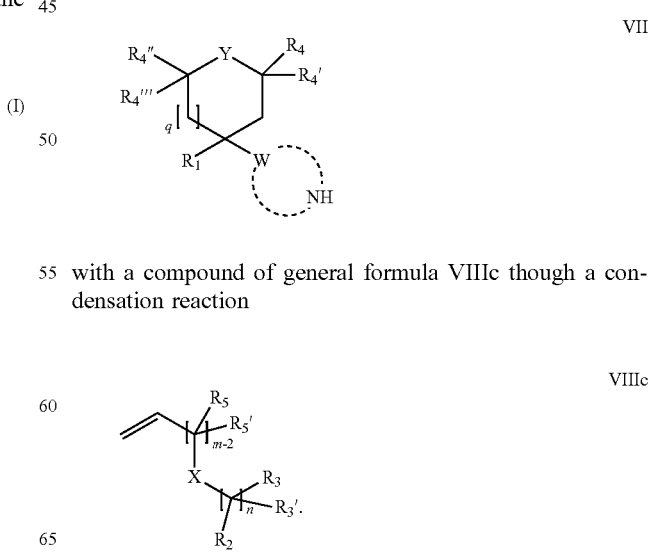

with a compound of general formula VIIIc though a condensation reaction

In a particular embodiment there is a process for the production of a compound of Formula (I) when W is carbon,

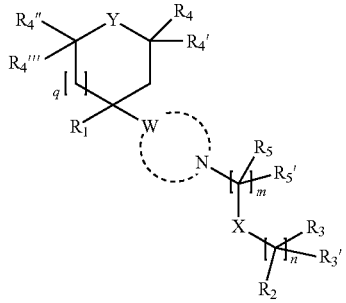
(I)

said process comprises the reductive alkylation of a cyano derivative of formula V

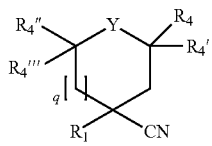
V with a compound of formula VIb

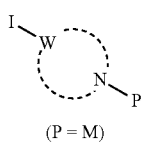
VIb (P = M)

In the presence of lithium naphthalenide.

In a particular embodiment there is a process for the production of a compound of Formula (IV) when $R_1$ is —C(O)$R_{1'}$,

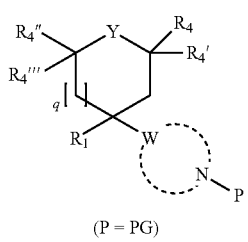
IV (P = PG)

said process comprises treating a compound of Formula IIa

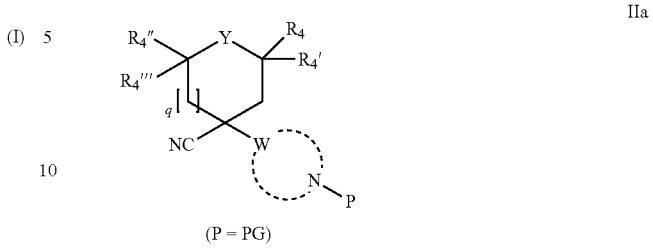
IIa (P = PG)

with a lithium salt generated from compounds of general formula IIIa $$Z—R_{1'}$$ IIIa with alkyl lithium, specially n-butyl lithium (nBuLi), and hydrolysing the obtained imine intermediate compound to a ketone compound of formula I in the presence of an aqueous inorganic acid.

In a particular embodiment there is a process for the production of a compound of Formula (IV) when $R_1$ is —C($R_6R_{6'}$)$_p R_{1'}$,

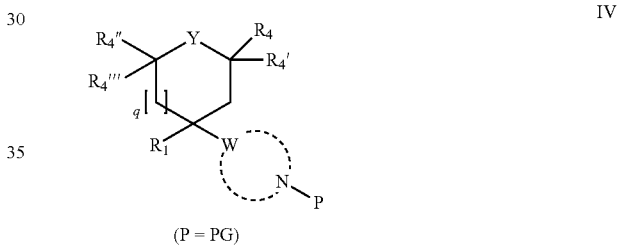
IV (P = PG)

said process comprises the reaction of compounds of general formula IIa

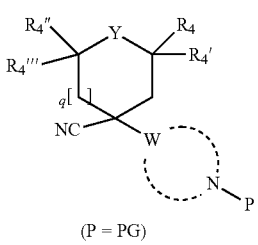
IIa (P = PG)

with Grignard reagents of formula IIIb $$Z—Mg—R_1$$ IIIb,

In a particular embodiment there is a process for the production of a compound of Formula (IV) when W is carbon,

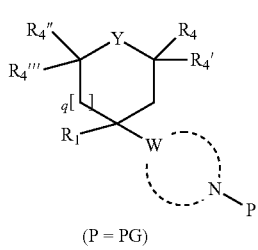

(P = PG)

said process comprises the reductive alkylation of a cyano derivative of formula V

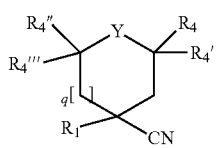

with a compound of formula VIa

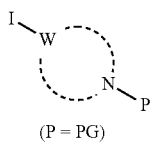

(P = PG)

In the presence of lithium naphthalenide.

In a particular embodiment there is a process for the production of a compound of Formula (VII)

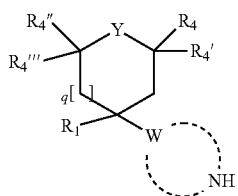

said process comprises the deprotection of a compound of formula IV

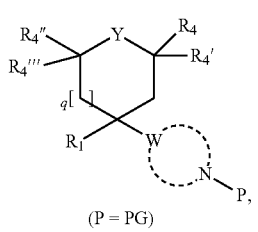

(P = PG)

In a particular embodiment there is a process for the production of a compound of Formula (IIa), preferably wherein W is carbon,

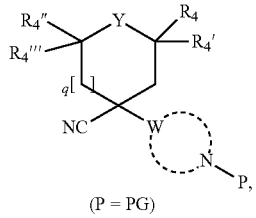

(P = PG)

said process comprises the reaction of a compound of formula V'

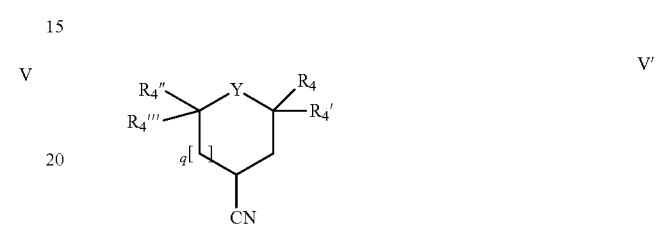

with a compound of formula VIa

(P = PG)

in the presence of a base, preferably lithium diisopropylamide, wherein M is

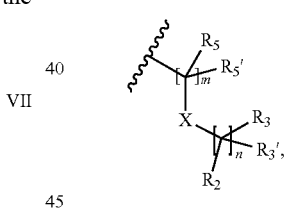

$R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X and Y are as defined in the previous claims, L is a leaving group such as halogen, mesylate, tosylate or triflate, Z is chloro or bromo, and PG is a protecting group.

In a particular embodiment there is a process for the production of a compound of Formula (IIb), preferably wherein W is carbon,

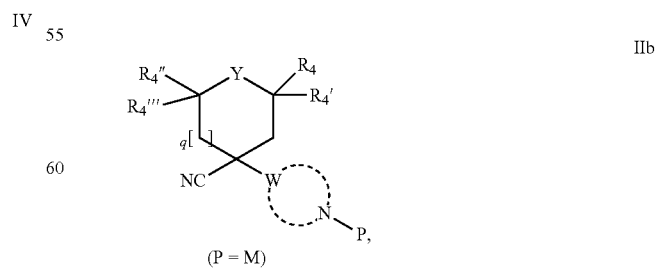

(P = M)

said process comprises the reaction of a compound of formula V'

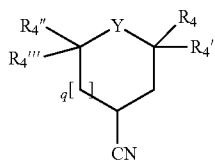

with a compound of formula VIb

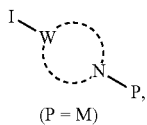

in the presence of a base, preferably lithium diisopropylamide, wherein M is

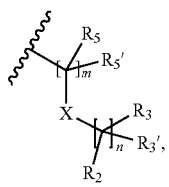

$R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X and Y are as defined in the previous claims, L is a leaving group such as halogen, mesylate, tosylate or triflate, Z is chloro or bromo, and PG is a protecting group.

In a particular embodiment there is a process for the production of a compound of Formula (IIa), wherein W is carbon,

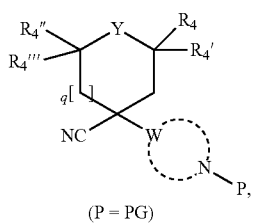

said process comprises the reaction of a compound of formula IX

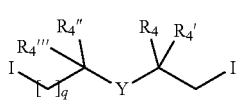

with a compound of formula Xa

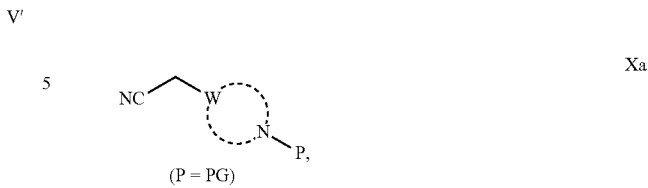

in the presence of a base, preferably lithium diisopropylamide, wherein M is

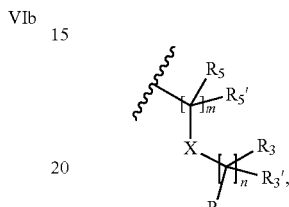

$R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X and Y are as defined in the previous claims, L is a leaving group such as halogen, mesylate, tosylate or triflate, Z is chloro or bromo, and PG is a protecting group.

In a particular embodiment there is a process for the production of a compound of Formula (IIb), preferably wherein W is carbon,

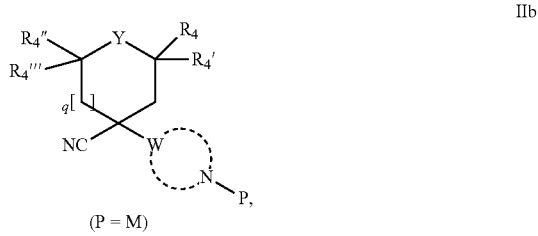

said process comprises the reaction of a compound of formula IX

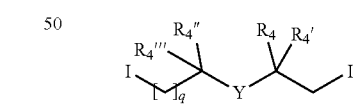

with a compound of formula Xb

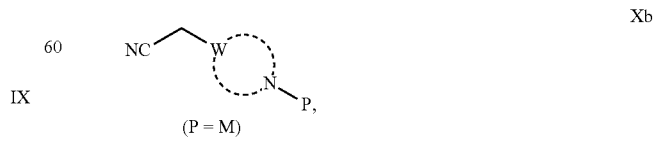

in the presence of a base, preferably lithium diisopropylamide, wherein M is

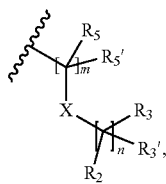

$R_1$, $R_1'$, $R_2$, $R_3$, $R_3'$, $R_4$, $R_4'$, $R_4''$, $R_4'''$, $R_5$, $R_5'$, $R_6$, $R_6'$, m, n, p, q, X and Y are as defined in the previous claims, L is a leaving group such as halogen, mesylate, tosylate or triflate, Z is chloro or bromo, and PG is a protecting group.

In a particular embodiment there is a process for the preparation of compound of Formula (I), preferably wherein W is carbon, and wherein said compound of Formula (I) is made from intermediate (IIa)

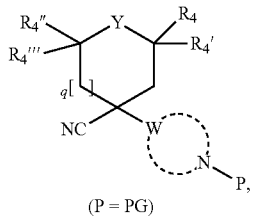

(P = PG)

IIa obtained from the reaction of a compound of formula V'

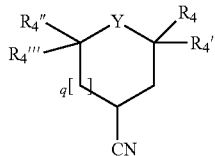

V' with a compound of formula VIa

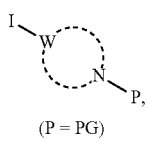

(P = PG)

VIa in the presence of a base, preferably lithium diisopropylamide, or wherein said compound of Formula (I) is made from intermediate (IIb)

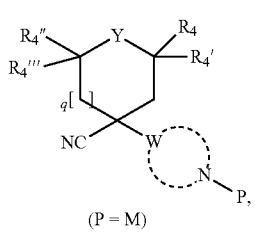

(P = M)

IIb obtained from the reaction of a compound of formula V'

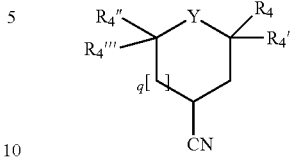

V' with a compound of formula VIb

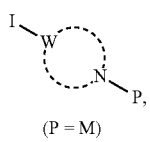

(P = M)

VIb in the presence of a base, preferably lithium diisopropylamide, or wherein said compound of Formula (I) is made from intermediate (IIa)

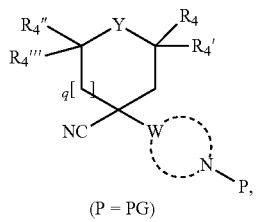

(P = PG)

IIa obtained from the reaction of a compound of formula IX

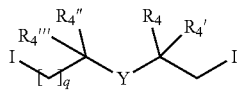

IX with a compound of formula Xa

(P = PG)

Xa in the presence of a base, preferably lithium diisopropylamide, or wherein said compound of Formula (I) is made from intermediate (IIb)

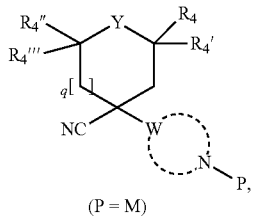

(P = M)

obtained from the reaction of a compound of formula IX

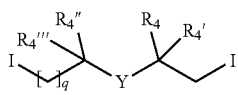

with a compound of formula Xb

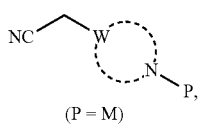

(P = M)

in the presence of a base, preferably lithium diisopropylamide, wherein M is

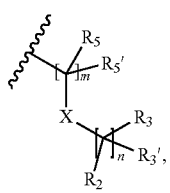

$R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X and Y are as defined in the previous claims, L is a leaving group such as halogen, mesylate, tosylate or triflate, Z is chloro or bromo, and PG is a protecting group.

The advantages of using the improved processes using intermediates V' or IX instead of V are:
- the synthesis of intermediates IIa and IIb are carried out in one step instead of four.
- all possible diastereoisomers are easily prepared.

In another particular embodiment a compound of Formula (IIa) or (IIb),

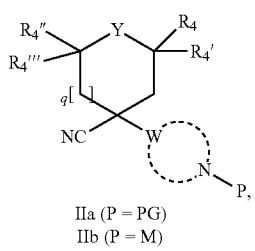

IIa (P = PG)
IIb (P = M)

is used for the preparation of a compound of Formula (I).

In another particular embodiment a compound of Formula (IIIa),

Z—R1'    IIIa is used for the preparation of a compound of Formula (I).

In another particular embodiment a compound of Formula (IIIb),

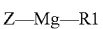

Z—Mg—R1    IIIb is used for the preparation of a compound of Formula (I).

In another particular embodiment a compound of Formula (IV),

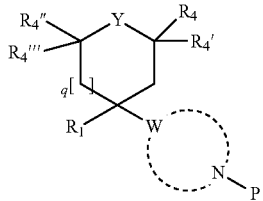

(P = PG)

is used for the preparation of a compound of Formula (I).

In another particular embodiment a compound of Formula (V),

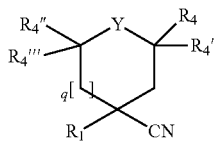

is used for the preparation of a compound of Formula (I).

In another particular embodiment a compound of Formula (VIa) or (VIb),

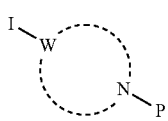

VIa (P = PG)
VIb (P = M)

is used for the preparation of a compound of Formula (I).

In another particular embodiment a compound of Formula (VII),

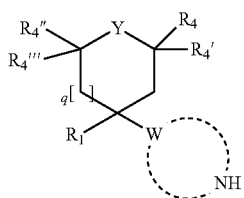

is used for the preparation of a compound of Formula (I).

In another particular embodiment a compound of Formula (VIIIa),

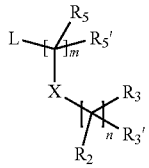

VIIIa is used for the preparation of a compound of Formula (I).

In another particular embodiment a compound of Formula (VIIIb),

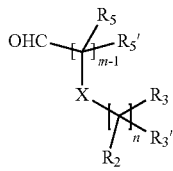

VIIIb is used for the preparation of a compound of Formula (I).

In another particular embodiment a compound of Formula (VIIIc),

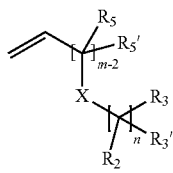

VIIIc is used for the preparation of a compound of Formula (I).

In another particular embodiment a compound of Formula (V'),

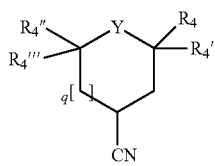

V' is used for the preparation of a compound of Formula (I).

In another particular embodiment a compound of Formula (IX),

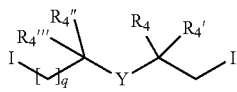

IX is used for the preparation of a compound of Formula (I).

In another particular embodiment a compound of Formula (Xa),

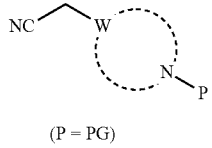

Xa (P = PG)

is used for the preparation of a compound of Formula (I).

In another particular embodiment a compound of Formula (Xb),

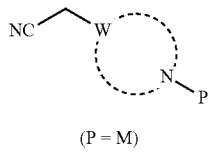

Xb (P = M)

is used for the preparation of a compound of Formula (I).

The obtained reaction products may, if desired, be purified by conventional methods, such as crystallisation and chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form of a compound of the invention is the crystalline form, including such form in pharmaceutical composition. In the case of salts and also solvates of the compounds of the invention the additional ionic and solvent moieties must also be non-toxic. The compounds of the invention may present different polymorphic forms, it is intended that the invention encompasses all such forms.

Another aspect of the invention refers to a pharmaceutical composition which comprises a compound according to the invention as described above according to general formula I or a pharmaceutically acceptable salt or steroisomer thereof, and a pharmaceutically acceptable carrier, adjuvant or vehicle. The present invention thus provides pharmaceutical compositions comprising a compound of this invention, or a pharmaceutically acceptable salt or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated and the weight of the sufferer. However, active compounds will typically be administered once or more times a day for example 1, 2, 3 or 4 times daily, with typical total daily doses in the range of from 0.1 to 1000 mg/kg/day.

The compounds and compositions of this invention may be used with other drugs to provide a combination therapy. The other drugs may form part of the same composition, or be provided as a separate composition for administration at the same time or at different time.

Another aspect of the invention refers to the use of a compound of the invention or a pharmaceutically acceptable salt or isomer thereof in the manufacture of a medicament.

Another aspect of the invention refers to a compound of the invention according as described above according to general formula I, or a pharmaceutically acceptable salt or isomer thereof, for use as a medicament for the treatment of pain. Preferably the pain is medium to severe pain, visceral pain, chronic pain, cancer pain, migraine, inflammatory pain, acute pain or neuropathic pain, allodynia or hyperalgesia. This may include mechanical allodynia or thermal hyperalgesia.

Another aspect of the invention refers to the use of a compound of the invention in the manufacture of a medicament for the treatment or prophylaxis of pain.

In a preferred embodiment the pain is selected from medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

Another aspect of this invention relates to a method of treating or preventing pain which method comprises administering to a patient in need of such a treatment a therapeutically effective amount of a compound as above defined or a pharmaceutical composition thereof. Among the pain syndromes that can be treated are medium to severe pain, visceral pain, chronic pain, cancer pain, migraine, inflammatory pain, acute pain or neuropathic pain, allodynia or hyperalgesia, whereas this could also include mechanical allodynia or thermal hyperalgesia.

The present invention is illustrated below with the aid of examples. These illustrations are given solely by way of example and do not limit the general spirit of the present invention.

EXAMPLES

General Experimental Part (Methods and Equipment of the Synthesis and Analysis

A process is described in Scheme 1 or Scheme 1' for the preparation of compounds of general formula I, wherein $R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, W, X and Y have the meanings defined above.

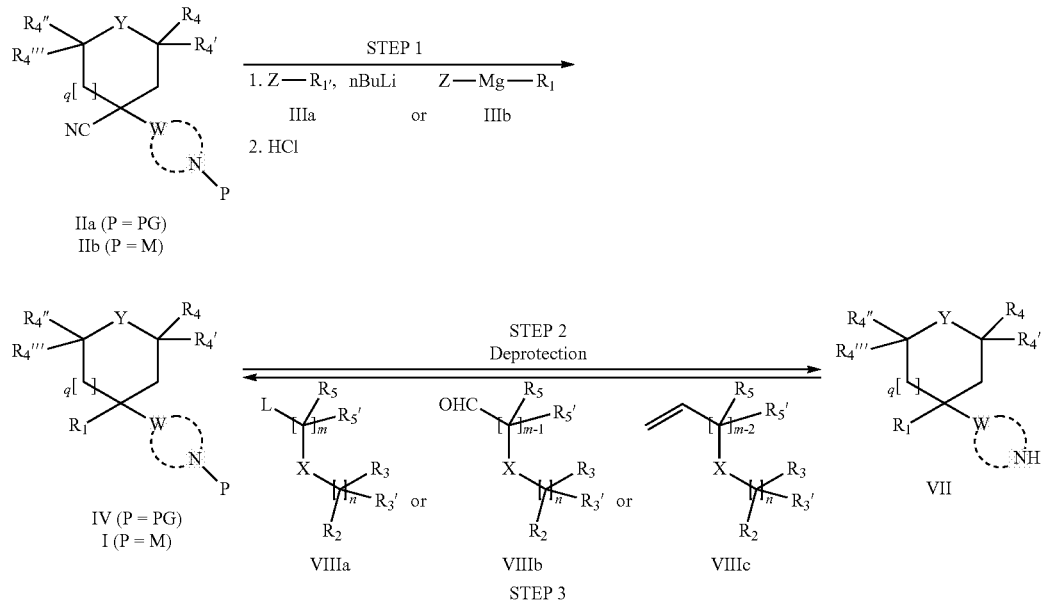

Scheme 1

-continued
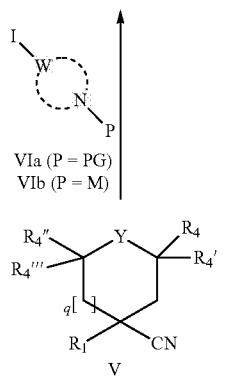
VIa (P = PG)
VIb (P = M)
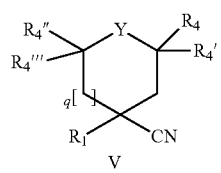
V
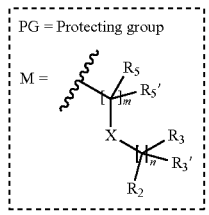
Scheme 1'
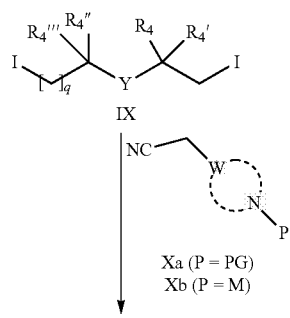
IX
Xa (P = PG)
Xb (P = M)
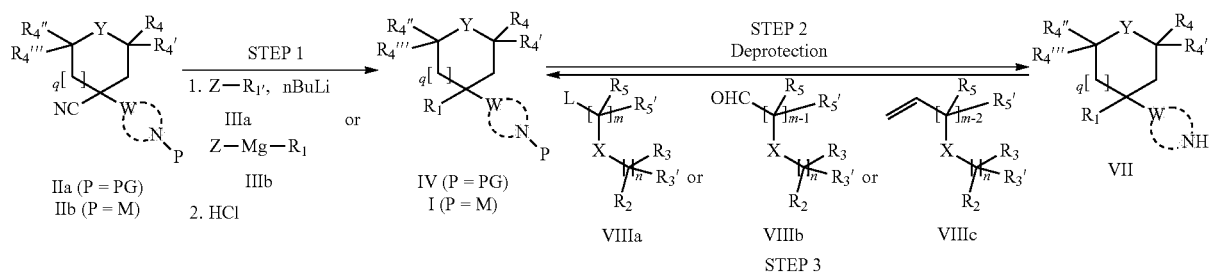
STEP 3

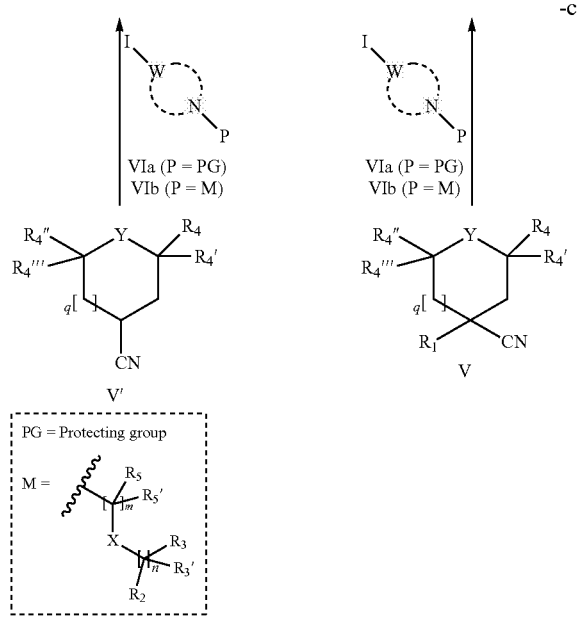

Where, L is a leaving group such as halogen, mesylate, tosylate or triflate and Z is chloro or bromo, M is the group indicated in a square in Scheme 1 and PG is a protecting group, such as benzyl or tert-butoxycarbonyl.

This process is carried out as described below:

Step 1:

The compounds of general formula IV or I are prepared by reacting a compound of general formula IIa or IIb, with a compound of formula IIIa or IIIb. Depending on the meaning of $R_1$, different reaction conditions will apply:

a) When $R_1$ is —$COR_{1'}$, compounds of general formula IIa or IIb are treated with a lithium salt in situ generated from compounds of general formula IIIa with nBuLi, in a suitable solvent, preferably in tetrahydrofuran, at a suitable temperature comprised between −78° C. and room temperature, preferably at room temperature. In a subsequent reaction, the obtained imine intermediate compound is hydrolized to ketone compounds of formula IV or I in the presence of an aqueous inorganic acid such as HCl.

b) When $R_1$ is —$C(R_6,R_{6'})_p$—$R_{1'}$, the reaction of compounds of general formula IIa or IIb with Grignard reagents of formula IIIb renders a compound of general formula IV or I. This reaction is carried out in a suitable solvent, preferably in tetrahydrofuran, at a suitable temperature comprised between 0° C. and room temperature.

Additionally, compounds of formula IV or I wherein W is carbon can be obtained by reductive alkylation of cyano derivatives of formula V with compounds of formula VIa or VIb, in the presence of lithium naphthalenide, in a suitable solvent such as tetrahydrofuran, and at a suitable temperature comprised between −40° C. and room temperature.

For compounds of general formula IV, wherein P is a protecting group, two additional steps are necessary to obtain compounds of formula I:

Step 2:

A compound of formula VII is prepared by deprotection of a compound of formula IV. If the protecting group is benzyl the deprotection is carried out under hydrogenation conditions, with hydrogen at a pressure comprised between 1 and 10 bar, in the presence of Pd and in a suitable solvent such as methanol or ethanol, optionally in the presence of an acid such as acetic or hydrochloric acid, at a suitable temperature comprised between room temperature and the reflux temperature. Alternative hydrogenation conditions involve the treatment with dichloroethyl formate as hydrogen source, in a suitable solvent such dichloroethane, at a suitable temperature comprised between room temperature and the reflux temperature, preferably at the reflux temperature. If the protecting group is Boc, the deprotection is carried out in the presence of an inorganic acid such as HCl or trifluoroacetic acid, in a suitable solvent such as dichloromethane, at a suitable temperature comprised between room temperature and the reflux temperature.

Step 3:

From deprotected compounds of formula VII, compounds of general formula I can be prepared by reaction with suitable reagents, such as those of formula VIIIa-c, using different conditions depending on the reagent nature. Thus:

The alkylation reaction with a compound of formula VIIIa is carried out in a suitable solvent, such as acetonitrile, dichloromethane, 1,4-dioxane, ethanol or dimethylformamide, preferably in acetonitrile, in the presence of an inorganic base such as $K_2CO_3$ or $Cs_2CO_3$, or an organic base such as triethylamine or diisopropylethylamine, preferably $K_2CO_3$, at a suitable temperature comprised between room temperature and the reflux temperature, preferably heating, or alternatively, this reaction can be carried out in a microwave reactor. Additionally, an activating agent such as NaI or KI can be used.

The reductive amination with a compound of formula VIIIb, is carried out in the presence of a reductive reagent, preferably sodium triacetoxyborohydride, in a suitable solvent, preferably methanol, at a suitable temperature comprised between room temperature and the reflux temperature, preferably in a microwave reactor.

The condensation reaction between a compound of general formula VII and a compound of formula VIIIc is carried out in a suitable solvent, such as ethanol, isopropanol, n-butanol or 2-methoxyethanol, preferably ethanol, optionally in the presence of an organic base such as triethylamine or diisopropylethylamine, at a suitable temperature comprised between room temperature and the reflux temperature, preferably heating, or alternatively, the reactions can be carried out in a microwave reactor.

The process described by Steps 1 to 3 represent the general route for the preparation of compounds of formula I. Additionally, the functional groups present in any of the positions can be interconverted using reactions known to those skilled in the art.

Compounds of formula IIa, IIb, IIIa, IIIb, V, VIa, VIb, VIIIa, VIIIb and VIIIc where $R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, W, Y and X have the meanings as defined above, are commercially available or can be prepared by conventional methods described in the bibliography. Compounds IIa or IIb, wherein W is nitrogen, can be prepared by Strecker reaction of conveniently substituted ketones with amino compounds. The preparation of compounds IIa or IIb wherein W is carbon, involves the treatment of a conveniently substituted nitrile compound with adequate ketones in the presence of a strong base such as LDA, dehydratation of the resulting tertiary alcohol and final reduction of the generated alkene. Additionally, compounds IIa or IIb wherein W is carbon, can be obtained by treatment of cyano derivatives with adequate iodopiperidines in the presence of a strong base, preferably lithium diisopropylamide. Cyano compounds of formula V can be prepared by reaction of conveniently substituted nitriles with suitable $R_1$—CN derivatives in the presence of a strong base.

EXAMPLES

Intermediates and Examples

The following abbreviations are used in the examples:
ACN: Acetonitrile
AcOH: Acetic acid
AcOEt: Ethyl acetate
BINAP: 2,2'-Bis(diphenylphosphino)-1,1'-binaphthyl
Conc: Concentrated
CH: Cyclohexane
DCM: Dichloromethane
DCE: 1,2-Dicloroethane
DIPEA: N,N-Diisopropylethylamine
DMF: Dimethylformamide
DMPU: N,N'-dimetilpropilenourea
DMSO: Dimethyl sulfoxide
EDC: 1-Ethyl-3-(3-dimethylaminopropyl)carbodiimide
EtOH: Ethanol
Et$_2$O: Diethyl ether
Ex: Example
h: Hour/s
HOBt: Hydroxybenzotriazole
HPLC: High-performance liquid chromatography
INT: Intermediate
LDA: Lithium diisopropilamide
LiHMDS: Lithium bis(trimethylsilyl)amide
MeOH: Methanol
MS: Mass spectrometry
Min: Minutes
Quant: Quantitative
Ret: Retention
rt: Room temperature
Sat: Saturated
TEA: Triethylamine
TFA: Trifluoroacetic acid
THF: Tetrahydrofuran
Wt: Weight
Xamphos: 4, 5-Bis(diphenylphosphino)-9,9-dimethylxanthene The following methods were used to obtain the HPLC-MS data:

A: Column Acquity UPLC BEH C18 2.1×50 mm, 1.7 µm; flow rate 0.61 mL/min; A: NH$_4$HCO$_3$ 10 mM; B: ACN; Gradient: 0.3 min in 98% A, 98% A to 5% A in 2.52 min, 1.02 min in 5% A, 5% A to 98% A in 0.34 min, 0.57 min in 98% A B: Column: Acquity BEH C18 2.1×50 mm 1.7 µm; flow rate 600 µl/min; A: NH$_4$HCO$_3$ 10 mM; B: ACN; Gradient: 0.3 min in 90% A, 90% A to 5% A in 2.7 min, 0.7 min in 5% A, 5% A to 90% A in 0.1 min, 1.2 min in 90% A C: Column: Gemini-NX 30×4.6 mm, 3 um; flow rate: 2.0 mL/min; A: NH$_4$HCO$_3$ pH 8; B: ACN; Gradient: 0.5 min in 95% A, 95% A to 0% A in 6.5 min, 1 min in 0% A; 40° C.; sample dissolved aprox. 1 mg/mL in NH$_4$HCO$_3$ pH 8/can D: Column Acquity UPLC BEH C18 2.1×50 mm, 1.7 µm; flow rate 0.61 mL/min; A: NH$_4$HCO$_3$ 10 mM; B: ACN; Gradient: 0.3 min in 98% A, 98% A to 0% A in 2.7 min, 2 min in 0% A, 0% A to 98% A in 0.2 min, 0.55 min in 98% A E: Column Acquity UPLC BEH C18 2.1×50 mm, 1.7 µm; flow rate 0.5 mL/min; A: NH$_4$HCO$_3$ 10 mM; B: ACN; Gradient: 90% A to 5% A in 4 min, 1 min in 5% A, 5% A to 90% A in 0.1 min, 1.9 min in 90% A Intermediate 1A. 4-(4-Benzylpiperazin-1-yl)-2,2-dimethyltetrahydro-2H-pyran-4-carbonitrile

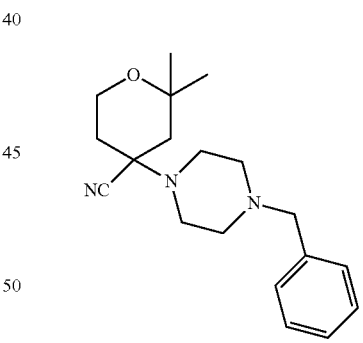

In a 2 L round bottomed flask, 2,2-dimethyldihydro-2H-pyran-4(3H)-one (10.4 g, 0.08 mol) was dissolved in water (500 mL) along with sodium metabisulfite (7.7 g, 0.04 mol). The mixture was allowed to stir at rt for 1.5 h, then benzylpiperazine (14.2 g, 0.08 mol) was added. The mixture was stirred for 2 h and potassium cyanide (8.42 g, 0.13 mol) was added to the reaction mixture. After stirring at rt for 2 days the solid formed was filtered and dried, to give the title compound as a white solid (15.4 g, yield 61%).

HPLC-MS (Method A): Ret, 1.98 min; ESI$^+$-MS m/z, 314.1 (M+1).

This method was used for the preparation of intermediates 1B-O using suitable starting materials:

| INT | Structure | Chemical name | Method | Ret (min) | MS (M + H) |
|---|---|---|---|---|---|
| 1B | 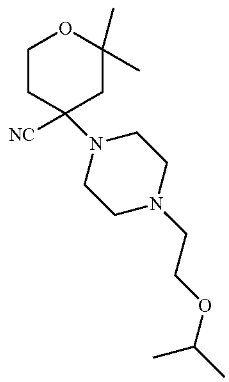 [SMILES: CC(C)OCCN1CCN(C2(C#N)CCOC(C)(C)C2)CC1] | 4-(4-(2-isopropoxyethyl)piperazin-1-yl)-2,2-dimethyltetrahydro-2H-pyran-4-carbonitrile | A | 1.59 | 310.5 |
| 1C | 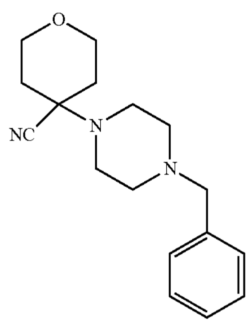 [SMILES: N#CC1(N2CCN(Cc3ccccc3)CC2)CCOCC1] | 4-(4-benzylpiperazin-1-yl)tetrahydro-2H-pyran-4-carbonitrile | A | 1.72 | 186 |
| 1D | 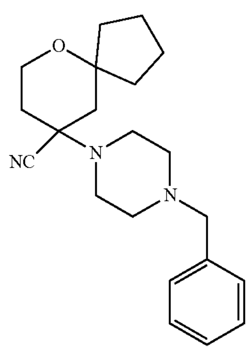 [SMILES: N#CC1(N2CCN(Cc3ccccc3)CC2)CCOC2(CCCC2)C1] | 9-(4-benzylpiperazin-1-yl)-6-oxaspiro[4.5]decane-9-carbonitrile | A | 2.21 | 340 |
| 1E | 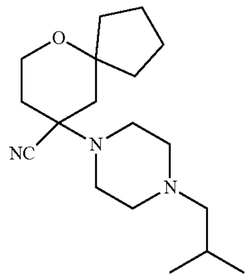 [SMILES: CC(C)CN1CCN(C2(C#N)CCOC3(CCCC3)C2)CC1] | 9-(4-isobutylpiperazin-1-yl)-6-oxaspiro[4.5]decane-9-carbonitrile | A | 2.34 | 306 |

-continued

| INT | Structure | Chemical name | Method | Ret (min) | MS (M + H) |
|---|---|---|---|---|---|
| 1F | 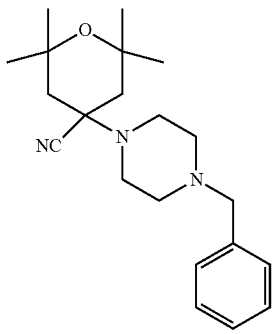 [SMILES: CC1(C)CC(C#N)(N2CCN(Cc3ccccc3)CC2)CC(C)(C)O1] | 1-benzyl-4-(4-isocyano-2,2,6,6-tetramethyltetrahydro-2H-pyran-4-yl)piperazine | A | 1.3 | 342 |
| 1G | 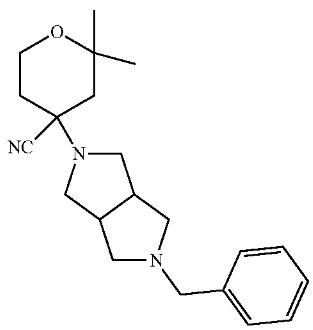 [SMILES: CC1(C)CC(C#N)(N2CC3CN(Cc4ccccc4)CC3C2)CCO1] | 4-(5-benzylhexahydropyrrolo[3,4-c]pyrrol-2(1H)-yl)-2,2-dimethyltetrahydro-2H-pyran-4-carbonitrile | A | 2.07 | 340 |
| 1H | 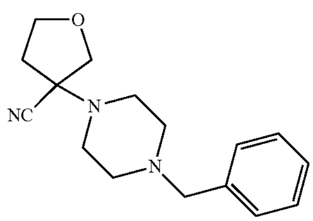 [SMILES: N#CC1(N2CCN(Cc3ccccc3)CC2)CCOC1] | 3-(4-benzylpiperazin-1-yl)tetrahydrofuran-3-carbonitrile | A | 1.71 | 272 |
| 1I | 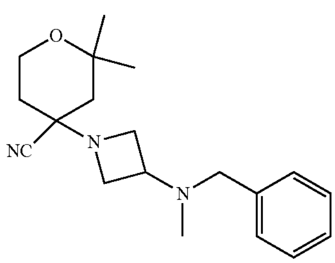 [SMILES: CN(Cc1ccccc1)C1CN(C2(C#N)CCOC(C)(C)C2)C1] | N-benzyl-1-(4-isocyano-2,2-dimethyltetrahydro-2H-pyran-4-yl)-N-methylazetidin-3-amine | A | 2.06 | 314 |
| 1J | 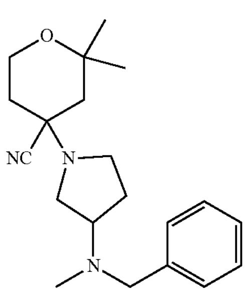 [SMILES: CN(Cc1ccccc1)C1CCN(C2(C#N)CCOC(C)(C)C2)C1] | 4-(3-(benzyl(methyl)amino)pyrrolidin-1-yl)-2,2-dimethyltetrahydro-2H-pyran-4-carbonitrile | A | 1.00 | 328.2 |

-continued

| INT | Structure | Chemical name | Method | Ret (min) | MS (M + H) |
|---|---|---|---|---|---|
| 1K | 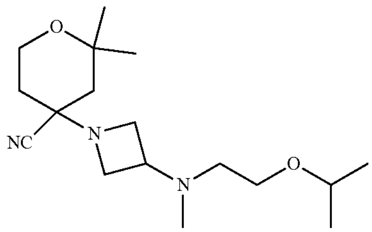 [SMILES: CC(C)OCCN(C)C1CN(C2(C#N)CCOC(C)(C)C2)C1] | 1-(4-isocyano-2,2-dimethyltetrahydro-2H-pyran-4-yl)-N-(2-isopropoxyethyl)-N-methylazetidin-3-amine | A | 1.76 | 310 |
| 1L | 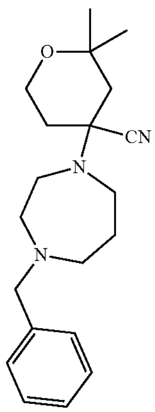 [SMILES: CC1(C)CC(C#N)(N2CCCN(Cc3ccccc3)CC2)CCO1] | 4-(4-benzyl-1,4-diazepan-1-yl)-2,2-dimethyltetrahydro-2H-pyran-4-carbonitrile | A | 1.07 | 328.2 |
| 1M | 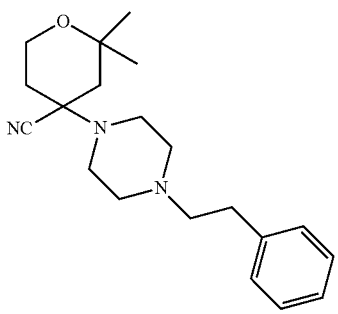 [SMILES: CC1(C)CC(C#N)(N2CCN(CCc3ccccc3)CC2)CCO1] | 2,2-dimethyl-4-(4-phenethylpiperazin-1-yl)tetrahydro-2H-pyran-4-carbonitrile | A | 2.02 | 328 |
| 1N | 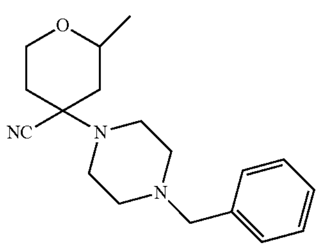 [SMILES: CC1CC(C#N)(N2CCN(Cc3ccccc3)CC2)CCO1] | 4-(4-benzylpiperazin-1-yl)-2-methyltetrahydro-2H-pyran-4-carbonitrile | A | 1.89 | 300 |
| 1O | 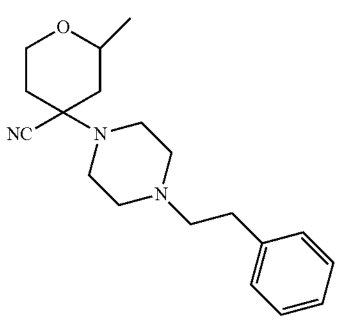 [SMILES: CC1CC(C#N)(N2CCN(CCc3ccccc3)CC2)CCO1] | 2-methyl-4-(4-phenethylpiperazin-1-yl)tetrahydro-2H-pyran-4-carbonitrile | A | 1.88 | 314.2 |

Intermediate 1P. 4-(1-Benzylpiperidin-4-yl)tetrahydro-2H-pyran-4-carbonitrile

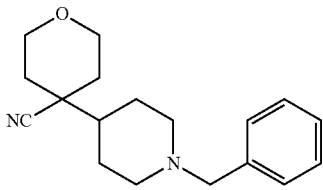 [SMILES: N#CC1(C2CCN(Cc3ccccc3)CC2)CCOCC1]

a) tert-Butyl-4-(4-cyanotetrahydro-2H-pyran-4-yl)-4-hydroxypiperidine-1 carboxylate To a solution of tetrahydro-2H-pyran-4-carbonitrile (4.85 g, 43.6 mmol) in dry THF (41 mL), cooled at −78° C., a LDA solution (30.5 mL, 1.5 M in a mixture of THF/ethylbenzene/heptane, 45.8 mmol) was added dropwise under a nitrogen atmosphere. The mixture was stirred at −50° C. for 45 min and then it was cooled at −78° C. A solution of tert-butyl 4-oxopiperidine-1-carboxylate (8.69 g, 43.6 mmol) in dry THF (5.2 mL) was added and the reaction mixture was stirred at −78° C. for 2 h. Then, NH$_4$Cl sat aqueous solution was added and the mixture was extracted with EtOAc. The organic phases were combined, dried over MgSO$_4$, filtered and concentrated to dryness. The residue was purified by flash chromatography, silica gel, gradient DCM to MeOH:DCM (1:9) to give the title compound (7.11 g, 53% yield).

HPLC-MS (Method C): Ret, 3.18 min; ESI$^+$-MS m/z, 255 (M+H-56).

b) tert-Butyl 4-(4-cyanotetrahydro-2H-pyran-4-yl)-5,6-dihydropyridine-1(2H)-carboxylate To a solution of the product obtained in step a (6.10 g, 19.7 mmol) in toluene (71 mL), (methoxycarbonylsulfamoyl)triethylammonium hydroxide inner salt ("Burgess reagent", 7.03 g, 29.5 mmol) was added and the mixture was heated at 90° C. overnight under a nitrogen atmosphere. It was then cooled to rt and water and DCM were added. The aqueous phase was back extracted with DCM. The organic phases were combined, washed with sat NaHCO$_3$ solution, dried over Na$_2$SO$_4$, filtered and concentrated to dryness to give the title compound (6.14 g crude product, 5.75 g theoretical weight; quant yield).

HPLC-MS (Method C): Ret, 3.91 min; ESI$^+$-MS m/z, 237.1 (M+H-56).

c) tert-Butyl 4-(4-cyanotetrahydro-2H-pyran-4-yl)piperidine-1-carboxylate

A mixture of the crude product obtained in step b (6.14 g crude, 19.7 mmol) and palladium (1.23 g, 5% wt on charcoal, wet) in EtOH (115 mL) was stirred at rt under 1 bar of H$_2$ overnight. Then, the solids were filtered off over a pad of celite and the solvent was evaporated to dryness. The residue was purified by flash chromatography, silica gel, gradient DCM to MeOH:DCM (1:9) to give the title compound (4.04 g, 70% yield).

HPLC-MS (Method C): Ret, 3.79 min; ESI$^+$-MS m/z, 239.1 (M+H-56).

d) 4-(Piperidin-4-yl)tetrahydro-2H-pyran-4-carbonitrile trifluoroacetate

To a solution of the product obtained in step c (4.0 g, 13.6 mmol) in DCM (40 mL), TFA (10.4 mL, 136 mmol) was added, and the reaction mixture was stirred at rt. for 1 h. The solvent was evaporated to dryness to give the title compound as a crude product (7.18 g, 4.19 g theoretical weight, quant yield), that was used in the following step without further purification.

HPLC-MS (Method C): Ret, 0.98 min (peak corresponds to TIC spectrum, no peak detected in UV detector at 210 nm) ESI-MS m/z, 195.1 (M+H).

e) Title Compound

To a solution of the crude product obtained in step d (7.18 g crude, 13.6 mmol) and benzaldehyde (1.3 mL, 17.7 mmol) in dry THF (92 mL), AcOH (1.73 mL, 30.2 mmol) was added. The mixture was stirred at rt for 15 min and then sodium triacetoxyborohydride (7.99 g, 40.8 mmol) was added in portions. The resulting mixture was stirred at rt overnight. Then, conc. NH$_4$OH (50 mL) was carefully added and it was extracted with EtOAc. The organic phases were combined, washed with brine, dried over MgSO$_4$, filtered and concentrated to dryness. The residue was purified by flash chromatography, silica gel, gradient DCM to MeOH:DCM (1:4) to give the title compound (1.75 g, 45% yield).

HPLC-MS (Method C): Ret, 3.83 min; ESI-MS m/z, 252.2 (M+H).

This method was used for the preparation of INT 1Q using suitable starting materials:

| INT | Structure | Chemical name | Method | Ret (min) | MS (M + H) |
|---|---|---|---|---|---|
| 1Q | 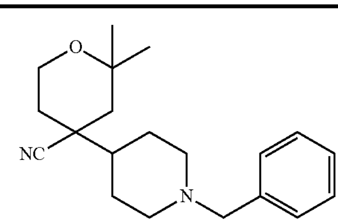 | 4-(1-benzylpiperidin-4-yl)-2,2-dimethyltetrahydro-2H-pyran-4-carbonitrile | C | 4.38 | 313.2 |

Alternative Method for the Obtention of Intermediate 1Q. 4-(1-benzylpiperidin-4-yl)-2,2-dimethyltetrahydro-2H-pyran-4-carbonitrile

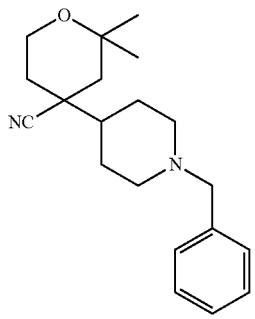 [SMILES: CC1(C)CC(C#N)(C2CCN(Cc3ccccc3)CC2)CCO1]

Intermediate 1S. 4-(1-Benzylpiperidin-4-yl)-2-methyltetrahydro-2H-pyran-4-carbonitrile (Diastereomeric Mixture)

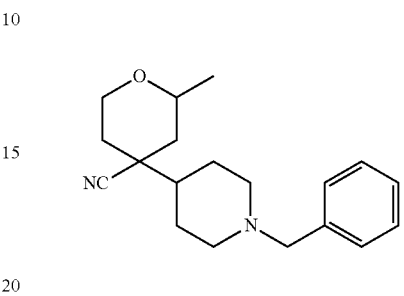

To a solution of 2,2-dimethyltetrahydro-2H-pyran-4-carbonitrile (800 mg, 5.7 mmol) in dry THF (15 mL) cooled at −0° C., a solution of lithium diisopropylamide (2 M in THF, 4.02 mL, 8 mmol) was added dropwise under nitrogen atmosphere. The mixture was stirred at rt temperature for 40 min. Then it was cooled down again to 0° C., and a solution of 1-benzyl-4-iodopiperidine (1.73 g, 5.7 mmol) in dry THF (15 mL) and DMPU (3.1 mL, 25.6 mmol) was added. The reaction mixture was allowed to reach rt and stirred overnight. The solvent was evaporated and the residue was diluted with water and AcOEt, extracted several times and the organic phases were combined and washed with NaHCO$_3$ aq sat solution. The solvent was evaporated and the residue thus obtained was purified by flash chromatography on silica gel, gradient DCM to DCM:MeOH (80:20) from 0 to 10% to give the title compound (800 mg, 45% yield).

HPLC-MS (Method B): Ret, 2.05 min; ESI$^+$-MS m/z, 312.3 (M+H).

This method was used for the preparation of intermediate 1R using the suitable tetrahydropyran derivative as starting material:

To a solution of 2-(1-benzylpiperidin-4-yl)acetonitrile (300 mg, 1.4 mmol) in THF (40 mL), a solution of LDA (2.8 mL, 4.2 mmol, 1.5 M in THF) was added dropwise at 0° C. and the mixture allowed to stir at rt for 40 min. Then, a solution of 1-iodo-2-(2-iodoethoxy)propane (500 mg, 1.47 mmol) in THF (20 mL) and DMPU (0.6 mL, 3.5 mmol) were added at 0° C. and the mixture was allowed to slowly reach rt and stirred for 16 h. The solvent was removed under vacuum and the crude product was extracted with EtOAc, washed with NH$_4$Cl and with a solution of NaHCO$_3$. The organic layer was concentrated under vacuum and the crude was purified by flash chromatography on silica gel (eluents Cyclohexane/EtOAc from 90/10 to 0/100). The title compound (63 mg, yield 15%) was isolated as a mixture of four diastereomers (two chromatographic peaks).

HPLC-MS (Method B): Diastereomers 1: Ret, 2.07 min; ESI$^+$-MS m/z, 299 (M+H). Diastereomers 2: Ret, 2.14 min; ESI$^+$-MS m/z, 299 (M+H).

Intermediates 1T-1Y were prepared according to the procedure described in intermediate 1A using suitable starting materials

| INT | Structure | Chemical name | Method | Ret (min) | MS (M + H) |
|---|---|---|---|---|---|
| 1R | 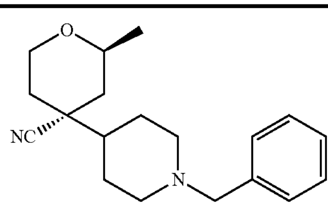 | 4-(1-benzylpiperidin-4-yl)-2-methyltetrahydro-2H-pyran-4-carbonitrile | A | 2.06 | 299.1 |

| INT | Structure | Chemical name | ¹H NMR |
|---|---|---|---|
| 1T | 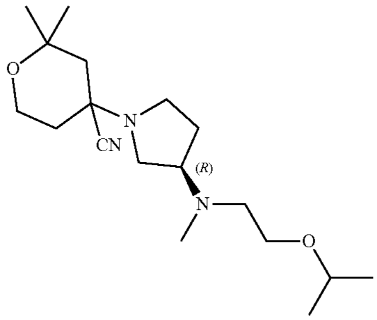 | 4-((R)-3-((2-isopropoxyethyl)(methyl)amino)pyrrolidin-1-yl)-2,2-dimethyltetrahydro-2H-pyran-4-carbonitrile | ¹H NMR (CDCl₃) δ: 3.87-3.77 (m, 4H), 3.62-3.53 (m, 2H), 3.51 (t, J = 6.3 Hz, 4H), 3.21-3.11 (m, 2H), 2.87-2.79 (m, 4H), 2.72-2.55 (m, 8H), 2.28 (s, 6H), 2.06-1.90 (m, 6H), 1.83-1.63 (m, 6H), 1.40 (s, 3H), 1.39 (s, 3H), 1.29 (s, 3H), 1.28 (s, 3H), 1.16 (d, J = 6.1 Hz, 12H) |
| 1U | 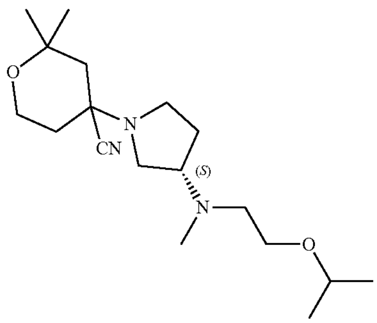 | 4-((S)-3-((2-isopropoxyethyl)(methyl)amino)pyrrolidin-1-yl)-2,2-dimethyltetrahydro-2H-pyran-4-carbonitrile | ¹H NMR (CDCl₃) δ: 3.87-3.77 (m, 4H), 3.62-3.53 (m, 2H), 3.51 (t, J = 6.3 Hz, 4H), 3.21-3.11 (m, 2H), 2.87-2.79 (m, 4H), 2.72-2.55 (m, 8H), 2.28 (s, 6H), 2.06-1.90 (m, 6H), 1.83-1.63 (m, 6H), 1.40 (s, 3H), 1.39 (s, 3H), 1.29 (s, 3H), 1.28 (s, 3H), 1.16 (d, J = 6.1 Hz, 12H) |
| 1V | 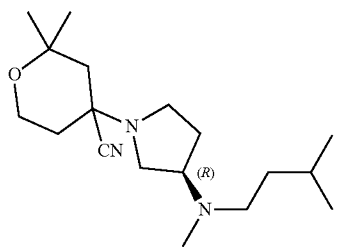 | 4-((R)-3-(isopentyl(methyl)amino)pyrrolidin-1-yl)-2,2-dimethyltetrahydro-2H-pyran-4-carbonitrile | ¹H NMR (CDCl₃) δ: 3.87-3.78 (m, 4H), 3.06 (dq, J = 14.6, 7.1 Hz, 2H), 2.91-2.77 (m, 4H), 2.74-2.58 (m, 4H), 2.47-2.27 (m, 4H), 2.20 (s, 6H), 2.05-1.90 (m, 6H), 1.84-1.63 (m, 6H), 1.56-1.47 (m, 2H), 1.40 (s, 3H), 1.39 (s, 3H), 1.38-1.32 (m, 4H), 1.29 (s, 3H), 1.29 (s, 3H), 0.90 (d, J = 6.6 Hz, 12H) |
| 1W | 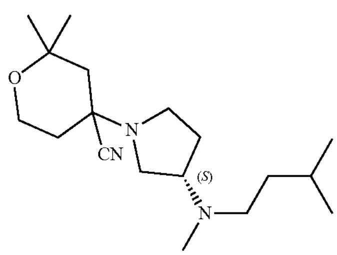 | 4-((S)-3-(isopentyl(methyl)amino)pyrrolidin-1-yl)-2,2-dimethyltetrahydro-2H-pyran-4-carbonitrile | ¹H NMR (CDCl₃) δ: 3.87-3.78 (m, 4H), 3.06 (dq, J = 14.6, 7.1 Hz, 2H), 2.91-2.77 (m, 4H), 2.74-2.58 (m, 4H), 2.47-2.27 (m, 4H), 2.20 (s, 6H), 2.05-1.90 (m, 6H), 1.84-1.63 (m, 6H), 1.56-1.47 (m, 2H), 1.40 (s, 3H), 1.39 (s, 3H), 1.38-1.32 (m, 4H), 1.29 (s, 3H), 1.29 (s, 3H), 0.90 (d, J = 6.6 Hz, 12H) |

| INT | Structure | Chemical name | Method | Ret (min) | MS (M + H) |
|---|---|---|---|---|---|
| 1X | 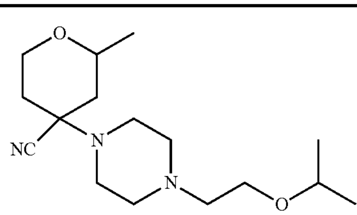 | 4-(4-(2-isopropoxyethyl)piperazin-1-yl)-2-methyltetrahydro-2H-pyran-4-carbonitrile | A | 1.61 | 296 |

-continued

| | | | | | |
|---|---|---|---|---|---|
| 1Y | 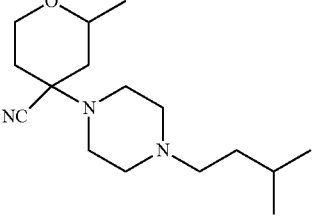 | 4-(4-isopentylpiperazin-1-yl)-2-methyltetrahydro-2H-pyran-4-carbonitrile | A | 1.97 | 280 |

Intermediate 2A. 2-(2,2-Dimethyl-4-(piperidin-4-yl)tetrahydro-2H-pyran-4-yl)pyridine

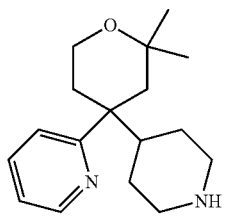 [SMILES: CC1(C)CC(c2ccccn2)(C2CCNCC2)CCO1]

a) 2,2-Dimethyl-4-(pyridin-2-yl)tetrahydro-2H-pyran-4-carbonitrile

To a solution of 2,2-dimethyltetrahydro-2H-pyran-4-carbonitrile (1.82 g, 13.1 mmol) and 2-cyanopyridine (1.36 g, 13.1 mmol) in dry THF (9 mL), cooled at −78° C., LiHMDS solution (14.4 mL, 1 M in THF, 14.4 mmol) was added dropwise under a nitrogen atmosphere. The mixture was then stirred at rt for 2 hours. NH$_4$Cl sat aqueous solution was added and it was extracted 3 times with EtOAc. The organic phases were combined, dried over MgSO$_4$, filtered and concentrated to dryness. The residue was purified by flash chromatography, silica gel, gradient Cyclohexane to EtOAc (9:1) to give the title compound (2.02 g, 71% yield).

HPLC retention time (method C): 3.11 min; MS: 217.1 (M+H).

b) tert-Butyl 4-(2,2-dimethyl-4-(pyridin-2-yl)tetrahydro-2H-pyran-4 yl)piperidine-1-carboxylate To a solution of the product obtained in step a (0.4 g, 1.85 mmol) in dry THF (18.5 mL), cooled at −40° C., lithium naphthalenide solution (11.1 mL, 0.5 M in THF, 5.55 mmol; prepared as described in *Tetrahedron Lett.* 1997, 38, 2253) was added dropwise under an argon atmosphere and it was stirred at −40° C. for 40 min. A solution of tert-butyl 4-iodopiperidine-1-carboxylate (2.3 g, 7.4 mmol) in dry THF (5 mL) was added at −40° C. and the mixture was further stirred at −40° C. for 1 h and then at rt overnight. NH$_4$Cl sat aqueous solution was added and it was extracted 3 times with DCM. The organic phases were combined, dried over Na$_2$SO$_4$, filtered and concentrated to dryness. The residue was purified by flash chromatography, silica gel, gradient DCM to MeOH:DCM (1:9) and then further purified by flash chromatography, C$_{18}$, gradient aqueous NH$_4$HCO$_3$ (pH 8) to acetonitrile to give the title compound (190 mg, 27% yield).

HPLC retention time (method A): 4.57 min; MS: 375.2 (M+H).

c) Title Compound

Boc deprotection was effected following the procedure described in INT 1P step d.

HPLC retention time (method A): 2.22 min; MS: 275.2 (M+H).

This method was used for the preparation of INT 2B using suitable starting materials:

| INT | Structure | Chemical name | Method | Ret (min) | MS (M + H) |
|---|---|---|---|---|---|
| 2B | 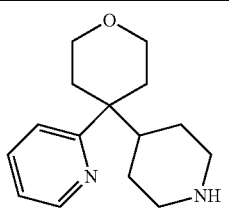 | 2-(4-(piperidin-4-yl)tetrahydro-2H-pyran-4-yl)pyridine | C | 1.75 | 247.1 |

Example 1. (4-(4-Benzylpiperazin-1-yl)-2,2-dimethyltetrahydro-2H-pyran-4-yl)(pyridin-2-yl)methanone

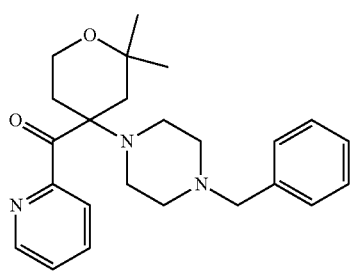 [SMILES: CC1(C)CC(C(=O)c2ccccn2)(N2CCN(Cc3ccccc3)CC2)CCO1]

a) (4-(4-Benzylpiperazin-1-yl)-2,2-dimethyltetrahydro-2H-pyran-4-yl)(pyridin-2-yl)methanimine 2-Bromopyridine (4.6 mL, 0.048 mol) in THF, under argon atmosphere, was cooled down to −78° C. and at this temperature n-BuLi (1.6 M, 31 mL, 0.049 mol) was added. The reaction was kept for 30 min at this temperature and a solution of 4-(4-benzylpiperazin-1-yl)-2,2-dimethyltetrahydro-2H-pyran-4-carbonitrile (INT 1A, 5 g, 0.016 mol.) in THF was added. The reaction was slowly allowed to reach rt. and stirred overnight. The mixture was quenched with NH$_4$Cl and extracted with ether. The combined organic fractions were dried over sodium sulphate. The solvent was removed under reduced pressure after filtration, to give the crude title compound as an oil, that was used in the following step without further purification.

HPLC-MS (Method A): Ret, 1.97 min; ESI$^+$-MS m/z, 394.3 (M+1).

b): Title Compound

The crude imine obtained in step a (6.3 g, 0.02 mol) was dissolved in THF (250 mL) and 3N HCl (ca. 124 mL) was added. The reaction was stirred until full conversion to ketone was achieved (HPLC analysis). The mixture was made alkaline with 10% NaOH and extracted twice with ether. The combined organic phases were dried over Na$_2$SO$_4$, filtered and concentrated to give a brown oil. The crude was purified by flash chromatography on silica gel, eluents CH:AcOEt, gradient to 80:20 to give the title compound (4.7 g, yield 75% over two steps).

HPLC-MS (Method A): Ret, 2.29 min; ESI$^+$-MS m/z, 394.3 (M+1).

Examples 2 and 3. (R) and (S) (4-(4-Benzylpiperazin-1-yl)-2,2-dimethyltetrahydro-2H-pyran-4-yl)(pyridin-2-yl)methanone The enantiomers of Ex 1 were separated by preparative HPLC using Chiralpak AS-H Column, flow rate 12 mL/min A: n-Heptano; B: (IPA+0.33% DEA) 98/2 v/v, rt to give:

| EX | Structure | Chemical name | Method | Ret (min) | MS (M + H) |
|---|---|---|---|---|---|
| 2 | 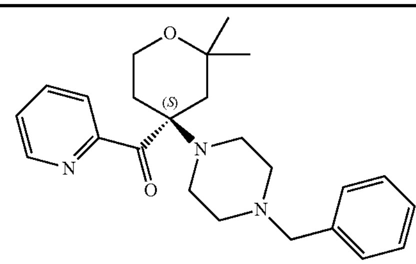 | (S)-(4-(4-benzylpiperazin-1-yl)-2,2-dimethyltetrahydro-2H-pyran-4-yl)(pyridin-2-yl)methanone | A | 2.29 | 394.3 |
| 3 | 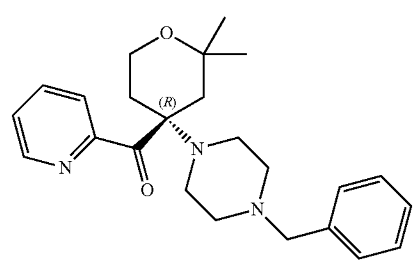 | (R)-(4-(4-benzylpiperazin-1-yl)-2,2-dimethyltetrahydro-2H-pyran-4-yl)(pyridin-2-yl)methanone | A | 2.29 | 394.3 |

Examples 4-22

Examples 4-22 were prepared using the method described for the preparation of example 1 and using the corresponding intermediates 1A-1Q as starting materials:

| EX | Structure | Chemical name | Method | Ret (min) | MS (M + H) |
|---|---|---|---|---|---|
| 4 | 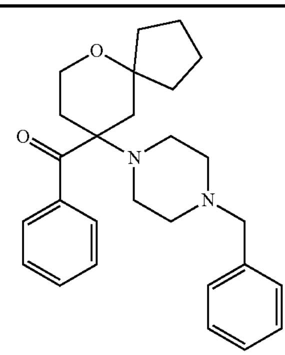 | (9-(4-benzylpiperazin-1-yl)-6-oxaspiro[4.5]decan-9-yl)(phenyl)methanone | A | 2.74 | 419.3 |

| EX | Structure | Chemical name | Method | Ret (min) | MS (M + H) |
|---|---|---|---|---|---|
| 5 | 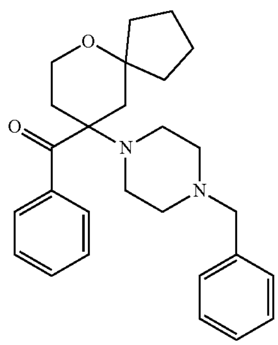 [SMILES: O=C(c1ccccc1)C1(N2CCN(Cc3ccccc3)CC2)CCOC2(CCCC2)C1] | (9-(4-benzylpiperazin-1-yl)-6-oxaspiro[4.5]decan-9-yl)(phenyl)methanone | A | 2.61 | 420.4 |
| 6 | 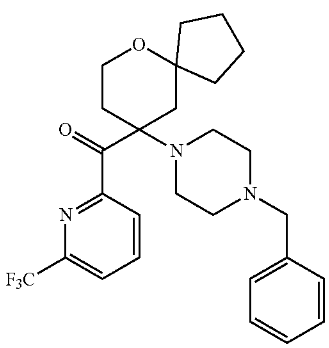 [SMILES: O=C(c1cccc(C(F)(F)F)n1)C1(N2CCN(Cc3ccccc3)CC2)CCOC2(CCCC2)C1] | (9-(4-benzylpiperazin-1-yl)-6-oxaspiro[4.5]decan-9-yl)(6-(trifluoromethyl)pyridin-2-yl)methanone | A | 2.82 | 488.2 |
| 7 | 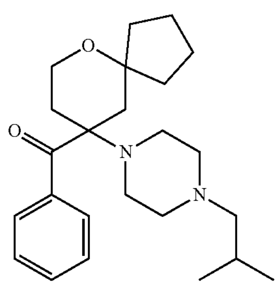 [SMILES: CC(C)CN1CCN(C2(C(=O)c3ccccc3)CCOC3(CCCC3)C2)CC1] | (9-(4-isobutylpiperazin-1-yl)-6-oxaspiro[4.5]decan-9-yl)(phenyl)methanone | A | 2.88 | 385.3 |
| 8 | 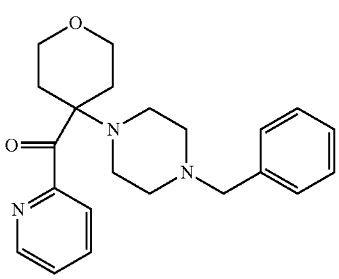 [SMILES: O=C(c1ccccn1)C1(N2CCN(Cc3ccccc3)CC2)CCOCC1] | (4-(4-benzylpiperazin-1-yl)tetrahydro-2H-pyran-4-yl)(pyridin-2-yl)methanone | A | 2.00 | 366.2 |
| 9 | 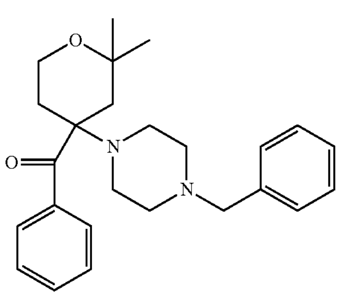 [SMILES: CC1(C)CC(C(=O)c2ccccc2)(N2CCN(Cc3ccccc3)CC2)CCO1] | (4-(4-benzylpiperazin-1-yl)-2,2-dimethyltetrahydro-2H-pyran-4-yl)(phenyl)methanone | A | 2.51 | 393.3 |

-continued

| EX | Structure | Chemical name | Method | Ret (min) | MS (M + H) |
|---|---|---|---|---|---|
| 10 | 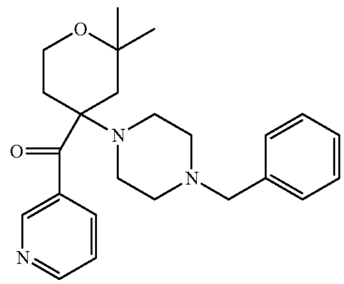 [SMILES: CC1(C)CC(C(=O)c2cccnc2)(N2CCN(Cc3ccccc3)CC2)CCO1] | (4-(4-benzylpiperazin-1-yl)-2,2-dimethyltetrahydro-2H-pyran-4-yl)(pyridin-3-yl)methanone | A | 2.15 | 394.3 |
| 11 | 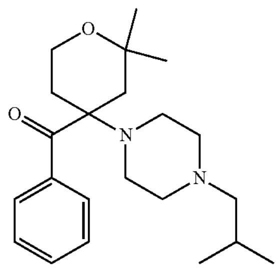 [SMILES: CC(C)CN1CCN(C2(C(=O)c3ccccc3)CCOC(C)(C)C2)CC1] | (4-(4-isobutylpiperazin-1-yl)-2,2-dimethyltetrahydro-2H-pyran-4-yl)(phenyl)methanone | A | 2.64 | 359.2 |
| 12 | 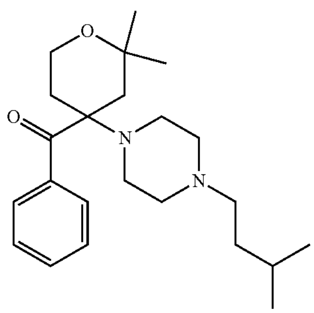 [SMILES: CC(C)CCN1CCN(C2(C(=O)c3ccccc3)CCOC(C)(C)C2)CC1] | (4-(4-isopentylpiperazin-1-yl)-2,2-dimethyltetrahydro-2H-pyran-4-yl)(phenyl)methanone | A | 2.56 | 373.3 |
| 13 | 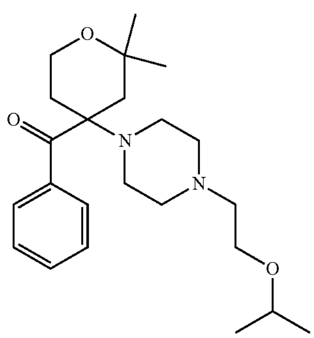 [SMILES: CC(C)OCCN1CCN(C2(C(=O)c3ccccc3)CCOC(C)(C)C2)CC1] | (4-(4-(2-isopropoxyethyl)piperazin-1-yl)-2,2-dimethyltetrahydro-2H-pyran-4-yl)(phenyl)methanone | A | 2.21 | 389.3 |
| 14 | 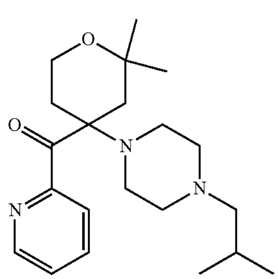 [SMILES: CC(C)CN1CCN(C2(C(=O)c3ccccn3)CCOC(C)(C)C2)CC1] | (4-(4-isobutylpiperazin-1-yl)-2,2-dimethyltetrahydro-2H-pyran-4-yl)(pyridin-2-yl)methanone | A | 2.35 | 360.2 |

| EX | Structure | Chemical name | Method | Ret (min) | MS (M + H) |
|---|---|---|---|---|---|
| 15 | 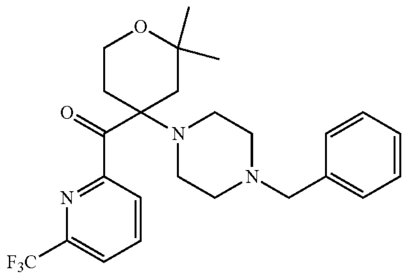 [SMILES: CC1(C)CC(C(=O)c2cccc(C(F)(F)F)n2)(N2CCN(Cc3ccccc3)CC2)CCO1] | (4-(4-benzylpiperazin-1-yl)-2,2-dimethyltetrahydro-2H-pyran-4-yl)(6-(trifluoromethyl)pyridin-2-yl)methanone | A | 2.62 | 462.1 |
| 16 | 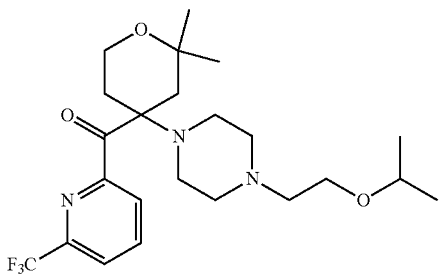 [SMILES: CC(C)OCCN1CCN(C2(C(=O)c3cccc(C(F)(F)F)n3)CCOC(C)(C)C2)CC1] | (4-(4-(2-isopropoxyethyl)piperazin-1-yl)-2,2-dimethyltetrahydro-2H-pyran-4-yl)(6-(trifluoromethyl)pyridin-2-yl)methanone | A | 2.30 | 458.3 |
| 17 | 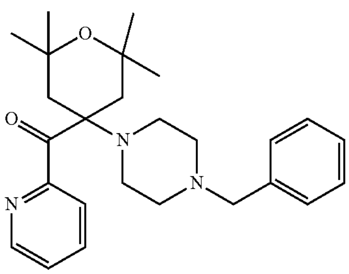 [SMILES: CC1(C)CC(C(=O)c2ccccn2)(N2CCN(Cc3ccccc3)CC2)CC(C)(C)O1] | (4-(4-benzylpiperazin-1-yl)-2,2,6,6-tetramethyltetrahydro-2H-pyran-4-yl)(pyridin-2-yl)methanone | A | 2.66 | 422.2 |
| 18 | 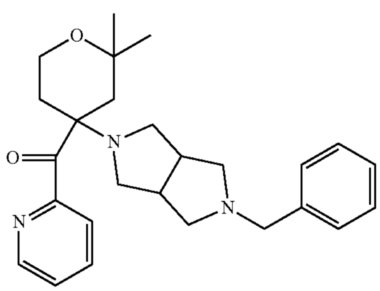 [SMILES: CC1(C)CC(C(=O)c2ccccn2)(N2CC3CN(Cc4ccccc4)CC3C2)CCO1] | (4-(5-benzylhexahydropyrrolo[3,4-c]pyrrol-2(1H)-yl)-2,2,-dimethyltetrahydro-2H-pyran-4-yl)(pyridin-2-yl)methanone | A | 2.23 | 420.2 |
| 19 | 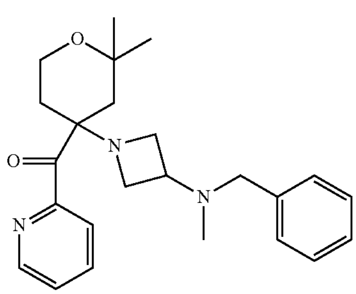 [SMILES: CN(Cc1ccccc1)C1CN(C2(C(=O)c3ccccn3)CCOC(C)(C)C2)C1] | (4-(3-(benzyl(methyl)amino)azetidin-1-yl)-2,2-dimethyltetrahydro-2H-pyran-4-yl)(pyridin-2-yl)methanone | A | 2.26 | 394.2 |

| EX | Structure | Chemical name | Method | Ret (min) | MS (M + H) |
|---|---|---|---|---|---|
| 20 | 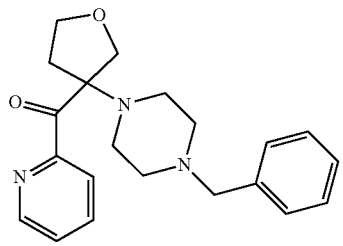 [SMILES: O=C(c1ccccn1)C1(N2CCN(Cc3ccccc3)CC2)CCOC1] | (3-(4-benzylpiperazin-1-yl)tetrahydrofuran-3-yl)(pyridin-2-yl)methanone | A | 1.90 | 352.2 |
| 21 | 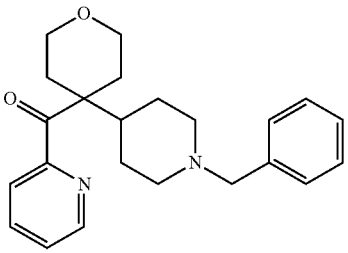 [SMILES: O=C(c1ccccn1)C1(C2CCN(Cc3ccccc3)CC2)CCOCC1] | (4-(1-benzylpiperidin-4-yl)tetrahydro-2H-pyran-4-yl)(pyridin-2-yl)methanone | C | 4.54 | 365.2 |
| 22 | 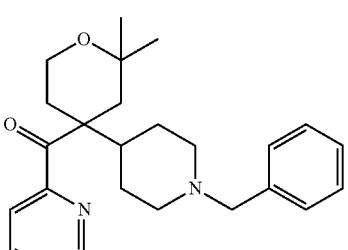 | (4-(1-benzylpiperidin-4-yl)-2,2-dimethyltetrahydro-2H-pyran-4-yl)(pyridin-2-yl)methanone | C | 5.03 | 393.2 |
| 23 | 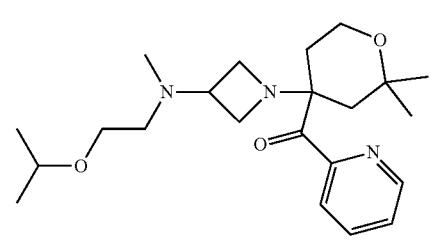 [SMILES: CC(C)OCCN(C)C1CN(C2(C(=O)c3ccccn3)CCOC(C)(C)C2)C1] | (4-(3-((2-isopropoxyethyl)(methyl)amino)azetidin-1-yl)-2,2-dimethyltetrahydro-2H-pyran-4-yl)(pyridin-2-yl)methanone | D | 1.96 | 390.4 |
| 24 | 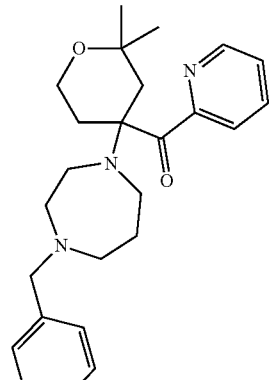 | (4-(4-benzyl-1,4-diazepan-1-yl)-2,2-dimethyltetrahydro-2H-pyran-4-yl)(pyridin-2-yl)methanone | D | 2.4 | 408.4 |

| EX | Structure | Chemical name | Method | Ret (min) | MS (M + H) |
|---|---|---|---|---|---|
| 25 | 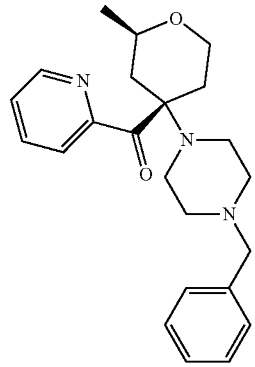 [SMILES: C[C@@H]1C[C@@](C(=O)c2ccccn2)(N2CCN(Cc3ccccc3)CC2)CCO1] | 4-(4-benzylpiperazin-1-yl)-2-methyltetrahydro-2H-pyran-4-yl)(pyridin-2-yl)methanone | | | |
| 26 | 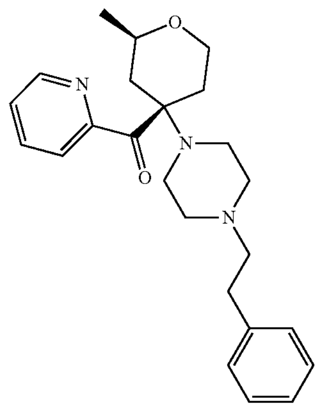 [SMILES: C[C@@H]1C[C@@](C(=O)c2ccccn2)(N2CCN(CCc3ccccc3)CC2)CCO1] | 2-methyl-4-(4-phenethylpiperazin-1-yl)tetrahydro-2H-pyran-4-yl)(pyridin-2-yl)methanone | D | 2.11 | 394.3 |

Examples 27 and 28. (2S,4R) and (2R,4S) 4-(4-Benzylpiperazin-1-yl)-2-methyltetrahydro-2H-pyran-4-yl)(pyridin-2-yl)methanone.

The enantiomers of example 25 were separated by preparative HPLC using Chiralpak IC Column, flow rate 12 mL/min A: n-Heptane; B: (EtOH+0.33% DEA) 90/10 v/v, rt to give examples 27 and 28:

| EX | Structure | Chemical name | Method | Ret (min) | MS (M + H) |
|---|---|---|---|---|---|
| 27 | 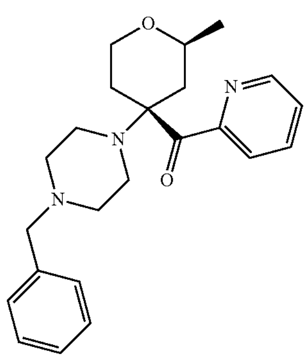 [SMILES: C[C@H]1C[C@](C(=O)c2ccccn2)(N2CCN(Cc3ccccc3)CC2)CCO1] | (2S,4R)-4-(4-benzylpiperazin-1-yl)-2-methyltetrahydro-2H-pyran-4-yl)(pyridin-2-yl)methanone | D | 2.16 | 380.3 |

-continued

| EX | Structure | Chemical name | Method | Ret (min) | MS (M + H) |
|---|---|---|---|---|---|
| 28 | 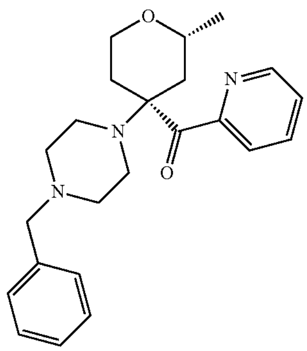 [SMILES: C[C@@H]1C[C@@](C(=O)c2ccccn2)(N2CCN(Cc3ccccc3)CC2)CCO1] | (2R,4S)-4-(4-benzylpiperazin-1-yl)-2-methyltetrahydro-2H-pyran-4-yl)(pyridin-2-yl)methanone | D | 2.16 | 380.3 |

Example 29. 1-Benzyl-4-(9-ethyl-6-oxaspiro[4.5]decan-9-yl)piperazine

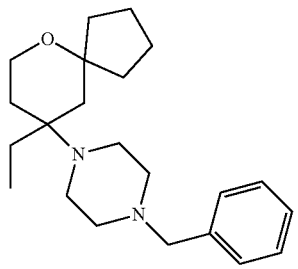 [SMILES: CCC1(N2CCN(Cc3ccccc3)CC2)CCOC2(CCCC2)C1]

A solution of 9-(4-benzylpiperazin-1-yl)-6-oxaspiro[4.5]decane-9-carbonitrile (INT 1 D, 70 mg, 0.206 mmol) in THF (3 mL) was cooled down to 0° C. and ethylmagnesium bromide (3M in ethyl ether, 206 µL, 0.619 mmol) was added. The resulting mixture was allowed to warm up and stirred at room temperature overnight under argon atmosphere. The reaction was quenched by addition of sat solution of $NH_4Cl$. The product was extracted with EtOAc and the combined organic layers were washed with brine (20 mL), dried over sodium sulfate, filtered and concentrated to give the title compound as yellow oil (70 mg, yield 96%)

HPLC-MS (Method A): Ret, 2.72 min; $ESI^+$-MS m/z, 343.3 (M+1).

This method was used for the preparation of examples 30-47 using the adequate magnesium reagents and the corresponding intermediates 1 as starting materials.

| Ex | Structure | Chemical name | Method | Ret (min) | MS (M + H) |
|---|---|---|---|---|---|
| 30 | 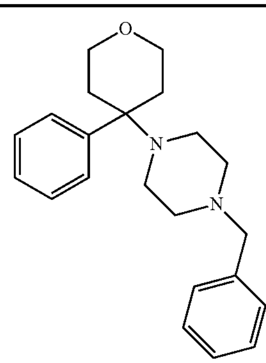 | 1-benzyl-4-(4-phenyltetrahydro-2H-pyran-4-yl)piperazine | A | 2.20 | 337.2 |
| 31 | 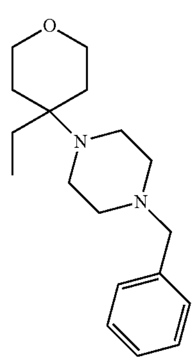 [SMILES: CCC1(N2CCN(Cc3ccccc3)CC2)CCOCC1] | 1-benzyl-4-(4-ethyltetrahydro-2H-pyran-4-yl)piperazine | A | 2.10 | 289.2 |

-continued

| Ex | Structure | Chemical name | Method | Ret (min) | MS (M + H) |
|---|---|---|---|---|---|
| 32 | 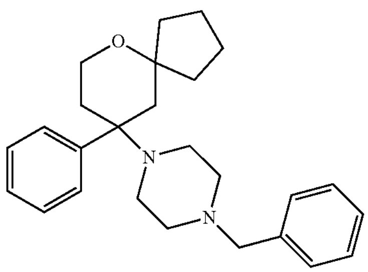 [SMILES: c1ccc(CN2CCN(C3(c4ccccc4)CCOC4(CCCC4)C3)CC2)cc1] | 1-benzyl-4-(9-phenyl-6-oxaspiro[4.5]decan-9-yl)piperazine | A | 2.74 | 391.3 |
| 33 | 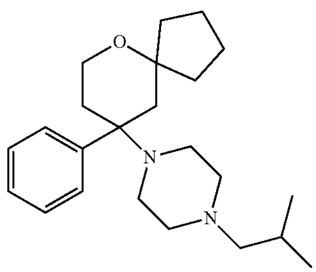 [SMILES: CC(C)CN1CCN(C2(c3ccccc3)CCOC3(CCCC3)C2)CC1] | 1-isobutyl-4-(9-phenyl-6-oxaspiro[4.5]decan-9-yl)piperazine | A | 2.81 | 357.3 |
| 34 | 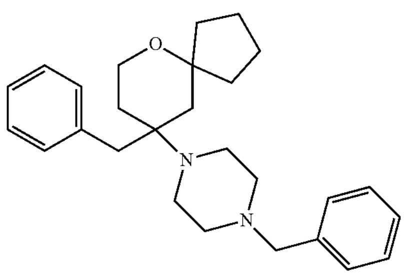 [SMILES: c1ccc(CN2CCN(C3(Cc4ccccc4)CCOC4(CCCC4)C3)CC2)cc1] | 1-benzyl-4-(9-benzyl-6-oxaspiro[4.5]decan-9-yl)piperazine | A | 2.87 | 405.3 |
| 35 | 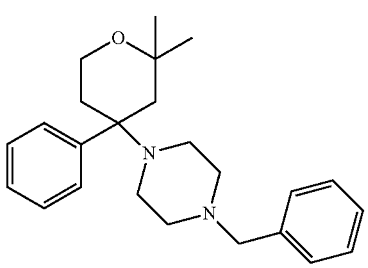 [SMILES: CC1(C)CC(c2ccccc2)(N2CCN(Cc3ccccc3)CC2)CCO1] | 1-benzyl-4-(2,2-dimethyl-4-phenyltetrahydro-2H-pyran-4-yl)piperazine | A | 2.48 | 365.3 |
| 36 | 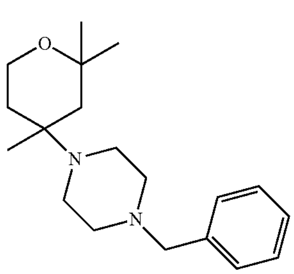 [SMILES: CC1(C)CC(C)(N2CCN(Cc3ccccc3)CC2)CCO1] | 1-benzyl-4-(2,2,4-trimethyltetrahydro-2H-pyran-4-yl)piperazine | B | 2.47 | 303.5 |

| Ex | Structure | Chemical name | Method | Ret (min) | MS (M + H) |
|---|---|---|---|---|---|
| 37 | 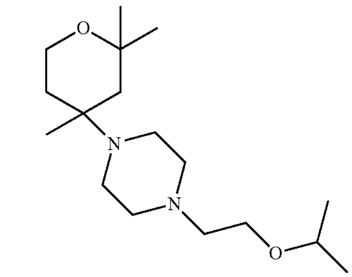 [SMILES: CC(C)OCCN1CCN(C2(C)CCOC(C)(C)C2)CC1] | 1-(2-isopropoxyethyl)-4-(2,2,4-trimethyltetrahydro-2H-pyran-4-yl)piperazine | A | 1.60 | 299.50 |
| 38 | 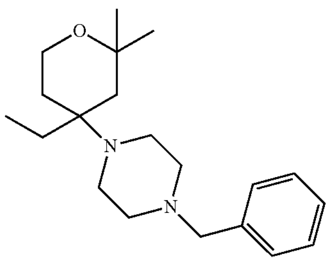 [SMILES: CCC1(N2CCN(Cc3ccccc3)CC2)CCOC(C)(C)C1] | 1-benzyl-4-(4-ethyl-2,2-dimethyltetrahydro-2H-pyran-4-yl)piperazine | A | 2.46 | 317.3 |
| 39 | 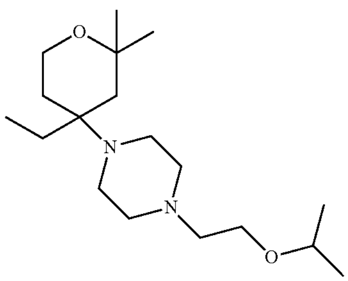 [SMILES: CCC1(N2CCN(CCOC(C)C)CC2)CCOC(C)(C)C1] | 1-(4-ethyl-2,2-dimethyltetrahydro-2H-pyran-4-yl)-4-(2-isopropoxyethyl)piperazine | A | 1.95 | 313 |
| 40 | 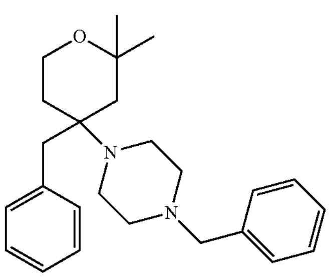 [SMILES: CC1(C)CC(Cc2ccccc2)(N2CCN(Cc3ccccc3)CC2)CCO1] | 1-benzyl-4-(4-benzyl-2,2-dimethyltetrahydro-2H-pyran-4-yl)piperazine | A | 2.64 | 379.3 |
| 41 | 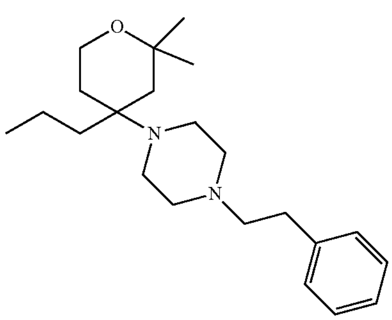 [SMILES: CCCC1(N2CCN(CCc3ccccc3)CC2)CCOC(C)(C)C1] | 1-(2,2-dimethyl-4-propyltetrahydro-2H-pyran-4-yl)-4-phenethylpiperazine | D | 2.53 | 345.3 |

-continued

| Ex | Structure | Chemical name | Method | Ret (min) | MS (M + H) |
|---|---|---|---|---|---|
| 42 | 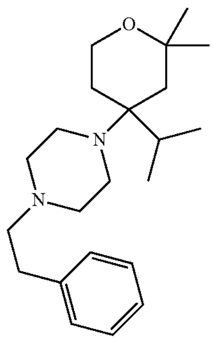 [SMILES: CC(C)C1(N2CCN(CCc3ccccc3)CC2)CCOC(C)(C)C1] | 1-(4-isopropyl-2,2-dimethyltetrahydro-2H-pyran-4-yl)-4-phenethylpiperazine | D | 2.53 | 345.3 |
| 43 | 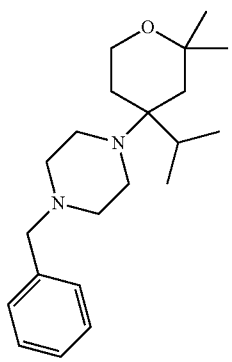 [SMILES: CC(C)C1(N2CCN(Cc3ccccc3)CC2)CCOC(C)(C)C1] | 1-benzyl-4-(4-isopropyl-2,2-dimethyltetrahydro-2H-pyran-4-yl)piperazine | D | 2.64 | 331.3 |
| 44 | 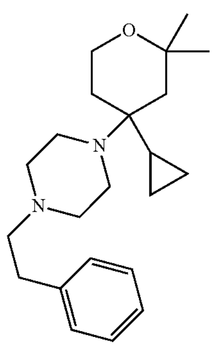 [SMILES: CC1(C)CC(C2CC2)(N2CCN(CCc3ccccc3)CC2)CCO1] | 1-(4-cyclopropyl-2,2-dimethyltetrahydro-2H-pyran-4-yl)-4-phenethylpiperazine | D | 2.42 | 343.3 |
| 45 | 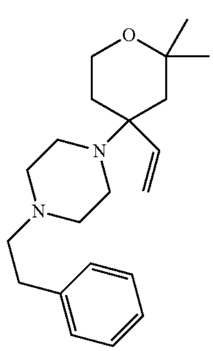 [SMILES: C=CC1(N2CCN(CCc3ccccc3)CC2)CCOC(C)(C)C1] | 1-(2,2-dimethyl-4-vinyltetrahydro-2H-pyran-4-yl)-4-phenethylpiperazine | D | 2.09 | 329 |

| Ex | Structure | Chemical name | Method | Ret (min) | MS (M + H) |
|---|---|---|---|---|---|
| 46 | 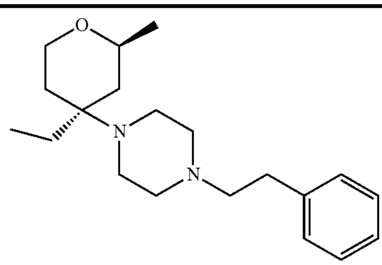 | 1-(4-ethyl-2-methyltetrahydro-2H-pyran-4-yl)-4-phenethylpiperazine | D | 2.27 | 317.3 |
| 47 | 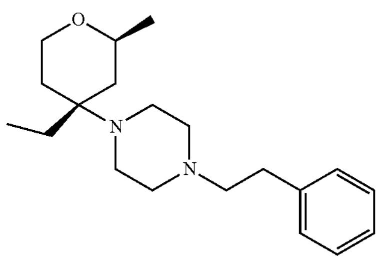 [SMILES: CC[C@@]1(N2CCN(CCc3ccccc3)CC2)CCO[C@@H](C)C1] | 1-(4-ethyl-2-methyltetrahydro-2H-pyran-4-yl)-4-phenethylpiperazine | D | 2.09 | 317.3 |

Example 48. 2-(2,2-Dimethyl-4-(4-phenethylpiperazin-1-yl)tetrahydro-2H-pyran-4-yl)ethanol

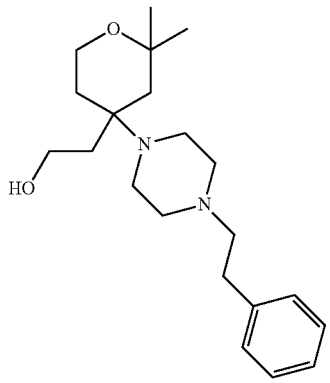 [SMILES: CC1(C)CC(CCO)(N2CCN(CCc3ccccc3)CC2)CCO1]

1-(2,2-Dimethyl-4-vinyltetrahydro-2H-pyran-4-yl)-4-phenethylpiperazine (Ex 45, 340 mg, 1.03 mmol) was dissolved in THF (30 mL) under argon atmosphere in a Schlenk tube. Then, a 9-BBN solution (7.76 mL, 3.1 mmol) was added dropwise and the reaction mixture was stirred overnight at rt. The reaction was cooled down to 0° C. and NaOH (10%, 2 mL) was added, followed by a $H_2O_2$ solution (30%, 1 mL) and the reaction stirred at r.t. for 3 h. The reaction mixture was quenched with water and extracted with EtOAc (3×). The combined organic fractions were dried over $Na_2SO_4$, filtered and concentrated under reduced pressure to give an oil was purified by flash chromatography on silica gel (eluents DCM:MeOH), to give the title compound (135 mg, yield 38%).

HPLC-MS (Method E): Ret, 3.5 min; ESI$^+$-MS m/z, 347.3 (M+1).

Example 49. 1-(4-(2-Methoxyethyl)-2,2-dimethyl-tetrahydro-2H-pyran-4-yl)-4-phenethylpiperazine

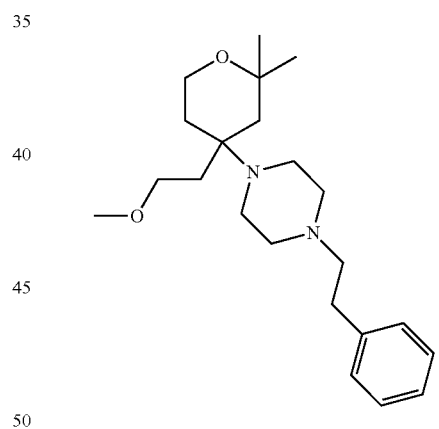

To a solution of 2-(2,2-dimethyl-4-(4-phenethylpiperazin-1-yl)tetrahydro-2H-pyran-4-yl)ethanol (Ex. 48, 46 mg, 1.13 mmol) in anhydrous DMF (1 mL) NaH (60% in mineral oil, 17 mg, 0.4 mmol) was added and the suspension was stirred at rt for 20 min. Then, $Me_2SO_4$ (37 µl, 0.4 mmol) was added and the reaction mixture was stirred at room temperature overnight. The reaction was quenched with water and aqueous sat $NaHCO_3$ solution extracted with EtOAc and washed twice with aqueous sat NaCl solution. The organic layer was dried over $Na_2SO_4$, filtered and concentrated. The crude residue was purified by flash chromatography on silica gel (eluents DCM:MeOH gradient to 90:10), to give the title compound as a colorless oil (4 mg, yield 8%).

HPLC-MS (Method D): Ret, 2.13 min; ESI$^+$-MS m/z, 361.3 (M+1).

Example 50. (2,2-Dimethyl-4-(4-(pyridin-2-ylmethyl)piperazin-1-yl)tetrahydro-2H-pyran-4-yl)(pyridin-2-yl)methanone

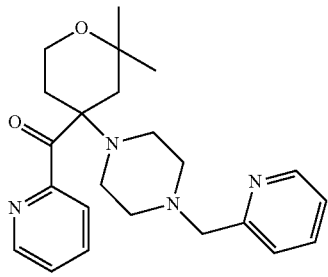 [SMILES: CC1(C)CC(C(=O)c2ccccn2)(N2CCN(Cc3ccccn3)CC2)CCO1]

a) (2,2-Dimethyl-4-(piperazin-1-yl)tetrahydro-2H-pyran-4-yl)(pyridin-2-yl)methanone hydrochloride To a solution of (4-(4-benzylpiperazin-1-yl)-2,2-dimethyltetrahydro-2H-pyran-4-yl)(pyridin-2-yl)methanone (Ex 1, 1.05 g, 2.67 mmol) in DCM (75 mL), dichloroethyl formate (600 µL, 5.561 mmol) was added and the reaction mixture heated to reflux for 3 h. After cooling down to rt, all volatiles were removed under reduced pressure. MeOH was then added and the reaction mixture heated again to reflux for 2 h. After cooling back to rt, the solvent was removed and the brown solid thus obtained was washed several times with ether and dried in vacuo (712 mg, yield 73%).

HPLC-MS (Method A): Ret, 1.12 min; ESI$^+$-MS m/z, 304.1 (M+1).

b) Title Compound 2-(Bromomethyl)pyridine hydrochloride (97 mg, 0.47 mmol) was added to a solution of the compound obtained in step a (106 mg, 0.31 mmol) and $K_2CO_3$ (215 mg, 1.56 mmol) in ACN (8 mL). The reaction mixture was stirred at 65° C. overnight and then it was cooled down to rt. AcOEt (10 mL) and sat aqueous $NaHCO_3$ solution (10 mL) were added and the phases were separated. The organic layer was dried over $Na_2SO_4$, filtered and concentrated. The crude residue was purified by flash chromatography on silica gel (eluents DCM:MeOH gradient to 80:20), to give the title compound as an oil (72 mg, yield 60%).

HPLC-MS (Method A): Ret, 1.82 min; ESI$^+$-MS m/z, 395.2 (M+1).

This method was used for the preparation of examples 51-111 using the adequate alkylating agents and the corresponding benzyl examples or INT 2 as starting materials.

| EX | Structure | Chemical name | Method | Ret (min) | MS (M + H) |
|---|---|---|---|---|---|
| 51 | 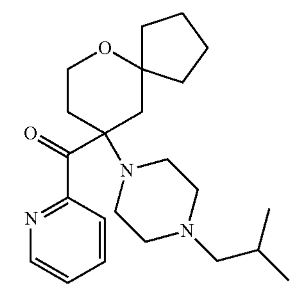 [SMILES: CC(C)CN1CCN(C2(C(=O)c3ccccn3)CCOC3(CCCC3)C2)CC1] | (9-(4-isobutylpiperazin-1-yl)-6-oxaspiro[4.5]decan-9-yl)(pyridin-2-yl)methanone | A | 2.65 | 386.2 |
| 52 | 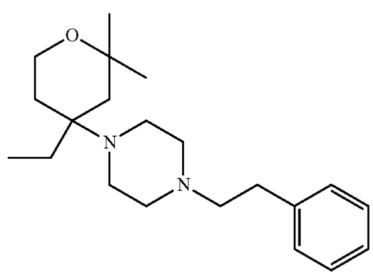 [SMILES: CCC1(N2CCN(CCc3ccccc3)CC2)CCOC(C)(C)C1] | 1-(4-ethyl-2,2-dimethyltetrahydro-2H-pyran-4-yl)-4-phenethylpiperazine | A | 2.37 | 331.3 |
| 53 | 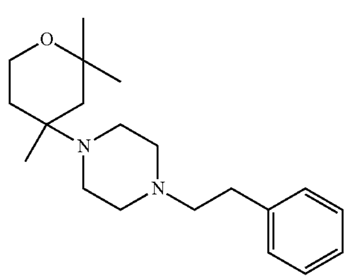 [SMILES: CC1(C)CC(C)(N2CCN(CCc3ccccc3)CC2)CCO1] | 1-phenethyl-4-(2,2,4-trimethyltetrahydro-2H-pyran-4-yl)piperazine | A | 2.03 | 317.4 |

| EX | Structure | Chemical name | Method | Ret (min) | MS (M + H) |
|---|---|---|---|---|---|
| 54 | 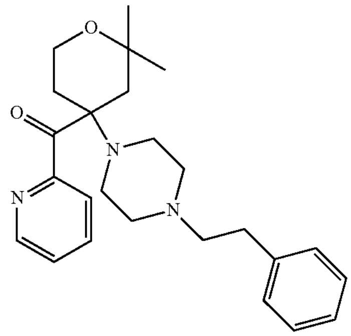 [SMILES: CC1(C)CC(C(=O)c2ccccn2)(N2CCN(CCc3ccccc3)CC2)CCO1] | (2,2-dimethyl-4-(4-phenethylpiperazin-1-yl)tetrahydro-2H-pyran-4-yl)(pyridin-2-yl)methanone | A | 2.26 | 408.6 |
| 55* | 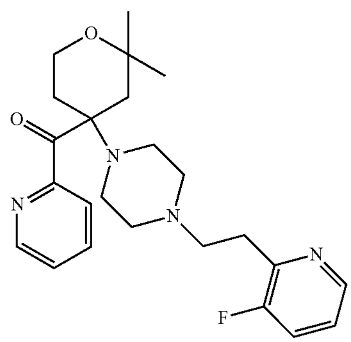 [SMILES: CC1(C)CC(C(=O)c2ccccn2)(N2CCN(CCc3ncccc3F)CC2)CCO1] | (4-(4-(2-(3-fluoropyridin-2-yl)ethyl)piperazin-1-yl)-2,2-dimethyltetrahydro-2H-pyran-4-yl)(pyridin-2-yl)methanone | A | 1.83 | 427.2 |
| 56* | 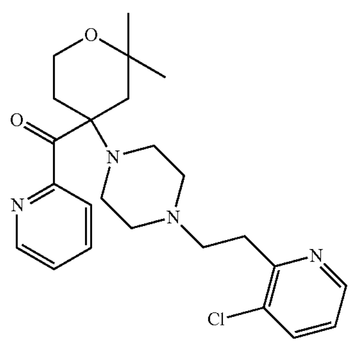 [SMILES: CC1(C)CC(C(=O)c2ccccn2)(N2CCN(CCc3ncccc3Cl)CC2)CCO1] | (4-(4-(2-(3-chloropyridin-2-yl)ethyl)piperazin-1-yl)-2,2-dimethyltetrahydro-2H-pyran-4-yl)(pyridin-2-yl)methanone | A | 1.98 | 443.2 |
| 57* | 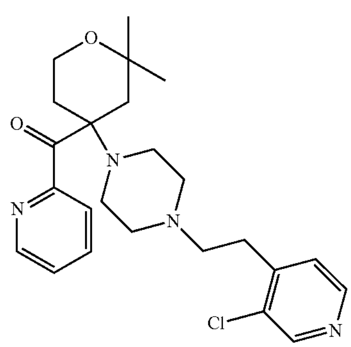 [SMILES: CC1(C)CC(C(=O)c2ccccn2)(N2CCN(CCc3ccncc3Cl)CC2)CCO1] | (4-(4-(2-(3-chloropyridin-4-yl)ethyl)piperazin-1-yl)-2,2-dimethyltetrahydro-2H-pyran-4-yl)(pyridin-2-yl)methanone | A | 1.97 | 443.2 |

-continued

| EX | Structure | Chemical name | Method | Ret (min) | MS (M + H) |
|---|---|---|---|---|---|
| 58 | 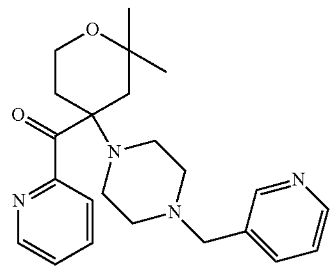 [SMILES: CC1(C)CC(C(=O)c2ccccn2)(N2CCN(Cc3cccnc3)CC2)CCO1] | (2,2-dimethyl-4-(4-(pyridin-3-ylmethyl)piperazin-1-yl)tetrahydro-2H-pyran-4-yl)(pyridin-2-yl)methanone | A | 1.68 | 395.2 |
| 59 | 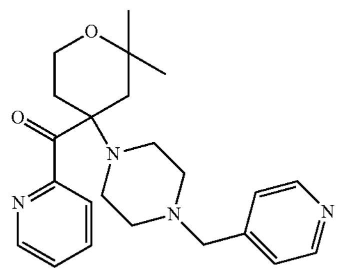 [SMILES: CC1(C)CC(C(=O)c2ccccn2)(N2CCN(Cc3ccncc3)CC2)CCO1] | (2,2-dimethyl-4-(4-(pyridin-4-ylmethyl)piperazin-1-yl)tetrahydro-2H-pyran-4-yl)(pyridin-2-yl)methanone | A | 1.73 | 395.2 |
| 60 | 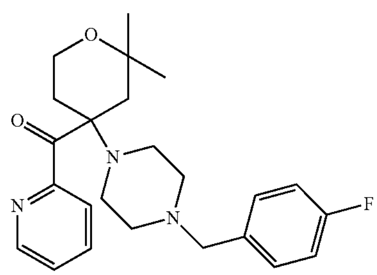 [SMILES: CC1(C)CC(C(=O)c2ccccn2)(N2CCN(Cc3ccc(F)cc3)CC2)CCO1] | (4-(4-(4-fluorobenzyl)piperazin-1-yl)-2,2-dimethyltetrahydro-2H-pyran-4-yl)(pyridin-2-yl)methanone | A | 2.31 | 412.2 |
| 61 | 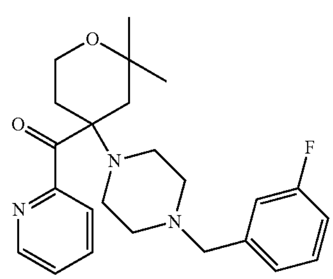 [SMILES: CC1(C)CC(C(=O)c2ccccn2)(N2CCN(Cc3cccc(F)c3)CC2)CCO1] | (4-(4-(3-fluorobenzyl)piperazin-1-yl)-2,2-dimethyltetrahydro-2H-pyran-4-yl)(pyridin-2-yl)methanone | A | 2.39 | 412.2 |
| 62 | 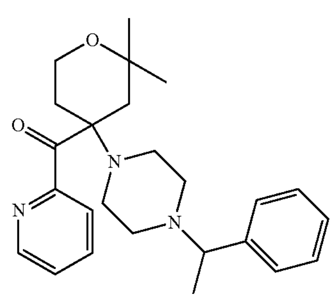 [SMILES: CC(c1ccccc1)N1CCN(C2(C(=O)c3ccccn3)CCOC(C)(C)C2)CC1] | (2,2-dimethyl-4-(4-(1-phenylethyl)piperazin-1-yl)tetrahydro-2H-pyran-4-yl)(pyridin-2-yl)methanone | A | 2.43 | 408.2 |

-continued

| EX | Structure | Chemical name | Method | Ret (min) | MS (M + H) |
|---|---|---|---|---|---|
| 63 | 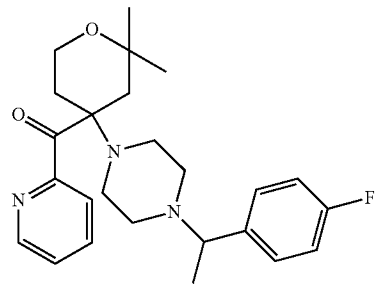 [SMILES: CC(c1ccc(F)cc1)N1CCN(C2(C(=O)c3ccccn3)CCOC(C)(C)C2)CC1] | (4-(4-(1-(4-fluorophenyl)ethyl)piperazin-1-yl)-2,2-dimethyltetrahydro-2H-pyran-4-yl)(pyridin-2-yl)methanone | A | 2.45 | 426.2 |
| 64 | 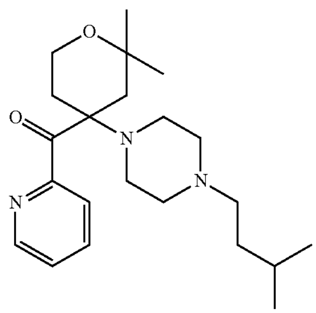 [SMILES: CC(C)CCN1CCN(C2(C(=O)c3ccccn3)CCOC(C)(C)C2)CC1] | (4-(4-isopentylpiperazin-1-yl)-2,2-dimethyltetrahydro-2H-pyran-4-yl)(pyridin-2-yl)methanone | A | 2.23 | 374.3 |
| 65 | 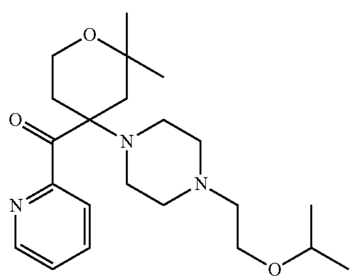 [SMILES: CC(C)OCCN1CCN(C2(C(=O)c3ccccn3)CCOC(C)(C)C2)CC1] | (4-(4-(2-isopropoxyethyl)piperazin-1-yl)-2,2-dimethyltetrahydro-2H-pyran-4-yl)(pyridin-2-yl)methanone | A | 1.94 | 390.3 |
| 66 | 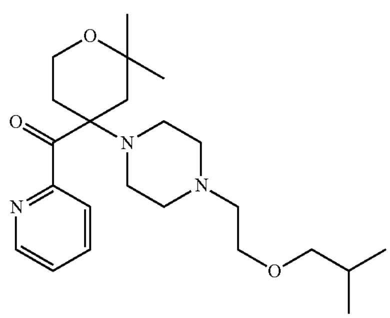 [SMILES: CC(C)COCCN1CCN(C2(C(=O)c3ccccn3)CCOC(C)(C)C2)CC1] | (4-(4-(2-isobutoxyethyl)piperazin-1-yl)-2,2-dimethyltetrahydro-2H-pyran-4-yl)(pyridin-2-yl)methanone | A | 2.22 | 404.2 |
| 67 | 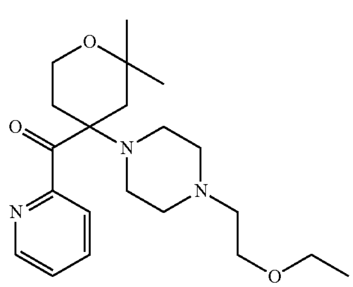 [SMILES: CCOCCN1CCN(C2(C(=O)c3ccccn3)CCOC(C)(C)C2)CC1] | (4-(4-(2-ethoxyethyl)piperazin-1-yl)-2,2-dimethyltetrahydro-2H-pyran-4-yl)(pyridin-2-yl)methanone | A | 1.75 | 376.2 |

-continued

| EX | Structure | Chemical name | Method | Ret (min) | MS (M + H) |
|---|---|---|---|---|---|
| 68 | 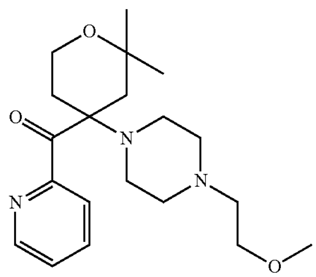 [SMILES: COCCN1CCN(C2(C(=O)c3ccccn3)CCOC(C)(C)C2)CC1] | (4-(4-(2-methoxyethyl)piperazin-1-yl)-2,2-dimethyltetrahydro-2H-pyran-4-yl)(pyridin-2-yl)methanone | A | 1.59 | 362.2 |
| 69 | 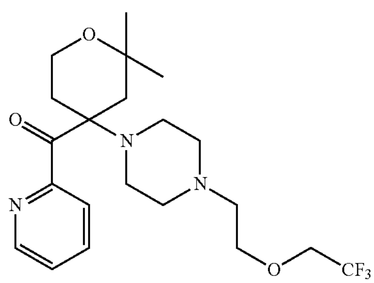 [SMILES: CC1(C)CC(C(=O)c2ccccn2)(N2CCN(CCOCC(F)(F)F)CC2)CCO1] | (2,2-dimethyl-4-(4-(2-(2,2,2-trifluoroethoxy)ethyl)piperazin-1-yl)tetrahydro-2H-pyran-4-yl)(pyridin-2-yl)methanone | A | 2.02 | 430.2 |
| 70 | 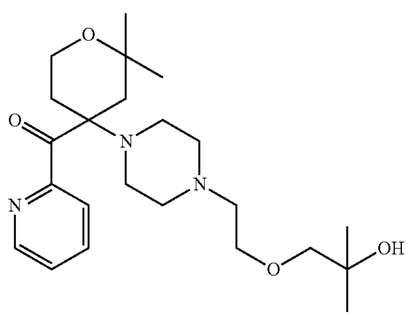 [SMILES: CC(C)(O)COCCN1CCN(C2(C(=O)c3ccccn3)CCOC(C)(C)C2)CC1] | (4-(4-(2-(2-hydroxy-2-methylpropoxy)ethyl)piperazin-1-yl)-2,2-dimethyltetrahydro-2H-pyran-4-yl)(pyridin-2-yl)methanone | A | 1.59 | 420.2 |
| 71 | 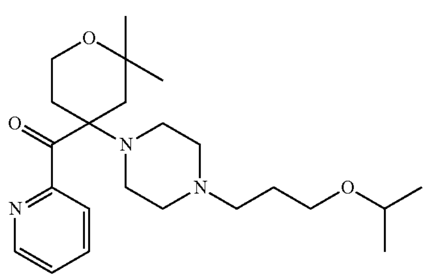 [SMILES: CC(C)OCCCN1CCN(C2(C(=O)c3ccccn3)CCOC(C)(C)C2)CC1] | (4-(4-(3-isopropoxypropyl)piperazin-1-yl)-2,2-dimethyltetrahydro-2H-pyran-4-yl)(pyridin-2-yl)methanone | A | 1.97 | 404.4 |
| 72 | 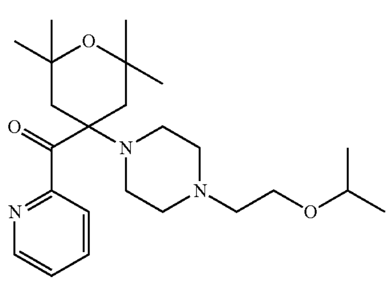 [SMILES: CC(C)OCCN1CCN(C2(C(=O)c3ccccn3)CC(C)(C)OC(C)(C)C2)CC1] | (4-(4-(2-isopropoxyethyl)piperazin-1-yl)-2,2,6,6-tetramethyltetrahydro-2H-pyran-4-yl)(pyridin-2-yl)methanone | A | 2.27 | 418.3 |

| EX | Structure | Chemical name | Method | Ret (min) | MS (M + H) |
|---|---|---|---|---|---|
| 73 | 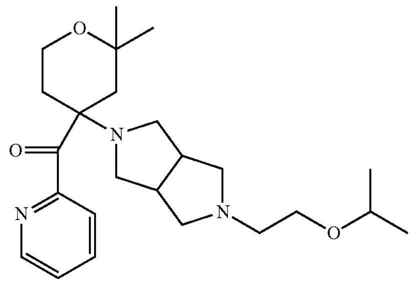 [SMILES: CC(C)OCCN1CC2CN(C3(C(=O)c4ccccn4)CCOC(C)(C)C3)CC2C1] | (4-(5-(2-isopropoxyethyl)hexa-hydropyrrolo[3,4-c]pyrrol-2(1H)-yl)-2,2-dimethyltetrahydro-2H-pyran-4-yl)(pyridin-2-yl)methanone | A | 1.75 | 416.3 |
| 74 | 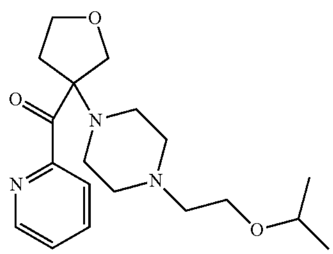 [SMILES: CC(C)OCCN1CCN(C2(C(=O)c3ccccn3)CCOC2)CC1] | (3-(4-(2-isopropoxyethyl)piperazin-1-yl)tetrahydrofuran-3-yl)(pyridin-2-yl)methanone | A | 1.86 | 348.3 |
| 75 | 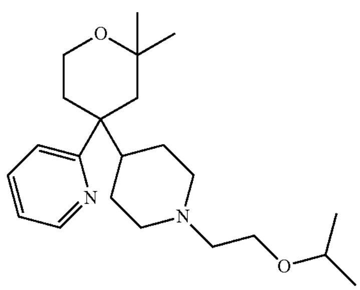 [SMILES: CC(C)OCCN1CCC(C2(c3ccccn3)CCOC(C)(C)C2)CC1] | 2-(4-(1-(2-isopropoxyethyl)piperidin-4-yl)-2,2-dimethyltetrahydro-2H-pyran-4-yl)pyridine | C | 3.47 | 361.2 |
| 76 | 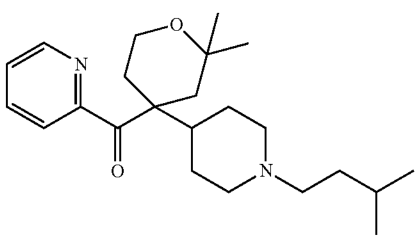 [SMILES: CC(C)CCN1CCC(C2(C(=O)c3ccccn3)CCOC(C)(C)C2)CC1] | (4-(1-isopentylpiperidin-4-yl)-2,2-dimethyltetrahydro-2H-pyran-4-yl)(pyridin-2-yl)methanone | C | 4.55 | 373.2 |
| 77 | 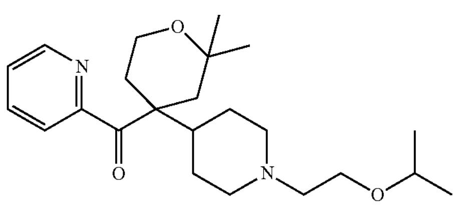 [SMILES: CC(C)OCCN1CCC(C2(C(=O)c3ccccn3)CCOC(C)(C)C2)CC1] | (4-(1-(2-isopropoxyethyl)piperidin-4-yl)-2,2-dimethyltetrahydro-2H-pyran-4-yl)(pyridin-2-yl)methanone | C | 3.67 | 389.2 |
| 78 | 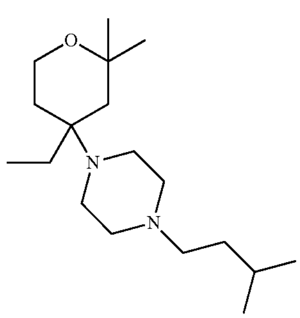 [SMILES: CCC1(N2CCN(CCC(C)C)CC2)CCOC(C)(C)C1] | 1-(4-ethyl-2,2-dimethyltetrahydro-2H-pyran-4-yl)-4-isopentylpiperazine | D | 2.32 | 297.4 |

| EX | Structure | Chemical name | Method | Ret (min) | MS (M + H) |
|---|---|---|---|---|---|
| 79 | 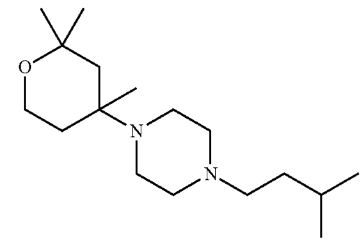 [SMILES: CC(C)CCN1CCN(C2(C)CCOC(C)(C)C2)CC1] | 1-isopentyl-4-(2,2,4-trimethyltetrahydro-2H-pyran-4-yl)piperazine | D | 1.88 | 283.3 |
| 80 | 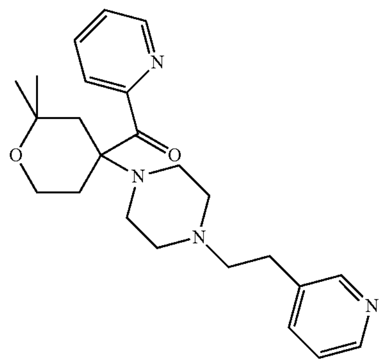 [SMILES: CC1(C)CC(C(=O)c2ccccn2)(N2CCN(CCc3cccnc3)CC2)CCO1] | (2,2-dimethyl-4-(4-(2-(pyridin-3-yl)ethyl)piperazin-1-yl)tetrahydro-2H-pyran-4-yl)(pyridin-2-yl)methanone | D | 1.71 | 409.5 |
| 81 | 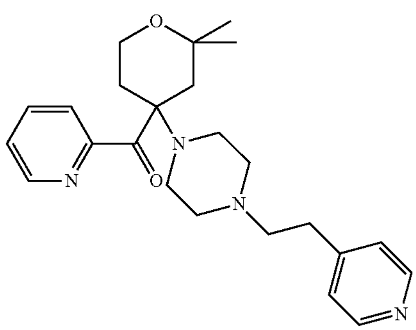 [SMILES: CC1(C)CC(C(=O)c2ccccn2)(N2CCN(CCc3ccncc3)CC2)CCO1] | (2,2-dimethyl-4-(4-(2-(pyridin-4-yl)ethyl)piperazin-1-yl)tetrahydro-2H-pyran-4-yl)(pyridin-2-yl)methanone | D | 1.71 | 409.5 |
| 82 | 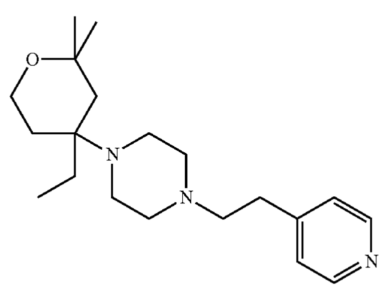 [SMILES: CCC1(N2CCN(CCc3ccncc3)CC2)CCOC(C)(C)C1] | 1-(4-ethyl-2,2-dimethyltetrahydro-2H-pyran-4-yl)-4-(2-(pyridin-4-yl)ethyl)piperazine | D | 1.77 | 332.3 |
| 83 | 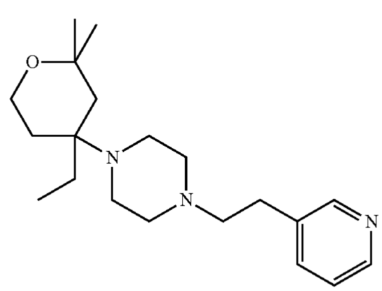 [SMILES: CCC1(N2CCN(CCc3cccnc3)CC2)CCOC(C)(C)C1] | 1-(4-ethyl-2,2-dimethyltetrahydro-2H-pyran-4-yl)-4-(2-(pyridin-3-yl)ethyl)piperazine | D | 1.76 | 332.3 |

-continued

| EX | Structure | Chemical name | Method | Ret (min) | MS (M + H) |
|---|---|---|---|---|---|
| 84* | 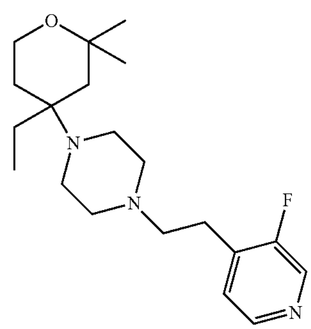 [SMILES: CCC1(N2CCN(CCc3ccncc3F)CC2)CCOC(C)(C)C1] | 1-(4-ethyl-2,2-dimethyltetrahydro-2H-pyran-4-yl)-4-(2-(3-fluoropyridin-4-yl)ethyl)piperazine | D | 1.97 | 350.3 |
| 85* | 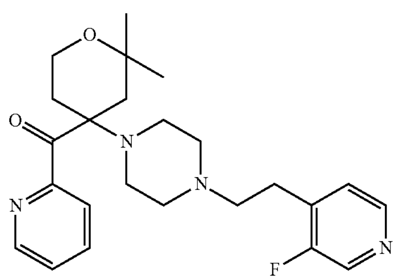 [SMILES: CC1(C)CC(C(=O)c2ccccn2)(N2CCN(CCc3ccncc3F)CC2)CCO1] | (4-(4-(2-(3-fluoropyridin-4-yl)ethyl)piperazin-1-yl)-2,2-dimethyltetrahydro-2H-pyran-4-yl)(pyridin-2-yl)methanone | D | 1.87 | 427.3 |
| 86 | 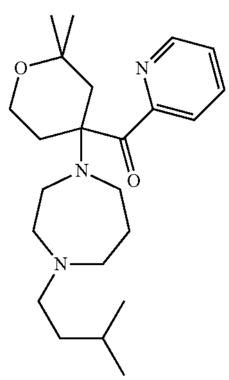 [SMILES: CC(C)CCN1CCCN(C2(C(=O)c3ccccn3)CCOC(C)(C)C2)CC1] | (4-(4-isopentyl-1,4-diazepan-1-yl)-2,2-dimethyltetrahydro-2H-pyran-4-yl)(pyridin-2-yl)methanone | D | 1.92 | 388.4 |
| 87* | 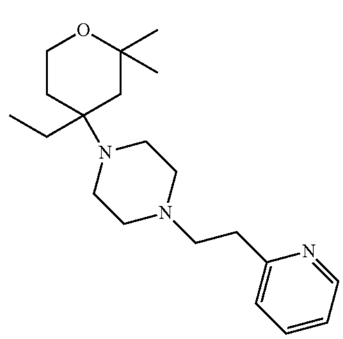 [SMILES: CCC1(N2CCN(CCc3ccccn3)CC2)CCOC(C)(C)C1] | 1-(4-ethyl-2,2-dimethyltetrahydro-2H-pyran-4-yl)-4-(2-(pyridin-2-yl)ethyl)piperazine | D | 1.73 | 332.3 |

-continued

| EX | Structure | Chemical name | Method | Ret (min) | MS (M + H) |
|----|-----------|---------------|--------|-----------|------------|
| 88 | 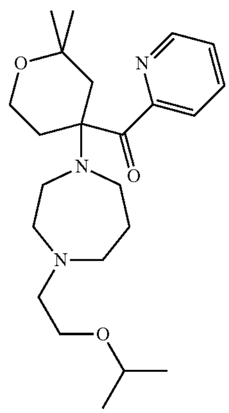 [SMILES: CC(C)OCCN1CCCN(C2(C(=O)c3ccccn3)CCOC(C)(C)C2)CC1] | (4-(4-(2-isopropoxyethyl)-1,4-diazepan-1-yl)-2,2-dimethyltetrahydro-2H-pyran-4-yl)(pyridin-2-yl)methanone | B | 2.20 | 404.4 |
| 89 | 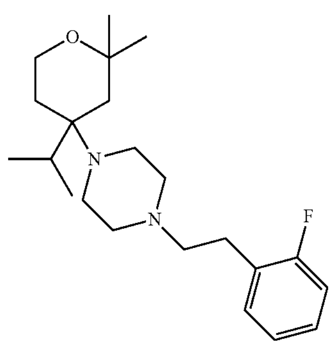 [SMILES: CC(C)C1(N2CCN(CCc3ccccc3F)CC2)CCOC(C)(C)C1] | 1-(2-fluorophenethyl)-4-(4-isopropyl-2,2-dimethyltetrahydro-2H-pyran-4-yl)piperazine | D | 2.60 | 363.4 |
| 90 | 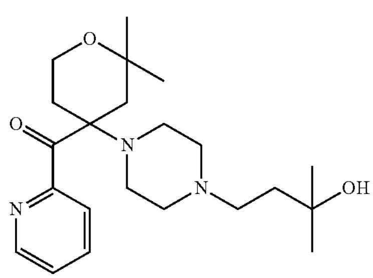 [SMILES: CC(C)(O)CCN1CCN(C2(C(=O)c3ccccn3)CCOC(C)(C)C2)CC1] | (4-(4-(3-hydroxy-3-methylbutyl)piperazin-1-yl)-2,2-dimethyltetrahydro-2H-pyran-4-yl)(pyridin-2-yl)methanone | D | 1.64 | 390.4 |
| 91 | 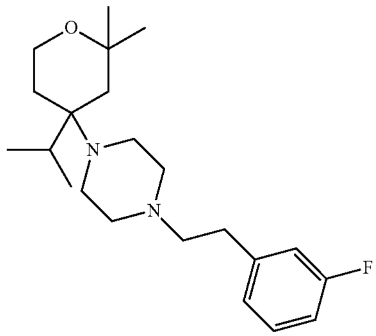 [SMILES: CC(C)C1(N2CCN(CCc3cccc(F)c3)CC2)CCOC(C)(C)C1] | 1-(3-fluorophenethyl)-4-(4-isopropyl-2,2-dimethyltetrahydro-2H-pyran-4-yl)piperazine | D | 2.57 | 363.3 |

| EX | Structure | Chemical name | Method | Ret (min) | MS (M + H) |
|---|---|---|---|---|---|
| 92 | 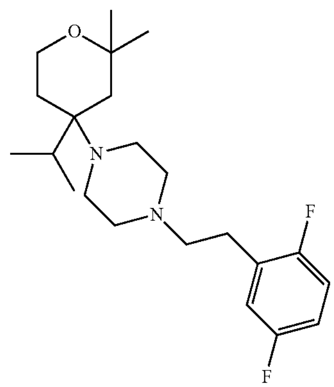 [SMILES: CC(C)C1(N2CCN(CCc3cc(F)ccc3F)CC2)CCOC(C)(C)C1] | 1-(2,5-difluorophenethyl)-4-(4-isopropyl-2,2-dimethyltetrahydro-2H-pyran-4-yl)piperazine | D | 2.65 | 381.3 |
| 93 | 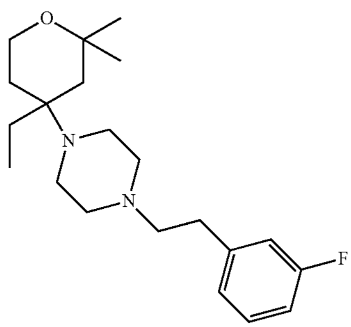 [SMILES: CCC1(N2CCN(CCc3cccc(F)c3)CC2)CCOC(C)(C)C1] | 1-(4-ethyl-2,2-dimethyltetrahydro-2H-pyran-4-yl)-4-(3-fluorophenethyl)piperazine | D | 2.45 | 349.3 |
| 94 | 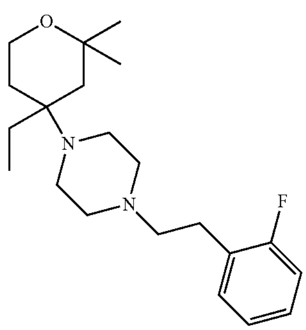 [SMILES: CCC1(N2CCN(CCc3ccccc3F)CC2)CCOC(C)(C)C1] | 1-(4-ethyl-2,2-dimethyltetrahydro-2H-pyran-4-yl)-4-(2-fluorophenethyl)piperazine | D | 2.47 | 349.3 |
| 95 | 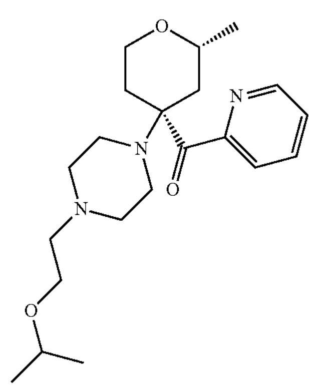 [SMILES: CC(C)OCCN1CCN([C@@]2(C(=O)c3ccccn3)CCO[C@H](C)C2)CC1] | (2R,4S)-4-(4-(2-isopropoxyethyl)piperazin-1-yl)-2-methyltetrahydro-2H-pyran-4-yl)(pyridin-2-yl)methanone | D | 1.77 | 376.3 |

-continued

| EX | Structure | Chemical name | Method | Ret (min) | MS (M + H) |
|---|---|---|---|---|---|
| 96 | 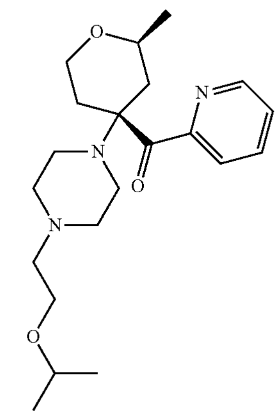 [SMILES: CC(C)OCCN1CCN([C@]2(C(=O)c3ccccn3)CCO[C@@H](C)C2)CC1] | (2S,4R)-4-(4-(2-isopropoxyethyl)piperazin-1-yl)-2-methyltetrahydro-2H-pyran-4-yl)(pyridin-2-yl)methanone | D | 1.76 | 376.3 |
| 97 | 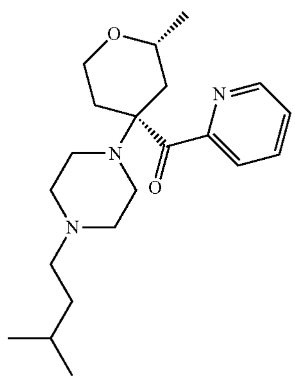 [SMILES: CC(C)CCN1CCN([C@@]2(C(=O)c3ccccn3)CCO[C@H](C)C2)CC1] | (2R,4S)-4-(4-isopentylpiperazin-1-yl)-2-methyltetrahydro-2H-pyran-4-yl)(pyridin-2-yl)methanone | D | 2.12 | 360.3 |
| 98 | 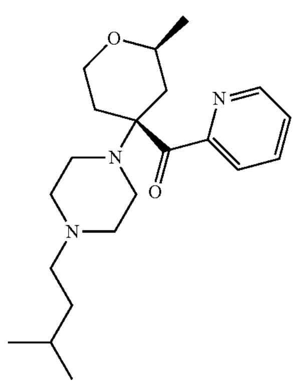 [SMILES: CC(C)CCN1CCN([C@]2(C(=O)c3ccccn3)CCO[C@@H](C)C2)CC1] | (2S,4R)-4-(4-isopentylpiperazin-1-yl)-2-methyltetrahydro-2H-pyran-4-yl)(pyridin-2-yl)methanone | D | 2.09 | 360.3 |
| 99 | 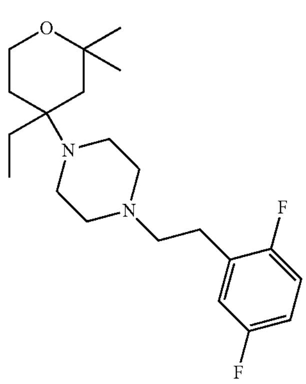 [SMILES: CCC1(N2CCN(CCc3cc(F)ccc3F)CC2)CCOC(C)(C)C1] | 1-(2,5-difluorophenethyl)-4-(4-ethyl-2,2-dimethyltetrahydro-2H-pyran-4-yl)piperazine | D | 2.53 | 367.3 |

| EX | Structure | Chemical name | Method | Ret (min) | MS (M + H) |
|---|---|---|---|---|---|
| 100 | 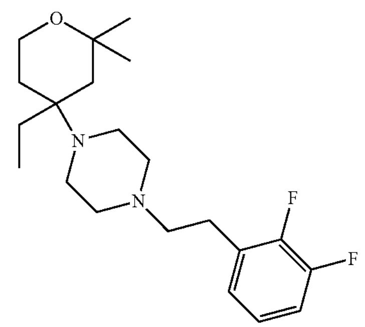 [SMILES: CCC1(N2CCN(CCc3cccc(F)c3F)CC2)CCOC(C)(C)C1] | 1-(2,3-difluorophenethyl)-4-(4-ethyl-2,2-dimethyltetrahydro-2H-pyran-4-yl)piperazine | E | 4.91 | 367.3 |
| 101 | 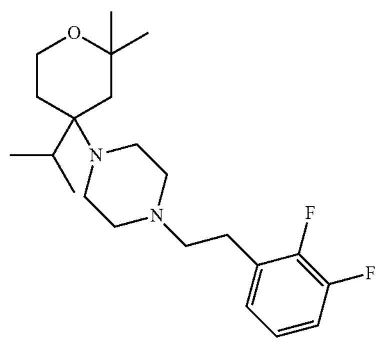 [SMILES: CC(C)C1(N2CCN(CCc3cccc(F)c3F)CC2)CCOC(C)(C)C1] | 1-(2,3-difluorophenethyl)-4-(4-isopropyl-2,2-dimethyltetrahydro-2H-pyran-4-yl)piperazine | D | 2.68 | 381.3 |
| 102 | 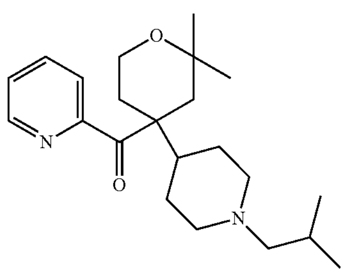 [SMILES: CC(C)CN1CCC(C2(C(=O)c3ccccn3)CCOC(C)(C)C2)CC1] | (4-(1-isobutylpiperidin-4-yl)-2,2-dimethyltetrahydro-2H-pyran-4-yl)(pyridin-2-yl)methanone | D | 2.09 | 359.3 |
| 103 | 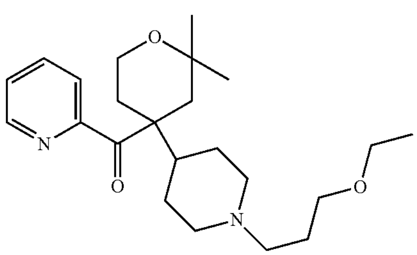 [SMILES: CCOCCCN1CCC(C2(C(=O)c3ccccn3)CCOC(C)(C)C2)CC1] | (4-(1-isobutylpiperidin-4-yl)-2,2-dimethyltetrahydro-2H-pyran-4-yl)(pyridin-2-yl)methanone | D | 1.74 | 389.3 |
| 104 | 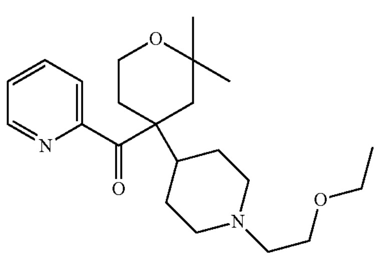 [SMILES: CCOCCN1CCC(C2(C(=O)c3ccccn3)CCOC(C)(C)C2)CC1] | (4-(1-(3-ethoxypropyl)piperidin-4-yl)-2,2-dimethyltetrahydro-2H-pyran-4-yl)(pyridin-2-yl)methanone | D | 1.77 | 375.2 |

| EX | Structure | Chemical name | Method | Ret (min) | MS (M + H) |
|---|---|---|---|---|---|
| 105 | 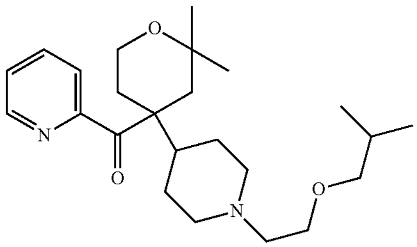 [SMILES: CC(C)COCCN1CCC(C2(C(=O)c3ccccn3)CCOC(C)(C)C2)CC1] | (4-(1-(2-ethoxyethyl)piperidin-4-yl)-2,2-dimethyltetrahydro-2H-pyran-4-yl)(pyridin-2-yl)methanone | D | 2.22 | 403.3 |
| 106 | 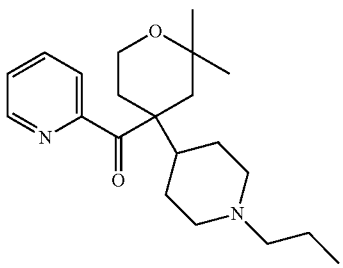 [SMILES: CCCN1CCC(C2(C(=O)c3ccccn3)CCOC(C)(C)C2)CC1] | (4-(1-(2-isobutoxyethyl)piperidin-4-yl)-2,2-dimethyltetrahydro-2H-pyran-4-yl)(pyridin-2-yl)methanone | D | 1.64 | 345.2 |
| 107 | 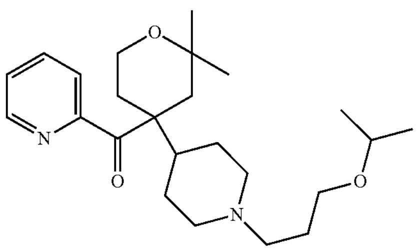 [SMILES: CC(C)OCCCN1CCC(C2(C(=O)c3ccccn3)CCOC(C)(C)C2)CC1] | (4-(1-(3-isopropoxypropyl)piperidin-4-yl)-2,2-dimethyltetrahydro-2H-pyran-4-yl)(pyridin-2-yl)methanone | D | 1.91 | 403.3 |
| 108 | 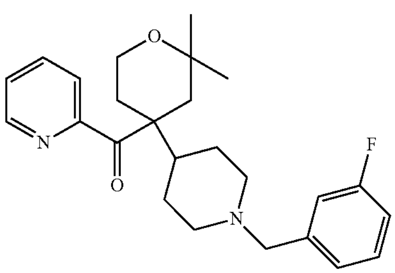 [SMILES: CC1(C)CC(C(=O)c2ccccn2)(C2CCN(Cc3cccc(F)c3)CC2)CCO1] | (4-(1-(3-fluorobenzyl)piperidin-4-yl)-2,2-dimethyltetrahydro-2H-pyran-4-yl)(pyridin-2-yl)methanone | D | 2.47 | 411.3 |
| 109 | 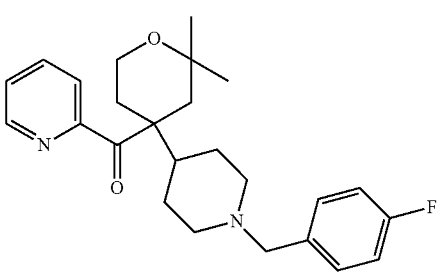 [SMILES: CC1(C)CC(C(=O)c2ccccn2)(C2CCN(Cc3ccc(F)cc3)CC2)CCO1] | (4-(1-(4-fluorobenzyl)piperidin-4-yl)-2,2-dimethyltetrahydro-2H-pyran-4-yl)(pyridin-2-yl)methanone | D | 2.40 | 411.3 |
| 110 | 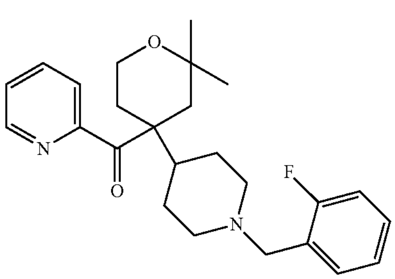 [SMILES: CC1(C)CC(C(=O)c2ccccn2)(C2CCN(Cc3ccccc3F)CC2)CCO1] | (4-(1-(2-fluorobenzyl)piperidin-4-yl)-2,2-dimethyltetrahydro-2H-pyran-4-yl)(pyridin-2-yl)methanone | B | 2.86 | 411.4 |

| EX | Structure | Chemical name | Method | Ret (min) | MS (M + H) |
|---|---|---|---|---|---|
| 111 | 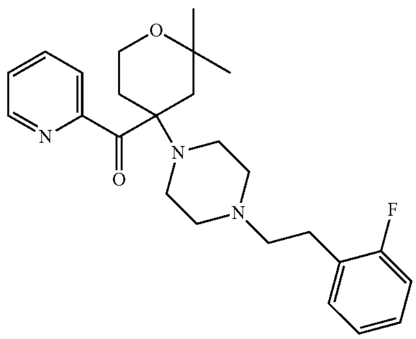 [SMILES: CC1(C)CC(C(=O)c2ccccn2)(N2CCN(CCc3ccccc3F)CC2)CCO1] | (4-(4-(2-fluorophenethyl)piperazin-1-yl)-2,2-dimethyltetrahydro-2H-pyran-4-yl)(pyridin-2-yl)methanone | D | 2.34 | 426.3 |

*Ex 55-56-57-84-85-87 were obtained by addition of vinyl reagents, using EtOH and TEA at 90° C. under microwave irradiating conditions.

Examples 112 and 113. (S) and (R) 1-(4-ethyl-2,2-dimethyltetrahydro-2H-pyran-4-yl)-4-phenethylpiperazine

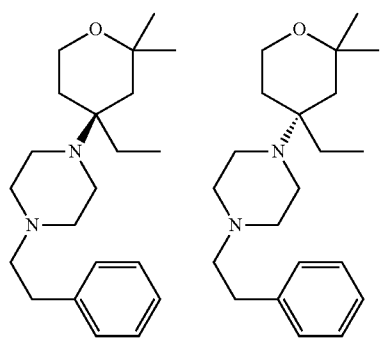 [SMILES: CC[C@]1(N2CCN(CCc3ccccc3)CC2)CCOC(C)(C)C1 ; CC[C@@]1(N2CCN(CCc3ccccc3)CC2)CCOC(C)(C)C1]

Examples 112 and 113 were obtained by chiral preparative HPLC from example 52.

Column: Chiralpak IA; Temperature: ambient; Flow: 13 mL/min; Mobile phase: n-Heptane/(EtOH+0.33% DEA) 97/3 v/v.

Example 112 HPLC-MS (Method D): Ret, 2.39 min; ESI⁺-MS m/z, 331.3 (M+1).

Example 113 HPLC-MS (Method D): Ret, 2.39 min; ESI⁺-MS m/z, 331.3 (M+1).

Examples 114 and 115. (S) and (R) (4-(1-isopentylpiperidin-4-yl)-2,2-dimethyltetrahydro-2H-pyran-4-yl)(pyridin-2-yl)methanone

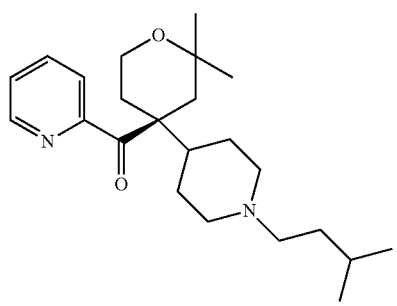

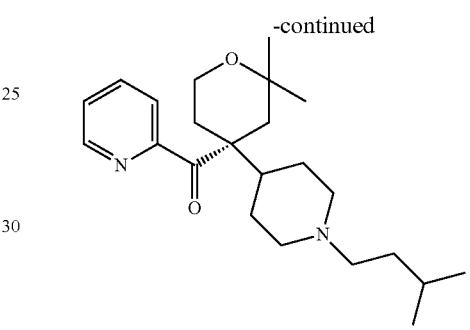

Examples 114 and 115 were obtained by chiral preparative HPLC from example 76.

Column: Chiralpak AD-H; Temperature: ambient; Flow: 11 mL/min; Mobile phase: n-Heptane/(EtOH+0.33% DEA) 98/2 v/v.

Example 114 HPLC-MS (Method D): Ret, 2.12 min; ESI⁺-MS m/z, 373.3 (M+1).

Example 115 HPLC-MS (Method D): Ret, 2.12 min; ESI⁺-MS m/z, 373.3 (M+1).

Example 116. (4-(4-(2-(2-Fluoro-2-methylpropoxy)ethyl)piperazin-1-yl)-2,2-dimethyltetrahydro-2H-pyran-4-yl)(pyridin-2-yl)methanone

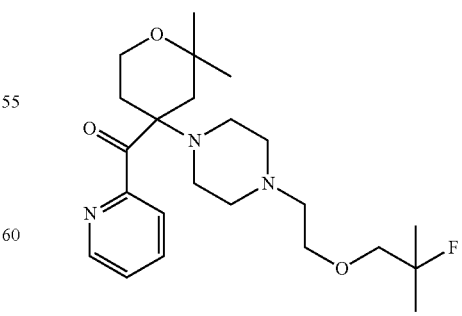

Deoxo-Fluor (bis(2-methoxyethyl)aminosulfur trifluoride, 50% in toluene, 132 μL) was added dropwise at 0° C. to a solution of (4-(4-(2-(2-hydroxy-2-methylpropoxy)

ethyl)piperazin-1-yl)-2,2-dimethyltetrahydro-2H-pyran-4-yl)(pyridin-2-yl)methanone (Example 70, 65 mg, 0.15 mmol) in toluene (4 mL). The mixture was stirred for 1 h at 0° C. and at rt overnight. Then, the solvent was concentrated in vacuo and the residue was partitioned between DCM and 0.1 N NaOH solution. The organic layer was separated, dried over Na$_2$SO$_4$, filtered and concentrated. The crude residue was purified by preparative HPLC (column X-Bridge C18, ACN: NH$_4$HCO$_3$ 10 mM from (2:98 to 95-5), flow 20 ml/min, rt) to give the title compound (14 mg, yield 17%).

HPLC-MS (Method A): Ret, 1.99 min; ESI$^+$-MS m/z, 422.2 (M+1).

This method was used for the preparation of example 117 using example 90 as starting material. Example 118 was also isolated.

a) 1-(9-Phenyl-6-oxaspiro[4.5]decan-9-yl)piperazine

The title compound was obtained following the procedure described in Ex 50 step a, using 1-benzyl-4-(9-phenyl-6-oxaspiro[4.5]decan-9-yl)piperazine (Ex 26) as starting material.

HPLC-MS (Method A): Ret, 1.51 min; ESI$^+$-MS m/z, 301.2 (M+1).

b) Title Compound

The compound obtained in step a (18 mg, 0.06 mmol) was introduced in a process vial, under argon atmosphere, and dissolved in MeOH (2 mL). Nicotinaldehyde (19 mg, 0.18 mmol) and sodium triacetoxyborohydride (15 mg, 0.24

| Ex | Structure | Chemical name | Method | Ret (min) | MS (M + H) |
|---|---|---|---|---|---|
| 117 | 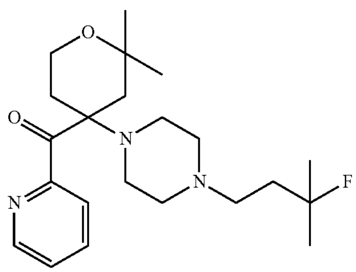 [SMILES: CC(C)(F)CCN1CCN(C2(C(=O)c3ccccn3)CCOC(C)(C)C2)CC1] | (4-(4-(3-fluoro-3-methylbutyl)piperazin-1-yl)-2,2-dimethyltetrahydro-2H-pyran-4-yl)(pyridin-2-yl)methanone | D | 2.06 | 392.3 |
| 118 | 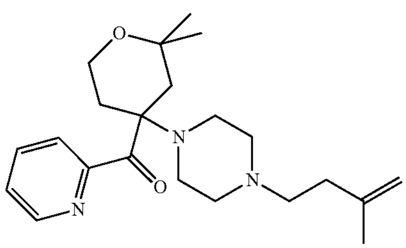 [SMILES: C=C(C)CCN1CCN(C2(C(=O)c3ccccn3)CCOC(C)(C)C2)CC1] | (2,2-Dimethyl-4-(4-(3-methylbut-3-enyl)piperazin-1-yl)tetrahydro-2H-pyran-4-yl)(pyridin-2-yl)methanone | D | 2.20 | 372.3 |

Example 119. 1-(9-Phenyl-6-oxaspiro[4.5]decan-9-yl)-4-(pyridin-3-ylmethyl)piperazine

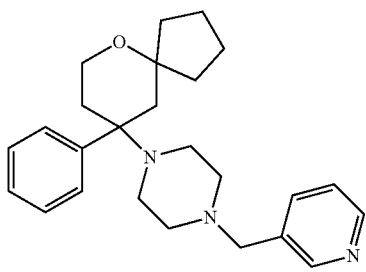

mmol) were added, and the vial was sealed with a septum. The suspension was subjected to microwave irradiating conditions for 30 min at 120° C. and then cooled. The crude product was evaporated to dryness and then suspended in aqueous NaHCO$_3$. The mixture was extracted with DCM and washed with sat aqueous NaHCO$_3$ solution. The organic layer was dried with Na$_2$SO$_4$, filtered and concentrated. The residue was purified by flash chromatography on silica gel, gradient DCM to DCM:MeOH (70:30), to afford the title compound (3 mg, yield 10%).

HPLC-MS (Method A): Ret, 2.12 min; ESI$^+$-MS m/z, 392.3 (M+1).

This method was used for the preparation of examples 120-128 using suitable aldehydes or ketones and the corresponding benzyl examples or INT 2 as starting materials:

| Ex | Structure | Chemical name | Method | Ret (min) | MS (M + H) |
|---|---|---|---|---|---|
| 120 | 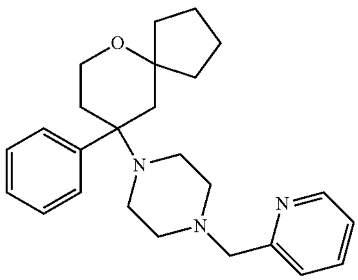 [SMILES: c1ccc(C2(N3CCN(Cc4ccccn4)CC3)CCOC3(CCCC3)C2)cc1] | 1-benzyl-4-(9-phenyl-6-oxaspiro[4.5]decan-9-yl)piperazine | A | 2.18 | 392.2 |
| 121 | 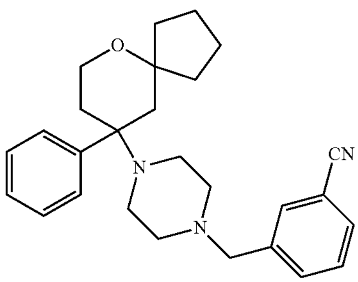 [SMILES: N#Cc1cccc(CN2CCN(C3(c4ccccc4)CCOC4(CCCC4)C3)CC2)c1] | 3-((4-(9-phenyl-6-oxaspiro[4.5]decan-9-yl)piperazin-1-yl)methyl)benzonitrile | A | 2.65 | 416.3 |
| 122 | 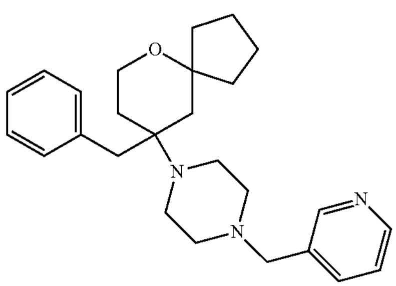 [SMILES: c1ccc(CC2(N3CCN(Cc4cccnc4)CC3)CCOC3(CCCC3)C2)cc1] | 1-(9-benzyl-6-oxaspiro[4.5]decan-9-yl)-4-(pyridin-3-ylmethyl)piperazine | A | 2.33 | 404.4 |
| 123 | 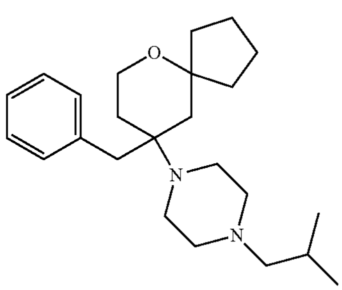 [SMILES: CC(C)CN1CCN(C2(Cc3ccccc3)CCOC3(CCCC3)C2)CC1] | 1-(9-benzyl-6-oxaspiro[4.5]decan-9-yl)-4-isobutyl-piperazine | A | 3.02 | 371.4 |
| 124 | 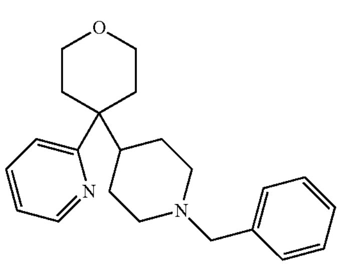 [SMILES: c1ccc(CN2CCC(C3(c4ccccn4)CCOCC3)CC2)cc1] | 2-(4-(1-benzylpiperidin-4-yl)tetrahydro-2H-pyran-4-yl)pyridine | C | 3.93 | 337.2 |

| Ex | Structure | Chemical name | Method | Ret (min) | MS (M + H) |
|---|---|---|---|---|---|
| 125 | 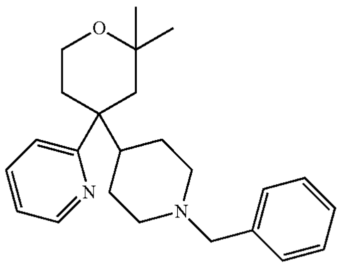 [SMILES: CC1(C)CC(c2ccccn2)(C2CCN(Cc3ccccc3)CC2)CCO1] | 2-(4-(1-benzylpiperidin-4-yl)-2,2-dimethyltetra-hydro-2H-pyran-4-yl)pyridine | C | 4.47 | 365.2 |
| 126 | 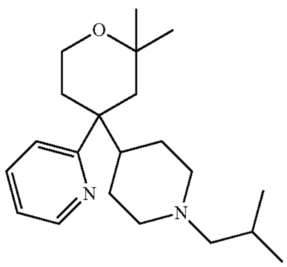 [SMILES: CC(C)CN1CCC(C2(c3ccccn3)CCOC(C)(C)C2)CC1] | 2-(4-(1-isobutylpiperidin-4-yl)-2,2-dimethyltetra-hydro-2H-pyran-4-yl)pyridine | C | 3.52 | 331.2 |
| 127 | 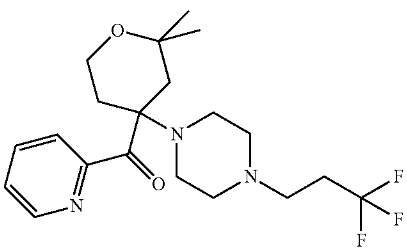 [SMILES: CC1(C)CC(C(=O)c2ccccn2)(N2CCN(CCC(F)(F)F)CC2)CCO1] | (2,2-dimethyl-4-(4-(3,3,3-trifluoropropyl)piperazin-1-yl)tetrahydro-2H-pyran-4-yl)(pyridin-2-yl)methanone | D | 2.15 | 400.3 |
| 128 | 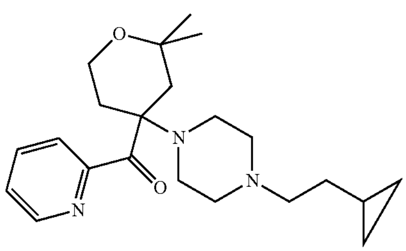 [SMILES: CC1(C)CC(C(=O)c2ccccn2)(N2CCN(CCC3CC3)CC2)CCO1] | (4-(4-(2-cyclopropylethyl)piperazin-1-yl)-2,2-dimethyltetra-hydro-2H-pyran-4-yl)(pyridin-2-yl)methanone | D | 2.16 | 372.3 |

Example 129. (4-(4-Benzylpiperazin-1-yl)-2,2-dimethyltetrahydro-2H-pyran-4-yl)(pyridin-2-yl)methanol

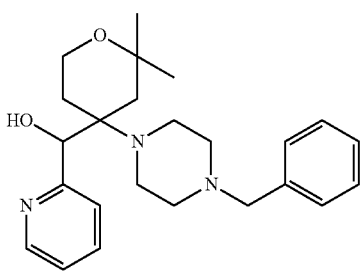 [SMILES: CC1(C)CC(C(O)c2ccccn2)(N2CCN(Cc3ccccc3)CC2)CCO1]

To a solution of (4-(4-benzylpiperazin-1-yl)-2,2-dimethyltetrahydro-2H-pyran-4-yl)(pyridin-2-yl)methanone (Ex 1, 161 mg, 0.409 mmol) in EtOH (10 mL), sodium tetrahydroborate (31 mg, 0.818 mmol) was added at 0° C. The reaction was stirred at rt for 2 h, it was quenched with water and stirred at rt for 2 days. Then, DCM was added and the aqueous layer was separated and extracted several times with DCM. The organic layers were combined, dried over $Na_2SO_4$, filtered and concentrated to give the title compound as a solid (140 mg, 86% yield).

HPLC-MS (Method B): Ret, 2.19 min; ESI$^+$-MS m/z, 396.2 (M+1).

This method was used for the preparation of Ex 130-131 using the corresponding examples 21 and 22 as starting materials:

| Ex | Structure | Chemical name | Method | Ret (min) | MS (M + H) |
|---|---|---|---|---|---|
| 130 | 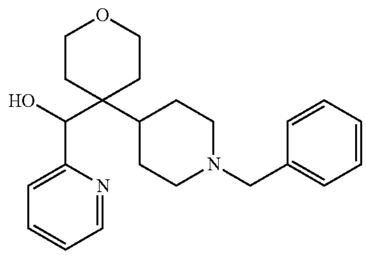 [SMILES: OC(c1ccccn1)C1(C2CCN(Cc3ccccc3)CC2)CCOCC1] | (4-(1-benzylpiperidin-4-yl)tetrahydro-2H-pyran-4-yl)(pyridin-2-yl)methanol | C | 3.24 | 367.2 |
| 131 | 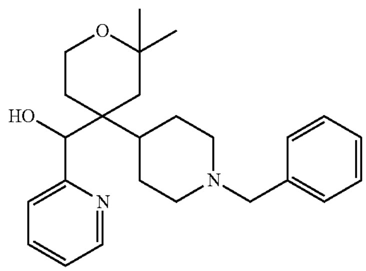 [SMILES: CC1(C)CC(C2CCN(Cc3ccccc3)CC2)(C(O)c2ccccn2)CCO1] | (4-(1-benzylpiperidin-4-yl)-2,2-dimethyltetrahydro-2H-pyran-4-yl)(pyridin-2-yl)methanol | C | 3.81 | 395.2 |

Examples 132 and 133. (S) and (R) (4-(4-isopentylpiperazin-1-yl)-2,2-dimethyltetrahydro-2H-pyran-4-yl)(pyridin-2-yl)methanone

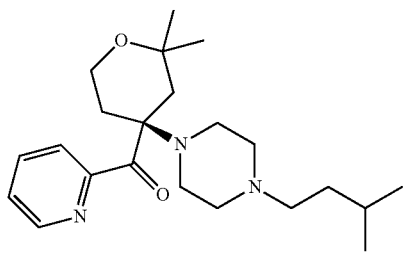

-continued

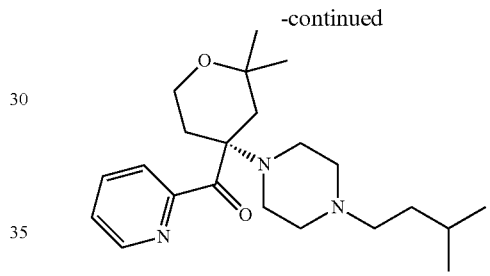

Examples 132 and 133 were obtained by chiral preparative HPLC from example 64.

Column: Chiralpak IA; Temperature: ambient; Flow: 12 mL/min; Mobile phase: n-Heptane/(EtOH+0.33% DEA) 90/10 v/v.

Example 75 HPLC-MS (Method A): Ret, 2.27 min; ESI$^+$-MS m/z, 374.2 (M+1).

Example 76 HPLC-MS (Method A): Ret, 2.27 min; ESI$^+$-MS m/z, 374.2 (M+1).

This method was used for the preparation of Ex 134 and 135 using example 65 as starting material:

| Ex | Structure | Chemical name | Method | Ret (min) | MS (M + H) |
|---|---|---|---|---|---|
| 134 | 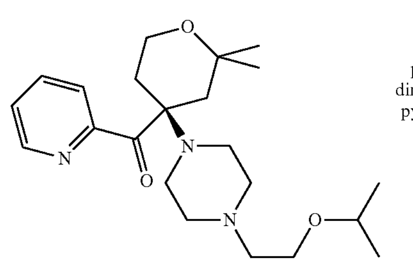 | (S)-(4-(4-(2-isopropoxyethyl)piperazin-1-yl)-2,2-dimethyltetrahydro-2H-pyran-4-yl)(pyridin-2-yl)methanone | A | 1.90 | 390.2 |

| Ex | Structure | Chemical name | Method | Ret (min) | MS (M + H) |
|---|---|---|---|---|---|
| 135 | 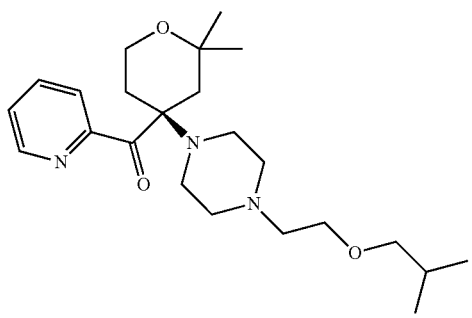 | (R)-(4-(4-(2-isopropoxyethyl)piperazin-1-yl)-2,2-dimethyltetrahydro-2H-pyran-4-yl)(pyridin-2-yl)methanone | A | 1.90 | 390.2 |

Examples 136 and 137. (S) and (R) (4-(4-(2-isobutoxyethyl)piperazin-1-yl)-2,2-dimethyltetrahydro-2H-pyran-4-yl)(pyridin-2-yl)methanone

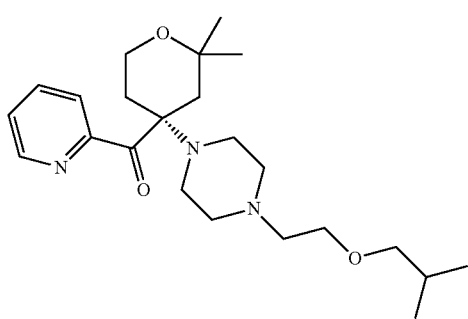

Examples 136 and 137 were obtained by chiral preparative HPLC from example 66.

Column: Chiralpak IC; Temperature: ambient; Flow: 12 mL/min; Mobile phase: n-Heptane/(IPA+0.33% DEA) 90/10 v/v.

Example 79 HPLC-MS (Method A): Ret, 2.22 min; ESI⁺-MS m/z, 404.2 (M+1).

Example 80 HPLC-MS (Method A): Ret, 2.22 min; ESI⁺-MS m/z, 404.2 (M+1).

Example 138. (4-((S)-3-(Benzyl(methyl)amino)pyrrolidin-1-yl)-2,2-dimethyltetrahydro-2H-pyran-4-yl)(pyridin-2-yl)methanone

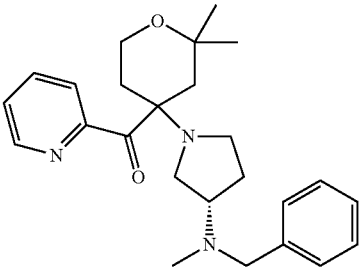 [SMILES: CN(Cc1ccccc1)[C@H]1CCN(C2(C(=O)c3ccccn3)CCOC(C)(C)C2)C1]

a) (S) tert-Butyl 3-(methylsulfonyloxy)pyrrolidine-1-carboxylate

Et$_3$N (5.58 mL, 40 mmol) was added to a solution of (S) tert-butyl 3-hydroxypyrrolidine-1-carboxylate (3 g, 16.02 mmol) in dry DCM (35 mL). The solution was cooled to 0° C., stirred for 10 min and then, methanesulfonyl chloride (2.1 mL, 27.24 mmol) was added and the reaction mixture was stirred at 0° C. After 1 h the reaction mixture was allowed to warm to rt and stirred for 0.5 h. The mixture was poured into ice-water and diluted with DCM. The organic layer was washed with water, dried over Na$_2$SO$_4$, filtered and evaporated to dryness to afford the title compound as a crude yellow oil (4.25 g) that was used in the next step without further purification.

$^1$H NMR (400 MHz, CDCl3) δ ppm 1.49 (s, 9H) 2.08-2.21 (m, 1H) 2.29 (br. s., 1H) 3.07 (s, 3H) 3.36-3.64 (m, 3H) 3.65-3.75 (m, 1H) 5.28 (tt, J=4.23, 2.08 Hz, 1H))

b) (S) tert-Butyl 3-(benzyl(methyl)amino)pyrrolidine-1-carboxylate

A mixture of the compound obtained in step a (4.25 g, 16.02 mmol)) and N-methyl-1-phenylmethanamine (6.20 mL, 48.07 mmol) was stirred and heated at 100° C. for 3 h, under nitrogen. The residue was partitioned between DCM/water. The aqueous phase was further extracted with dichloromethane. The combined extracts were washed with brine, dried (Na$_2$SO$_4$) filtered and evaporated. The crude product thus obtained was purified by flash chromatography on silica gel, gradient CH:AcOEt from (100:0) to (70:30) to give the title compound as yellow oil (2.93 g, 63% yield).

HPLC-MS (Method A): Ret, 2.20 min; ESI⁺-MS m/z, 291 (M+1).

c) (S) N-Benzyl-N-methylpyrrolidin-3-amine

Over a suspension of (the compound obtained in step b (2.5 g, 8.71 mmol) in DCM (20 mL), TFA (16.7 mL, 218 mmol) was added and the mixture was stirred at rt for 1 h. The solvent was concentrated off and the crude residue was diluted with H$_2$O (30 mL), taken up to pH 12 with 10% aqueous NaOH solution and extracted with DCM (30 mL). The combined organic layers were dried over Na$_2$SO$_4$, filtered and concentrated to give the title compound as brown oil (1.66 g, quant yield).

HPLC-MS (Method A): Ret, 1.01 min; ESI⁺-MS m/z, 191 (M+1).

d) 4-((S)-3-(Benzyl(methyl)amino)pyrrolidin-1-yl)-2,2-dimethyltetrahydro-2H-pyran-4-carbonitrile The title compound was obtained following the procedure described in INT 1, using compound obtained in step c as starting material.

e) Title Compound

The title compound was obtained following the procedure described in Ex 1, using compound obtained in step d as starting material.

HPLC-MS (Method A): Ret, 2.33 min; ESI⁺-MS m/z, 408.2 (M+1).

This method was used for the preparation of example 139 using (R) tert-butyl 3-hydroxypyrrolidine-1-carboxylate as starting material.

| Ex | Structure | Chemical name | Method | Ret (min) | MS (M + H) |
|---|---|---|---|---|---|
| 139 | 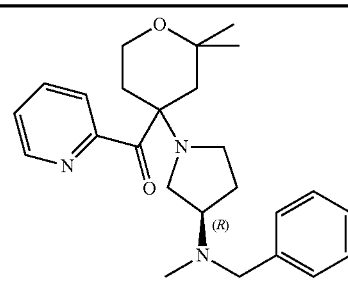 | (R)-(4-(4-(2-isopropoxyethyl)piperazin-1-yl)-2,2-dimethyltetrahydro-2H-pyran-4-yl)(pyridin-2-yl)methanone | D | | 408.4 |

Examples 140 and 141. ((S)-4-((S)-3-(benzyl(methyl)amino)pyrrolidin-1-yl)-2,2-dimethyltetrahydro-2H-pyran-4-yl)(pyridin-2-yl)methanone and ((R)-4-((S)-3-(benzyl(methyl)amino)pyrrolidin-1-yl)-2,2-dimethyltetrahydro-2H-pyran-4-yl)(pyridin-2-yl)methanone The diastereoisomers of example 138 were separated by preparative HPLC using Chiralpak IC Column, flow rate 12 mL/min A: n-Heptane B: (IPA+0.33% DEA) 95/5 v/v, rt to give:

| Ex | Structure | Chemical name | Method | Ret (min) | MS (M + H) |
|---|---|---|---|---|---|
| 140 | 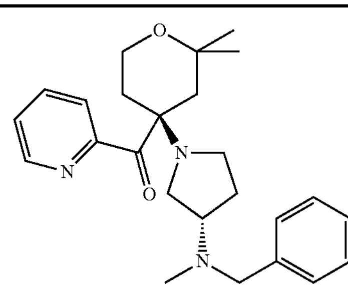 | ((S)-4-((S)-3-(benzyl(methyl)amino)pyrrolidin-1-yl)-2,2-dimethyltetrahydro-2H-pyran-4-yl)(pyridin-2-yl)methanone | A | 2.33 | 408 |

| Ex | Structure | Chemical name | Method | Ret (min) | MS (M + H) |
|---|---|---|---|---|---|
| 141 | 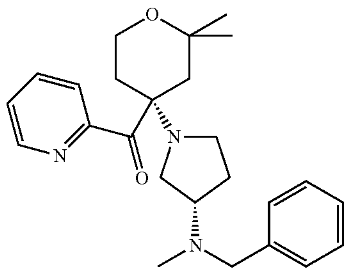 [SMILES: CN(Cc1ccccc1)[C@H]1CCN([C@]2(C(=O)c3ccccn3)CCOC(C)(C)C2)C1] | ((R)-4-((S)-3-(benzyl(methyl)amino)pyrrolidin-1-yl)-2,2-dimethyltetrahydro-2H-pyran-4-yl)(pyridin-2-yl)methanone | A | 2.33 | 408 |

Examples 142 and 143. ((R)-4-((R)-3-(benzyl(methyl)amino)pyrrolidin-1-yl)-2,2-dimethyltetrahydro-2H-pyran-4-yl)(pyridin-2-yl)methanone and ((S)-4-((R)-3-(benzyl(methyl)amino)pyrrolidin-1-yl)-2,2-dimethyltetrahydro-2H-pyran-4-yl)(pyridin-2-yl)methanone The diastereoisomers of example 139 were separated by preparative HPLC using Chiralpak IC Column, flow rate 12 mL/min A: n-Heptano; B: (IPA+0.33% DEA) 95/5 v/v, rt to give:

Examples 144-155 were prepared according to the procedure described in example 1, using suitable intermediates 1 as starting materials. The compounds were obtained as diastereomeric mixtures or racemates, and were separated by preparative HPLC to give the final examples. HPLC conditions were: Chiralpak IC Column, flow rate 10 or 11 or 12 mL/min, A: n-Heptane B: (IPA+0.33% DEA) 95/5 v/v or A: ACN B: (IPA+5% DEA) 98/2 v/v or A: n-Heptane B: (EtOH+0.33% DEA) 90/10 v/v rt. For examples 146 and 147, the conditions were: Lux C4 column, flow rate 21 mL/min, A: ACN B: (IPA+0.1% NH3) 90/10 v/v, rt.

| Ex | Structure | Chemical name | Method | Ret (min) | MS (M + H) |
|---|---|---|---|---|---|
| 142 | 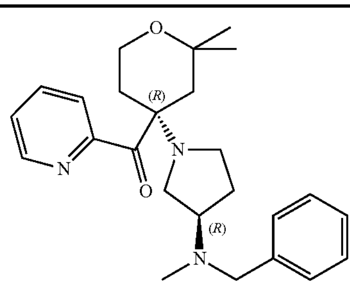 | ((R)-4-((R)-3-(benzyl(methyl)amino)pyrrolidin-1-yl)-2,2-dimethyltetrahydro-2H-pyran-4-yl)(pyridin-2-yl)methanone | D | 2.37 | 408.4 |
| 143 | 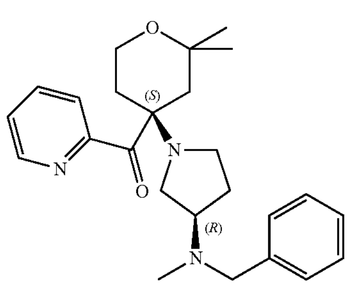 | ((S)-4-((R)-3-(benzyl(methyl)amino)pyrrolidin-1-yl)-2,2-dimethyltetrahydro-2H-pyran-4-yl)(pyridin-2-yl)methanone | D | 2.38 | 408.4 |

| Ex | Structure | Chemical name | Method | Ret (min) | MS (M + H) |
|---|---|---|---|---|---|
| 144 | 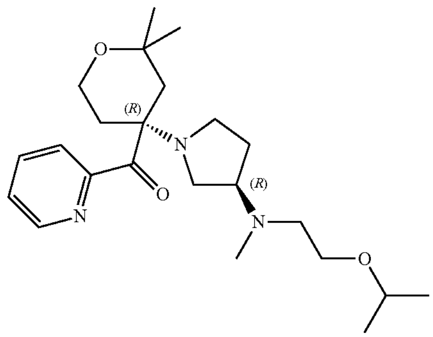 | ((R)-4-((R)-3-((2-isopropoxyethyl)(methyl)amino)pyrrolidin-1-yl)-2,2-dimethyltetrahydro-2H-pyran-4-yl)(pyridin-2-yl)methanone | A | 2.10 | 404.2 |
| 145 | 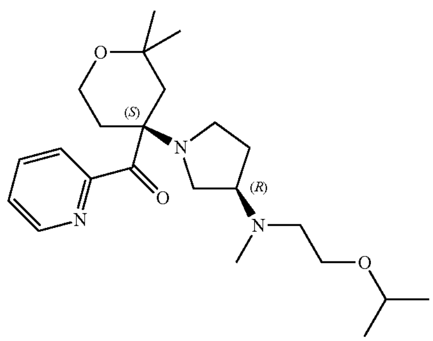 | ((S)-4-((R)-3-((2-isopropoxyethyl)(methyl)amino)pyrrolidin-1-yl)-2,2-dimethyltetrahydro-2H-pyran-4-yl)(pyridin-2-yl)methanone | A | 2.10 | 404.2 |
| 146 | 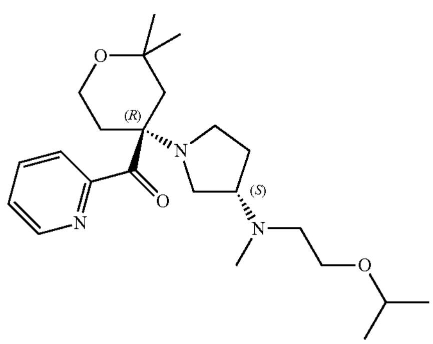 | ((R)-4-((S)-3-((2-isopropoxyethyl)(methyl)amino)pyrrolidin-1-yl)-2,2-dimethyltetrahydro-2H-pyran-4-yl)(pyridin-2-yl)methanone | A | 2.63 | 404.2 |
| 147 | 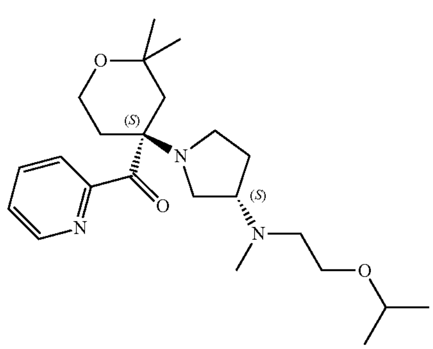 | ((S)-2-((S)-3-((2-isopropoxyethyl)(methyl)amino)pyrrolidin-1-yl)-2,2-dimethyltetrahydro-2H-pyran-4-yl)(pyridin-2-yl)methanone | A | 2.63 | 404.2 |

-continued

| Ex | Structure | Chemical name | Method | Ret (min) | MS (M + H) |
|---|---|---|---|---|---|
| 148 | 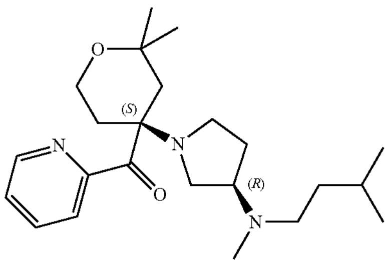 | ((S)-4-((R)-3-(isopentyl(methyl)amino)pyrrolidin-1-yl)-2,2-dimethyltetrahydro-2H-pyran-4-yl)(pyridin-2-yl)methanone | A | 2.96 | 388.2 |
| 149 | 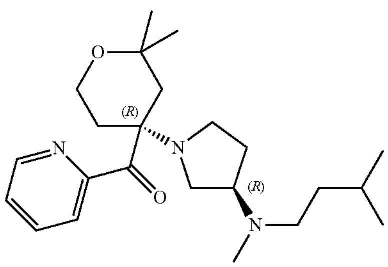 | ((R)-4-((R)-3-(isopentyl(methyl)amino)pyrrolidin-1-yl)-2,2-dimethyltetrahydro-2H-pyran-4-yl)(pyridin-2-yl)methanone | A | 2.96 | 388.2 |
| 150 | 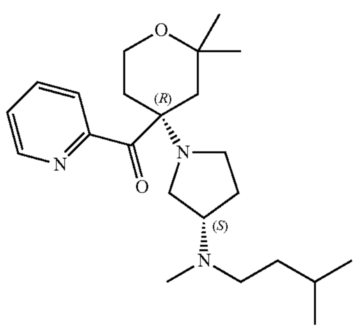 | ((R)-4-((S)-3-(isopentyl(methyl)amino)pyrrolidin-1-yl)-2,2-dimethyltetrahydro-2H-pyran-4-yl)(pyridin-2-yl)methanone | A | 2.13 | 388.3 |
| 151 | 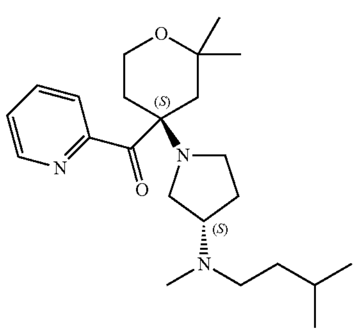 | ((S)-4-((S)-3-(isopentyl(methyl)amino)pyrrolidin-1-yl)-2,2-dimethyltetrahydro-2H-pyran-4-yl)(pyridin-2-yl)methanone | A | 2.12 | 388.4 |

| Ex | Structure | Chemical name | Method | Ret (min) | MS (M + H) |
|---|---|---|---|---|---|
| 152 | 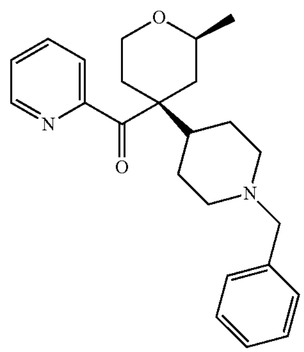 [SMILES: C[C@H]1C[C@@](C(=O)c2ccccn2)(C2CCN(Cc3ccccc3)CC2)CCO1] | 4-(1-benzylpiperidin-4-yl)-2-methyltetrahydro-2H-pyran-4-yl)(pyridin-2-yl)methanone | A | 2.43 | 379.1 |
| 153 | 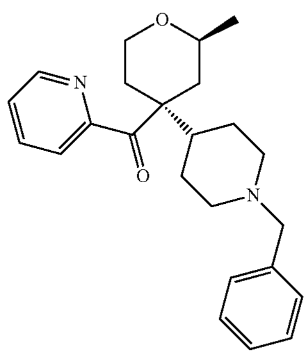 [SMILES: C[C@H]1C[C@](C(=O)c2ccccn2)(C2CCN(Cc3ccccc3)CC2)CCO1] | 4-(1-benzylpiperidin-4-yl)-2-methyltetrahydro-2H-pyran-4-yl)(pyridin-2-yl)methanone | A | 2.27 | 379.2 |
| 154 | 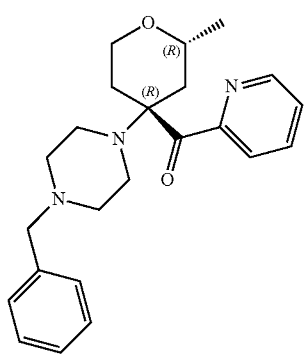 | ((2R,4R)-2-(4-benzylpiperazin-1-yl)-2-methyltetrahydro-2H-pyran-4-yl)(pyridin-2-yl)methanone | D | 2.16 | 380.3 |
| 155 | 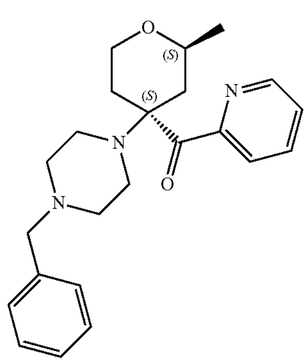 | ((2S,4S)-4-(4-benzylpiperazin-1-yl)-2-methyltetrahydro-2H-pyran-4-yl)(pyridin-2-yl)methanone | D | 2.16 | 380.3 |

Examples 156-166 were prepared according to the procedure described in example 29, using suitable intermediates 1 as starting materials.

| Ex | Structure | Chemical name | Method | Ret (min) | MS (M + H) |
|---|---|---|---|---|---|
| 156 | 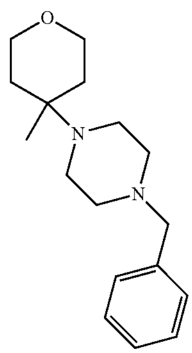 [SMILES: CC1(N2CCN(Cc3ccccc3)CC2)CCOCC1] | 1-Benzyl-4-(4-methyltetrahydro-2H-pyran-4-yl)piperazine | A | 1.67 | 275 |
| 157 | 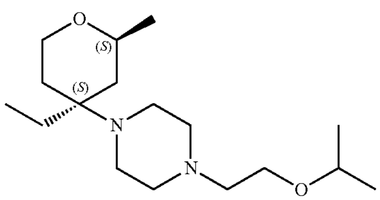 | 1-((2S,4S)-4-ethyl-2-methyltetrahydro-2H-pyran-4-yl)-4-(2-isopropoxyethyl)piperazine | A | 1.69 | 299.2 |
| 158 | 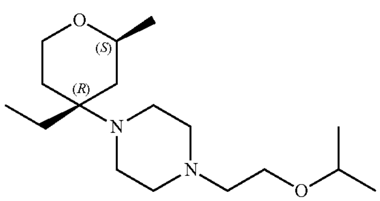 | 1-((2S,4R)-4-ethyl-2-methyltetrahydro-2H-pyran-4-yl)-4-(2-isopropoxyethyl)piperazine | A | 1.94 | 299.2 |
| 159 | 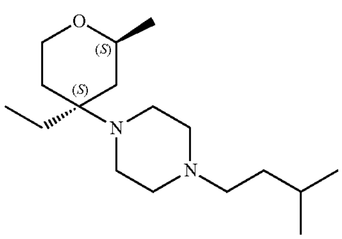 | 1-((2S,4S)-4-ethyl-2-methyltetrahydro-2H-pyran-4-yl)-4-isopentylpiperazine | A | 2.02 | 283.2 |
| 160 | 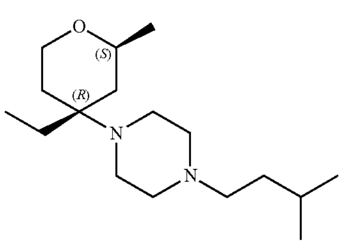 | 1-((2S,4R)-4-ethyl-2-methyltetrahydro-2H-pyran-4-yl)-4-isopentylpiperazine | A | 2.15 | 283.2 |
| 161 | 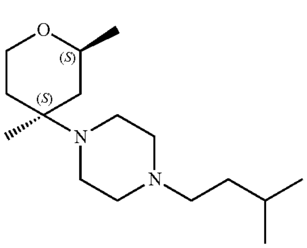 | 1-((2S,4S)-2,4-dimethyltetrahydro-2H-pyran-4-yl)-4-isopentylpiperazine | A | 1.64 | 269.2 |

-continued

| Ex | Structure | Chemical name | Method | Ret (min) | MS (M + H) |
|---|---|---|---|---|---|
| 162 | 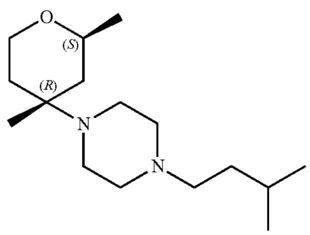 | 1-((2S,4R)-2,4-dimethyltetrahydro-2H-pyran-4-yl)-4-isopentylpiperazine | A | 1.96 | 269.2 |
| 163 | 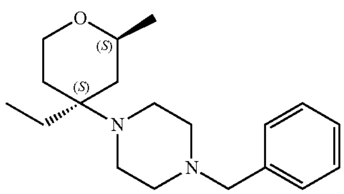 | 1-benzyl-4-((2S,4S)-4-ethyl-2-methyltetrahydro-2H-pyran-4-yl)piperazine | A | 2.19 | 303.2 |
| 164 | 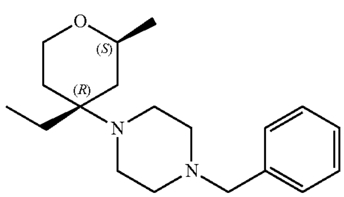 | 1-benzyl-4-((2S,4R)-4-ethyl-2-methyltetrahydro-2H-pyran-4-yl)piperazine | A | 2.44 | 303.2 |
| 165 | 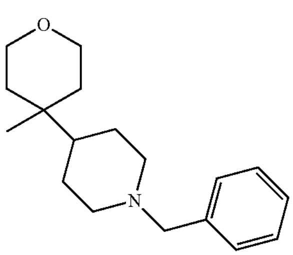 [SMILES: CC1(C2CCN(Cc3ccccc3)CC2)CCOCC1] | 1-benzyl-4-(4-methyltetrahydro-2H-pyran-4-yl)piperidine | | | 274.2 |
| 166 | 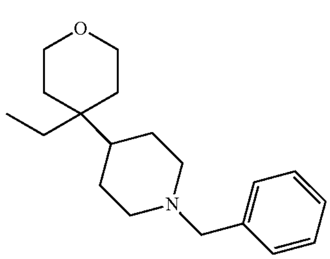 [SMILES: CCC1(C2CCN(Cc3ccccc3)CC2)CCOCC1] | 1-benzyl-4-(4-ethyltetrahydro-2H-pyran-4-yl)piperidine | | | 288.2 |

Example 167. 1-Benzyl-4-(4-ethyl-2,2-dimethyltetrahydro-2H-pyran-4-yl)piperidine

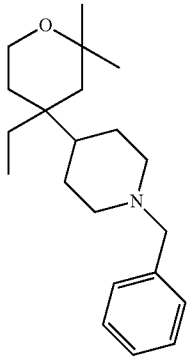 [SMILES: CCC1(C2CCN(Cc3ccccc3)CC2)CCOC(C)(C)C1]

a) 1-(4-(1-Benzylpiperidin-4-yl)-2,2-dimethyltetrahydro-2H-pyran-4-yl)ethanimine 4-(1-Benzylpiperidin-4-yl)-2,2-dimethyltetrahydro-2H-pyran-4-carbonitrile (INT 1Q, 375 mg, 1.2 mmol) was dissolved in THF, under argon atmosphere and cooled down to 0° C. At this temperature methyllithium (1.6 M in ether, 7.5 mL, 12 mmol) was added. The reaction was slowly allowed to reach rt. and stirred overnight. The mixture was quenched with NH$_4$Cl and volatiles were removed under vacuum. The crude residue was extracted with AcOEt, dried over sodium sulphate, filtered and concentrated to give a crude product that was used in following step without further purification (337 mg, 68% purity, yield 58%).

HPLC-MS (Method A): Ret 2.04 min; ESI$^+$-MS m/z, 329 (M+1).

b) 1-(4-(1-Benzylpiperidin-4-yl)-2,2-dimethyltetrahydro-2H-pyran-4-yl)ethanone The crude imine obtained in step a (337 mg, 0.7 mmol) was dissolved in THF (10 mL) and 3 N HCl (ca. 4 mL) was added. The reaction mixture was stirred until full conversion to ketone was achieved (HPLC analysis). The mixture was made alkaline with 10% NaOH and extracted twice with AcOEt. The combined organic phases were dried over Na$_2$SO$_4$, filtered and concentrated. The crude product was purified by flash chromatography on silica gel, eluents DCM/MeOH, from 0 to 35% MeOH, to give the title compound (210 mg, yield 91%).

HPLC-MS (Method A): Ret, 2.38 min; ESI$^+$-MS m/z, 330 (M+1).

c) 1-(4-(1-Benzylpiperidin-4-yl)-2,2-dimethyltetrahydro-2H-pyran-4-yl)ethanol A solution of LiAlH$_4$ (1M in THF, 1.9 mL, 1.9 mmol) was added dropwise at 0° C. to a solution of the compound obtained in step b (210 mg, 0.64 mmol), in dry THF (6 mL). The mixture was allowed to reach rt and stirred overnight. Then, the solution was quenched with NaOH (2.5 M, 2 mL) at 0° C., filtered and washed with more THF (4×10 mL). The filtrate was evaporated to dryness to give the title compound (203 mg, yield 96%).

HPLC-MS (Method A): Ret, 2.08 min; ESI$^+$-MS m/z, 332 (M+1).

d) O-(1-(4-(1-Benzylpiperidin-4-yl)-2,2-dimethyltetrahydro-2H-pyran-4-yl)ethyl) 1H-imidazole-1-carbothioate In a kimax tube, a solution of the compound obtained in step c, obtained in step c (200 mg, 0.6 mmol), thiocarbonyldiimidazolide (323 mg, 1.8 mmol), and 4-(dimethylamino)pyridine (22 mg, 0.18 mmol) in a minimum amount of ether was evaporated to dryness. The resulting solid was heated at 50-55° C. for 2.5 h under nitrogen atmosphere. Then, the residue was purified by column chromatography, DCM/MeOH, from 0 to 10% to give the title compound (203 mg, yield 76%).

HPLC-MS (Method A): Ret, 2.84 min; ESI$^+$-MS m/z, 442.6 (M+1).

e) Title Compound

To a solution of the compound obtained in step d (180 mg, 0.41 mmol) and (E)-3,3'-(diazene-1,2-diyl)bis(2-methylpropanenitrile) (AIBN, 7 mg, 0.04 mmol) in anh. Toluene (5 mL), 1,1,1,3,3,3-hexamethyl-2-(trimethylsilyl)trisilane ((TMS)$_3$SiH, 0.6 mL, 2 mmol) was added. The solution was fully degassed with Ar and it was refluxed for 4 h. Volatiles were removed under vacuum. The residue was extracted in EtOAc (50 mL), washed with aq sat NaHCO$_3$ solution and the organic layer was dried and concentrated under vacuum. The crude product was purified by column chromatography in DCM/MeOH, from 0 to 50% to give title compound (117 mg, yield 90%).

HPLC-MS (Method A): Ret, 2.53 min; ESI$^+$-MS m/z, 316.2 (M+1).

Examples 168-239 were prepared according to the procedure described in example 50, using the adequate alkylating agents and the corresponding benzyl examples as starting materials

| Ex | Structure | Chemical name | Method | Ret (min) | MS (M + H) |
|---|---|---|---|---|---|
| 168 | 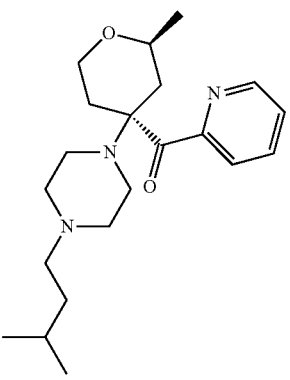 [SMILES: CC(C)CCN1CCN([C@@]2(C(=O)c3ccccn3)CCO[C@@H](C)C2)CC1] | 4-(4-isopentylpiperazin-1-yl)-2-methyltetrahydro-2H-pyran-4-yl)(pyridin-2-yl)methanone | A | 2.12 | 360 |
| 169 | 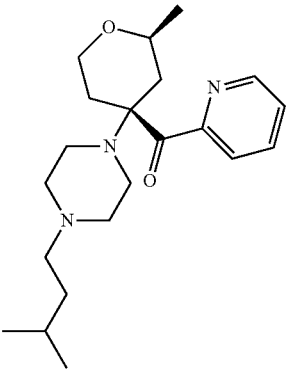 [SMILES: CC(C)CCN1CCN([C@]2(C(=O)c3ccccn3)CCO[C@@H](C)C2)CC1] | 4-(4-isopentylpiperazin-1-yl)-2-methyltetrahydro-2H-pyran-4-yl)(pyridin-2-yl)methanone | A | 2.22 | 360 |
| 170 | 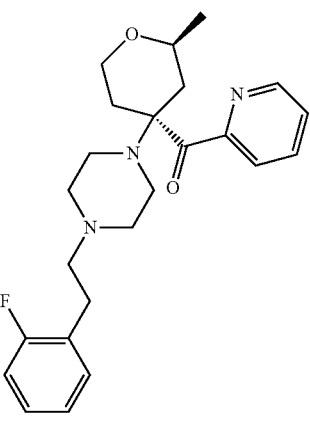 [SMILES: C[C@H]1C[C@@](C(=O)c2ccccn2)(N2CCN(CCc3ccccc3F)CC2)CCO1] | 4-(4-(2-fluorophenethyl)piperazin-1-yl)-2-methyltetrahydro-2H-pyran-4-yl)(pyridin-2-yl)methanone | A | 2.23 | 412 |
| 171 | 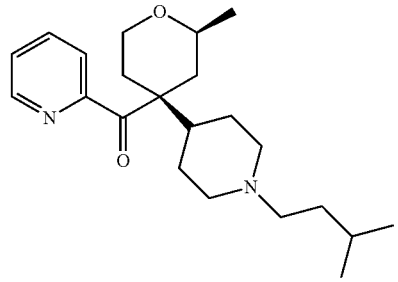 [SMILES: CC(C)CCN1CCC([C@@]2(C(=O)c3ccccn3)CCO[C@@H](C)C2)CC1] | 4-(1-isopentylpiperidin-4-yl)-2-methyltetrahydro-2H-pyran-4-yl)(pyridin-2-yl)methanone | A | 2.66 | 359.2 |

| Ex | Structure | Chemical name | Method | Ret (min) | MS (M + H) |
|---|---|---|---|---|---|
| 172 | 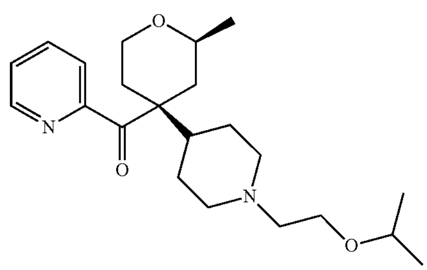 [SMILES: CC(C)OCCN1CCC([C@@]2(C(=O)c3ccccn3)CCO[C@@H](C)C2)CC1] | 4-(1-(2-isopropoxyethyl)piperidin-4-yl)-2-methyltetrahydro-2H-pyran-4-yl)(pyridin-2-yl)methanone | A | 2.29 | 375.2 |
| 173 | 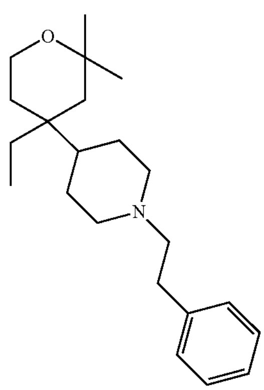 [SMILES: CCC1(C2CCN(CCc3ccccc3)CC2)CCOC(C)(C)C1] | 4-(4-ethyl-2,2-dimethyltetrahydro-2H-pyran-4-yl)-1-phenethylpiperidine | A | 2.68 | 330.2 |
| 174 | 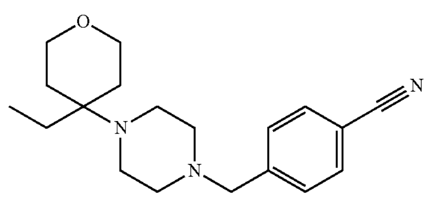 [SMILES: CCC1(N2CCN(Cc3ccc(C#N)cc3)CC2)CCOCC1] | 4-((4-(4-ethyltetrahydro-2H-pyran-4-yl)piperazin-1-yl)methyl)benzonitrile | B | 2.72 | 314.3 |
| 175 | 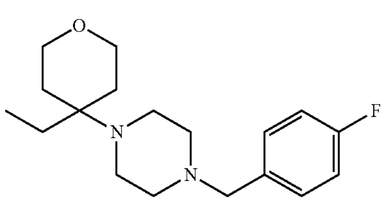 [SMILES: CCC1(N2CCN(Cc3ccc(F)cc3)CC2)CCOCC1] | 1-(4-ethyltetrahydro-2H-pyran-4-yl)-4-(4-fluorobenzyl)piperazine | A | 2.26 | 307.3 |
| 176 | 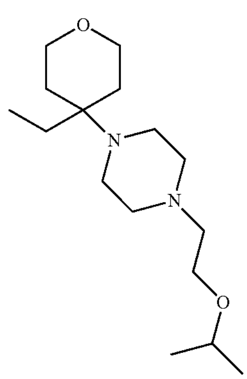 [SMILES: CCC1(N2CCN(CCOC(C)C)CC2)CCOCC1] | 1-(4-ethyltetrahydro-2H-pyran-4-yl)-4-(2-isopropoxyethyl)piperazine | A | 1.67 | 285.3 |

-continued

| Ex | Structure | Chemical name | Method | Ret (min) | MS (M + H) |
|----|-----------|---------------|--------|-----------|------------|
| 177 | 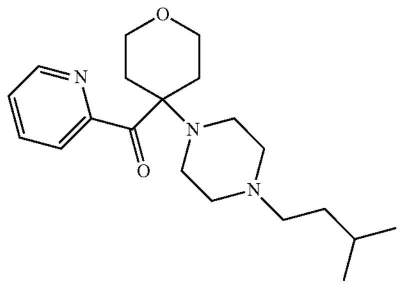 [SMILES: CC(C)CCN1CCN(C2(C(=O)c3ccccn3)CCOCC2)CC1] | (4-(4-isopentylpiperazin-1-yl)tetrahydro-2H-pyran-4-yl)(pyridin-2-yl)methanone | A | 2.05 | 346.3 |
| 178 | 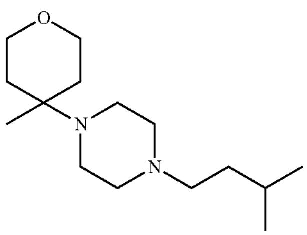 [SMILES: CC(C)CCN1CCN(C2(C)CCOCC2)CC1] | 1-isopentyl-4-(4-methyltetrahydro-2H-pyran-4-yl)piperazine | A | 1.49 | 255.3 |
| 179 | 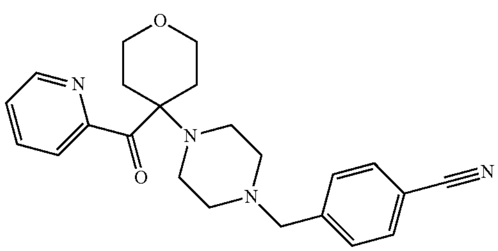 [SMILES: N#Cc1ccc(CN2CCN(C3(C(=O)c4ccccn4)CCOCC3)CC2)cc1] | 4-((4-(4-picolinoyltetrahydro-2H-pyran-4-yl)piperazin-1-yl)methyl)benzonitrile | A | 2.02 | 391.2 |
| 180 | 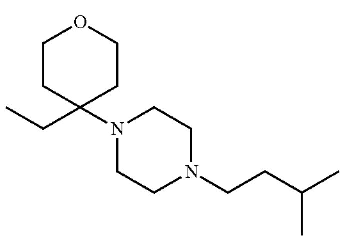 [SMILES: CCC1(N2CCN(CCC(C)C)CC2)CCOCC1] | 1-(4-ethyltetrahydro-2H-pyran-4-yl)-4-isopentylpiperazine | A | 1.91 | 269.3 |
| 181 | 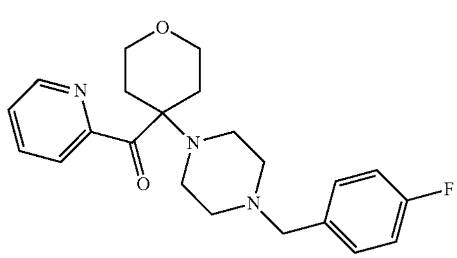 [SMILES: O=C(c1ccccn1)C1(N2CCN(Cc3ccc(F)cc3)CC2)CCOCC1] | (4-(4-(4-fluorobenzyl)piperazin-1-yl)tetrahydro-2H-pyran-4-yl)(pyridin-2-yl)methanone | A | 2.17 | 384.1 |
| 182 | 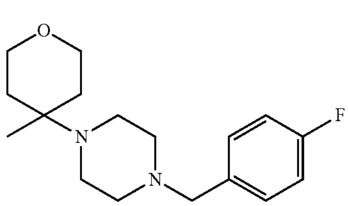 [SMILES: CC1(N2CCN(Cc3ccc(F)cc3)CC2)CCOCC1] | 1-(4-fluorobenzyl)-4-(4-methyltetrahydro-2H-pyran-4-yl)piperazine | A | 1.76 | 293.1 |

-continued

| Ex | Structure | Chemical name | Method | Ret (min) | MS (M + H) |
|---|---|---|---|---|---|
| 183 | 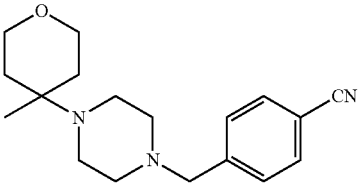 [SMILES: CC1(N2CCN(Cc3ccc(C#N)cc3)CC2)CCOCC1] | 4-((4-(4-methyltetrahydro-2H-pyran-4-yl)piperazin-1-yl)methyl)benzonitrile | A | 1.63 | 300.1 |
| 184 | 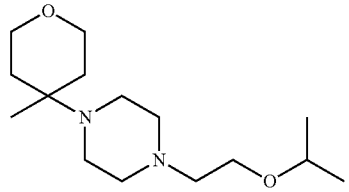 | 1-(2-isopropoxyethyl)-4-(4-methyltetrahydro-2H-pyran-4-yl)piperazine | A | 1.25 | 271.2 |
| 185 | 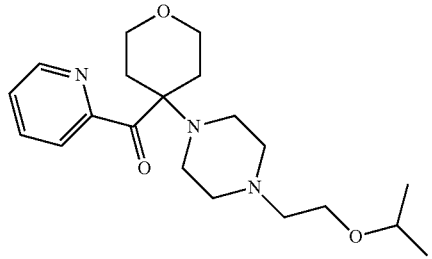 [SMILES: CC(C)OCCN1CCN(C2(C(=O)c3ccccn3)CCOCC2)CC1] | (4-(4-(2-isopropoxyethyl)piperazin-1-yl)tetrahydro-2H-pyran-4-yl)(pyridin-2-yl)methanone | A | 1.73 | 362.2 |
| 186 | 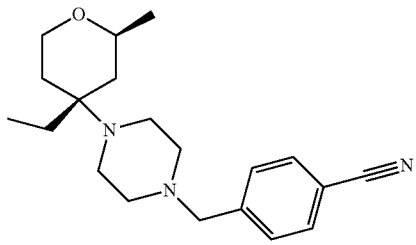 [SMILES: CC[C@@]1(N2CCN(Cc3ccc(C#N)cc3)CC2)CCO[C@@H](C)C1] | 4-((4-(4-ethyl-2-methyltetrahydro-2H-pyran-4-yl)piperazin-1-yl)methyl)benzonitrile | A | 2.36 | 328.1 |
| 187 | 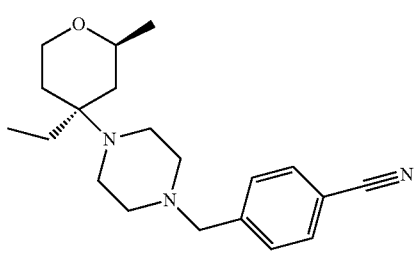 [SMILES: CC[C@]1(N2CCN(Cc3ccc(C#N)cc3)CC2)CCO[C@@H](C)C1] | 4-((4-(4-ethyl-2-methyltetrahydro-2H-pyran-4-yl)piperazin-1-yl)methyl)benzonitrile | | | 328.2 |
| 188 | 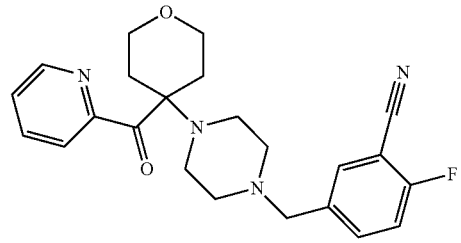 [SMILES: N#Cc1cc(CN2CCN(C3(C(=O)c4ccccn4)CCOCC3)CC2)ccc1F] | 2-fluoro-5-((4-(4-picolinoyltetrahydro-2H-pyran-4-yl)piperazin-1-yl)methyl)benzonitrile | A | 2.07 | 409.4 |

| Ex | Structure | Chemical name | Method | Ret (min) | MS (M + H) |
|---|---|---|---|---|---|
| 189 | 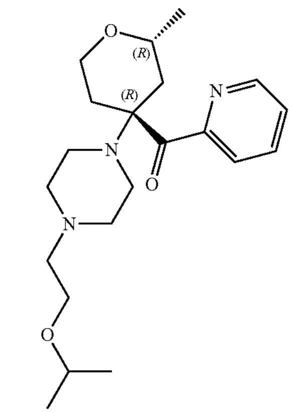 | ((2R,4R)-4-(4-(2-isopropoxyethyl)piperazin-1-yl)-2-methyltetrahydro-2H-pyran-4-yl)(pyridin-2-yl)methanone | D | 1.76 | 376.3 |
| 190 | 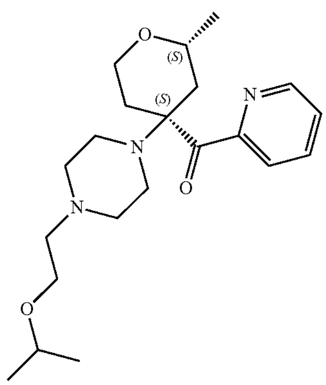 | ((2S,4S)-4-(4-(2-isopropoxyethyl)piperazin-1-yl)-2-methyltetrahydro-2H-pyran-4-yl)(pyridin-2-y)methanone | D | 1.76 | 376.3 |
| 191 | 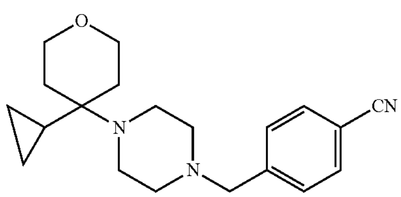 [SMILES: N#Cc1ccc(CN2CCN(C3(C4CC4)CCOCC3)CC2)cc1] | 4-((4-(4-cyclopropyltetrahydro-2H-pyran-4-yl)piperazin-1-yl)methyl)benzonitrile | | | 326.2 |
| 192 | 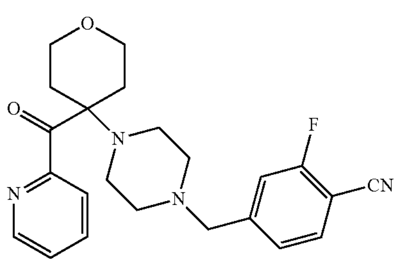 [SMILES: N#Cc1ccc(CN2CCN(C3(C(=O)c4ccccn4)CCOCC3)CC2)cc1F] | 2-fluoro-4-((4-(4-picolinoyltetrahydro-2-pyran-4-yl)piperazin-1-yl)methyl)benzonitrile | A | 2.11 | 409.3 |
| 193 | 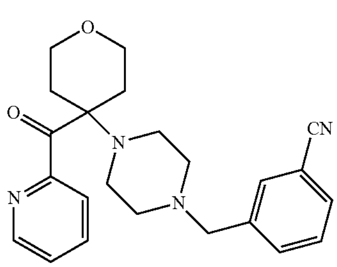 [SMILES: N#Cc1cccc(CN2CCN(C3(C(=O)c4ccccn4)CCOCC3)CC2)c1] | 3-((4-(4-picolinoyltetrahydro-2H-pyran-4-yl)piperazin-1-yl)methyl)benzonitrile | | | 391.2 |

| Ex | Structure | Chemical name | Method | Ret (min) | MS (M + H) |
|---|---|---|---|---|---|
| 194 | 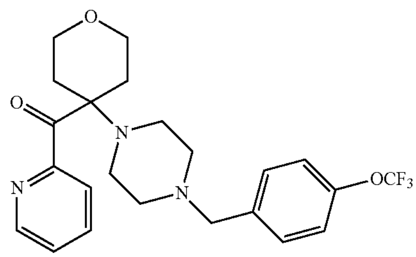 [SMILES: O=C(c1ccccn1)C1(N2CCN(Cc3ccc(OC(F)(F)F)cc3)CC2)CCOCC1] | pyridin-2-yl(4-(4-(4-(trifluoro-methoxy)benzyl)piperazin-1-yl)tetrahydro-2H-pyran-4-yl)methanone | | | 450.2 |
| 195 | 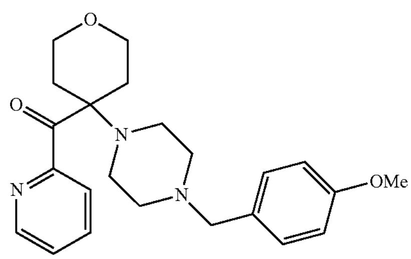 [SMILES: COc1ccc(CN2CCN(C3(C(=O)c4ccccn4)CCOCC3)CC2)cc1] | (4-(4-(4-methoxybenzyl)piperazin-1-yl)tetrahydro-2H-pyran-4-yl)(pyridin-2-yl)methanone | | | 396.2 |
| 196 | 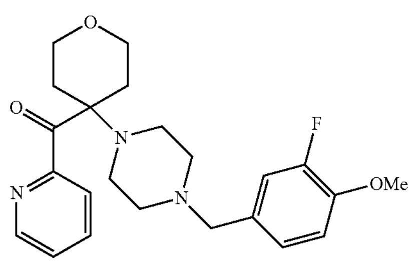 [SMILES: COc1ccc(CN2CCN(C3(C(=O)c4ccccn4)CCOCC3)CC2)cc1F] | (4-(4-(3-fluoro-4-methoxybenzyl)piperazin-1-yl)tetrahydro-2H-pyran-4-yl)(pyridin-2-yl)methanone | | | 414.2 |
| 197 | 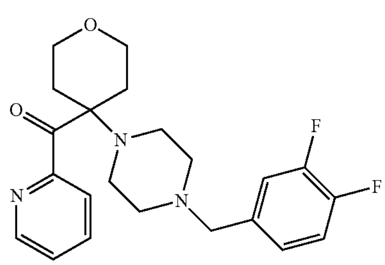 [SMILES: O=C(c1ccccn1)C1(N2CCN(Cc3ccc(F)c(F)c3)CC2)CCOCC1] | (4-(4-(3,4-difluorobenzyl)piperazin-1-yl)tetrahydro-2H-pyran-4-yl)(pyridin-2-yl)methanone | | | 402.2 |
| 198 | 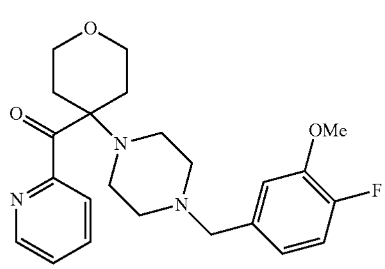 [SMILES: COc1cc(CN2CCN(C3(C(=O)c4ccccn4)CCOCC3)CC2)ccc1F] | (4-(4-(4-fluoro-3-methoxybenzyl)piperazin-1-yl)tetrahydro-2H-pyran-4-yl)(pyridin-2-yl)methanone | A | 2.10 | 414 |

| Ex | Structure | Chemical name | Method | Ret (min) | MS (M + H) |
|---|---|---|---|---|---|
| 199 | 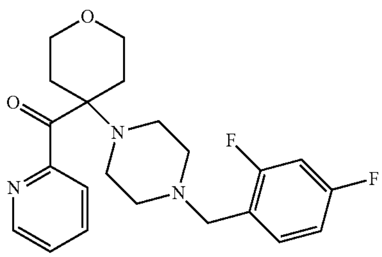 [SMILES: O=C(c1ccccn1)C1(N2CCN(Cc3ccc(F)cc3F)CC2)CCOCC1] | (4-(4-(2,4-difluorobenzyl)piperazin-1-yl)tetrahydro-2H-pyran-4-yl)(pyridin-2-yl)methanone | A | 2.21 | 403 |
| 200 | 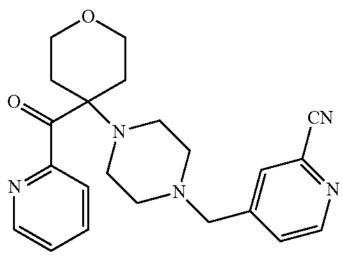 [SMILES: N#Cc1cc(CN2CCN(C3(C(=O)c4ccccn4)CCOCC3)CC2)ccn1] | 4-((4-(4-picolinoyltetrahydro-2H-pyran-4-yl)piperazin-1-yl)methyl)picolinonitrile | | | 392.2 |
| 201 | 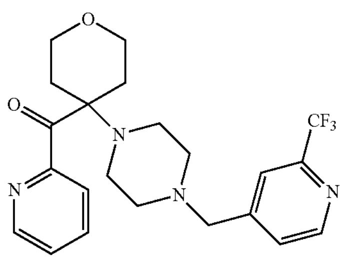 | pyridin-2-yl(4-(4-((2-(trifluoromethyl)pyridin-4-yl)methyl)piperazin-1-yl)tetrahydro-2H-pyran-4-yl)methanone | | | 435.2 |
| 202 | 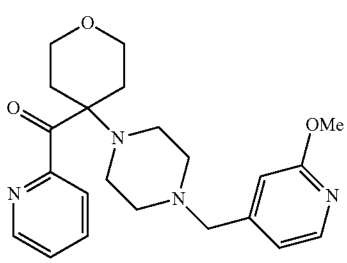 [SMILES: COc1cc(CN2CCN(C3(C(=O)c4ccccn4)CCOCC3)CC2)ccn1] | 4-(4-((2-methoxypyridin-4-y)methyl)piperazin-1-yl)tetrahydro-2H-pyran-4-yl)(pyridin-2-yl)methanone | | | 397.2 |
| 203 | 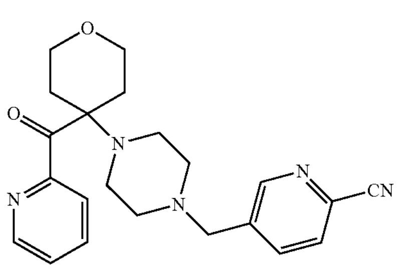 [SMILES: N#Cc1ccc(CN2CCN(C3(C(=O)c4ccccn4)CCOCC3)CC2)cn1] | 5-((4-(4-picolinoyltetrahydro-2H-pyran-4-yl)piperazin-1-yl)methyl)picolinonitrile | | | 392.2 |

| Ex | Structure | Chemical name | Method | Ret (min) | MS (M + H) |
|---|---|---|---|---|---|
| 204 | 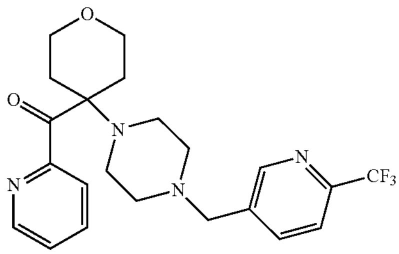 [SMILES: O=C(c1ccccn1)C1(N2CCN(Cc3ccc(C(F)(F)F)nc3)CC2)CCOCC1] | pyridin-2-yl(4-(4-((6-(trifluoromethyl)pyridin-3-yl)methyl)piperazin-1-yl)tetrahydro-2H-pyran-4-yl)methanone | | | 435.2 |
| 205 | 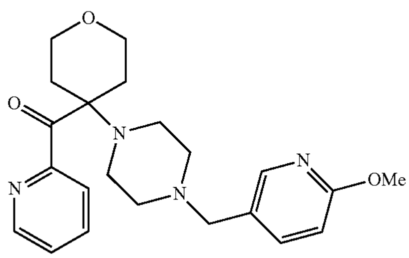 [SMILES: COc1ccc(CN2CCN(C3(C(=O)c4ccccn4)CCOCC3)CC2)cn1] | (4-(4-((6-methoxypyridin-3-yl)methyl)piperazin-1-yl)tetrahydro-2H-pyran-4-yl)(pyridin-2-yl)methanone | | | 397.2 |
| 206 | 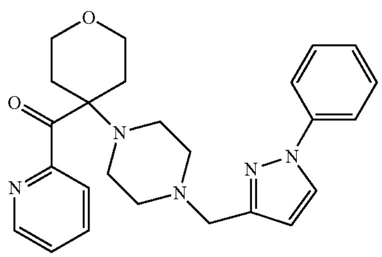 [SMILES: O=C(c1ccccn1)C1(N2CCN(Cc3ccn(-c4ccccc4)n3)CC2)CCOCC1] | 4-(4-((1-phenyl-1H-pyrazol-3-yl)methyl)piperazin-1-yl)tetrahydro-2H-pyran-4-yl)(pyridin-2-yl)methanone | | | 432.2 |
| 207 | 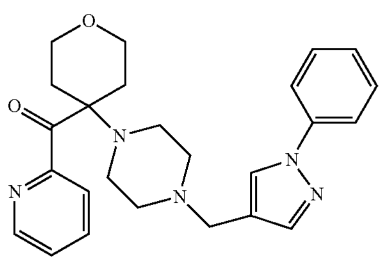 [SMILES: O=C(c1ccccn1)C1(N2CCN(Cc3cnn(-c4ccccc4)c3)CC2)CCOCC1] | 4-(4-((1-phenyl-1H-pyrazol-4-y)methyl)piperazin-1-yl)tetrahydro-2H-pyran-4-yl)(pyridin-2-yl)methanone | | | 432.2 |
| 208 | 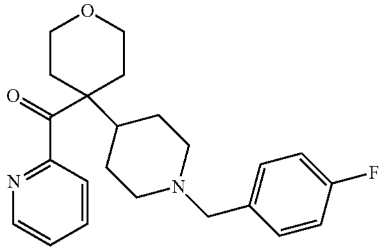 [SMILES: O=C(c1ccccn1)C1(C2CCN(Cc3ccc(F)cc3)CC2)CCOCC1] | 4-(1-(4-fluorobenzyl)piperidin-4-yl)tetrahydro-2H-pyran-4-yl)(pyridin-2-yl)methanone | | | 383.2 |

| Ex | Structure | Chemical name | Method | Ret (min) | MS (M + H) |
|---|---|---|---|---|---|
| 209 | 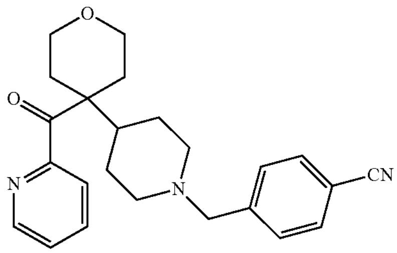 [SMILES: N#Cc1ccc(CN2CCC(C3(C(=O)c4ccccn4)CCOCC3)CC2)cc1] | 4-((4-(4-picolinoyltetrahydro-2H-pyran-4-yl)piperidin-1-yl)methyl)benzonitrile | | | 390.2 |
| 210 | 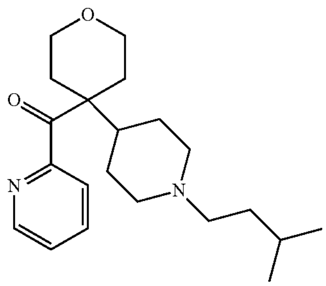 [SMILES: CC(C)CCN1CCC(C2(C(=O)c3ccccn3)CCOCC2)CC1] | (4-(1-isopentylpiperidin-4-yl)tetrahydro-2H-pyran-4-yl)(pyridin-2-yl)methanone | | | 345.2 |
| 211 | 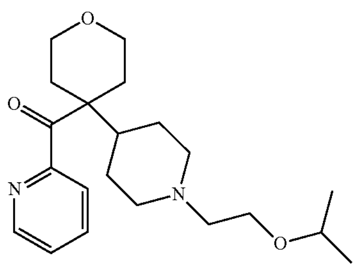 [SMILES: CC(C)OCCN1CCC(C2(C(=O)c3ccccn3)CCOCC2)CC1] | (4-(1-(2-isopropoxyethyl)piperidin-4-yl)tetrahydro-2H-pyran-4-yl)(pyridin-2-yl)methanone | | 361.2 | |
| 212 | 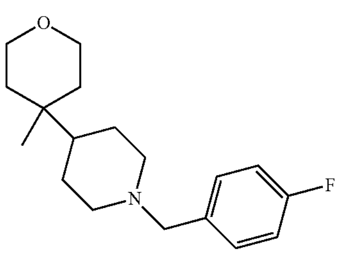 [SMILES: CC1(C2CCN(Cc3ccc(F)cc3)CC2)CCOCC1] | 1-(4-fluorobenzyl)-4-(4-methyltetrahydro-2H-pyran-4-yl)piperidine | | | 292.2 |
| 213 | 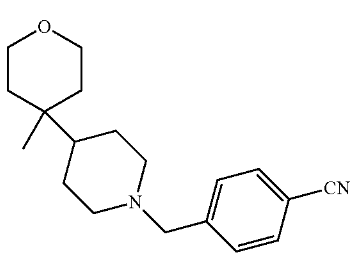 [SMILES: CC1(C2CCN(Cc3ccc(C#N)cc3)CC2)CCOCC1] | 4-((4-(4-methyltetrahydro-2H-pyran-4-yl)piperidin-1-yl)methyl)benzonitrile | | | 299.2 |

| Ex | Structure | Chemical name | Method | Ret (min) | MS (M + H) |
|---|---|---|---|---|---|
| 214 | 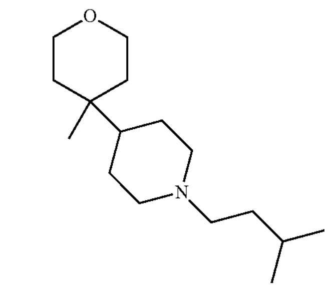 [SMILES: CC(C)CCN1CCC(C2(C)CCOCC2)CC1] | 1-isopentyl-4-(4-methyltetrahydro-2H-pyran-4-yl)piperidine | | | 254.2 |
| 215 | 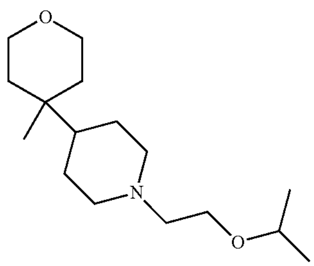 [SMILES: CC(C)OCCN1CCC(C2(C)CCOCC2)CC1] | 1-(2-isopropoxyethyl)-4-(4-methyltetrahydro-2H-pyran-4-yl)piperidine | | | 270.2 |
| 216 | 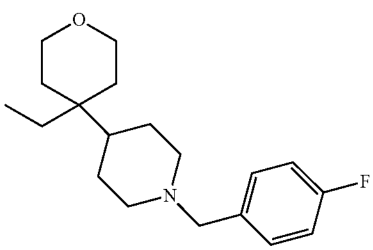 [SMILES: CCC1(C2CCN(Cc3ccc(F)cc3)CC2)CCOCC1] | 4-(4-ethyltetrahydro-2H-pyran-4-yl)-1-(4-fluorobenzyl)piperidine | | | 306.2 |
| 217 | 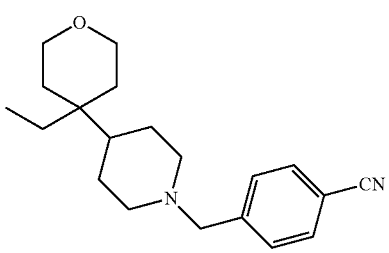 [SMILES: CCC1(C2CCN(Cc3ccc(C#N)cc3)CC2)CCOCC1] | 4-((4-(4-ethyltetrahydro-2H-pyran-4-yl)piperidin-1-yl)methyl)benzonitrile | | | 313.2 |
| 218 | 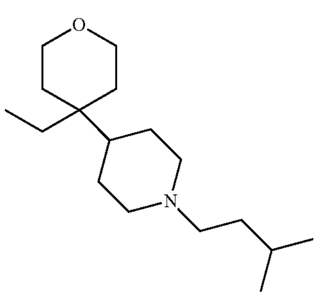 [SMILES: CCC1(C2CCN(CCC(C)C)CC2)CCOCC1] | 4-(4-ethyltetrahydro-2H-pyran-4-yl)-1-isopentylpiperidine | | | 268.3 |

-continued

| Ex | Structure | Chemical name | Method | Ret (min) | MS (M + H) |
|---|---|---|---|---|---|
| 219 | 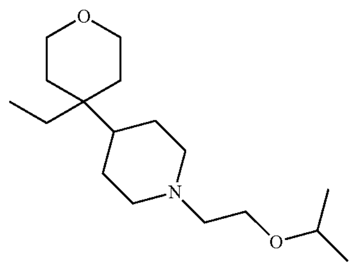 [SMILES: CCC1(C2CCN(CCOC(C)C)CC2)CCOCC1] | 4-(4-ethyltetrahydro-2H-pyran-4-yl)-1-(2-isopropoxyethyl)piperidine | | | 284.3 |
| 220 | 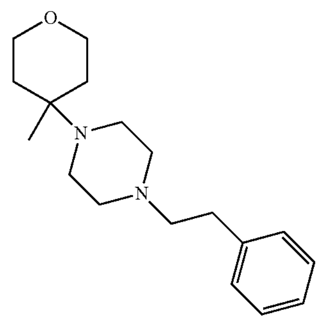 [SMILES: CC1(N2CCN(CCc3ccccc3)CC2)CCOCC1] | 1-(4-methyltetrahydro-2H-pyran-4-yl)-4-phenethylpiperazine | | | 289.2 |
| 221 | 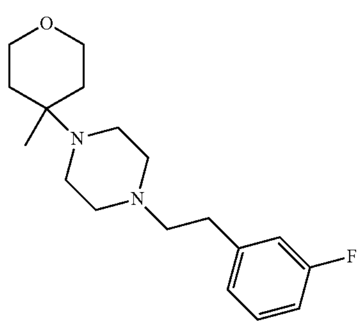 [SMILES: CC1(N2CCN(CCc3cccc(F)c3)CC2)CCOCC1] | 1-(3-fluorophenethyl)-4-(4-methyltetrahydro-2H-pyran-4-yl)piperazine | | | 307.2 |
| 222 | 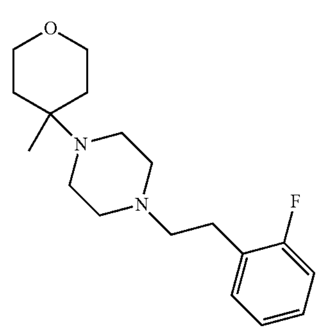 [SMILES: CC1(N2CCN(CCc3ccccc3F)CC2)CCOCC1] | 1-(2-fluorophenethyl)-4-(4-methyltetrahydro-2H-pyran-4-yl)piperazine | | | 307.2 |

-continued

| Ex | Structure | Chemical name | Method | Ret (min) | MS (M + H) |
|---|---|---|---|---|---|
| 223 | 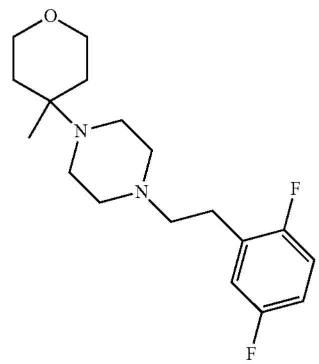 [SMILES: CC1(N2CCN(CCc3cc(F)ccc3F)CC2)CCOCC1] | 1-(2,5-difluorophenethyl)-4-(4-methyltetrahydro-2H-pyran-4-yl)piperazine | | | 325.2 |
| 224 | 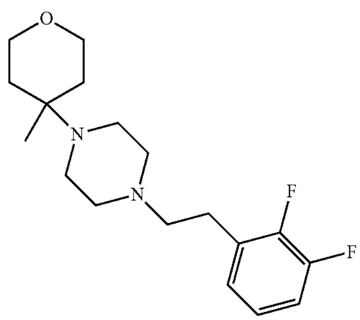 [SMILES: CC1(N2CCN(CCc3cccc(F)c3F)CC2)CCOCC1] | 1-(2,3-difluorophenethyl)-4-(4-methyltetrahydro-2H-pyran-4-yl)piperazine | | | 325.2 |
| 225 | 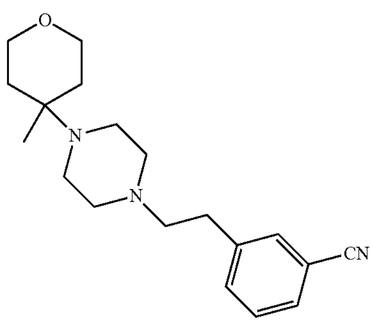 [SMILES: CC1(N2CCN(CCc3cccc(C#N)c3)CC2)CCOCC1] | 3-(2-(4-(4-methyltetrahydro-2H-pyran-4-yl)piperazin-1-yl)ethyl)benzonitrile | | | 314.2 |
| 226 | 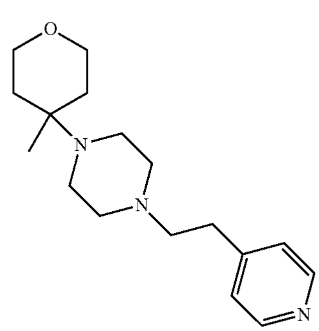 [SMILES: CC1(N2CCN(CCc3ccncc3)CC2)CCOCC1] | 1-(4-methyltetrahydro-2H-pyran-4-yl)-4-(2-(pyridin-4-yl)ethyl)piperazine | | | 290.2 |

-continued

| Ex | Structure | Chemical name | Method | Ret (min) | MS (M + H) |
|---|---|---|---|---|---|
| 227 | 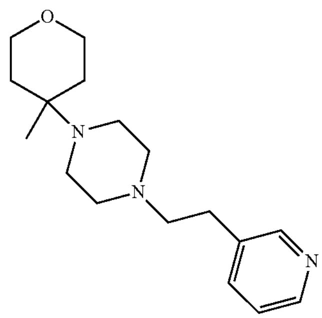 [SMILES: CC1(N2CCN(CCc3cccnc3)CC2)CCOCC1] | 1-(4-methyltetrahydro-2H-pyran-4-yl)-4-(2-(pyridin-3-yl)ethyl)piperazine | | | 290.2 |
| 228 | 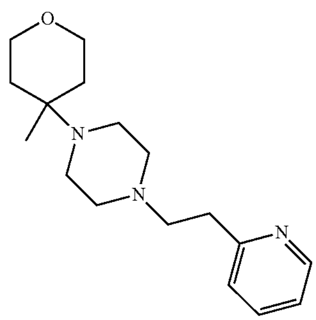 [SMILES: CC1(N2CCN(CCc3ccccn3)CC2)CCOCC1] | 1-(4-methyltetrahydro-2H-pyran-4-yl)-4-(2-(pyridin-2-yl)ethyl)piperazine | | | 290.2 |
| 229 | 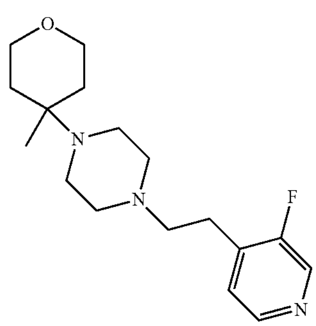 [SMILES: CC1(N2CCN(CCc3ccncc3F)CC2)CCOCC1] | 1-(2-(3-fluoropyridin-4-yl)ethyl)-4-(4-methyltetrahydro-2H-pyran-4-yl)piperazine | | | 308.2 |
| 230 | 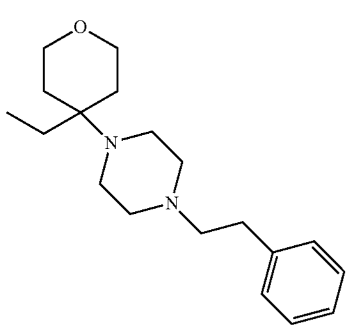 | 1-(4-ethyltetrahydro-2H-pyran-4-yl)-4-phenethylpiperazine | | | 303.2 |

-continued

| Ex | Structure | Chemical name | Method | Ret (min) | MS (M + H) |
|---|---|---|---|---|---|
| 231 | 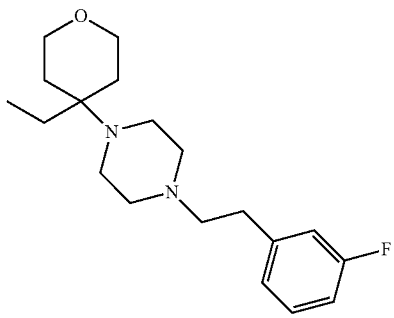 [SMILES: CCC1(N2CCN(CCc3cccc(F)c3)CC2)CCOCC1] | 1-(4-ethyltetrahydro-2H-pyran-4-yl)-4-(3-fluorophenethyl)piperazine | | | 321.2 |
| 232 | 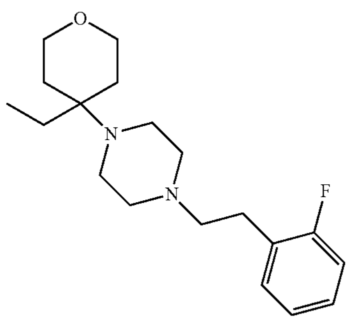 [SMILES: CCC1(N2CCN(CCc3ccccc3F)CC2)CCOCC1] | 1-(4-ethyltetrahydro-2H-pyran-4-yl)-4-(2-fluorophenethyl)piperazine | | | 321.2 |
| 233 | 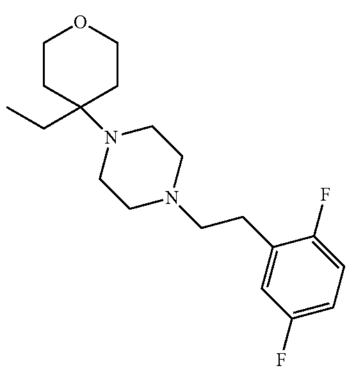 [SMILES: CCC1(N2CCN(CCc3cc(F)ccc3F)CC2)CCOCC1] | 1-(2,5-difluorophenethyl)-4-(4-ethyltetrahydro-2H-pyran-4-yl)piperazine | | | 339.2 |
| 234 | 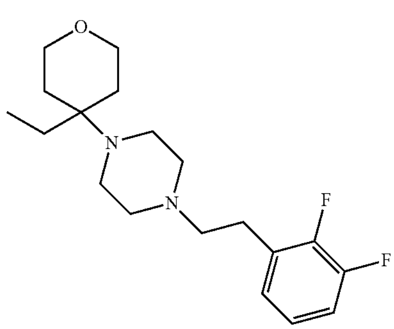 [SMILES: CCC1(N2CCN(CCc3cccc(F)c3F)CC2)CCOCC1] | 1-(2,3-difluorophenethyl)-4-(4-ethyltetrahydro-2H-pyran-4-yl)piperazine | | | 339.2 |

| Ex | Structure | Chemical name | Method | Ret (min) | MS (M + H) |
|---|---|---|---|---|---|
| 235 | 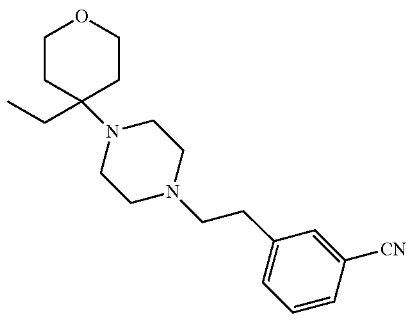 [SMILES: CCC1(N2CCN(CCc3cccc(C#N)c3)CC2)CCOCC1] | 3-(2-(4-(4-ethyltetrahydro-2H-pyran-4-yl)piperazin-1-yl)ethyl)benzonitrile | | | 328.2 |
| 236 | 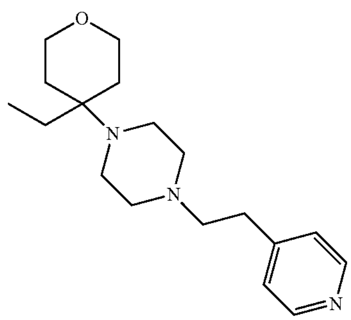 | 1-(4-ethyltetrahydro-2H-pyran-4-yl)-4-(2-(pyridin-4-yl)ethyl)piperazine | | | 304.2 |
| 237 | 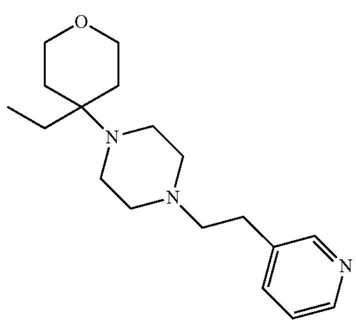 [SMILES: CCC1(N2CCN(CCc3cccnc3)CC2)CCOCC1] | 1-(4-ethyltetrahydro-2H-pyran-4-yl)-4-(2-(pyridin-3-yl)ethyl)piperazine | | | 304.2 |
| 238 | 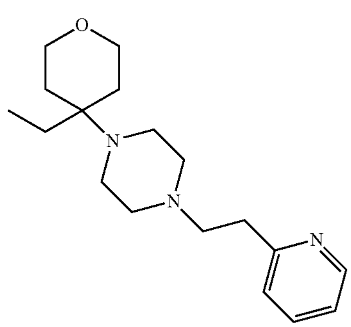 | 1-(4-ethyltetrahydro-2H-pyran-4-yl)-4-(2-(pyridin-2-yl)ethyl)piperazine | | | 304.2 |

| Ex | Structure | Chemical name | Method | Ret (min) | MS (M + H) |
|---|---|---|---|---|---|
| 239 | 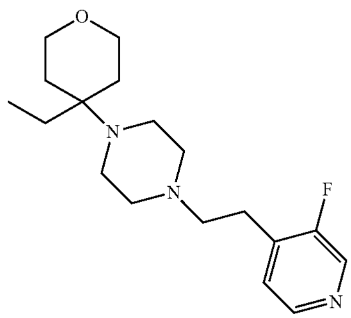 | 1-(4-ethyltetrahydro-2H-pyran-4-yl)-4-(2-(3-fluoropyridin-4-yl)ethyl)piperazine | | | 322.2 |

Examples 240-251

The enantiomers of racemic compounds in examples 26, 74, 77, 168, 172 and 186 were separated by preparative HPLC using Chiralpak IC Column, flow rates 10 or 11 or 12 mL/min A: n-Heptane B: (IPA+0.33% DEA) 70/30 or A: n-Heptane B: (EtOH+5% DEA) 95/5 v/v or A: n-Heptane B: (EtOH+0.33% DEA) 95/5 v/v or A: n-Heptane B: (EtOH+0.33% DEA) 90/10 v/v, rt to give:

| Ex | Structure | Chemical name | Method | Ret (min) | MS (M + H) |
|---|---|---|---|---|---|
| 240 | 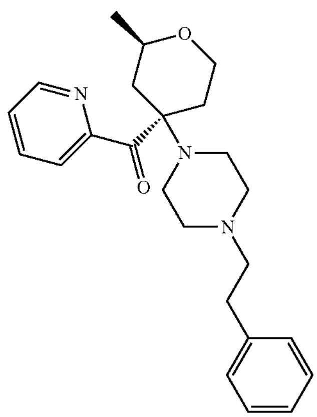 [SMILES: C[C@@H]1C[C@](C(=O)c2ccccn2)(N2CCN(CCc3ccccc3)CC2)CCO1] | ((2R,4R)-2-methyl-4-(4-phenethylpiperazin-1-yl)tetrahydro-2H-pyran-4-yl)(pyridin-2-yl)methanone | A | 2.37 | 394.1 |
| 241 | 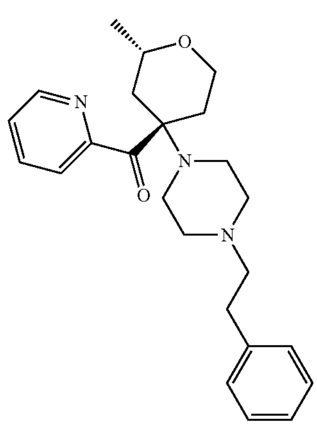 [SMILES: C[C@H]1C[C@@](C(=O)c2ccccn2)(N2CCN(CCc3ccccc3)CC2)CCO1] | ((2S,4S)-2-methyl-4-(4-phenethylpiperazin-1-yl)tetrahydro-2H-pyran-4-yl)(pyridin-2-yl)methanone | A | 2.37 | 394.1 |

-continued

| Ex | Structure | Chemical name | Method | Ret (min) | MS (M + H) |
|---|---|---|---|---|---|
| 242 | 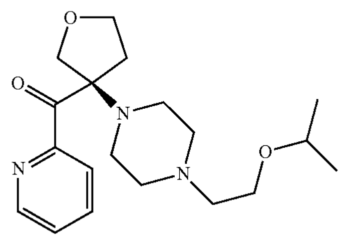 [SMILES: CC(C)OCCN1CCN([C@]2(C(=O)c3ccccn3)CCOC2)CC1] | (R)-(3-(4-(2-isopropoxyethyl)piperazin-1-yl)tetrahydrofuran-3-yl)(pyridin-2-yl)methanone | A | 1.61 | 348 |
| 243 | 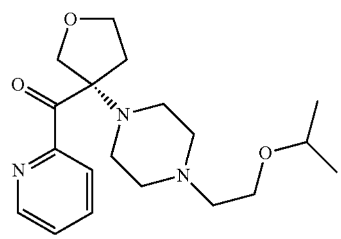 [SMILES: CC(C)OCCN1CCN([C@@]2(C(=O)c3ccccn3)CCOC2)CC1] | (S)-(3-(4-(2-isopropoxyethyl)piperazin-1-yl)tetrahydrofuran-3-yl)(pyridin-2-yl)methanone | A | 1.61 | 348 |
| 244 | 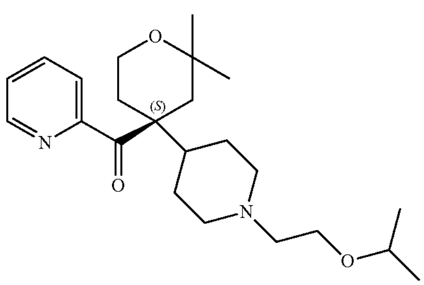 | (S)-(4-(1-(2-isopropoxyethyl)piperidin-4-yl)-2,2-dimethyltetrahydro-2H-pyran-4-yl)(pyridin-2-yl)methanone | A | 1.99 | 389.3 |
| 245 | 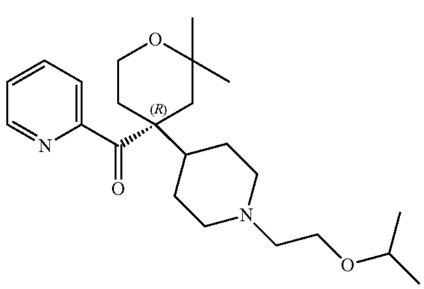 | (R)-(4-(1-(2-isopropoxyethyl)piperidin-4-yl)-2,2-dimethyltetrahydro-2H-pyran-4-yl)(pyridin-2-yl)methanone | A | 1.99 | 389.3 |
| 246 | 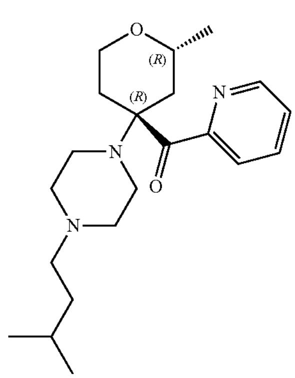 | ((2R,4R)-4-(4-isopentylpiperazin-1-yl)-2-methyltetrahydro-2H-pyran-4-yl)(pyridin-2-yl)methanone | D | 2.24 | 360.3 |

-continued

| Ex | Structure | Chemical name | Method | Ret (min) | MS (M + H) |
|---|---|---|---|---|---|
| 247 | 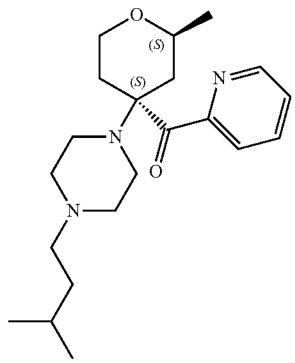 | ((2S,4S)-4-(4-isopentylpiperazin-1-yl)-2-methyltetrahydro-2H-pyran-4-yl)(pyridin-2-yl)methanone | D | 2.24 | 360.3 |
| 248 | 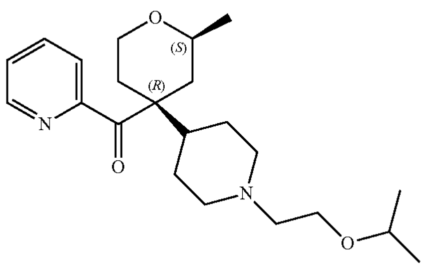 | ((2S,4R)-4-(1-(2-isopropoxyethyl)piperidin-4-yl)-2-methyltetrahydro-2H-pyran-4-yl)(pyridin-2-yl)methanone | A | 1.91 | 375.2 |
| 249 | 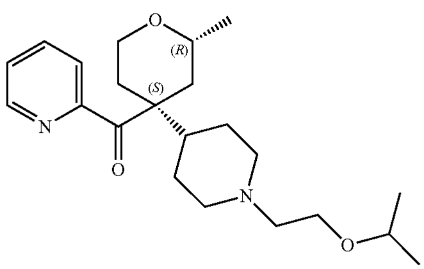 | ((2R,4S)-4-(1-(2-isopropoxyethyl)piperidin-4-yl)-2-methyltetrahydro-2H-pyran-4-yl)(pyridin-2-yl)methanone | A | 1.91 | 375.2 |
| 250 | 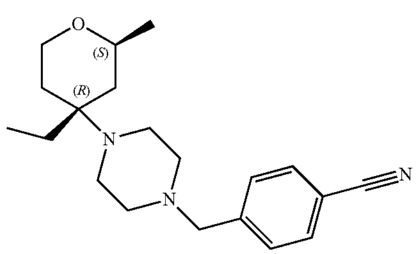 | 4-((4-((2S,4R)-4-ethyl-2-methyltetrahydro-2H-pyran-4-yl)piperazin-1-yl)methyl)benzonitrile | A | 2.36 | 328.4 |
| 251 | 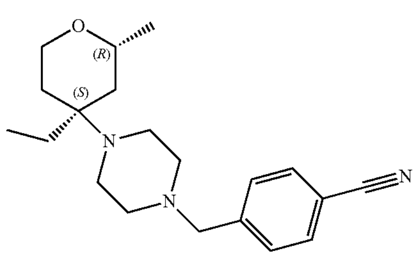 | 4-((4-((2R,4S)-4-ethyl-2-methyltetrahydro-2H-pyran-4-yl)piperazin-1-yl)methyl)benzonitrile | A | 2.36 | 328.4 |

Table of Examples with Binding to the μ-Opioid Receptor and the $\sigma_1$-Receptor:

BIOLOGICAL ACTIVITY

Pharmacological Study
Human $\sigma_1$ Receptor Radioligand Assay

To investigate binding properties of test compounds to human $\sigma_1$ receptor, transfected HEK-293 membranes and [$^3$H](+)-pentazocine (Perkin Elmer, NET-1056), as the radioligand, were used. The assay was carried out with 7 μg of membrane suspension, 5 nM of [$^3$H](+)-pentazocine in either absence or presence of either buffer or 10 μM Haloperidol for total and non-specific binding, respectively. Binding buffer contained Tris-HCl 50 mM at pH 8. Plates were incubated at 37° C. for 120 minutes. After the incubation period, the reaction mix was then transferred to MultiScreen HTS, FC plates (Millipore), filtered and plates were washed 3 times with ice-cold 10 mM Tris-HCL (pH7.4). Filters were dried and counted at approximately 40% efficiency in a MicroBeta scintillation counter (Perkin-Elmer) using EcoScint liquid scintillation cocktail Human μ-Opioid Receptor Radioligand Assay To investigate binding properties of test compounds to human μ-opioid receptor, transfected CHO-K1 cell membranes and [$^3$H]-DAMGO (Perkin Elmer, ES-542-C), as the radioligand, were used. The assay was carried out with 20 μg of membrane suspension, 1 nM of [$^3$H]-DAMGO in either absence or presence of either buffer or 10 μM Naloxone for total and non-specific binding, respectively. Binding buffer contained Tris-HCl 50 mM, MgCl2 5 mM at pH 7.4. Plates were incubated at 27° C. for 60 minutes. After the incubation period, the reaction mix was then transferred to MultiScreen HTS, FC plates (Millipore), filtered and plates were washed 3 times with ice-cold 10 mM Tris-HCL (pH 7.4). Filters were dried and counted at approximately 40% efficiency in a MicroBeta scintillation counter (Perkin-Elmer) using EcoScint liquid scintillation cocktail.

Results:

As this invention is aimed at providing a compound or a chemically related series of compounds which act as dual ligands of the $\sigma_1$ receptor and the μ-opioid receptor it is a very preferred embodiment in which the compounds are selected which act as dual ligands of the $\sigma_1$ receptor and the μ-opioid receptor and especially compounds which have a binding expressed as $K_i$ which is preferably <1000 nM for both receptors, more preferably <500 nM, even more preferably <100 nM.

The following scale as been adopted for representing the binding to the $\sigma_1$ receptor and the μ-opioid receptor expressed as $K_i$:

+ Both $K_i$-μ and $K_i$-$\sigma_1$ >=500 nM
++ One $K_i$<500 nM while the other $K_i$ is >=500 nM
+++ Both $K_i$-μ and $K_i$-$\sigma_1$<500 nM
++++ Both $K_i$-μ and $K_i$-$\sigma_1$<100 nM All compounds prepared in the present application exhibit binding to the $\sigma_1$ receptor and the μ-opioid receptor, in particular the following binding results are shown:

| EX | μ and $\sigma_1$ dual binding |
|---|---|
| 1 | ++++ |
| 2 | ++ |
| 3 | ++++ |
| 4 | ++++ |
| 5 | ++++ |
| 6 | ++++ |
| 7 | ++++ |
| 8 | ++ |
| 9 | ++ |
| 10 | ++ |
| 11 | ++ |
| 12 | +++ |
| 13 | ++ |
| 14 | + |
| 15 | ++++ |
| 16 | +++ |
| 17 | ++ |
| 18 | +++ |
| 19 | ++ |
| 20 | ++ |
| 21 | ++ |
| 22 | +++ |
| 23 | + |
| 24 | +++ |
| 25 | + |
| 26 | +++ |
| 27 | +++ |
| 28 | ++ |
| 29 | +++ |
| 30 | ++ |
| 31 | ++ |
| 32 | ++++ |
| 33 | +++ |
| 34 | +++ |
| 35 | +++ |
| 36 | ++ |
| 37 | ++ |
| 38 | ++ |
| 39 | ++ |
| 40 | ++++ |
| 41 | +++ |
| 42 | ++++ |
| 43 | +++ |
| 44 | +++ |
| 45 | + |
| 46 | ++ |
| 47 | ++ |
| 48 | + |
| 49 | +++ |
| 50 | ++ |
| 51 | +++ |
| 52 | +++ |
| 53 | ++ |
| 54 | +++ |
| 55 | ++ |
| 56 | + |
| 57 | +++ |
| 58 | + |
| 59 | + |
| 60 | +++ |
| 61 | +++ |
| 62 | +++ |
| 63 | ++ |
| 64 | +++ |
| 65 | +++ |
| 66 | +++ |
| 67 | + |
| 68 | + |
| 69 | ++ |
| 70 | ++ |
| 71 | +++ |
| 72 | ++ |
| 73 | ++ |
| 74 | ++ |
| 75 | + |
| 76 | ++++ |
| 77 | +++ |
| 78 | ++ |

| EX | μ and σ₁ dual binding |
|---|---|
| 79 | ++ |
| 80 | + |
| 81 | + |
| 82 | ++ |
| 83 | ++ |
| 84 | ++ |
| 85 | +++ |
| 86 | ++++ |
| 87 | ++ |
| 88 | +++ |
| 89 | +++ |
| 90 | ++ |
| 91 | +++ |
| 92 | +++ |
| 93 | +++ |
| 94 | +++ |
| 95 | ++ |
| 96 | + |
| 97 | ++ |
| 98 | +++ |
| 99 | +++ |
| 100 | +++ |
| 101 | ++ |
| 102 | ++ |
| 103 | + |
| 104 | ++ |
| 105 | ++ |
| 106 | + |
| 107 | + |
| 108 | +++ |
| 109 | ++ |
| 110 | ++ |
| 111 | +++ |
| 112 | +++ |
| 113 | ++ |
| 114 | +++ |
| 115 | +++ |
| 116 | +++ |
| 117 | +++ |
| 118 | +++ |
| 119 | ++ |
| 120 | ++ |
| 121 | ++ |
| 122 | +++ |
| 123 | ++ |
| 124 | ++ |
| 125 | + |
| 126 | + |
| 127 | + |
| 128 | +++ |
| 129 | ++ |
| 130 | ++ |
| 131 | ++ |
| 132 | +++ |
| 133 | ++++ |
| 134 | ++ |
| 135 | +++ |
| 136 | ++ |
| 137 | +++ |
| 138 | + |
| 139 | + |
| 140 | +++ |
| 141 | ++ |
| 142 | ++++ |
| 143 | ++ |
| 144 | +++ |
| 145 | + |
| 146 | ++ |
| 147 | ++ |
| 148 | +++ |
| 149 | ++ |
| 150 | +++ |
| 151 | +++ |
| 152 | ++ |
| 153 | +++ |
| 154 | +++ |
| 155 | ++ |
| 156 | ++ |
| 157 | ++++ |
| 158 | ++ |
| 159 | ++ |
| 160 | ++ |
| 161 | ++ |
| 162 | ++ |
| 163 | ++ |
| 164 | ++ |
| 165 | + |
| 166 | + |
| 167 | ++ |
| 168 | ++ |
| 169 | +++ |
| 170 | +++ |
| 171 | ++ |
| 172 | ++ |
| 173 | ++ |
| 174 | ++ |
| 175 | ++ |
| 176 | ++ |
| 177 | ++ |
| 178 | ++ |
| 179 | ++ |
| 180 | ++ |
| 181 | ++ |
| 182 | ++ |
| 183 | ++ |
| 184 | ++ |
| 185 | ++ |
| 186 | ++ |
| 187 | + |
| 188 | + |
| 189 | + |
| 190 | ++ |
| 191 | + |
| 192 | + |
| 193 | + |
| 194 | + |
| 195 | + |
| 196 | + |
| 197 | + |
| 198 | + |
| 199 | ++ |
| 240 | ++ |
| 241 | +++ |
| 242 | ++ |
| 243 | ++ |
| 244 | ++ |
| 245 | ++ |
| 246 | +++ |
| 247 | ++ |
| 248 | +++ |
| 249 | ++ |
| 250 | + |
| 251 | + |

The invention claimed is:
1. Compound of Formula (I):

(I)

wherein
$R_1$ is m is 1, 2 or 3;
n is 0, 1 or 2;
p is 0, 1 or 2;
q is 0 or 1;
W is nitrogen or carbon;
X is a bond, —C($R_xR_{x'}$)—, C=O or —O—;
  wherein $R_x$ is selected from the group consisting of halogen, —$OR_7$, substituted or unsubstituted $C_{1-6}$ alkyl, substituted or unsubstituted $C_{2-6}$ alkenyl and substituted or unsubstituted $C_{2-6}$ alkynyl;
  $R_{x'}$ is selected from the group consisting of hydrogen, halogen, substituted or unsubstituted $C_{1-6}$ alkyl, substituted or unsubstituted $C_{2-6}$ alkenyl and substituted or unsubstituted $C_{2-6}$ alkynyl;
  $R_7$ is selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
Y is —S— or —O—;
$R_{1'}$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl;
  wherein the cycloalkyl, aryl or heterocyclyl in $R_{1'}$, if substituted, is substituted with one or more substituent/s selected from the group consisting of halogen, —$R_{11}$, —$OR_{11}$, —$NO_2$, —$NR_{11}R_{11'''}$, $NR_{11}C(O)R_{11'}$, —$NR_{11}S(O)_2R_{11'}$, —$S(O)_2NR_{11}R_{11'}$, —$NR_{11}C(O)NR_{11'}R_{11'''}$, —$SR_{11}$, —$S(O)R_{11}$, $S(O)_2R_{11}$, —CN, haloalkyl, haloalkoxy, —$C(O)OR_{11}$, —$C(O)NR_{11}R_{11'}$, —$OCH_2CH_2OH$, —$NR_{11}S(O)_2NR_{11'}R_{11''}$ and $C(CH_3)_2OR_{11}$;
  additionally, the cycloalkyl or non-aromatic heterocyclyl in $R_{1'}$, if substituted, may also be substituted with or =O;
  wherein the alkyl, alkenyl or alkynyl in $R_{1'}$, if substituted, is substituted with one or more substituent/s selected from the group consisting of —$OR_{11}$, halogen, —CN, haloalkyl, haloalkoxy, —$SR_{11}$, —$S(O)R_{11}$, and —$S(O)_2R_{11}$;
  wherein $R_{11}$, $R_{11'}$ and $R_{11''}$ are independently selected from the group consisting of hydrogen, unsubstituted $C_{1-6}$ alkyl, unsubstituted $C_{2-6}$ alkenyl and unsubstituted $C_{2-6}$ alkynyl;
  and wherein $R_{11'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;
$R_2$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl,
  wherein the cycloalkyl, aryl or heterocyclyl in $R_2$, if substituted, is substituted with one or more substituent/s selected from the group consisting of halogen, —$R_{12}$, —$OR_{12}$, —$NO_2$, —$NR_{12}R_{12'''}$, —$NR_{12}C(O)R_{12'}$, —$NR_{12}S(O)_2R_{12'}$, —$S(O)_2NR_{12}R_{12'}$, —$NR_{12}C(O)NR_{12'}R_{12'''}$, —$SR_{12}$, —$S(O)R_{12}$, —$S(O)_2R_{12}$, —CN, haloalkyl, haloalkoxy, —$C(O)OR_{12}$, —$C(O)NR_{12}R_{12'}$, —$OCH_2CH_2OH$, —$NR_{12}S(O)_2NR_{12'}R_{12''}$ and —$C(CH_3)_2OR_{12}$;
  additionally, the cycloalkyl or non-aromatic heterocyclyl in $R_2$, if substituted, may also be substituted with or =O;
  wherein the alkyl, alkenyl or alkynyl in $R_2$, if substituted, is substituted with one or more substituent/s selected from the group consisting of —$OR_{12}$, halogen, —CN, haloalkyl, haloalkoxy, —$SR_{12}$, —$S(O)R_{12}$, and —$S(O)_2R_{12}$;
  wherein $R_{12}$, $R_{12'}$ and $R_{12''}$ are independently selected from the group consisting of hydrogen, unsubstituted $C_{1-6}$ alkyl, unsubstituted $C_{2-6}$ alkenyl and unsubstituted $C_{2-6}$ alkynyl;
  and wherein $R_{12'''}$ is selected from the group consisting of hydrogen, unsubstituted $C_{1-6}$ alkyl, unsubstituted $C_{2-6}$ alkenyl, unsubstituted $C_{2-6}$ alkynyl and -Boc;
$R_3$ and $R_{3'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl;
$R_4$ and $R_{4'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl,
alternatively, $R_4$ and $R_{4'}$, together with the carbon atom to which they are attached, form a substituted or unsubstituted cycloalkyl;
$R_{4''}$ and $R_{4'''}$ are independently selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl, alternatively, R$_{4''}$ and R$_{4'''}$, together with the carbon atom to which they are attached, form a substituted or unsubstituted cycloalkyl;

R$_5$ and R$_{5'}$ are independently selected from the group consisting of hydrogen, substituted or unsubstituted C$_{1-6}$ alkyl, substituted or unsubstituted C$_{2-6}$ alkenyl, substituted or unsubstituted C$_{2-6}$ alkynyl, —CHOR$_8$ and —C(O)OR$_8$;

wherein R$_8$ is selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl;

R$_6$ and R$_{6'}$ are independently selected from the group consisting of hydrogen, —OR$_9$, substituted or unsubstituted C$_{1-6}$ alkyl, substituted or unsubstituted C$_{2-6}$ alkenyl and substituted or unsubstituted C$_{2-6}$ alkynyl;

wherein R$_9$ and R$_{9'}$ are independently selected from the group consisting of hydrogen, substituted or unsubstituted C$_{1-6}$ alkyl, substituted or unsubstituted C$_{2-6}$ alkenyl and substituted or unsubstituted C$_{2-6}$ alkynyl;

and wherein

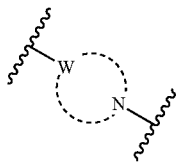

is selected from the group consisting of

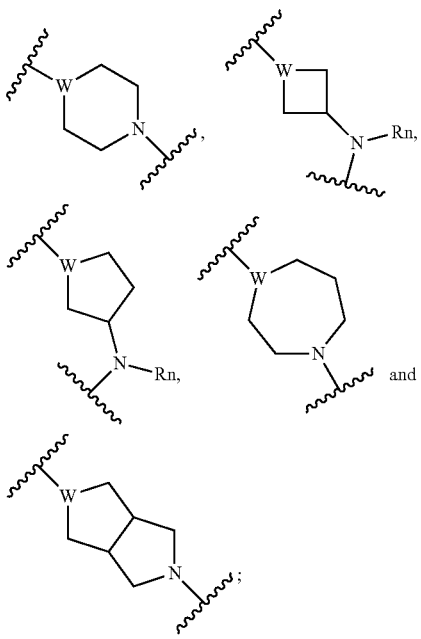

wherein R$_n$ is selected from the group consisting of unsubstituted C$_{1-6}$ alkyl, unsubstituted C$_{2-6}$ alkenyl and unsubstituted C$_{2-6}$ alkynyl;

the alkyl, alkenyl or alkynyl, other than those defined in R$_{1'}$ or R$_2$, if substituted, is substituted with one or more substituent/s selected from the group consisting of —OR$_{13}$, halogen, —CN, haloalkyl, haloalkoxy, —SR$_{13}$, —S(O)R$_{13}$, and —S(O)$_2$R$_{13}$;

wherein R$_{13}$, and R$_{13'}$ are independently selected from the group consisting of hydrogen, unsubstituted C$_{1-6}$ alkyl, unsubstituted C$_{2-6}$ alkenyl, and unsubstituted C$_{2-6}$ alkynyl;

the aryl, heterocyclyl or cycloalkyl other than those defined in R$_{1'}$ or R$_2$, if substituted, is substituted with one or more substituent/s selected from the group consisting of halogen, —R$_{14}$, —OR$_{14}$, —NO$_2$, —NR$_{14}$R$_{14'''}$, NR$_{14}$C(O)R$_{14'}$, —NR$_{14}$S(O)$_2$R$_{14'}$, —S(O)$_2$NR$_{14}$R$_{14'}$, —NR$_{14}$C(O)NR$_{14'}$R$_{14''}$, —SR$_{14}$, —S(O)R$_{14}$, S(O)$_2$R$_{14}$, —CN, haloalkyl, haloalkoxy, —C(O)OR$_{14}$, —C(O)NR$_{14}$R$_{14'}$, —OCH$_2$CH$_2$OH, —NR$_{14}$S(O)$_2$NR$_{14'}$R$_{14''}$ and C(CH$_3$)$_2$OR$_{14}$;

additionally, wherein the cycloalkyl or non-aromatic heterocyclyl, other than those defined in R$_{1'}$ or R$_2$, if substituted, may also be substituted with

or =O;

wherein R$_{14}$, R$_{14'}$ and R$_{14''}$ are independently selected from the group consisting of hydrogen, unsubstituted C$_{1-6}$ alkyl, unsubstituted C$_{2-6}$ alkenyl, unsubstituted C$_{2-6}$ alkynyl, unsubstituted aryl, unsubstituted cycloalkyl and unsubstituted heterocyclyl;

and wherein R$_{14'''}$ is selected from the group consisting of hydrogen, unsubstituted C$_{1-6}$ alkyl, unsubstituted C$_{2-6}$ alkenyl, unsubstituted C$_{2-6}$ alkynyl and -Boc;

optionally as a stereoisomer, including enantiomers and diastereomers, a racemate or as a mixture of at two of stereoisomers, including enantiomers and/or diastereomers, in any mixing ratio, or a corresponding salt thereof, or a corresponding solvate thereof;

wherein the following compound is excluded:

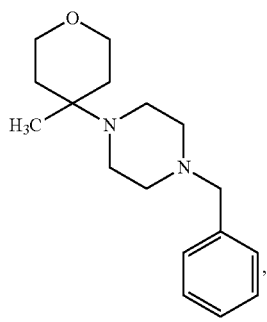 [SMILES: CC1(N2CCN(Cc3ccccc3)CC2)CCOCC1]

and the following compound is excluded:

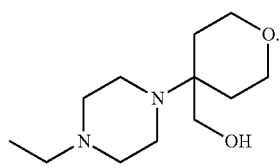

2. The compound according to claim 1, wherein

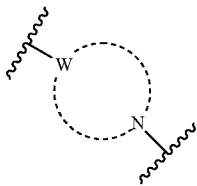

is

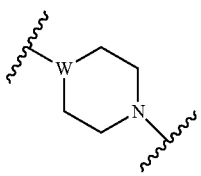

and W is nitrogen or carbon.

3. The compound according to claim 2, wherein W is nitrogen.

4. The compound according to claim 1, wherein
X is a bond or —O—.

5. The compound according to claim 4, wherein X is a bond.

6. The compound according to claim 1, wherein
$R_{1'}$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl.

7. The compound according to claim 6, wherein $R_{1'}$ is selected from the group consisting of substituted or unsubstituted methyl, substituted or unsubstituted ethyl, substituted or unsubstituted isopropyl, substituted or unsubstituted vinyl, substituted or unsubstituted cyclopropyl, substituted or unsubstituted phenyl and substituted or unsubstituted pyridine.

8. The compound according to claim 1, wherein
$R_2$ is selected from the group consisting of substituted or unsubstituted $C_{1-6}$ alkyl, substituted or unsubstituted $C_{2-6}$ alkenyl, substituted or unsubstituted $C_{2-6}$ alkynyl, substituted or unsubstituted cycloalkyl, substituted or unsubstituted aryl and substituted or unsubstituted heterocyclyl.

9. The compound according to claim 8, wherein $R_2$ is selected from the group consisting of substituted or unsubstituted methyl, substituted or unsubstituted 2-methylprop-1-enyl, substituted or unsubstituted ethyl, substituted or unsubstituted isopropyl, substituted or unsubstituted isobutyl, —CH$_2$C(CH$_3$)$_2$F, —CH$_2$C(CH$_3$)$_2$OH, substituted or unsubstituted phenyl or substituted or unsubstituted pyridine.

10. The compound according to claim 1, wherein
$R_3$ and $R_{3'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl.

11. The compound according to claim 10, wherein $R_3$ is substituted or unsubstituted methyl.

12. The compound according to claim 1, wherein
$R_4$ and $R_{4'}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl
and/or
$R_{4''}$ and $R_{4'''}$ are independently selected from the group consisting of hydrogen, substituted or unsubstituted $C_{1-6}$ alkyl, substituted or unsubstituted $C_{2-6}$ alkenyl and substituted or unsubstituted $C_{2-6}$ alkynyl.

13. The compound according to claim 12, wherein
$R_4$ and $R_{4'}$ are both hydrogen or substituted or unsubstituted methyl; and/or
$R_{4''}$ and $R_{4'''}$ are both hydrogen or substituted or unsubstituted methyl.

14. The compound according to claim 1, wherein
$R_4$ and $R_{4'}$, together with the carbon atom to which they are attached, form a substituted or unsubstituted cycloalkyl.

15. The compound according to claim 14, wherein $R_4$ and $R_{4'}$, together with the carbon atom to which they are attached, form a substituted or unsubstituted cyclopentyl.

16. The compound according to claim 1, wherein
$R_5$ and $R_{5'}$ are independently selected from the group consisting of hydrogen, substituted or unsubstituted $C_{1-6}$ alkyl, substituted or unsubstituted $C_{2-6}$ alkenyl, substituted or unsubstituted $C_{2-6}$ alkynyl, —CHOR$_8$ and —C(O)OR$_8$.

17. The compound according to claim 16, wherein $R_5$ and $R_{5'}$ are selected from the group consisting of hydrogen or substituted or unsubstituted methyl.

18. The compound according to claim 1, wherein the compound is selected from the group consisting of:
(4-(4-benzylpiperazin-1-yl)-2,2-dimethyltetrahydro-2H-pyran-4-yl)(pyridin-2-yl)methanone,
(S)-(4-(4-benzylpiperazin-1-yl)-2,2-dimethyltetrahydro-2H-pyran-4-yl)(pyridin-2-yl)methanone,
(R)-(4-(4-benzylpiperazin-1-yl)-2,2-dimethyltetrahydro-2H-pyran-4-yl)(pyridin-2-yl)methanone,
(9-(4-benzylpiperazin-1-yl)-6-oxaspiro[4.5]decan-9-yl)(phenyl)methanone,
(9-(4-benzylpiperazin-1-yl)-6-oxaspiro[4.5]decan-9-yl)(pyridin-2-yl)methanone,
(9-(4-benzylpiperazin-1-yl)-6-oxaspiro[4.5]decan-9-yl)(6-(trifluoromethyl)pyridin-2-yl)methanone,
(9-(4-isobutylpiperazin-1-yl)-6-oxaspiro[4.5]decan-9-yl)(phenyl)methanone,
(4-(4-benzylpiperazin-1-yl)tetrahydro-2H-pyran-4-yl)(pyridin-2-yl)methanone,
(4-(4-benzylpiperazin-1-yl)-2,2-dimethyltetrahydro-2H-pyran-4-yl)(phenyl)methanone,
(4-(4-benzylpiperazin-1-yl)-2,2-dimethyltetrahydro-2H-pyran-4-yl)(pyridin-3-yl)methanone,
(4-(4-isobutylpiperazin-1-yl)-2,2-dimethyltetrahydro-2H-pyran-4-yl)(phenyl)methanone,
(4-(4-isopentylpiperazin-1-yl)-2,2-dimethyltetrahydro-2H-pyran-4-yl)(phenyl)methanone,
(4-(4-(2-isopropoxyethyl)piperazin-1-yl)-2,2-dimethyltetrahydro-2H-pyran-4-yl)(phenyl)methanone,
(4-(4-isobutylpiperazin-1-yl)-2,2-dimethyltetrahydro-2H-pyran-4-yl)(pyridin-2-yl)methanone,
(4-(4-benzylpiperazin-1-yl)-2,2-dimethyltetrahydro-2H-pyran-4-yl)(6-(trifluoromethyl)pyridin-2-yl)methanone,
(4-(4-(2-isopropoxyethyl)piperazin-1-yl)-2,2-dimethyltetrahydro-2H-pyran-4-yl)(6-(trifluoromethyl)pyridin-2-yl)methanone, (4-(4-benzylpiperazin-1-yl)-2,2,6,6-tetramethyltetrahydro-2H-pyran-4-yl)(pyridin-2-yl)methanone,
(4-(5-benzylhexahydropyrrolo[3,4-c]pyrrol-2(1H)-yl)-2,2-dimethyltetrahydro-2H-pyran-4-yl)(pyridin-2-yl)methanone,
(4-(3-(benzyl(methyl)amino)azetidin-1-yl)-2,2-dimethyltetrahydro-2H-pyran-4-yl)(pyridin-2-yl)methanone,
(3-(4-benzylpiperazin-1-yl)tetrahydrofuran-3-yl)(pyridin-2-yl)methanone,
(4-(1-benzylpiperidin-4-yl)tetrahydro-2H-pyran-4-yl)(pyridin-2-yl)methanone,
(4-(1-benzylpiperidin-4-yl)-2,2-dimethyltetrahydro-2H-pyran-4-yl)(pyridin-2-yl)methanone,
(4-(3-((2-isopropoxyethyl)(methyl)amino)azetidin-1-yl)-2,2-dimethyltetrahydro-2H-pyran-4-yl)(pyridin-2-yl)methanone,
(4-(4-benzyl-1,4-diazepan-1-yl)-2,2-dimethyltetrahydro-2H-pyran-4-yl)(pyridin-2-yl)methanone,
4-(4-benzylpiperazin-1-yl)-2-methyltetrahydro-2H-pyran-4-yl)(pyridin-2-yl)methanone,
2-methyl-4-(4-phenethylpiperazin-1-yl)tetrahydro-2H-pyran-4-yl)(pyridin-2-yl)methanone,
(2S,4R)-4-(4-benzylpiperazin-1-yl)-2-methyltetrahydro-2H-pyran-4-yl)(pyridin-2-yl)methanone,
(2R,4S)-4-(4-benzylpiperazin-1-yl)-2-methyltetrahydro-2H-pyran-4-yl)(pyridin-2-yl)methanone,
1-benzyl-4-(9-ethyl-6-oxaspiro[4.5]decan-9-yl)piperazine,
1-benzyl-4-(4-phenyltetrahydro-2H-pyran-4-yl)piperazine,
1-benzyl-4-(4-ethyltetrahydro-2H-pyran-4-yl)piperazine,
1-benzyl-4-(9-phenyl-6-oxaspiro[4.5]decan-9-yl)piperazine,
1-isobutyl-4-(9-phenyl-6-oxaspiro[4.5]decan-9-yl)piperazine,
1-benzyl-4-(9-benzyl-6-oxaspiro[4.5]decan-9-yl)piperazine,
1-benzyl-4-(2,2-dimethyl-4-phenyltetrahydro-2H-pyran-4-yl)piperazine,
1-benzyl-4-(2,2,4-trimethyltetrahydro-2H-pyran-4-yl)piperazine,
1-(2-isopropoxyethyl)-4-(2,2,4-trimethyltetrahydro-2H-pyran-4-yl)piperazine,
1-benzyl-4-(4-ethyl-2,2-dimethyltetrahydro-2H-pyran-4-yl)piperazine,
1-(4-ethyl-2,2-dimethyltetrahydro-2H-pyran-4-yl)-4-(2-isopropoxyethyl)piperazine,
1-benzyl-4-(4-benzyl-2,2-dimethyltetrahydro-2H-pyran-4-yl)piperazine,
1-(2,2-dimethyl-4-propyltetrahydro-2H-pyran-4-yl)-4-phenethylpiperazine,
1-(4-isopropyl-2,2-dimethyltetrahydro-2H-pyran-4-yl)-4-phenethylpiperazine,
1-benzyl-4-(4-isopropyl-2,2-dimethyltetrahydro-2H-pyran-4-yl)piperazine,
1-(4-cyclopropyl-2,2-dimethyltetrahydro-2H-pyran-4-yl)-4-phenethylpiperazine,
1-(2,2-dimethyl-4-vinyltetrahydro-2H-pyran-4-yl)-4-phenethylpiperazine,
1-(4-ethyl-2-methyltetrahydro-2H-pyran-4-yl)-4-phenethylpiperazine,
1-(4-ethyl-2-methyltetrahydro-2H-pyran-4-yl)-4-phenethylpiperazine,
2-(2,2-dimethyl-4-(4-phenethylpiperazin-1-yl)tetrahydro-2H-pyran-4-yl)ethanol,
1-(4-(2-Methoxyethyl)-2,2-dimethyltetrahydro-2H-pyran-4-yl)-4-phenethylpiperazine,
(2,2-dimethyl-4-(4-(pyridin-2-ylmethyl)piperazin-1-yl)tetrahydro-2H-pyran-4-yl)(pyridin-2-yl)methanone,
(9-(4-isobutylpiperazin-1-yl)-6-oxaspiro[4.5]decan-9-yl)(pyridin-2-yl)methanone,
1-(4-ethyl-2,2-dimethyltetrahydro-2H-pyran-4-yl)-4-phenethylpiperazine,
1-phenethyl-4-(2,2,4-trimethyltetrahydro-2H-pyran-4-yl)piperazine,
(2,2-dimethyl-4-(4-phenethylpiperazin-1-yl)tetrahydro-2H-pyran-4-yl)(pyridin-2-yl)methanone,
(4-(4-(2-(3-fluoropyridin-2-yl)ethyl)piperazin-1-yl)-2,2-dimethyltetrahydro-2H-pyran-4-yl)(pyridin-2-yl)methanone,
(4-(4-(2-(3-chloropyridin-2-yl)ethyl)piperazin-1-yl)-2,2-dimethyltetrahydro-2H-pyran-4-yl)(pyridin-2-yl)methanone,
(4-(4-(2-(3-chloropyridin-4-yl)ethyl)piperazin-1-yl)-2,2-dimethyltetrahydro-2H-pyran-4-yl)(pyridin-2-yl)methanone,
(2,2-dimethyl-4-(4-(pyridin-3-ylmethyl)piperazin-1-yl)tetrahydro-2H-pyran-4-yl)(pyridin-2-yl)methanone,
(2,2-dimethyl-4-(4-(pyridin-4-ylmethyl)piperazin-1-yl)tetrahydro-2H-pyran-4-yl)(pyridin-2-yl)methanone,
(4-(4-(4-fluorobenzyl)piperazin-1-yl)-2,2-dimethyltetrahydro-2H-pyran-4-yl)(pyridin-2-yl)methanone,
(4-(4-(3-fluorobenzyl)piperazin-1-yl)-2,2-dimethyltetrahydro-2H-pyran-4-yl)(pyridin-2-yl)methanone,
(2,2-dimethyl-4-(4-(1-phenylethyl)piperazin-1-yl)tetrahydro-2H-pyran-4-yl)(pyridin-2-yl)methanone,
(4-(4-(1-(4-fluorophenyl)ethyl)piperazin-1-yl)-2,2-dimethyltetrahydro-2H-pyran-4-yl)(pyridin-2-yl)methanone,
(4-(4-isopentylpiperazin-1-yl)-2,2-dimethyl tetrahydro-2H-pyran-4-yl)(pyridin-2-yl)methanone,
(4-(4-(2-isopropoxyethyl)piperazin-1-yl)-2,2-dimethyltetrahydro-2H-pyran-4-yl)(pyridin-2-yl)methanone,
(4-(4-(2-isobutoxyethyl)piperazin-1-yl)-2,2-dimethyltetrahydro-2H-pyran-4-yl)(pyridin-2-yl)methanone,
(4-(4-(2-ethoxyethyl)piperazin-1-yl)-2,2-dimethyltetrahydro-2H-pyran-4-yl)(pyridin-2-yl)methanone,
(4-(4-(2-methoxyethyl)piperazin-1-yl)-2,2-dimethyltetrahydro-2H-pyran-4-yl)(pyridin-2-yl)methanone,
(2,2-dimethyl-4-(4-(2-(2,2,2-trifluoroethoxy)ethyl)piperazin-1-yl)tetrahydro-2H-pyran-4-yl)(pyridin-2-yl)methanone,
(4-(4-(2-(2-hydroxy-2-methyl propoxy)ethyl)piperazin-1-yl)-2,2-dimethyltetrahydro-2H-pyran-4-yl)(pyridin-2-yl)methanone,
(4-(4-(3-isopropoxypropyl)piperazin-1-yl)-2,2-dimethyltetrahydro-2H-pyran-4-yl)(pyridin-2-yl)methanone,
(4-(4-(2-isopropoxyethyl)piperazin-1-yl)-2,2,6,6-tetramethyltetrahydro-2H-pyran-4-yl)(pyridin-2-yl)methanone,
(4-(5-(2-isopropoxyethyl)hexahydropyrrolo[3,4-c]pyrrol-2(1H)-yl)-2,2-dimethyltetrahydro-2H-pyran-4-yl)(pyridin-2-yl)methanone,
(3-(4-(2-isopropoxyethyl)piperazin-1-yl)tetrahydrofuran-3-yl)(pyridin-2-yl)methanone,
2-(4-(1-(2-isopropoxyethyl)piperidin-4-yl)-2,2-dimethyltetrahydro-2H-pyran-4-yl)pyridine,
(4-(1-isopentylpiperidin-4-yl)-2,2-dimethyltetrahydro-2H-pyran-4-yl)(pyridin-2-yl)methanone,
(4-(1-(2-isopropoxyethyl)piperidin-4-yl)-2,2-dimethyltetrahydro-2H-pyran-4-yl)(pyridin-2-yl)methanone,
1-(4-ethyl-2,2-dimethyltetrahydro-2H-pyran-4-yl)-4-isopentylpiperazine, 1-isopentyl-4-(2,2,4-trimethyltetrahydro-2H-pyran-4-yl) piperazine,
(2,2-dimethyl-4-(4-(2-(pyridin-3-yl)ethyl)piperazin-1-yl) tetrahydro-2H-pyran-4-yl)(pyridin-2-yl)methanone,
(2,2-dimethyl-4-(4-(2-(pyridin-4-yl)ethyl)piperazin-1-yl) tetrahydro-2H-pyran-4-yl)(pyridin-2-yl)methanone,
1-(4-ethyl-2,2-dimethyltetrahydro-2H-pyran-4-yl)-4-(2-(pyridin-4-yl)ethyl)piperazine,
1-(4-ethyl-2,2-dimethyltetrahydro-2H-pyran-4-yl)-4-(2-(pyridin-3-yl)ethyl)piperazine,
1-(4-ethyl-2,2-dimethyltetrahydro-2H-pyran-4-yl)-4-(2-(3-fluoropyridin-4-yl)ethyl)piperazine,
(4-(4-(2-(3-fluoropyridin-4-yl)ethyl)piperazin-1-yl)-2,2-dimethyltetrahydro-2H-pyran-4-yl)(pyridin-2-yl) methanone,
(4-(4-isopentyl-1,4-diazepan-1-yl)-2,2-dimethyltetrahydro-2H-pyran-4-yl)(pyridin-2-yl)methanone,
1-(4-ethyl-2,2-dimethyltetrahydro-2H-pyran-4-yl)-4-(2-(pyridin-2-yl)ethyl)piperazine,
(4-(4-(2-isopropoxyethyl)-1,4-diazepan-1-yl)-2,2-dimethyltetrahydro-2H-pyran-4-yl)(pyridin-2-yl)methanone,
1-(2-fluorophenethyl)-4-(4-isopropyl-2,2-dimethyltetrahydro-2H-pyran-4-yl)piperazine,
(4-(4-(3-hydroxy-3-methylbutyl)piperazin-1-yl)-2,2-dimethyltetrahydro-2H-pyran-4-yl)(pyridin-2-yl)methanone,
1-(3-fluorophenethyl)-4-(4-isopropyl-2,2-dimethyltetrahydro-2H-pyran-4-yl)piperazine,
1-(2,5-difluorophenethyl)-4-(4-isopropyl-2,2-dimethyltetrahydro-2H-pyran-4-yl)piperazine,
1-(4-ethyl-2,2-dimethyltetrahydro-2H-pyran-4-yl)-4-(3-fluorophenethyl)piperazine,
1-(4-ethyl-2,2-dimethyltetrahydro-2H-pyran-4-yl)-4-(2-fluorophenethyl)piperazine,
(2R,4S)-4-(4-(2-isopropoxyethyl)piperazin-1-yl)-2-methyltetrahydro-2H-pyran-4-yl)(pyridin-2-yl)methanone,
(2S,4R)-4-(4-(2-isopropoxyethyl)piperazin-1-yl)-2-methyltetrahydro-2H-pyran-4-yl)(pyridin-2-yl)methanone,
(2R,4S)-4-(4-isopentylpiperazin-1-yl)-2-methyltetrahydro-2H-pyran-4-yl)(pyridin-2-yl)methanone,
(2S,4R)-4-(4-isopentylpiperazin-1-yl)-2-methyltetrahydro-2H-pyran-4-yl)(pyridin-2-yl)methanone,
1-(2,5-difluorophenethyl)-4-(4-ethyl-2,2-dimethyltetrahydro-2H-pyran-4-yl)piperazine,
1-(2,3-difluorophenethyl)-4-(4-ethyl-2,2-dimethyltetrahydro-2H-pyran-4-yl)piperazine,
1-(2,3-difluorophenethyl)-4-(4-isopropyl-2,2-dimethyltetrahydro-2H-pyran-4-yl)piperazine,
(4-(1-isobutylpiperidin-4-yl)-2,2-dimethyltetrahydro-2H-pyran-4-yl)(pyridin-2-yl)methanone,
(4-(1-isobutylpiperidin-4-yl)-2,2-dimethyltetrahydro-2H-pyran-4-yl)(pyridin-2-yl)methanone,
(4-(1-(3-ethoxypropyl)piperidin-4-yl)-2,2-dimethyltetrahydro-2H-pyran-4-yl)(pyridin-2-yl)methanone,
(4-(1-(2-ethoxyethyl)piperidin-4-yl)-2,2-dimethyltetrahydro-2H-pyran-4-yl)(pyridin-2-yl)methanone,
(4-(1-(2-isobutoxyethyl)piperidin-4-yl)-2,2-dimethyltetrahydro-2H-pyran-4-yl)(pyridin-2-yl)methanone,
(4-(1-(3-isopropoxypropyl)piperidin-4-yl)-2,2-dimethyltetrahydro-2H-pyran-4-yl)(pyridin-2-yl)methanone,
(4-(1-(3-fluorobenzyl)piperidin-4-yl)-2,2-dimethyltetrahydro-2H-pyran-4-yl)(pyridin-2-yl)methanone,
(4-(1-(4-fluorobenzyl)piperidin-4-yl)-2,2-dimethyltetrahydro-2H-pyran-4-yl)(pyridin-2-yl)methanone,
(4-(1-(2-fluorobenzyl)piperidin-4-yl)-2,2-dimethyltetrahydro-2H-pyran-4-yl)(pyridin-2-yl)methanone,
(4-(4-(2-fluorophenethyl)piperazin-1-yl)-2,2-dimethyltetrahydro-2H-pyran-4-yl)(pyridin-2-yl)methanone,
(S)-1-(4-ethyl-2,2-dimethyltetrahydro-2H-pyran-4-yl)-4-phenethylpiperazine,
(R) 1-(4-ethyl-2,2-dimethyltetrahydro-2H-pyran-4-yl)-4-phenethylpiperazine,
(S)-(4-(1-isopentylpiperidin-4-yl)-2,2-dimethyltetrahydro-2H-pyran-4-yl)(pyridin-2-yl)methanone,
(R)-(4-(1-isopentylpiperidin-4-yl)-2,2-dimethyltetrahydro-2H-pyran-4-yl)(pyridin-2-yl)methanone,
(4-(4-(2-(2-fluoro-2-methylpropoxy)ethyl)piperazin-1-yl)-2,2-dimethyltetrahydro-2H-pyran-4-yl)(pyridin-2-yl)methanone,
(4-(4-(3-fluoro-3-methylbutyl)piperazin-1-yl)-2,2-dimethyltetrahydro-2H-pyran-4-yl)(pyridin-2-yl)methanone,
(2,2-Dimethyl-4-(4-(3-methylbut-3-enyl)piperazin-1-yl) tetrahydro-2H-pyran-4-yl)(pyridin-2-yl)methanone,
1-(9-phenyl-6-oxaspiro[4.5]decan-9-yl)-4-(pyridin-3-ylmethyl)piperazine,
1-(9-phenyl-6-oxaspiro[4.5]decan-9-yl)-4-(pyridin-2-ylmethyl)piperazine,
3-((4-(9-phenyl-6-oxaspiro[4.5]decan-9-yl)piperazin-1-yl)methyl)benzonitrile,
1-(9-benzyl-6-oxaspiro[4.5]decan-9-yl)-4-(pyridin-3-ylmethyl)piperazine,
1-(9-benzyl-6-oxaspiro[4.5]decan-9-yl)-4-isobutylpiperazine,
2-(4-(1-benzylpiperidin-4-yl)tetrahydro-2H-pyran-4-yl) pyridine,
2-(4-(1-benzylpiperidin-4-yl)-2,2-dimethyltetrahydro-2H-pyran-4-yl)pyridine,
2-(4-(1-isobutylpiperidin-4-yl)-2,2-dimethyltetrahydro-2H-pyran-4-yl)pyridine,
(2,2-dimethyl-4-(4-(3,3,3-trifluoropropyl)piperazin-1-yl) tetrahydro-2H-pyran-4-yl)(pyridin-2-yl)methanone,
(4-(4-(2-cyclopropylethyl)piperazin-1-yl)-2,2-dimethyltetrahydro-2H-pyran-4-yl)(pyridin-2-yl)methanone,
(4-(4-benzylpiperazin-1-yl)-2,2-dimethyltetrahydro-2H-pyran-4-yl)(pyridin-2-yl)methanol,
(4-(1-benzylpiperidin-4-yl)tetrahydro-2H-pyran-4-yl) (pyridin-2-yl)methanol,
(4-(1-benzylpiperidin-4-yl)-2,2-dimethyltetrahydro-2H-pyran-4-yl)(pyridin-2-yl)methanol,
(S)-(4-(4-isopentylpiperazin-1-yl)-2,2-dimethyltetrahydro-2H-pyran-4-yl)(pyridin-2-yl)methanone,
(R)-(4-(4-isopentylpiperazin-1-yl)-2,2-dimethyltetrahydro-2H-pyran-4-yl)(pyridin-2-yl)methanone,
(S)-(4-(4-(2-isopropoxyethyl)piperazin-1-yl)-2,2-dimethyltetrahydro-2H-pyran-4-yl)(pyridin-2-yl)methanone,
(R)-(4-(4-(2-isopropoxyethyl)piperazin-1-yl)-2,2-dimethyltetrahydro-2H-pyran-4-yl)(pyridin-2-yl)methanone,
(S)-(4-(4-(2-isobutoxyethyl)piperazin-1-yl)-2,2-dimethyltetrahydro-2H-pyran-4-yl)(pyridin-2-yl)methanone,
(R)-(4-(4-(2-isobutoxyethyl)piperazin-1-yl)-2,2-dimethyltetrahydro-2H-pyran-4-yl)(pyridin-2-yl)methanone,
(4-((S)-3-(benzyl(methyl)amino)pyrrolidin-1-yl)-2,2-dimethyltetrahydro-2H-pyran-4-yl)(pyridin-2-yl)methanone,
(R)-(4-(4-(2-isopropoxyethyl)piperazin-1-yl)-2,2-dimethyltetrahydro-2H-pyran-4-yl)(pyridin-2-yl)methanone,
((S)-4-((S)-3-(benzyl(methyl)amino)pyrrolidin-1-yl)-2,2-dimethyltetrahydro-2H-pyran-4-yl)(pyridin-2-yl) methanone, ((R)-4-((S)-3-(benzyl(methyl)amino)pyrrolidin-1-yl)-2,
2-dimethyltetrahydro-2H-pyran-4-yl)(pyridin-2-yl)
methanone,
(R) 4-((R)-3-(benzyl(methyl)amino)pyrrolidin-1-yl)-2,2-
dimethyltetrahydro-2H-pyran-4-yl)(pyridin-2-yl)
methanone,
(S) 4-((R)-3-(benzyl(methyl)amino)pyrrolidin-1-yl)-2,2-
dimethyltetrahydro-2H-pyran-4-yl)(pyridin-2-yl)
methanone,
((R)-4-((R)-3-((2-isopropoxyethyl)(methyl)amino)pyr-
rolidin-1-yl)-2,2-dimethyltetrahydro-2H-pyran-4-yl)
(pyridin-2-yl)methanone,
((S)-4-((R)-3-((2-isopropoxyethyl)(methyl)amino)pyr-
rolidin-1-yl)-2,2-dimethyltetrahydro-2H-pyran-4-yl)
(pyridin-2-yl)methanone,
((R)-4-((S)-3-((2-isopropoxyethyl)(methyl)amino)pyr-
rolidin-1-yl)-2,2-dimethyltetrahydro-2H-pyran-4-yl)
(pyridin-2-yl)methanone,
((S)-4-((S)-3-((2-isopropoxyethyl)(methyl)amino)pyr-
rolidin-1-yl)-2,2-dimethyl tetrahydro-2H-pyran-4-
yl)(pyridin-2-yl)methanone,
((S)-4-((R)-3-(isopentyl(methyl)amino)pyrrolidin-1-
yl)-2,2-dimethyltetrahydro-2H-pyran-4-yl)(pyridin-
2-yl)methanone,
((R)-4-((R)-3-(isopentyl(methyl)amino)pyrrolidin-1-yl)-
2,2-dimethyl tetrahydro-2H-pyran-4-yl)(pyridin-2-yl)
methanone,
((R)-4-((S)-3-(isopentyl(methyl)amino)pyrrolidin-1-
yl)-2,2-dimethyltetrahydro-2H-pyran-4-yl)(pyridin-
2-yl)methanone,
((S)-4-((S)-3-(isopentyl(methyl)amino)pyrrolidin-1-
yl)-2,2-dimethyltetrahydro-2H-pyran-4-yl)(pyridin-
2-yl)methanone,
4-(1-benzylpiperidin-4-yl)-2-methyltetrahydro-2H-
pyran-4-yl)(pyridin-2-yl)methanone,
4-(1-benzylpiperidin-4-yl)-2-methyltetrahydro-2H-
pyran-4-yl)(pyridin-2-yl)methanone,
((2R,4R)-4-(4-benzylpiperazin-1-yl)-2-methyltetra-
hydro-2H-pyran-4-yl)(pyridin-2-yl)methanone,
((2S,4S)-4-(4-benzylpiperazin-1-yl)-2-methyltetra-
hydro-2H-pyran-4-yl)(pyridin-2-yl)methanone,
1-Benzyl-4-(4-methyltetrahydro-2H-pyran-4-yl)pip-
erazine,
1-((2S,4S)-4-ethyl-2-methyltetrahydro-2H-pyran-4-
yl)-4-(2-isopropoxyethyl)piperazine,
1-((2S,4R)-4-ethyl-2-methyltetrahydro-2H-pyran-4-
yl)-4-(2-isopropoxyethyl)piperazine,
1-((2S,4S)-4-ethyl-2-methyltetrahydro-2H-pyran-4-
yl)-4-isopentylpiperazine,
1-((2S,4R)-4-ethyl-2-methyltetrahydro-2H-pyran-4-
yl)-4-isopentylpiperazine,
1-((2S,4S)-2,4-dimethyltetrahydro-2H-pyran-4-yl)-4-
isopentylpiperazine,
1-((2S,4R)-2,4-dimethyltetrahydro-2H-pyran-4-yl)-4-
isopentylpiperazine,
1-benzyl-4-((2S,4S)-4-ethyl-2-methyltetrahydro-2H-
pyran-4-yl)piperazine,
1-benzyl-4-((2S,4R)-4-ethyl-2-methyltetrahydro-2H-
pyran-4-yl)piperazine,
1-benzyl-4-(4-methyltetrahydro-2H-pyran-4-yl)piperi-
dine,
1-benzyl-4-(4-ethyltetrahydro-2H-pyran-4-yl)piperi-
dine,
1-Benzyl-4-(4-ethyl-2,2-dimethyltetrahydro-2H-
pyran-4-yl)piperidine,
4-(4-isopentylpiperazin-1-yl)-2-methyltetrahydro-2H-
pyran-4-yl)(pyridin-2-yl)methanone,
4-(4-isopentylpiperazin-1-yl)-2-methyltetrahydro-2H-
pyran-4-yl)(pyridin-2-yl)methanone,
4-(4-(2-fluorophenethyl)piperazin-1-yl)-2-methyltetra-
hydro-2H-pyran-4-yl)(pyridin-2-yl)methanone,
4-(1-isopentylpiperidin-4-yl)-2-methyltetrahydro-2H-
pyran-4-yl)(pyridin-2-yl)methanone,
4-(1-(2-isopropoxyethyl)piperidin-4-yl)-2-methyltetra-
hydro-2H-pyran-4-yl)(pyridin-2-yl)methanone,
4-(4-ethyl-2,2-dimethyltetrahydro-2H-pyran-4-yl)-1-
phenethylpiperidine,
4-((4-(4-ethyltetrahydro-2H-pyran-4-yl)piperazin-1-
yl)methyl)benzonitrile,
1-(4-ethyltetrahydro-2H-pyran-4-yl)-4-(4-fluoroben-
zyl)piperazine,
1-(4-ethyltetrahydro-2H-pyran-4-yl)-4-(2-isopropoxy-
ethyl)piperazine,
(4-(4-isopentylpiperazin-1-yl)tetrahydro-2H-pyran-4-
yl)(pyridin-2-yl)methanone,
1-isopentyl-4-(4-methyltetrahydro-2H-pyran-4-yl)pip-
erazine,
4-((4-(4-picolinoyltetrahydro-2H-pyran-4-yl)piper-
azin-1-yl)methyl)benzonitrile,
1-(4-ethyltetrahydro-2H-pyran-4-yl)-4-isopentylpip-
erazine,
(4-(4-(4-fluorobenzyl)piperazin-1-yl)tetrahydro-2H-
pyran-4-yl)(pyridin-2-yl)methanone,
1-(4-fluorobenzyl)-4-(4-methyltetrahydro-2H-pyran-4-
yl)piperazine,
4-((4-(4-methyltetrahydro-2H-pyran-4-yl)piperazin-1-
yl)methyl)benzonitrile,
1-(2-isopropoxyethyl)-4-(4-methyltetrahydro-2H-
pyran-4-yl)piperazine,
(4-(4-(2-isopropoxyethyl)piperazin-1-yl)tetrahydro-
2H-pyran-4-yl)(pyridin-2-yl)methanone,
4-((4-(4-ethyl-2-methyltetrahydro-2H-pyran-4-yl)pip-
erazin-1-yl)methyl)benzonitrile,
4-((4-(4-ethyl-2-methyltetrahydro-2H-pyran-4-yl)pip-
erazin-1-yl)methyl)benzonitrile,
2-fluoro-5-((4-(4-picolinoyltetrahydro-2H-pyran-4-yl)
piperazin-1-yl)methyl)benzonitrile,
((2R,4R)-4-(4-(2-isopropoxyethyl)piperazin-1-yl)-2-
methyltetrahydro-2H-pyran-4-yl)(pyridin-2-yl)
methanone,
((2S,4S)-4-(4-(2-isopropoxyethyl)piperazin-1-yl)-2-
methyltetrahydro-2H-pyran-4-yl)(pyridin-2-yl)
methanone,
4-((4-(4-cyclopropyltetrahydro-2H-pyran-4-yl)piper-
azin-1-yl)methyl)benzonitrile,
2-fluoro-4-((4-(4-picolinoyltetrahydro-2-pyran-4-yl)
piperazin-1-yl)methyl)benzonitrile,
3-((4-(4-picolinoyltetrahydro-2H-pyran-4-yl)piper-
azin-1-yl)methyl)benzonitrile,
pyridin-2-yl(4-(4-(4-(trifluoromethoxy)benzyl)piper-
azin-1-yl)tetrahydro-2H-pyran-4-yl)methanone,
(4-(4-(4-methoxybenzyl)piperazin-1-yl)tetrahydro-2H-
pyran-4-yl)(pyridin-2-yl)methanone,
(4-(4-(3-fluoro-4-methoxybenzyl)piperazin-1-yl)tetra-
hydro-2H-pyran-4-yl)(pyridin-2-yl)methanone,
(4-(4-(3,4-difluorobenzyl)piperazin-1-yl)tetrahydro-
2H-pyran-4-yl)(pyridin-2-yl)methanone,
(4-(4-(4-fluoro-3-methoxybenzyl)piperazin-1-yl)tetra-
hydro-2H-pyran-4-yl)(pyridin-2-yl)methanone,
(4-(4-(2,4-difluorobenzyl)piperazin-1-yl)tetrahydro-
2H-pyran-4-yl)(pyridin-2-yl)methanone,
4-((4-(4-picolinoyltetrahydro-2H-pyran-4-yl)piper-
azin-1-yl)methyl)picolinonitrile, pyridin-2-yl(4-(4-((2-(trifluoromethyl)pyridin-4-yl)methyl)piperazin-1-yl)tetrahydro-2H-pyran-4-yl)methanone,
4-(4-((2-methoxypyridin-4-yl)methyl)piperazin-1-yl)tetrahydro-2H-pyran-4-yl)(pyridin-2-yl)methanone,
5-((4-(4-picolinoyltetrahydro-2H-pyran-4-yl)piperazin-1-yl)methyl)picolinonitrile,
pyridin-2-yl(4-(4-((6-(trifluoromethyl)pyridin-3-yl)methyl)piperazin-1-yl)tetrahydro-2H-pyran-4-yl)methanone,
(4-(4-((6-methoxypyridin-3-yl)methyl)piperazin-1-yl)tetrahydro-2H-pyran-4-yl)(pyridin-2-yl)methanone,
4-(4-((1-phenyl-1H-pyrazol-3-yl)methyl)piperazin-1-yl)tetrahydro-2H-pyran-4-yl)(pyridin-2-yl)methanone,
4-(4-((1-phenyl-1H-pyrazol-4-yl)methyl)piperazin-1-yl)tetrahydro-2H-pyran-4-yl)(pyridin-2-yl)methanone,
4-(1-(4-fluorobenzyl)piperidin-4-yl)tetrahydro-2H-pyran-4-yl)(pyridin-2-yl)methanone,
4-((4-(4-picolinoyltetrahydro-2H-pyran-4-yl)piperidin-1-yl)methyl)benzonitrile,
(4-(1-isopentylpiperidin-4-yl)tetrahydro-2H-pyran-4-yl)(pyridin-2-yl)methanone,
(4-(1-(2-isopropoxyethyl)piperidin-4-yl)tetrahydro-2H-pyran-4-yl)(pyridin-2-yl)methanone,
1-(4-fluorobenzyl)-4-(4-methyltetrahydro-2H-pyran-4-yl)piperidine,
4-((4-(4-methyltetrahydro-2H-pyran-4-yl)piperidin-1-yl)methyl)benzonitrile,
1-isopentyl-4-(4-methyltetrahydro-2H-pyran-4-yl)piperidine,
1-(2-isopropoxyethyl)-4-(4-methyltetrahydro-2H-pyran-4-yl)piperidine,
4-(4-ethyltetrahydro-2H-pyran-4-yl)-1-(4-fluorobenzyl)piperidine,
4-((4-(4-ethyltetrahydro-2H-pyran-4-yl)piperidin-1-yl)methyl)benzonitrile,
4-(4-ethyltetrahydro-2H-pyran-4-yl)-1-isopentylpiperidine,
4-(4-ethyltetrahydro-2H-pyran-4-yl)-1-(2-isopropoxyethyl)piperidine,
1-(4-methyltetrahydro-2H-pyran-4-yl)-4-phenethylpiperazine,
1-(3-fluorophenethyl)-4-(4-methyltetrahydro-2H-pyran-4-yl)piperazine,
1-(2-fluorophenethyl)-4-(4-methyltetrahydro-2H-pyran-4-yl)piperazine,
1-(2,5-difluorophenethyl)-4-(4-methyltetrahydro-2H-pyran-4-yl)piperazine,
1-(2,3-difluorophenethyl)-4-(4-methyltetrahydro-2H-pyran-4-yl)piperazine,
3-(2-(4-(4-methyltetrahydro-2H-pyran-4-yl)piperazin-1-yl)ethyl)benzonitrile,
1-(4-methyltetrahydro-2H-pyran-4-yl)-4-(2-(pyridin-4-yl)ethyl)piperazine,
1-(4-methyltetrahydro-2H-pyran-4-yl)-4-(2-(pyridin-3-yl)ethyl)piperazine,
1-(4-methyltetrahydro-2H-pyran-4-yl)-4-(2-(pyridin-2-yl)ethyl)piperazine,
1-(2-(3-fluoropyridin-4-yl)ethyl)-4-(4-methyltetrahydro-2H-pyran-4-yl)piperazine,
1-(4-ethyltetrahydro-2H-pyran-4-yl)-4-phenethylpiperazine,
1-(4-ethyltetrahydro-2H-pyran-4-yl)-4-(3-fluorophenethyl)piperazine,
1-(4-ethyltetrahydro-2H-pyran-4-yl)-4-(2-fluorophenethyl)piperazine,
1-(2,5-difluorophenethyl)-4-(4-ethyltetrahydro-2H-pyran-4-yl)piperazine,
1-(2,3-difluorophenethyl)-4-(4-ethyltetrahydro-2H-pyran-4-yl)piperazine,
3-(2-(4-(4-ethyltetrahydro-2H-pyran-4-yl)piperazin-1-yl)ethyl)benzonitrile,
1-(4-ethyltetrahydro-2H-pyran-4-yl)-4-(2-(pyridin-4-yl)ethyl)piperazine,
1-(4-ethyltetrahydro-2H-pyran-4-yl)-4-(2-(pyridin-3-yl)ethyl)piperazine,
1-(4-ethyltetrahydro-2H-pyran-4-yl)-4-(2-(pyridin-2-yl)ethyl)piperazine,
1-(4-ethyltetrahydro-2H-pyran-4-yl)-4-(2-(3-fluoropyridin-4-yl)ethyl)piperazine,
((2R,4R)-2-methyl-4-(4-phenethylpiperazin-1-yl)tetrahydro-2H-pyran-4-yl)(pyridin-2-yl)methanone,
((2S,4S)-2-methyl-4-(4-phenethylpiperazin-1-yl)tetrahydro-2H-pyran-4-yl)(pyridin-2-yl)methanone,
(R)-(3-(4-(2-isopropoxyethyl)piperazin-1-yl)tetrahydrofuran-3-yl)(pyridin-2-yl)methanone,
(S)-(3-(4-(2-isopropoxyethyl)piperazin-1-yl)tetrahydrofuran-3-yl)(pyridin-2-yl)methanone,
(S)-(4-(1-(2-isopropoxyethyl)piperidin-4-yl)-2,2-dimethyltetrahydro-2H-pyran-4-yl)(pyridin-2-yl)methanone,
(R)-(4-(1-(2-isopropoxyethyl)piperidin-4-yl)-2,2-dimethyltetrahydro-2H-pyran-4-yl)(pyridin-2-yl)methanone,
((2R,4R)-4-(4-isopentylpiperazin-1-yl)-2-methyltetrahydro-2H-pyran-4-yl)(pyridin-2-yl)methanone,
((2S,4S)-4-(4-isopentylpiperazin-1-yl)-2-methyltetrahydro-2H-pyran-4-yl)(pyridin-2-yl)methanone,
((2S,4R)-4-(1-(2-isopropoxyethyl)piperidin-4-yl)-2-methyltetrahydro-2H-pyran-4-yl)(pyridin-2-yl)methanone,
((2R,4S)-4-(1-(2-isopropoxyethyl)piperidin-4-yl)-2-methyltetrahydro-2H-pyran-4-yl)(pyridin-2-yl)methanone,
4-((4-((2S,4R)-4-ethyl-2-methyltetrahydro-2H-pyran-4-yl)piperazin-1-yl)methyl)benzonitrile and
4-((4-((2R,4S)-4-ethyl-2-methyltetrahydro-2H-pyran-4-yl)piperazin-1-yl)methyl)benzonitrile.

19. A process for the preparation of the compound of Formula (I) according to claim 1, wherein
a) when $R_1$ is —C(O)$R_{1'}$, said process comprises treating a compound of Formula IIb

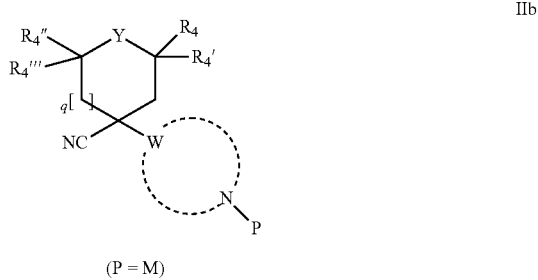

with a lithium salt generated from compounds of general formula IIIa

Z—$R_{1'}$    IIIa with nBuLi, and hydrolysing the obtained imine intermediate compound to a ketone compound of formula I in the presence of an aqueous inorganic acid,
or b) when $R_1$ is —$C(R_6R_{6'})_pR_{1'}$, said process comprises the reaction of compounds of general formula IIIb

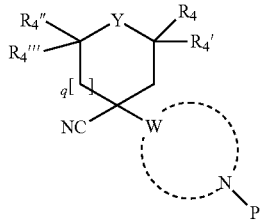

IIb (P = M)

with Grignard reagents of formula IIIb

Z—Mg—$R_1$    IIIb, or c) said process comprises reacting a compound of general formula VII

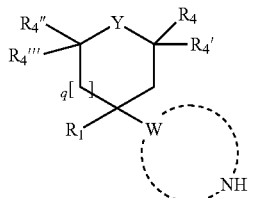

VII with a compound of general formula VIIIa through an alkylation reaction in the presence of an inorganic or organic base

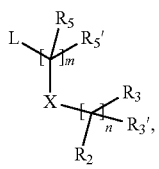

VIIIa or with a compound of general formula VIIIb through a reductive amination reaction in the presence of a reductive agent

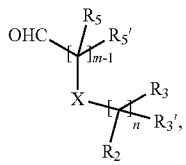

VIIIb or with a compound of general formula VIII through a condensation reaction

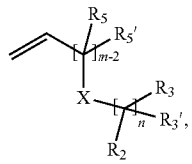

VIIIc or d) when W is carbon, said process comprises the reductive alkylation of a cyano derivatives of formula V

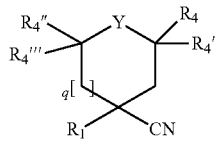

V with a compound of formula VIb

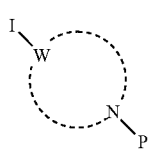

VIb (P = M)

in the presence of lithium naphthalenide, wherein $R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X, Y and W are as defined in claim 17, L is a leaving group, including halogen, mesylate, tosylate and triflate, Z is chloro or bromo, M is

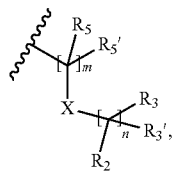

and PG is a protecting group.

20. A process for the preparation of the compound of Formula (I) according to claim 1, employing a compound of Formula IIa, IIb, IIIa, IIIb, IV, V, VIa, VIb, VII, VIIIa, VIIIb or VIIIc,

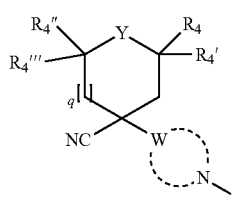

IIa (P = PG)
IIb (P = Y)

-continued

Z—R1',

Z—Mg—R1,

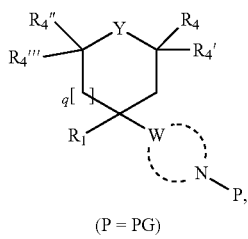

(P = PG)

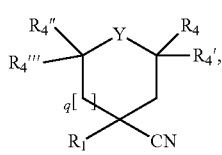

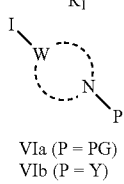

VIa (P = PG)
VIb (P = Y)

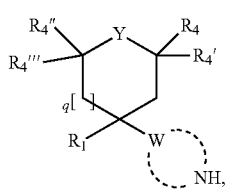

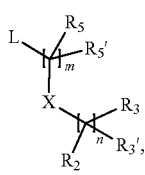

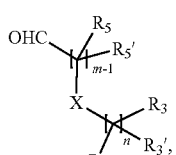

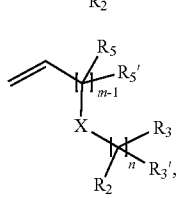

and/or a compound of Formula V', IX, Xa or Xb,

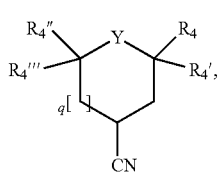

-continued

IIIa
IIIb
IV

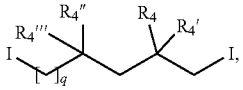  IX

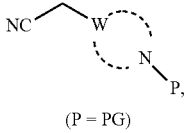  Xa (P = PG)

V  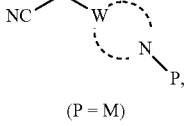  Xb (P = M)

wherein $R_1$, $R_{1'}$, $R_2$, $R_3$, $R_{3'}$, $R_4$, $R_{4'}$, $R_{4''}$, $R_{4'''}$, $R_5$, $R_{5'}$, m, n, p, q, X, Y and W are as defined in claim 17, L is a leaving group, including halogen, mesylate, tosylate and triflate, Z is chloro or bromo, M is

VII

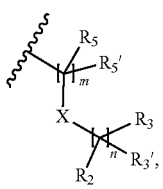

VIIIa and PG is a protecting group.

21. A pharmaceutical composition which comprises the compound according to claim 1, or a pharmaceutically acceptable salt thereof, and a pharmaceutically acceptable carrier or adjuvant.

VIIIb

22. A method of treating pain in a subject in need thereof, comprising administration of an effective amount of the compound according to claim 1.

23. The method according to claim 22, wherein the pain is selected from the group consisting of medium to severe pain, visceral pain, chronic pain, cancer pain, migraine, inflammatory pain, acute pain or neuropathic pain, allodynia and hyperalgesia.

VIIIc

24. A process for the preparation of the compound of Formula (I) according to claim 1, wherein said compound of Formula (I) is made from intermediate (IIa)

IIa

V'  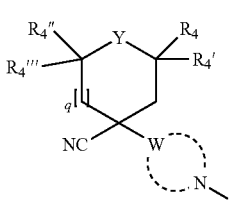

(P = PG)

obtained from the reaction of a compound of formula V'

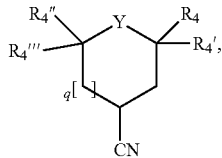

with a compound of formula VIa

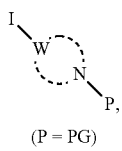

in the presence of a base
or wherein said compound of Formula (I) is made from intermediate (IIb)

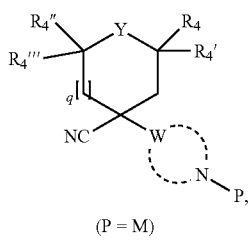

obtained from the reaction of a compound of formula V'

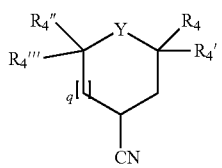

with a compound of formula VIb

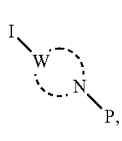

in the presence of a base, or
wherein said compound of Formula (I) is made from intermediate (IIa)

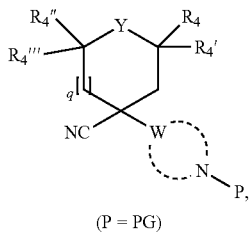

obtained from the reaction of a compound of formula IX

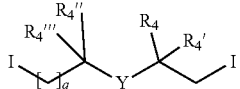

with a compound of formula Xa

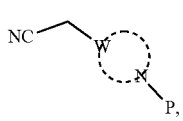

in the presence of a base, or
wherein said compound of Formula (I) is made from intermediate (IIb)

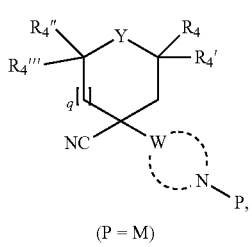

obtained from the reaction of a compound of formula IX

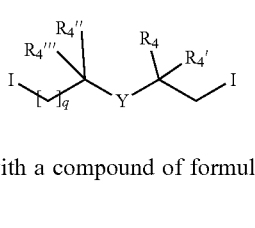

with a compound of formula Xb

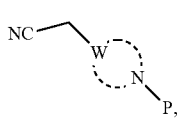

in the presence of a base, wherein M is
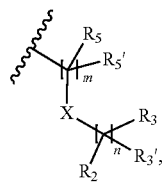
$R_1$, $R_{1'}$, $R_2$, $R_3$, $R_{3'}$, $R_4$, $R_{4'}$, $R_{4''}$, $R_{4'''}$, $R_5$, $R_{5'}$, $R_6$, $R_{6'}$, m, n, p, q, X and Y are as defined in claim 17, L is a leaving group, including halogen, mesylate, tosylate and triflate, Z is chloro or bromo, and PG is a protecting group.
* * * * *